US011078198B2

(12) United States Patent
Carpenter et al.

(10) Patent No.: US 11,078,198 B2
(45) Date of Patent: Aug. 3, 2021

(54) SPIROCYCLIC COMPOUNDS AS FARNESOID X RECEPTOR MODULATORS

(71) Applicant: BRISTOL-MYERS SQUIBB COMPANY, Princeton, NJ (US)

(72) Inventors: Joseph E. Carpenter, Plainsboro, NJ (US); Yanting Huang, Pennington, NJ (US); Ying Wang, New Hope, PA (US); Gang Wu, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 139 days.

(21) Appl. No.: 16/175,910

(22) Filed: Oct. 31, 2018

(65) Prior Publication Data

US 2019/0127362 A1 May 2, 2019

Related U.S. Application Data

(60) Provisional application No. 62/580,068, filed on Nov. 1, 2017.

(51) Int. Cl.
C07D 261/08 (2006.01)
C07D 263/32 (2006.01)
C07D 401/14 (2006.01)
C07D 413/08 (2006.01)
C07D 413/12 (2006.01)
C07D 413/14 (2006.01)
C07D 417/12 (2006.01)
C07D 417/14 (2006.01)
C07D 471/04 (2006.01)
C07D 487/04 (2006.01)
C07D 487/10 (2006.01)
C07D 491/107 (2006.01)
C07D 491/113 (2006.01)
C07D 491/20 (2006.01)
C07D 513/04 (2006.01)
A61K 31/42 (2006.01)
A61K 31/428 (2006.01)
A61K 31/429 (2006.01)
C07H 15/26 (2006.01)

(52) U.S. Cl.
CPC ............ C07D 417/14 (2013.01); A61K 31/42 (2013.01); A61K 31/428 (2013.01); A61K 31/429 (2013.01); C07D 261/08 (2013.01); C07D 263/32 (2013.01); C07D 401/14 (2013.01); C07D 413/08 (2013.01); C07D 413/12 (2013.01); C07D 413/14 (2013.01); C07D 417/12 (2013.01); C07D 471/04 (2013.01); C07D 487/04 (2013.01); C07D 487/10 (2013.01); C07D 491/107 (2013.01); C07D 491/113 (2013.01); C07D 491/20 (2013.01); C07D 513/04 (2013.01); C07H 15/26 (2013.01)

(58) Field of Classification Search
CPC ................ C07D 417/14; C07D 261/08; C07D 491/107; C07D 487/04; C07D 471/04; C07D 413/08; C07D 487/10; C07D 491/113; C07D 491/20; C07D 513/04; C07D 417/12; C07D 263/32; C07D 413/12; C07D 401/14; C07D 413/14
See application file for complete search history.

(56) References Cited

U.S. PATENT DOCUMENTS

| 8,158,665 | B2 | 4/2012 | Caldwell et al. |
| 8,907,095 | B2 | 12/2014 | Xia et al. |
| 9,539,244 | B2 | 1/2017 | Kinzel et al. |
| 9,751,874 | B2 | 9/2017 | Gege et al. |
| 2010/0152166 | A1 | 6/2010 | Genin et al. |
| 2011/0034507 | A1 | 2/2011 | Akwabi-Ameyaw et al. |
| 2015/0329529 | A1* | 11/2015 | Bala .................. A61P 11/00 514/378 |
| 2015/0366856 | A1 | 12/2015 | Tully et al. |

(Continued)

FOREIGN PATENT DOCUMENTS

| CN | 106146483 A | 11/2016 |
| CN | 106632294 A | 5/2017 |

(Continued)

OTHER PUBLICATIONS

Chen et al. "Synthesis of New Heterocyclic Compounds Having 1,2,3-Triazole and Isoxazole Rings in a Single Molecule" J. Het. Chem. 2008, 45, 77-83. (Year: 2008).*

(Continued)

Primary Examiner — Amanda L. Aguirre
(74) Attorney, Agent, or Firm — Gary Greenblatt

(57) ABSTRACT

The present invention provides compounds of Formula (I):

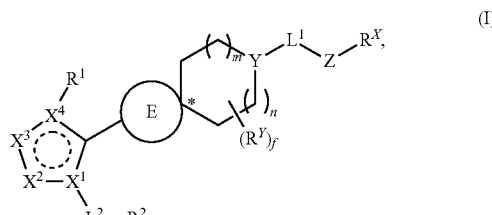

or stereoisomers, tautomers, or pharmaceutically acceptable salts or solvates thereof, wherein all the variables are as defined herein. These compounds modulate the activity of farnesoid X receptor (FXR), for example, as agonists. This invention also relates to pharmaceutical compositions comprising these compounds and methods of treating a disease, disorder, or condition associated with FXR dysregulation, such as pathological fibrosis, transplant rejection, cancer, osteoporosis, and inflammatory disorders, by using the compounds and pharmaceutical compositions.

12 Claims, No Drawings

(56) References Cited

U.S. PATENT DOCUMENTS

| | | |
|---|---|---|
| 2016/0176861 A1 | 6/2016 | Gege et al. |
| 2017/0298068 A1 | 10/2017 | Gege et al. |
| 2017/0304270 A1 | 10/2017 | Or et al. |
| 2017/0304271 A1 | 10/2017 | Or et al. |
| 2017/0304272 A1 | 10/2017 | Or et al. |
| 2017/0333399 A1 | 11/2017 | Or et al. |
| 2017/0355693 A1 | 12/2017 | Blomgren et al. |
| 2017/0355694 A1 | 12/2017 | Gege |
| 2017/0368038 A1 | 12/2017 | Badman et al. |
| 2019/0002452 A1 | 1/2019 | Zhang et al. |

FOREIGN PATENT DOCUMENTS

| | | |
|---|---|---|
| CN | 107021958 A | 8/2017 |
| EP | 3401315 A1 | 11/2018 |
| WO | WO9313101 A1 | 7/1993 |
| WO | WO9817276 A1 | 4/1998 |
| WO | WO2006006490 A1 | 1/2006 |
| WO | WO2008094556 A2 | 8/2008 |
| WO | WO2009009059 A1 | 1/2009 |
| WO | WO2010058318 A1 | 5/2010 |
| WO | WO2011045292 A1 | 4/2011 |
| WO | WO2013186159 A1 | 12/2013 |
| WO | WO2014054053 A1 | 4/2014 |
| WO | WO2015172747 A1 | 11/2015 |
| WO | WO2017133521 A1 | 8/2017 |
| WO | WO2017145040 A1 | 8/2017 |
| WO | WO2017145041 A1 | 8/2017 |
| WO | WO2018059314 A1 | 4/2018 |

OTHER PUBLICATIONS

Claudel, Thierry et al., "The Farnesoid X Receptor: A Novel Drug Target?", Expert Opin. Investig. Drugs, vol. 13(9), pp. 1135-1148, (2004).

International Search Report for Application No. PCT/US2018/058326, dated Oct. 31, 2018.

Sepe, Valentina et al., "Farnesoid X Receptor Modulators 2014-present: A Patent Review," Expert Opinion on Therapeutic Patents, vol. 28, No. 5, pp. 351-364 (2018).

Tully, David C. et al., "Discovery of Tropifexor (LJN452), a Highly Potent Non-bile Acid FXR Agonist for the Treatment of Cholestatic Liver Diseases and Nonalcoholic Steatohepatitis (NASH)", Journal of Medicinal Chemistry, vol. 60, pp. 9960-9973 (2017).

\* cited by examiner

SPIROCYCLIC COMPOUNDS AS FARNESOID X RECEPTOR MODULATORS

CROSS REFERENCE

This application claims the benefit of U.S. Provisional Application Ser. No. 62/580,068 filed Nov. 1, 2017 which is incorporated herein in its entirety.

DESCRIPTION

The present invention relates generally to compounds useful as farnesoid X receptor (FXR) modulators, pharmaceutical compositions comprising such compounds and to their use in therapy, especially in the treatment or prophylaxis of diseases, disorders, and conditions for which an FXR modulator is indicated.

FXR or NR1H4 (nuclear receptor subfamily 1, group H, member 4) is a nuclear receptor that can activate the expression of specific target genes in a ligand-dependent manner. FXR is expressed in the liver, throughout the gastrointestinal tract, colon, ovary, adrenal gland, kidney, and in the gall bladder and biliary tree in humans. FXR forms a heterodimer with Retinoid X Receptor (RXR) and binds to specific response elements in target genes to regulate gene transcription (B. M. Forman et al., Cell 1995; 81: 687; W. Seol et al., Mol. Endocrinol. 1995; 9: 72). The FXR/RXR heterodimer typically binds to an inverted repeat of a consensus hexanucleotide sequence (AGGTCA) separated by a single nucleotide, i.e. an IR-1 sequence. The relevant physiological ligands of FXR are bile acids including chenodeoxycholic acid and its taurine-conjugate (D. J. Parks et al., Science 1999; 284: 1365; M. Makishima et al., Science 1999; 284: 1362). FXR activation regulates the expression of multiple genes that encode enzymes and transporters involved in bile acid synthesis, influx, and efflux from the liver and intestine resulting in a net decrease in total endogenous bile acids in a negative feedback loop. FXR is involved in paracrine and endocrine signaling by upregulating the expression of the cytokine Fibroblast Growth Factor 15 (rodents) or 19 (primates), which can also contribute to the regulation of bile acid concentrations (Holt et al., Genes Dev. 2003; 17: 1581; Inagaki et al., Cell Metab 2005; 2: 217). Therefore, FXR is considered to be a master regulator of bile acid homeostasis.

One use of FXR agonists is for the treatment of diseases in which bile acids are dysregulated, including cholestatic diseases (e.g. primary biliary cirrhosis and primary sclerosing cholangitis) that can lead to fibrosis, cirrhosis, cholangiocarcinoma, hepatocellular carcinoma, liver failure, and death. While elevated bile acid concentrations in the liver have deleterious effects, bile acids also affect the microflora and integrity of the small intestine. Obstruction of bile flow in humans or rodents causes proliferation of intestinal bacteria and mucosal injury, which can lead to bacterial translocation across the mucosal barrier and systemic infection (Berg, Trends Microbiol. 1995; 3: 149-154). Mice lacking FXR have increased ileal levels of bacteria and a compromised epithelial barrier, while activation of intestinal FXR plays an important role in preventing bacterial overgrowth and maintaining the integrity of the intestinal epithelium (Inagaki et al., Proc Natl Acad Sci 2006; 103: 3920-3925). Over time, FXR null mice spontaneously develop hepatocellular carcinoma, and this can be abrogated by selective re-activation of FXR in the intestine (Degirolamo et al., Hepatology 61: 161-170). Pharmacological activation of FXR with a small molecule agonist or transgenic expression of FXR in the intestine can normalize bile acid concentrations, decrease cellular proliferation in hepatic bile ducts, and reduce inflammatory cell infiltration, necrotic area, and liver fibrosis in rodent models of cholestasis (Liu et al., J. Clin. Invest. 2003; 112:1678-1687; Modica et al., Gastroenterology. 2012; 142: 355-365). Some of these beneficial effects observed in preclinical models of cholestasis have translated to human patients, and the FXR agonist, obeticholic acid (OCA or OCALIVA™), has been approved for the treatment of primary biliary cirrhosis (https://www.fda.gov/newsevents/newsroom/pressannouncements/ucm503964.htm).

In addition to controlling bile acid homeostasis, FXR agonists regulate the hepatic expression of hundreds of genes encoding proteins involved in cholesterol and lipid metabolism and transport, glucose homeostasis, inflammation, chemotaxis, and apoptosis among other pathways (Zhan et al., PLoS One 2014; 9: e105930; Ijssennagger et al., J Hepatol 2016; 64: 1158-1166). Consistent with these broad effects on gene expression, FXR agonists have also been investigated in preclinical models of fibrosis, cancer, inflammatory diseases, and metabolic disorders, including dyslipidemia, obesity, type 2 diabetes, nonalcoholic fatty liver disease (NAFLD) and metabolic syndrome (Crawley, Expert Opin. Ther. Patents 2010; 20:1047-1057).

FXR agonists are also being investigated in human clinical trials for the treatment of NAFLD, a more advanced form of fatty liver disease, nonalcoholic steatohepatitis (NASH), and associated complications. NAFLD is one of the most common causes of chronic liver disease in the world today (Vemon et al., Aliment Pharmacol Ther 2011; 34:274-285). The risk factors for developing NAFLD include obesity, type 2 diabetes mellitus (T2DM), insulin resistance, hypertension, and dyslipidemia. In a 6-week clinical trial in T2DM patients with NAFLD, the FXR agonist OCA statistically significantly improved insulin sensitivity and reduced body weight, showing beneficial effects on some of these risk factors (Mudaliar et al., Gastroenterology 2013; 145: 574-582). NASH is the most severe and progressive form of NAFLD and includes the histological findings of hepatic steatosis, inflammation, and ballooning degeneration with varying amounts of pericellular fibrosis (Sanyal et al., Hepatology 2015; 61:1392-1405). In a 72-week clinical trial in patients with NASH, OCA statistically significantly improved hepatic steatosis, lobular inflammation, hepatocyte ballooning, and fibrosis as assessed by histological analyses of liver biopsies (Neuschwander-Tetri et al., Lancet 2015; 385: 956-965). These data also suggest the potential for FXR agonists to show benefit on clinical outcomes given that NASH is the second leading cause of hepatocellular carcinoma (HCC) and liver transplantation in the United States (Wong et al., Hepatology 2014; 59: 2188-2195).

The present invention provides novel compounds for treating a disease, disorder, or condition associated with farnesoid X receptor (FXR) activity in a patient in need thereof.

SUMMARY OF THE INVENTION

In one aspect, the present invention provides compounds of Formula (I), Formula (II) and Formula (III) as well as the subgenera and species thereof, including stereoisomers, tautomers, pharmaceutically acceptable salts, and solvates thereof, which are useful as FXR modulators.

In another aspect, the present invention also provides processes and intermediates for making the compounds of the present invention.

In another aspect, the present invention also provides pharmaceutical compositions comprising a pharmaceutically acceptable carrier and at least one of the compounds of the present invention or stereoisomers, tautomers, pharmaceutically acceptable salts, or solvates thereof.

In another aspect, the compounds of the invention may be used in therapy, either alone or in combination with one or more additional therapeutic agents.

The compounds of the invention may be used in the treatment of a disease, disorder, or condition associated with activity of farnesoid X receptor (FXR) in a patient in need of such treatment by administering a therapeutically effective amount of the compound, or a stereoisomer, a tautomer, or a pharmaceutically acceptable salt or solvate thereof, to the patient. The disease, disorder, or condition may be related to pathological fibrosis. The compounds of the invention can be used alone, in combination with one or more compounds of the present invention, or in combination with one or more, e.g., one to two, other therapeutic agents.

The compounds of the invention may be used, either as a single agent or in combination with other agents, in the treatment of a disease, disorder, or condition selected from nonalcoholic steatohepatitis (NASH), non-alcoholic fatty liver disease (NAFLD), chronic kidney disease, diabetic kidney disease, primary sclerosing cholangitis (PSC), and primary biliary cirrhosis (PBC). The compounds of the invention may be used, either as a single agent or in combination with other agents, in the treatment of idiopathic pulmonary fibrosis (IPF).

The compounds of the invention may be used for the manufacture of a medicament for the treatment of a disease, disorder, or condition in a patient in need of such treatment.

Other features and advantages of the invention will be apparent from the following detailed description and claims.

DETAILED DESCRIPTION

The present application provides compounds, including all stereoisomers, solvates, prodrugs and pharmaceutically acceptable salt and solvate forms thereof, according to Formula (I). The present application also provides pharmaceutical compositions containing at least one compound according to Formula (I), or a stereoisomer, a tautomer, or a pharmaceutically acceptable salt or a solvate thereof, and optionally at least one additional therapeutic agent. Additionally, the present application provides methods for treating a patient suffering from a FXR-modulated disease or disorder such as for example, biliary fibrosis, liver fibrosis, renal fibrosis, Non-Alcoholic Fatty Liver Disease (NAFLD), Non-Alcoholic Steato-Hepatitis (NASH), primary sclerosing cholangitis (PSC), primary biliary cirrhosis (PBC), and pancreatic fibrosis, by administering to a patient in need of such treatment a therapeutically effective amount of a compound of the present invention, or a stereoisomer, a tautomer, or a pharmaceutically acceptable salt or a solvate thereof, and optionally in combination with at least one additional therapeutic agent.

I. Compounds of the Invention

In one embodiment, the present invention provides a compound of Formula (I):

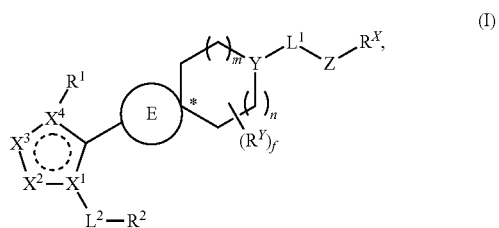

$X^1$ and $X^4$ are each independently C or N;

$X^2$ and $X^3$ are each independently $CR^5$, N, $NR^6$, O, or S;

E ring is a 4- to 6-membered carbocyclyl or heterocyclyl, wherein the carbocyclyl and heterocyclyl are each independently substituted with 0 to 3 $R^3$;

* denotes a spiro carbon atom;

Y is $CR^7$ or N;

m and n are each independently an integer of 0, 1, or 2;

f is an integer of 0, 1, 2, or 3;

Z is 6- to 10-membered aryl, 5- to 10-membered heteroaryl containing 1 to 3 heteroatoms independently selected from N, O, and S, 3- to 10-membered carbocyclyl, or 4- to 10-membered heterocyclyl containing 1 to 3 heteroatoms independently selected from N, O, and S, wherein the aryl, heteroaryl carbocyclyl, and heterocyclyl are independently substituted with 0 to 5 $R^8$;

$L^1$ is a covalent bond, O, S, $NR^{16}$, —$S(O)_2$—, $C_{1-3}$ alkylene, $C_{1-3}$ heteroalkylene, $C_{2-4}$ alkenylene, $C_{2-4}$ alkynylene, aryl, or a 5- to 6-membered heteroaryl containing 1 to 3 heteroatoms independently selected from N, O, and S containing 1 to 4 heteroatoms independently selected from N, O, and S; wherein the alkylene, alkenylene, aryl, heteroalkylene, and heteroaryl are each independently substituted with 0 to 3 $R^{11}$;

$L^2$ is a covalent bond, O, S, $NR^{17}$, $C_{1-3}$ alkylene, or $C_{1-3}$ heteroalkylene, wherein the alkylene and heteroalkylene are independently substituted with 0 to 3 $R^{15}$;

$R^X$ is -$L^3$-R;

$L^3$ is a covalent bond, a $C_{1-3}$ alkylene, —C(O)$NR^{12}$—$CH_2$—, or —$OCH_2$—, wherein the $C_{1-3}$ alkylene is substituted with 0 to 3 $R^4$;

$R^Z$ is —CN, —C(O)$OR^{13}$, —C(O)$NR^{14a}R^{14b}$,

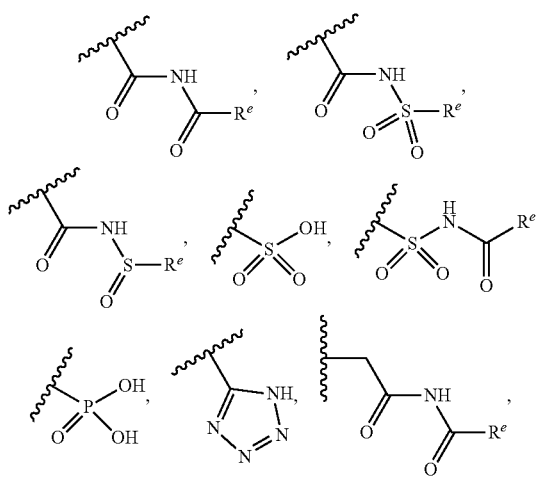

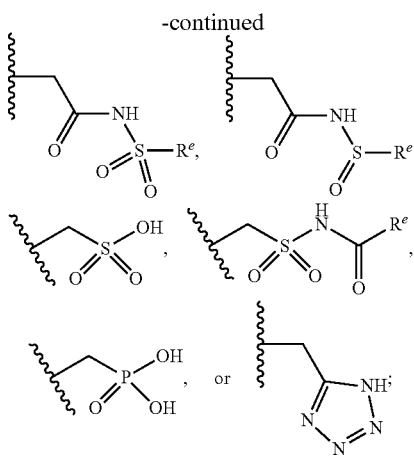

$R^e$ is $C_{1-6}$ alkyl, $C_{3-6}$ cycloalkyl, haloalkyl, hydroxyalkyl, aminoalkyl, alkoxyalkyl, or haloalkoxyalkyl;

each $R^Y$ is independently hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy; or alternatively two $R^Y$, together with the carbon atoms to which they are attached, form a bridge moiety; and with the proviso that when Y is N and $R^Y$ is attached to a carbon atom adjacent to Y, then $R^Y$ is not halo, cyano, hydroxyl, amino, alkoxy, or haloalkoxy;

$R^1$ is $C_{1-6}$ alkyl, $C_{3-5}$ cycloalkyl, or $C_{4-6}$ heterocyclyl, wherein the alkyl or cycloalkyl is substituted with 0 to 3 $R^9$;

$R^2$ is 6- to 10-membered aryl, 5- to 10-membered heteroaryl containing 1 to 3 heteroatoms independently selected from N, O, and S, 3- to 10-membered carbocyclyl, or 4- to 10-membered heterocyclyl containing 1 to 3 heteroatoms independently selected from N, O, and S, wherein the aryl, heteroaryl, carbocyclyl, and heterocyclyl are independently substituted with 0 to 5 $R^{10}$;

$R^3$, $R^5$ and $R^7$ are each independently hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy;

$R^4$ is each independently halo, oxo, cyano, hydroxyl, amino, alkyl, alkoxy, or alkylamino; or alternatively, two $R^4$ taken together with the atom(s) to which they are attached, form a carbocyclyl or heterocyclyl moiety;

$R^6$, $R^{16}$ and $R^{17}$ are each independently hydrogen, $C_{1-6}$ alkyl, haloalkyl, hydroxyalkyl, aminoalkyl, alkoxyalkyl, or haloalkoxyalkyl;

$R^8$ and $R^{10}$ are each independently halo, cyano, hydroxyl, amino, oxo, —$OR^a$, —$SR^a$, =S, —$NR^cR^c$, =NH, =N—OH, =$NR^a$, =N—$OR^a$, —$NO_2$, —$S(O)_2R^a$, —$S(O)_2NHR^b$, —$S(O)_2NR^cR^c$, —$S(O)_2OR^b$, —$OS(O)_2R^b$, —$OS(O)_2OR^b$, —$P(O)(OR^b)(OR^b)$, —$C(O)R^b$, —$C(NR^b)R^b$, —$C(O)OR^b$, —$C(O)NR^cR^c$, —$C(NR^b)NR^cR^c$, —$OC(O)R^b$, —$NR^bC(O)R^b$, —$OC(O)OR^b$, —$NR^bC(O)OR^b$, —$OC(O)NR^cR^c$, —$NR^bC(O)NR^cR^c$, —$NR^bC(NR^b)R^b$, —$NR^bC(NR^b)NR^cR^c$, $C_{1-6}$ alkyl, $C_{1-6}$ haloalkyl, aryl, arylalkyl, heteroaryl, carbocyclyl, or heterocyclyl; wherein the alkyl, aryl, heteroaryl, carbocyclyl, and heterocyclyl, by themselves or as part of another group, are each independently substituted with 0 to 5 $R^d$;

$R^a$ is each independently $C_{1-6}$ alkyl, haloalkyl, hydroxyalkyl, aminoalkyl, alkoxyalkyl, haloalkoxyalkyl, aryl, arylalkyl, heteroaryl, heteroarylalkyl, carbocyclyl, carbocyclylalkyl, heterocyclyl, or heterocyclylalkyl;

$R^b$ is each independently hydrogen or $R^a$;

$R^c$ is each independently $R^b$ or alternatively, the two $R^c$ are taken together with the nitrogen atom to which they are bonded form a 4-, 5-, 6- or 7-membered heterocyclyl containing 1 to 3 heteroatoms independently selected from N, O, and S;

$R^d$ is each independently selected from $R^a$, alkoxy, haloalkoxy, alkylamino, cycloalkylamino, heterocyclylamino, haloalkyl, hydroxyalkyl, aminoalkyl, cycloalkoxy, heterocyclyloxy, haloalkoxy, alkoxyalkoxy, haloalkylamino, alkoxyalkylamino, haloalkoxyalkylamino, aryloxy, aralkyloxy, heteroaryloxy, heteroarylalkyloxy, alkylthio, halo, cyano, hydroxyl, amino, oxo, —$OR^a$, —$SR^a$, =S, —$NR^cR^c$, =NH, =N—OH, =$NR^a$, =N—$OR^a$, —$NO_2$, —$S(O)_2R^a$, —$S(O)_2NHR^b$, —$S(O)_2NR^cR^c$, —$S(O)_2OR^b$, —$OS(O)_2R^b$, —$OS(O)_2OR^b$, —$P(O)(OR^b)(OR^b)$, —$C(O)R^b$, —$C(NR^b)R^b$, —$C(O)OR^b$, —$C(O)NR^cR^c$, —$C(NR^b)NR^cR^c$, —$OC(O)R^b$, —$NR^bC(O)R^b$, —$OC(O)OR^b$, —$NR^bC(O)OR^b$, —$NR^bC(O)NR^cR^c$, —$NR^bC(NR^b)R^b$, and —$NR^bC(NR^b)NR^cR^c$;

$R^9$ is each independently halo, cyano, hydroxyl, amino, or $C_{1-6}$ alkyl;

$R^{11}$ and $R^{15}$ are each independently halo, oxo, cyano, hydroxyl, amino, $C_{1-6}$ alkyl, $C_{3-6}$ cycloalkyl, $C_{4-6}$ heterocyclyl, alkylamino, haloalkyl, hydroxyalkyl, aminoalkyl, alkoxyalkyl, haloalkoxyalkyl, alkoxy, or haloalkoxy;

$R^{12}$ is hydrogen or $C_{1-4}$ alkyl;

$R^{13}$ is hydrogen, $C_{1-10}$ alkyl, glycosyl, or carboxy(trihydroxy)tetrahydropyranyl; and $R^{14a}$ and $R^{14b}$ are each independently hydrogen, $C_{1-6}$ alkyl, $C_{3-6}$ cycloalkyl, $C_{4-6}$ heterocyclyl, alkylamino, haloalkyl, hydroxyalkyl, aminoalkyl, alkoxyalkyl, haloalkoxyalkyl, alkoxy, or haloalkoxy.

It should be understood by one skilled in the art that the dashed circle denotes an aromatic ring formed by $X^1$, $X^2$, $X^3$, $X^4$, and the carbon atom; and the dashed straight lines are each independently an optional covalent bond.

In one embodiment of Formula (I), $X^2$ is N or $NR^6$.

In one embodiment of Formula (I), two $R^Y$, together form a $C_{1-3}$ alkylene bridge moiety. $(R^Y)_f$ denotes one or more optional substituent groups on any of the suitable ring member atoms, and each of $R^Y$ is independent and can be the same or different.

In any one of the preceding embodiments of Formula (I), the

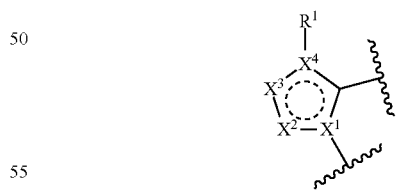

moiety is

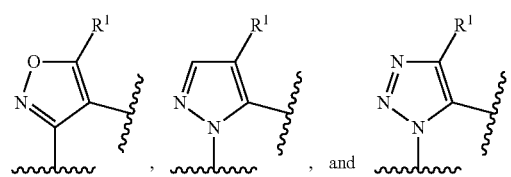

In any one of the preceding embodiments of Formula (I), $L^1$ is a covalent bond, O, S, NH, $C_{1-3}$ alkylene, —($C_{1-3}$ alkylene)$_a$-O—($C_{1-3}$ alkylene)$_b$-, —($C_{1-3}$ alkylene)$_a$-S—($C_{1-3}$ alkylene)$_b$-, or —($C_{1-3}$ alkylene)$_a$-NH—($C_{1-3}$ alkylene)$_b$-, wherein the $C_{1-3}$ alkylene is substituted with 0 to 3 $R^{11}$; a is an integer of 0 or 1; b is an integer of 0 or 1; provided that a and b are not both 1; and $L^2$ is a covalent bond.

In any one of the preceding embodiments of Formula (I), the E ring is a moiety selected from:

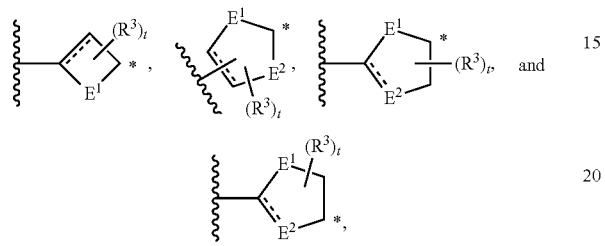

$E^1$ and $E^2$ are independently $CR^3$, $CHR^3$, N, $NR^3$, O or S;

the dashed line is an optional covalent bond; that is, the dashed line denotes a covalent bond which is either present or absent;

t is 0, 1 or 2; and each $R^3$ is independently hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy.

In any one of the preceding embodiments of Formula (I), the

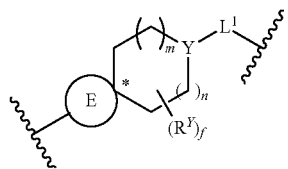

moiety is selected from

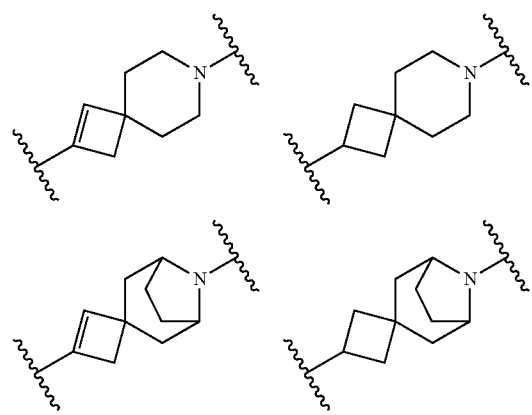

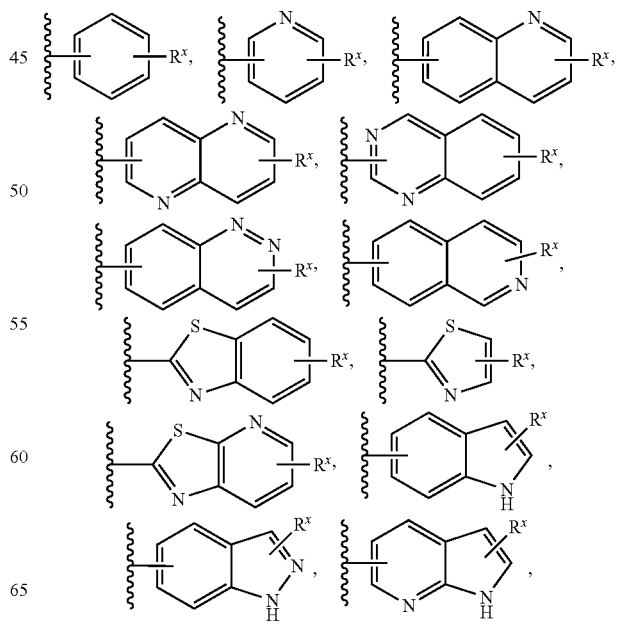

wherein the nitrogen atom is attached to $L^1$.

In any one of the preceding embodiments of Formula (I), Z is phenyl or 5- to 10-membered heteroaryl containing 1 to 3 heteroatoms independently selected from N, O, and S containing 1 to 3 heteroatoms independently selected from N, O, and S, wherein the phenyl and heteroaryl are independently substituted with 0 to 5 $R^8$, wherein $R^8$ is the same as defined above.

In any one of the preceding embodiments of Formula (I), $L^1$ is a covalent bond.

In any one of the preceding embodiments of Formula (I), —Z—$R^x$ is

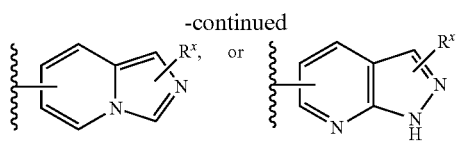

wherein the Z moiety is further substituted with 0 to 3 $R^8$, and $R^8$ is the same as defined above.

In any one of the preceding embodiments of Formula (I), Y is N.

In any one of the preceding embodiments of Formula (I), Y is CH; and $L^1$ is a covalent bond, O, S, NH, —O—($C_{1-3}$ alkylene)-, —S—($C_{1-3}$ alkylene)-, or —NH—($C_{1-3}$ alkylene)-.

In any one of the preceding embodiments of Formula (I), $R^2$ is phenyl or 6-membered heteroaryl containing 1 to 3 heteroatoms independently selected from N, O, and S containing 1 to 3 heteroatoms independently selected from N, O, and S, wherein the phenyl or heteroaryl is substituted with 0 to 3 $R^{10}$.

In any one of the preceding embodiments of Formula (I), $L^2$ is a covalent bond.

In one embodiment of Formula (I), the compound is represented by Formula (II):

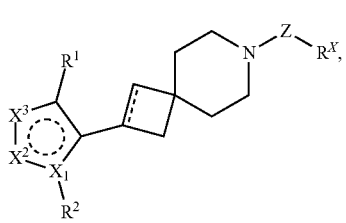

(II)

$X^1$ is C or N;
$X^2$ and $X^3$ are each independently CH, N, O, or S;
Z is phenyl or a 5- to 10-membered heteroaryl containing 1 to 3 heteroatoms independently selected from N, O, and S containing 1 to 3 heteroatoms independently selected from N, O, and S, wherein the phenyl and heteroaryl are independently substituted with 0 to 3 $R^8$;
$R^X$ is —C(O)O$R^{13}$ or —C(O)NH—S(O)$_2R^e$;
$R^e$ is $C_{1-6}$ alkyl or $C_{3-6}$ cycloalkyl;
$R^1$ is $C_{1-6}$ alkyl or $C_{3-5}$ cycloalkyl, wherein the alkyl or cycloalkyl is substituted with 0 to 3 $R^9$;
$R^2$ is phenyl or 6-membered heteroaryl containing 1 to 3 heteroatoms independently selected from N, O, and S containing 1 to 3 heteroatoms independently selected from N, O, and S, wherein the phenyl or heteroaryl is substituted with 0 to 3 $R^{10}$; and
$R^8$, $R^9$, $R^{10}$, and $R^{13}$ are the same as defined above.

In any one of the preceding embodiments of Formula (II), the

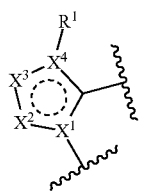

moiety is

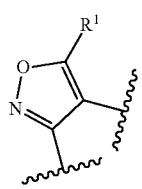

or

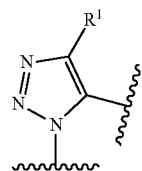

In any one of the preceding embodiments of Formula (II), $R^2$ is phenyl or pyridinyl, each of which is independently substituted with 0 to 3 $R^{10}$.

In any one of the preceding embodiments of Formula (I), the

[structure]

moiety is

[structure]

In any one of the preceding embodiments of Formula (I), Z is 8- to 10-membered bicyclic heteroaryl, wherein the heteroaryl is independently substituted with 0 to 3 $R^8$.

In any one of the preceding embodiments of Formula (I), $R^X$ is —C(O)OH.

In one embodiment, the present compounds are represented by Formula (III):

[structure]

(III)

or a stereoisomer, a tautomer, or a pharmaceutically acceptable salt or solvate thereof; wherein:
Z is 6-membered monocyclic heteroaryl containing 1 or 2 nitrogen atoms, or a 9- to 10-membered bicyclic heteroaryl containing 1 or 3 heteroatoms independently selected from N, O, and S, wherein the monocyclic or bicyclic heteroaryl is independently substituted with 0 to 3 $R^8$;
$R^2$ is phenyl or pyridinyl, wherein the phenyl and pyridinyl are each independently substituted with 0 to 2 $R^{10}$;
$R^8$ is each independently halo, cyano, hydroxyl, $C_{1-4}$ alkyl, $C_{1-4}$ haloalkyl, $C_{1-4}$ alkoxy, or $C_{1-4}$ haloalkoxy;
$R^{10}$ is each independently halo, $C_{1-4}$ alkyl, $C_{1-4}$ haloalkyl, $C_{1-4}$ alkoxy, or $C_{1-4}$ haloalkoxy;
$R^X$ is —C(O)OH or —C(O)NH—S(O)$_2R^e$; and
$R^e$ is $C_{1-6}$ alkyl or $C_{3-6}$ cycloalkyl.

In some embodiments of Formula (III), Z is a heteroaryl selected from pyridinyl, benzthiazolyl, pyrrolopyridinyl, pyrrolopyrimidinyl, indolyl, quinolinyl, imidazopyridinyl, pyrazolopyrimidinyl, and pyrrolotriazinyl, wherein the heteroaryl is independently substituted with 0 to 3 $R^8$. In some embodiments, the heteroaryl is independently substituted with 0, 1, or 2 $R^8$.

In some embodiments of Formula (III), $R^2$ is phenyl or pyridinyl, wherein the phenyl and pyridinyl are each independently substituted with 1 or 2 $R^{10}$.

In some embodiments of Formula (III), $R^8$ is each independently F, —$CH_3$, —$OCH_3$, —$OCH_2CH_3$, —OCH$(CH_3)_2$, —$CF_3$, —$OCF_3$, or —$OCHF_2$.

In some embodiments of Formula (III), $R^{10}$ is each independently $C_1$, —$CH_3$, —$CF_3$, or —$OCF_3$.

In some embodiments of Formula (III), $R^X$ is —C(O)OH or —C(O)NH—S(O)$_2R^e$; and $R^e$ is methyl, ethyl, isopropyl, or cyclopropyl.

In one embodiment of Formula (I) or Formula (II), $X^1$ is C.

In one embodiment of Formula (I) or Formula (II), $X^2$ is N.

In one embodiment of Formula (I) or Formula (II), $X^3$ is O.

In one embodiment of Formula (I), $X^4$ is C.

In one embodiment of Formula (I), $X^1$ is C and $X^4$ is C.

In one embodiment of Formula (I) or Formula (II), one of $X^2$ and $X^3$ is N and the other of $X^2$ and $X^3$ is O.

In one embodiment of Formula (I) or Formula (II), $X^2$ is N and $X^3$ is O.

In one embodiment of Formula (I) or Formula (II), $X^2$ is O and $X^3$ is N.

In one embodiment of Formula (I) or Formula (II), $X^1$ is C; $X^2$ is N; and $X^3$ is O.

In one embodiment of Formula (I), $X^1$ is C; one of $X^2$ and $X^3$ is N and the other of $X^2$ and $X^3$ is O; and $X^4$ is C.

In one embodiment of Formula (I), $X^1$ is C; $X^2$ is N; $X^3$ is O; and $X^4$ is C.

In one embodiment of Formula (I), $X^1$ is C; $X^2$ is O; $X^3$ is N; and $X^4$ is C.

In one embodiment of Formula (I) or Formula (III), $X^1$ is N; $X^2$ is N; and $X^3$ is N.

In one embodiment of Formula (I), the

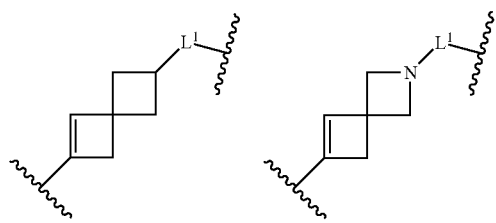

moiety is selected from:

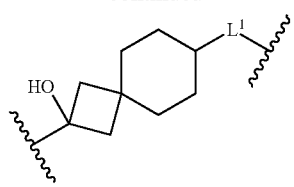

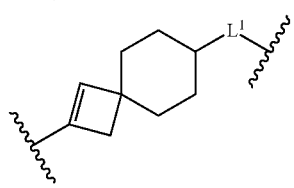

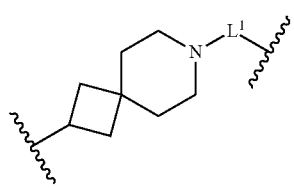

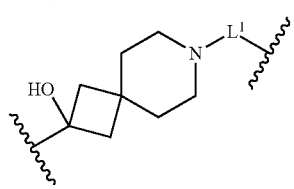

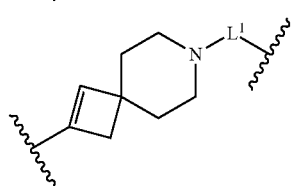

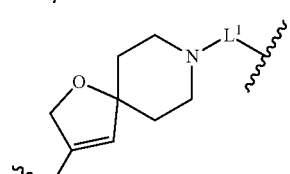

and

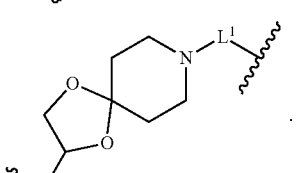

In one embodiment of Formula (I), $L^1$ is a covalent bond, O, —$CH_2$—, —$CH_2CH_2$—, —$OCH_2$—, —$CH_2OCH_2$—, or —$NR^{16}$—. Included in this embodiment are compounds in which $L^1$ is a covalent bond, O, or —$OCH_2$—. Also included in this embodiment are compounds in which $L^1$ is a covalent bond.

In one embodiment of Formula (I), the
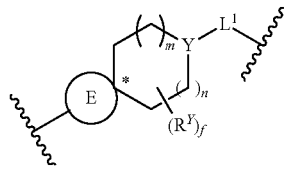
moiety is selected from:
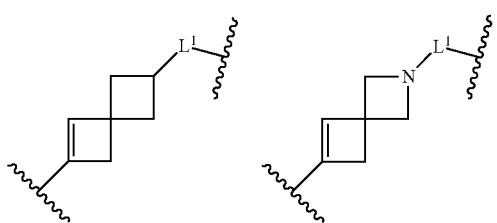
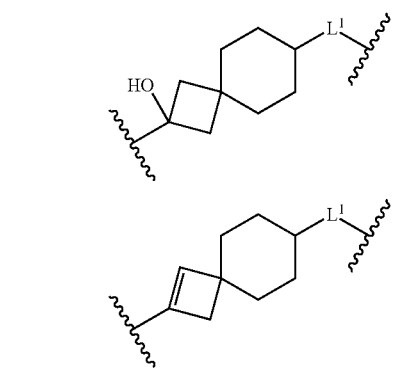
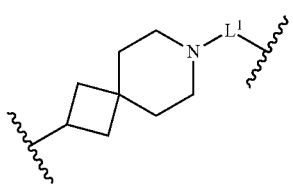
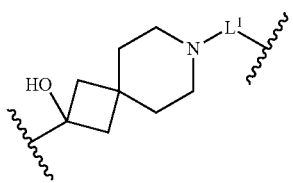
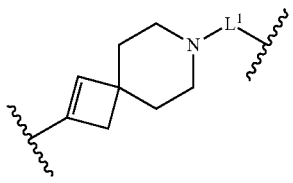
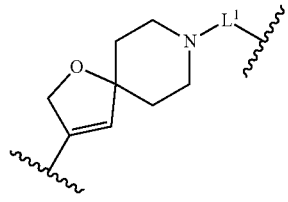
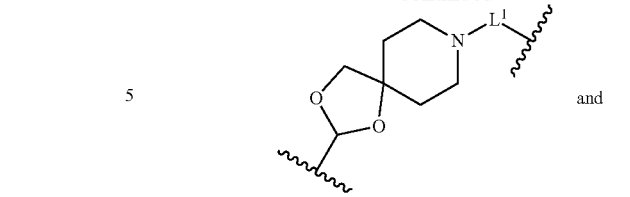
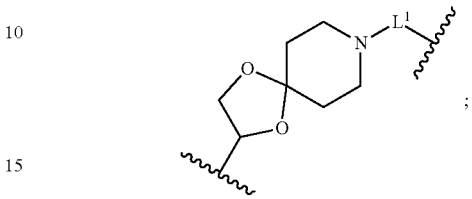
and
$L^1$ is a covalent bond, O, —CH$_2$—, —CH$_2$CH$_2$—, —OCH$_2$—, —CH$_2$OCH$_2$—, or NR$^{16}$—. Included in this embodiment are compounds in which $L^1$ is a covalent bond, O, or —OCH$_2$—. Also included in this embodiment are compounds in which $L^1$ is a covalent bond.
In one embodiment of Formula (I), the
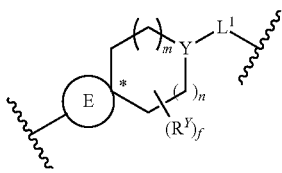
moiety is selected from:
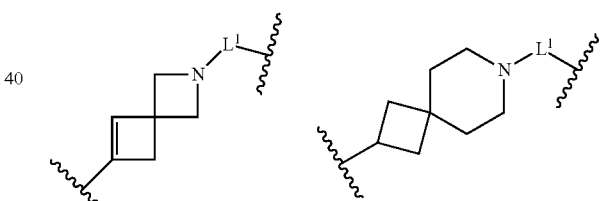
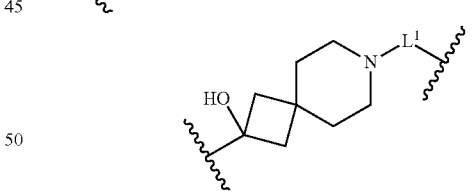
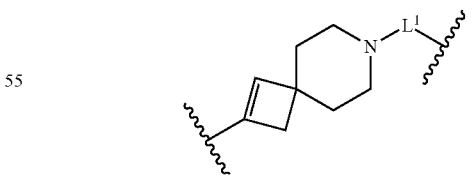
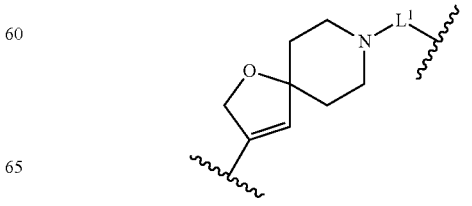

-continued

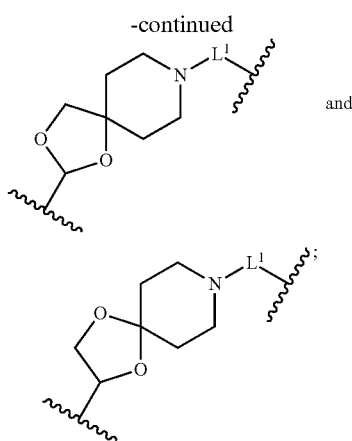

and $L^1$ is a covalent bond, —CH₂—, —CH₂CH₂—, —OCH₂—, —CH₂OCH₂—. Included in this embodiment are compounds in which $L^1$ is a covalent bond.

In one embodiment of Formula (I), the

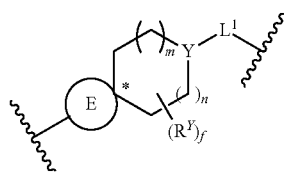

moiety is selected from:

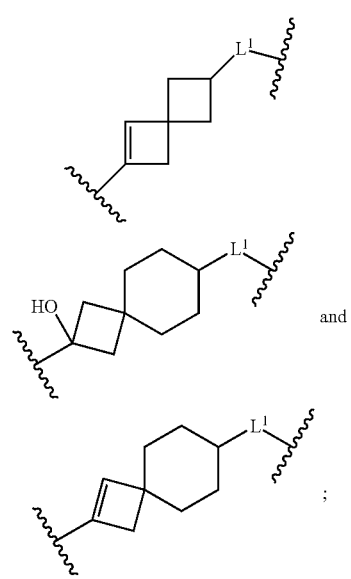

and $L^1$ is a covalent bond, O, —CH₂—, —CH₂CH₂—, —OCH₂—, —CH₂OCH₂—, or —NR$^{16}$—. Included in this embodiment are compounds in which $L^1$ is a covalent bond, O, or —OCH₂—. Also included in this embodiment are compounds in which $L^1$ is a covalent bond.

In one embodiment of Formula (I), Formula (II), or Formula (III), Z is aryl or 5- to 10-membered heteroaryl containing 1 to 3 heteroatoms independently selected from N, O, and S, wherein the phenyl and heteroaryl are independently substituted with 0 to 5 $R^8$. Included in this embodiment are compounds in which Z is phenyl, pyridinyl, pyridazinyl, pyrimidinyl, pyrazinyl, benzo[d]imidazolyl, benzo[d]isoxazolyl, benzo[d]oxadiazolyl, benzo[d]thiazolyl, imidazolo[1,5-a]pyridinyl, indazolyl, indolyl, pyrazolo[4,3-b]pyridinyl, pyrrolo[2,1-f][1,2,4]triazinyl, pyrrolo[2,3-b]pyridinyl, pyrrolo[2,3-c]pyridinyl, pyrrolo[2,3-d]pyrimidinyl, pyrrolo[3,2-c]pyridinyl, thiazolo[4,5-b]pyridinyl, thiazolo[5,4-b]pyridinyl, cinnolinyl, isoquinolinyl, quinolinyl, or quinoxalinyl, each substituted with zero to 1 $R^8$.

In one embodiment of Formula (I), the

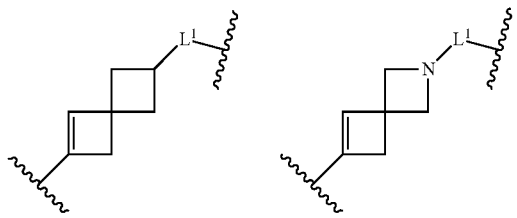

moiety is selected from:

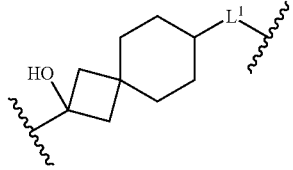

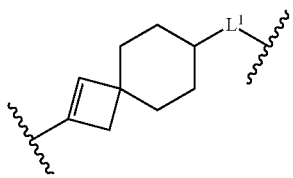

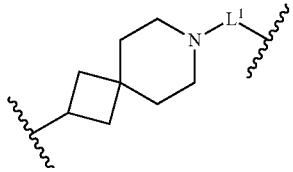

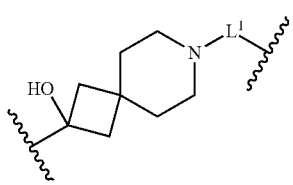

-continued

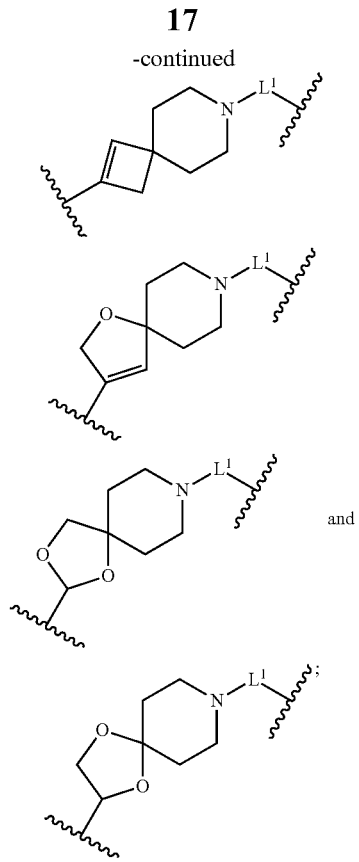

L¹ is a covalent bond, O, or —OCH₂—; and

Z is phenyl, pyridinyl, pyridazinyl, pyrimidinyl, pyrazinyl, benzo[d]imidazolyl, benzo[d]isoxazolyl, benzo[d]oxadiazolyl, benzo[d]thiazolyl, imidazolo[1,5-a]pyridinyl, indazolyl, indolyl, pyrazolo[4,3-b]pyridinyl, pyrrolo[2,1-f][1,2,4]triazinyl, pyrrolo[2,3-b]pyridinyl, pyrrolo[2,3-c]pyridinyl, pyrrolo[2,3-d]pyrimidinyl, pyrrolo[3,2-c]pyridinyl, thiazolo[4,5-b]pyridinyl, thiazolo[5,4-b]pyridinyl, cinnolinyl, isoquinolinyl, quinolinyl, or quinoxalinyl, each substituted with zero to 1 R⁸.

In one embodiment of Formula (I), Formula (II), or Formula (III), L³ is a covalent bond, —CH₂—, —CH₂CH₂—, —C(O)NHCH₂—, or —OCH₂—.

In one embodiment of Formula (I), Formula (II), or Formula (III), L³ is a covalent bond.

In one embodiment of Formula (I), Formula (II), or Formula (III), L³ is —CH₂—, —CH₂CH₂—, —C(O)NHCH₂—, or —OCH₂—.

In one embodiment of Formula (I), Formula (II), or Formula (III), L³ is a covalent bond or —C(O)NHCH₂—.

In one embodiment of Formula (I), Formula (II), or Formula (III), R$^Z$ is —CN, —C(O)OR¹³, —C(O)NR$^{14a}$R$^{14b}$,

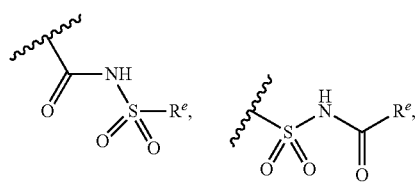

-continued

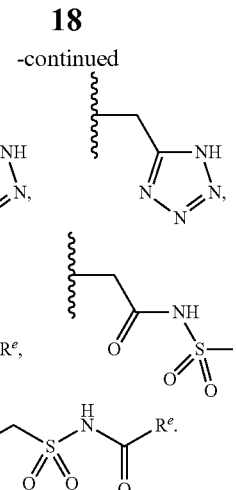

Included in this embodiment are compounds in which L³ is a covalent bond.

In one embodiment of Formula (I), Formula (II), or Formula (III), R$^x$ is —CN, —C(O)OH, —C(O)O(C$_{1-3}$ alkyl), —C(O)NH₂, —C(O)NH(C$_{1-3}$ alkyl), —C(O)NH(C$_{3-6}$ cyclopropyl), —C(O)NHCH₂C(O)OH, —C(O)NHS(O)₂(C$_{1-3}$ alkyl), —C(O)NHS(O)₂(C$_{3-6}$ cyclopropyl), —OCH₂C(O)OH, or —C(O)O(carboxy(trihydroxy)tetrahydropyranyl). Included in this embodiment are compounds in which R$^x$ is —CN, —C(O)OH, —C(O)OCH₂CH₃, —C(O)NH₂, —C(O)NH(CH₃), —C(O)NHCH₂CH₃, —C(O)NHCH(CH₃)₂, —C(O)NH(cyclopropyl), —C(O)NHCH₂C(O)OH, —C(O)NHS(O)₂CH₃, —C(O)NHS(O)₂(cyclopropyl), —OCH₂C(O)OH, or —C(O)O(carboxy(trihydroxy)tetrahydropyranyl).

In one embodiment of Formula (I), Formula (II), or Formula (III), L² is a covalent bond or —CH(cyclopropyl)-.

In one embodiment of Formula (I), Formula (II), or Formula (III), L² is a covalent bond.

In one embodiment of Formula (I), Formula (II), or Formula (III), L² is —CH(cyclopropyl)- and R² is cyclopropyl.

In one embodiment of Formula (I), Formula (II), or Formula (III), R² is C$_{3-6}$ cycloalkyl, phenyl, or pyridinyl, wherein the phenyl and the pyridinyl are independently substituted with 1 to 3 R¹⁰.

In one embodiment of Formula (I), Formula (II), or Formula (III), R² is cyclopropyl, cyclohexyl, phenyl, or pyridinyl, wherein the phenyl and the pyridinyl are independently substituted with 1 to 3 R¹⁰.

In one embodiment of Formula (I), Formula (II), or Formula (III), R² is cyclohexyl, phenyl, or pyridinyl, wherein the phenyl and the pyridinyl are independently substituted with 1 to 3 R¹⁰; and L² is a covalent bond.

In one embodiment of Formula (I), Formula (II), or Formula (III), R¹ is C$_{1-3}$ alkyl, C$_{3-4}$ cycloalkyl, or C$_{4-5}$ heterocyclyl, wherein the alkyl, cycloalkyl, and heterocyclyl are each substituted with 0 to 3 R⁹;

In one embodiment of Formula (I), Formula (II), or Formula (III), R¹ is —CHF₂, —CH(CH₃)₂, cyclopropyl, or methylcyclopropyl.

One embodiment provides a compound according to Formula (I) wherein: X¹ is C, X² is N, X³ is O, and X⁴ is C; or X¹ is N, X² is N, X³ is C, and X⁴ is C; Y is CH or N; the

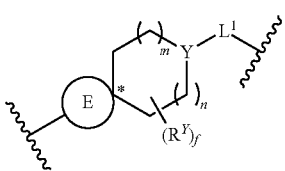

moiety is selected from:

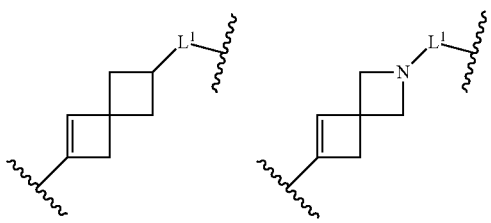

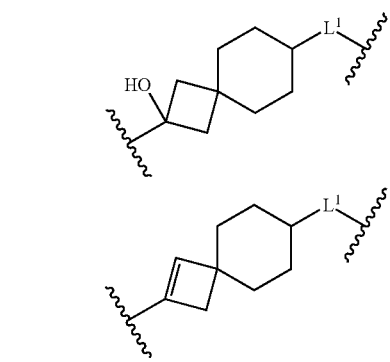

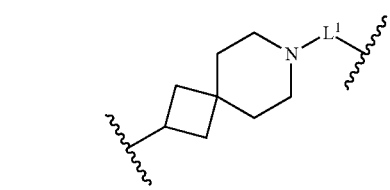

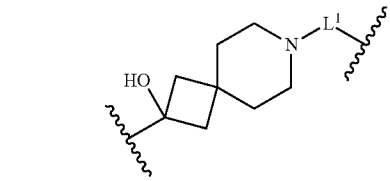

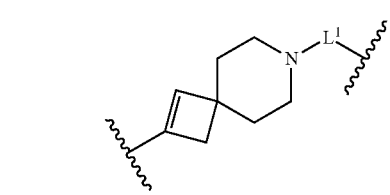

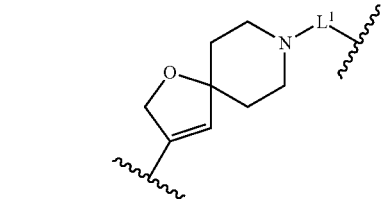

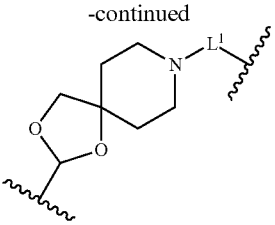

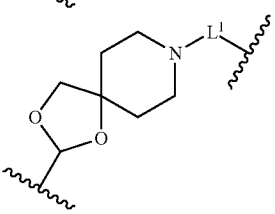

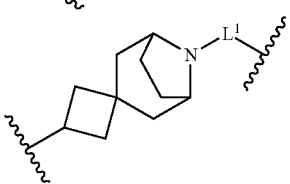

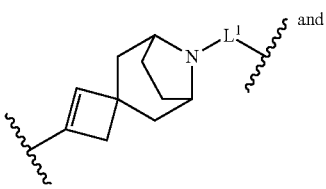 and

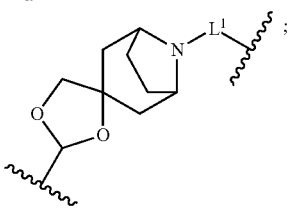;

$L^1$ is a covalent bond, O, or —OCH$_2$—, provided that $L^1$ is a covalent bond when Y is N;

Z is phenyl, pyridinyl, pyridazinyl, pyrimidinyl, pyrazinyl, benzo[d]imidazolyl, benzo[d]isoxazolyl, benzo[d]oxadiazolyl, benzo[d]thiazolyl, imidazolo[1,5-a]pyridinyl, indazolyl, indolyl, pyrazolo[4,3-b]pyridinyl, pyrrolo[2,1-f][1,2,4]triazinyl, pyrrolo[2,3-b]pyridinyl, pyrrolo[2,3-c]pyridinyl, pyrrolo[2,3-d]pyrimidinyl, pyrrolo[3,2-c]pyridinyl, thiazolo[4,5-b]pyridinyl, thiazolo[5,4-b]pyridinyl, cinnolinyl, isoquinolinyl, quinolinyl, or quinoxalinyl, each substituted with zero to 1 $R^8$;

$R^8$ is F, —CH$_3$, —CF$_3$, —OCH$_3$, —OCH$_2$CH$_3$, —OCH(CH$_3$)$_2$, —OCHF$_2$, —OCF$_3$, —OCH$_2$CH$_2$OH, or —CH$_2$OCH$_2$CH$_2$Si(CH$_3$)$_3$;

$R^x$ is —CN, —C(O)OH, —C(O)OCH$_2$CH$_3$, —C(O)NH$_2$, —C(O)NH(CH$_3$), —C(O)NHCH$_2$CH$_3$, —C(O)NHCH(CH$_3$)$_2$, —C(O)NH(cyclopropyl), —C(O)NHCH$_2$C(O)OH, —C(O)NHS(O)$_2$CH$_3$, —C(O)NHS(O)$_2$(cyclopropyl), —OCH$_2$C(O)OH, or —C(O)O(carboxy(trihydroxy)tetrahydropyranyl);

$L^2$ is a covalent bond;

$R^1$ is —CHF$_2$, —CH(CH$_3$)$_2$, cyclopropyl, or methylcyclopropyl;

$R^2$ is cyclohexyl, phenyl, or pyridinyl, wherein the phenyl and the pyridinyl are independently substituted with 1 to 3 $R^{10}$; and $R^{10}$ is each independently F, C$_1$, —CH$_3$, —CF$_3$, —OCH$_3$, or —OCF$_3$.

In one embodiment, the present compounds are represented by Formula (III) or a stereoisomer, a tautomer, or a pharmaceutically acceptable salt or solvate thereof; wherein:
Z is a 9- to 10-membered bicyclic heteroaryl containing 1 or 3 heteroatoms independently selected from N, O, and S, wherein the bicyclic heteroaryl is independently substituted with 0 to 3 $R^8$;
$R^2$ is phenyl or pyridinyl, wherein the phenyl and pyridinyl are each independently substituted with 0 to 2 $R^{10}$;
$R^8$ is each independently F, $C_1$, cyano, hydroxyl, $C_{1-3}$ alkyl, $C_{1-2}$ haloalkyl, $C_{1-3}$ alkoxy, or $C_{1-2}$ haloalkoxy;
$R^{10}$ is each independently F, $C_1$, $C_{1-3}$ alkyl, $C_{1-2}$ fluoroalkyl, $C_{1-4}$ alkoxy, or $C_{1-2}$ fluoroalkoxy;
$R^X$ is —C(O)OH.

In one embodiment, the present compounds are represented by Formula (III) or a stereoisomer, a tautomer, or a pharmaceutically acceptable salt or solvate thereof; wherein:
Z is a 9-membered bicyclic heteroaryl containing 1 or 3 heteroatoms independently selected from N, O, and S, wherein the bicyclic heteroaryl is independently substituted with 0 to 3 $R^8$;
$R^2$ is phenyl or pyridinyl, wherein the phenyl and pyridinyl are each independently substituted with 0 to 2 $R^{10}$;
$R^8$ is each independently F, $C_1$, cyano, hydroxyl, $C_{1-3}$ alkyl, $C_{1-2}$ haloalkyl, $C_{1-3}$ alkoxy, or $C_{1-2}$ haloalkoxy;
$R^{10}$ is each independently F, $C_1$, $C_{1-3}$ alkyl, $C_{1-2}$ fluoroalkyl, $C_{1-4}$ alkoxy, or $C_{1-2}$ fluoroalkoxy; and
$R^X$ is —C(O)OH.

In one embodiment, the present invention provides compounds selected from:

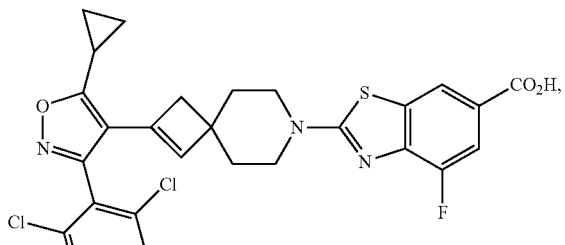

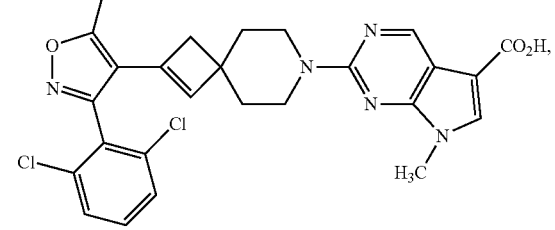

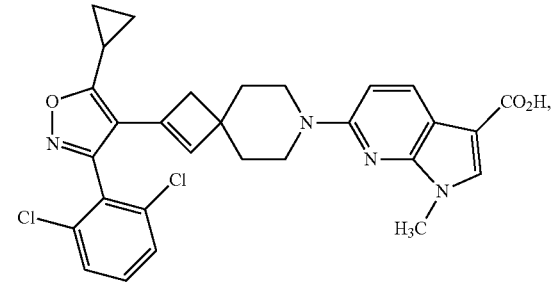

-continued

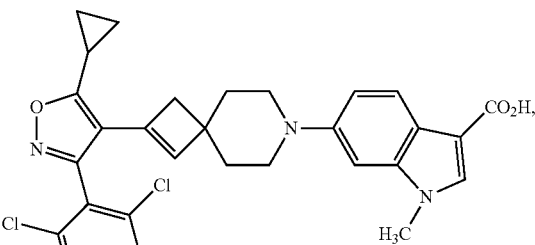

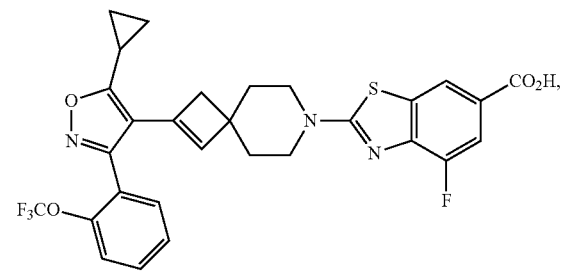

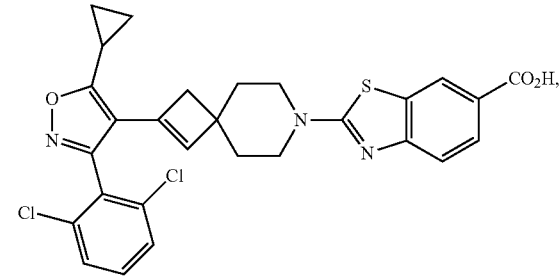

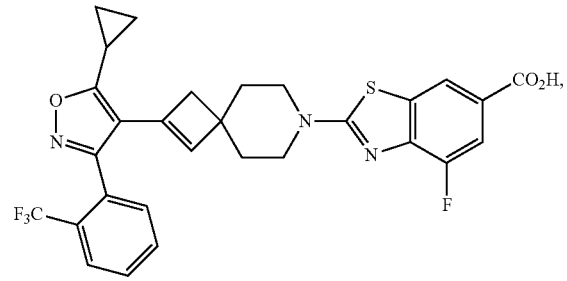

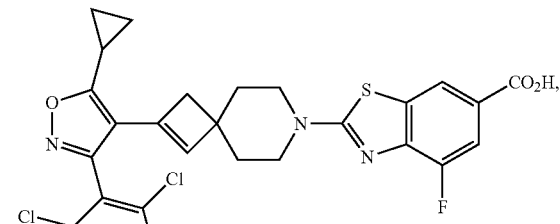

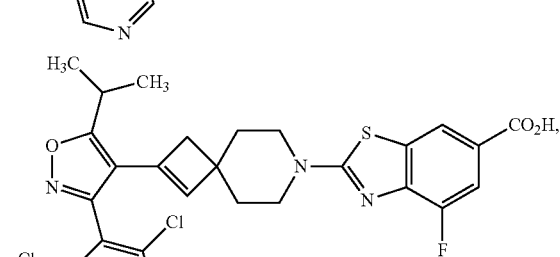

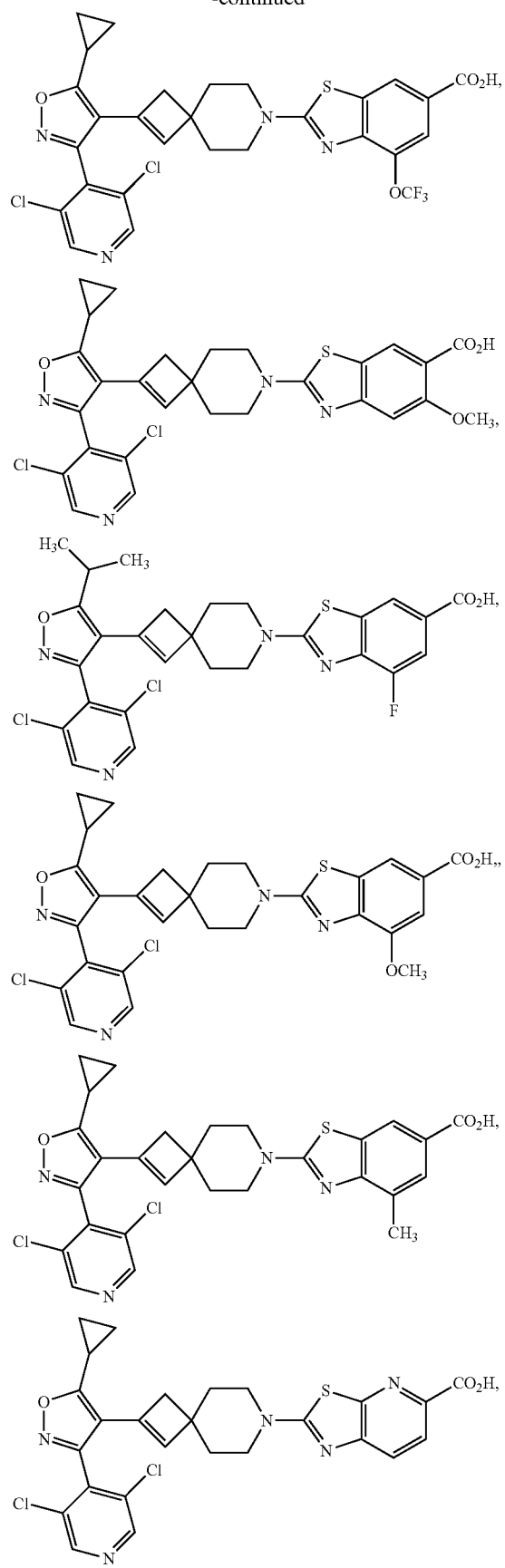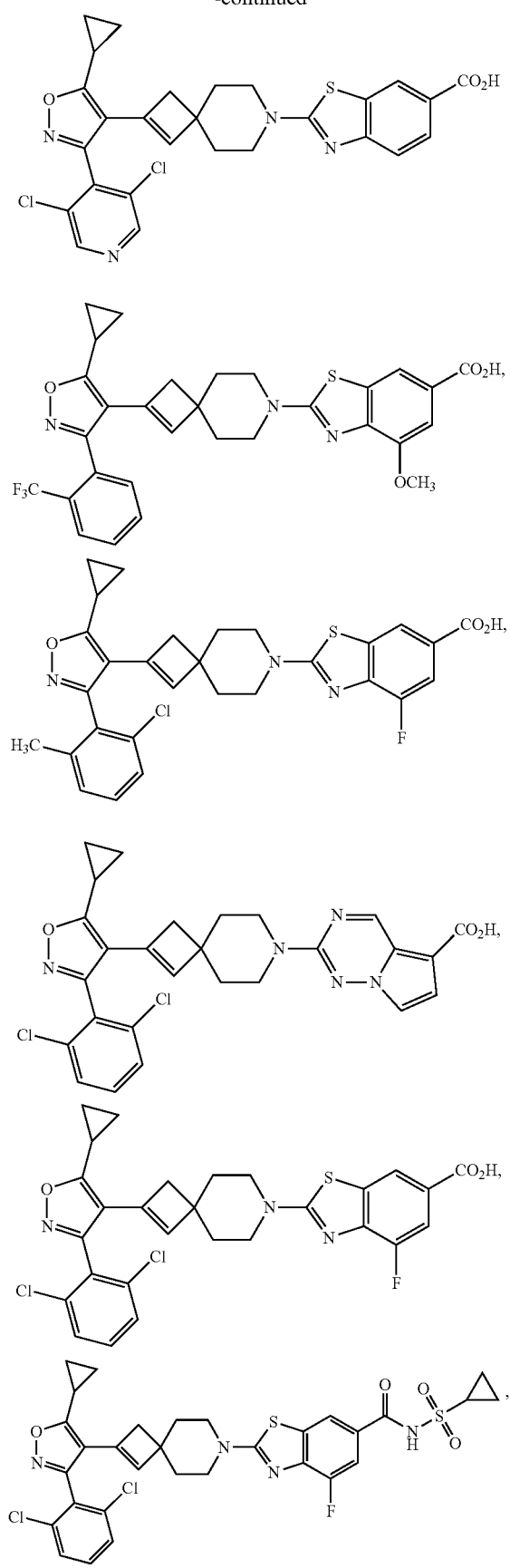

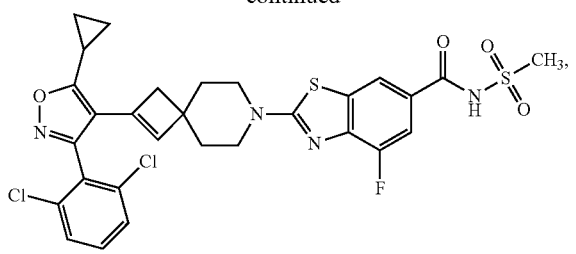
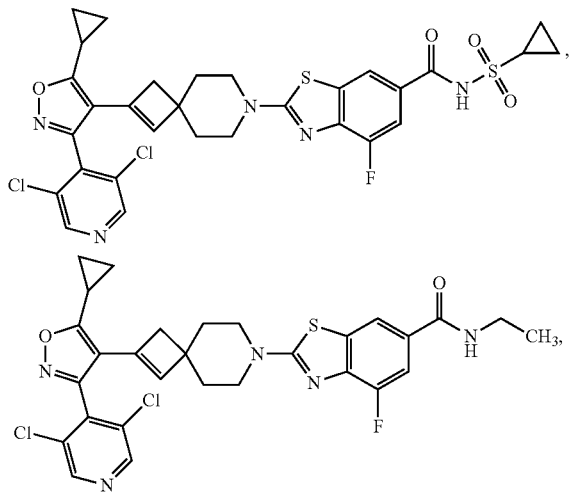
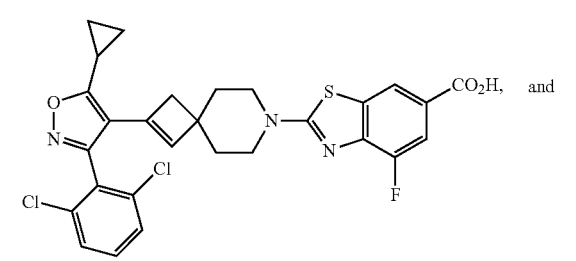
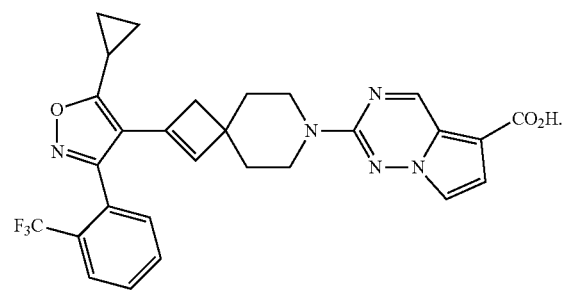
and
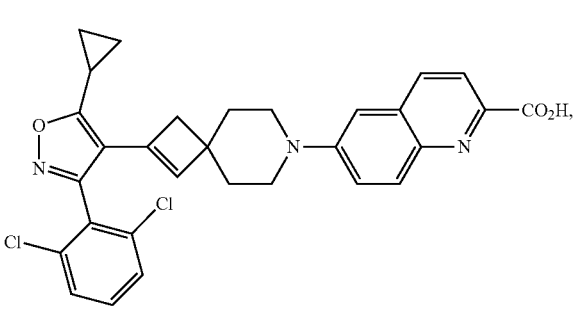
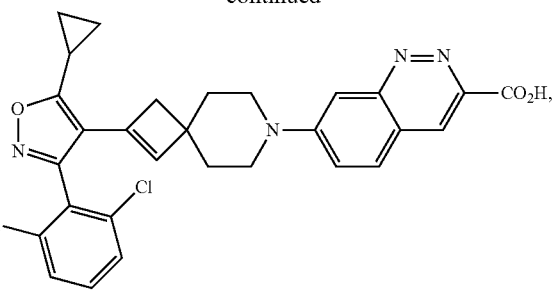
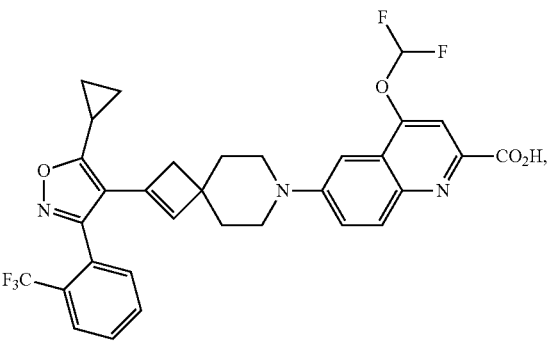
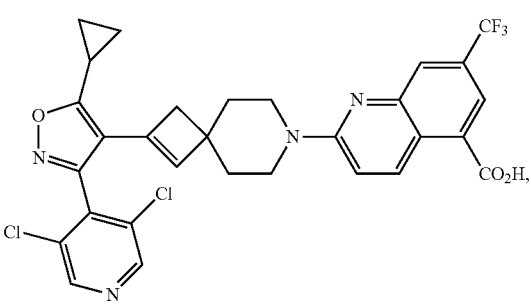
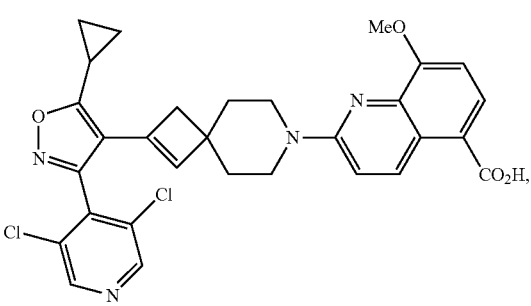
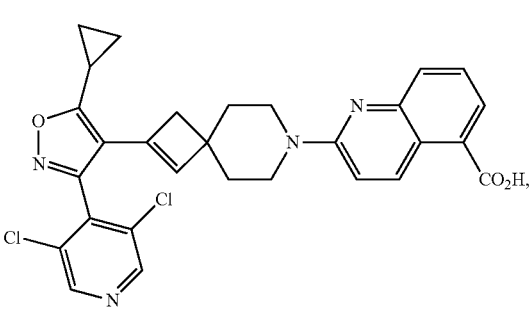

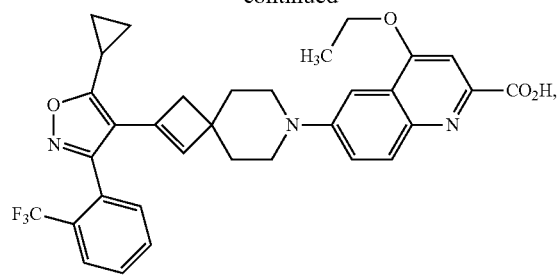
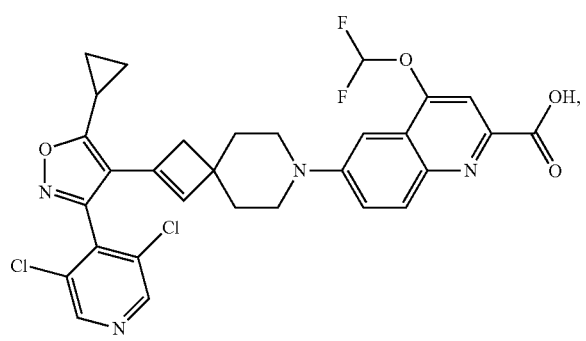
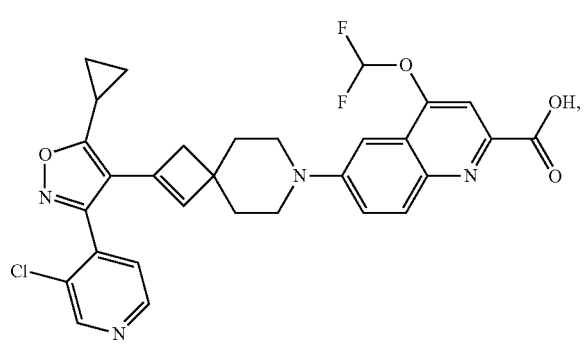
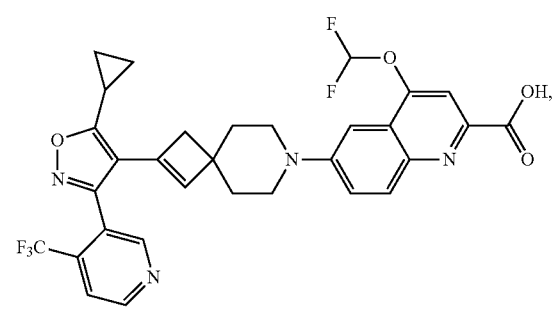
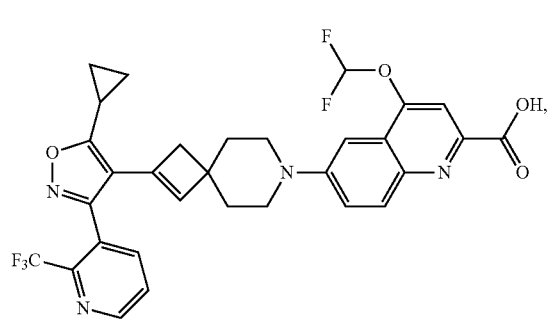
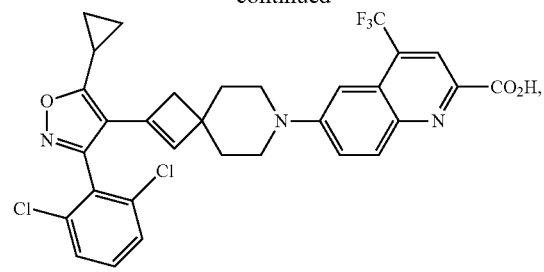
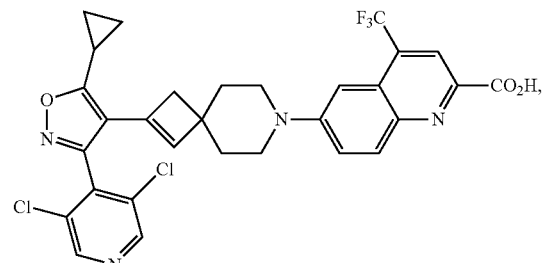
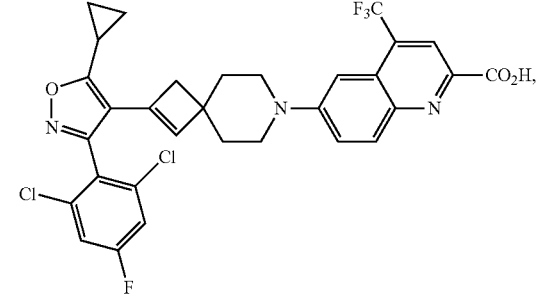
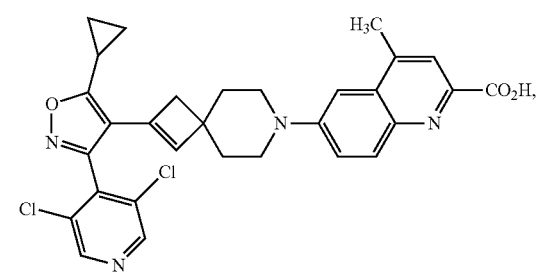
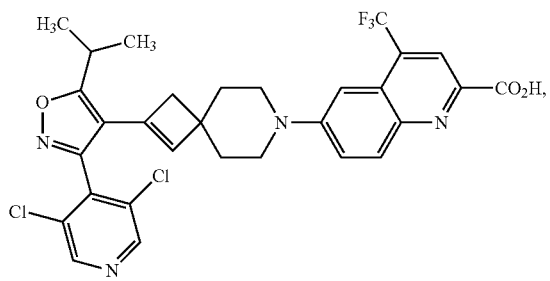
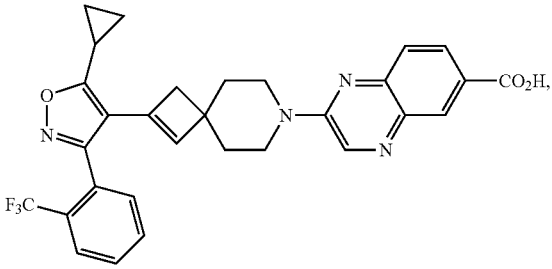

-continued
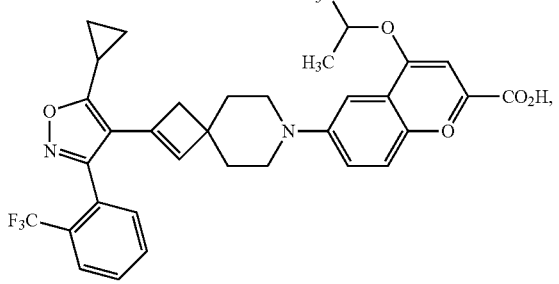
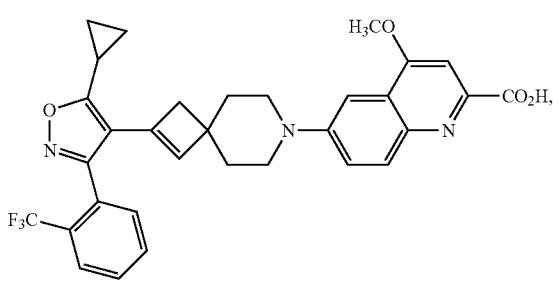
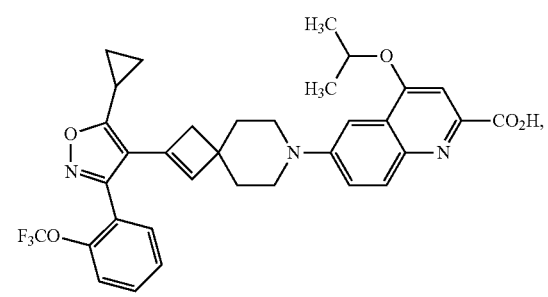
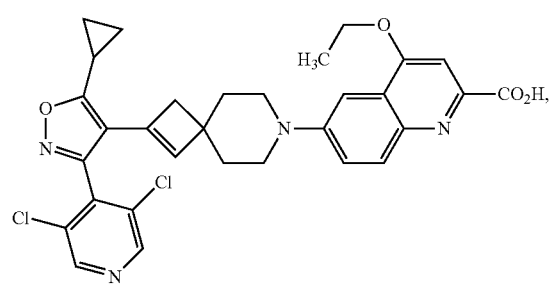
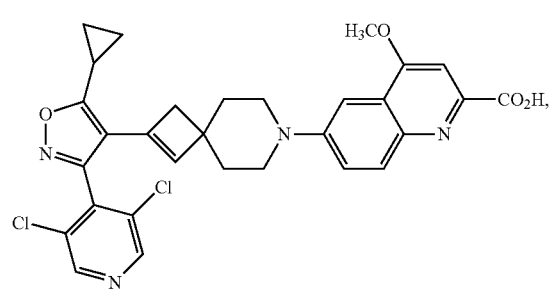
-continued
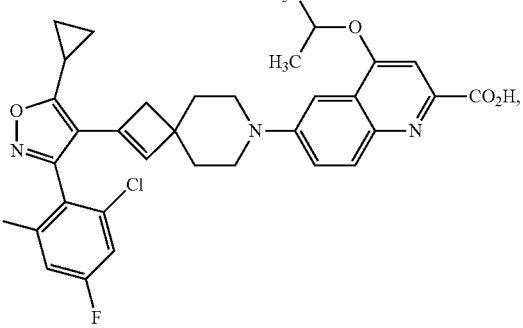
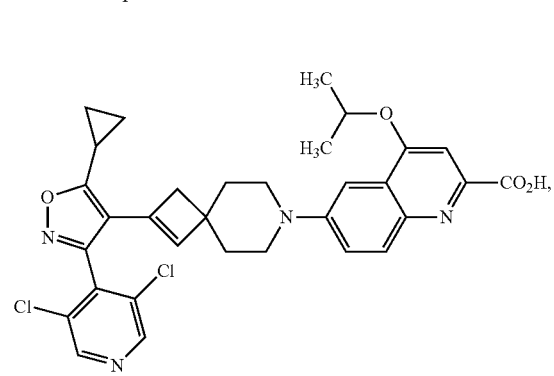
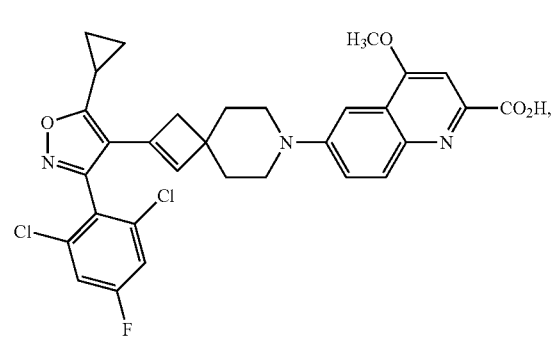
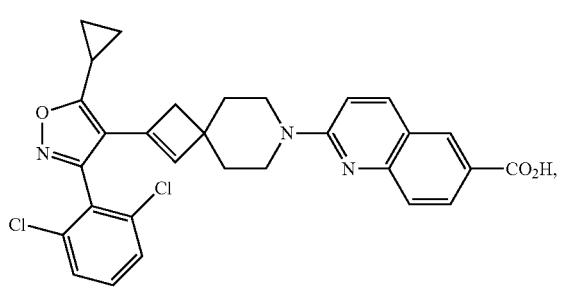
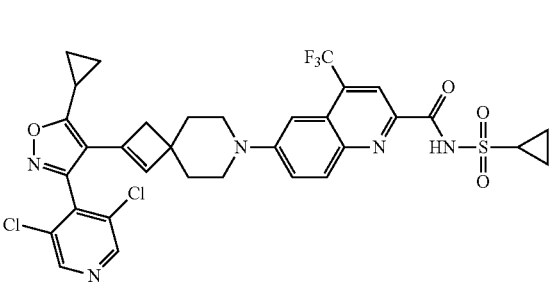

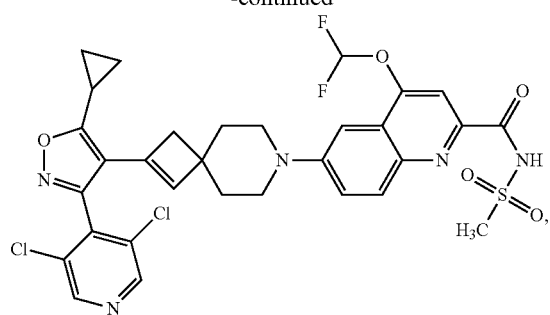
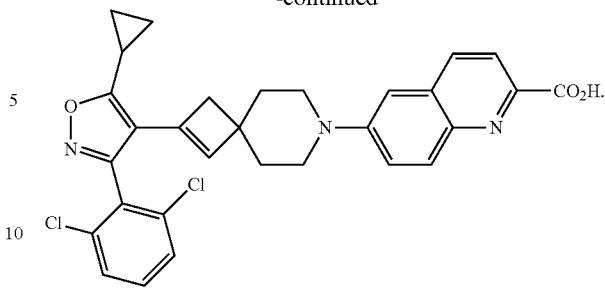
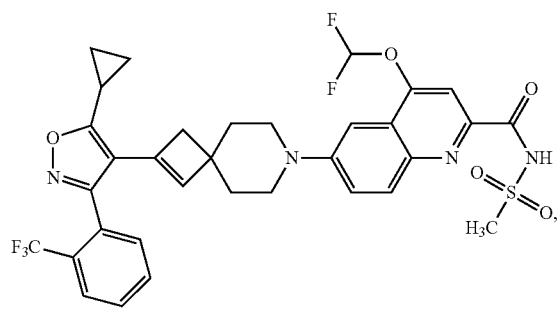
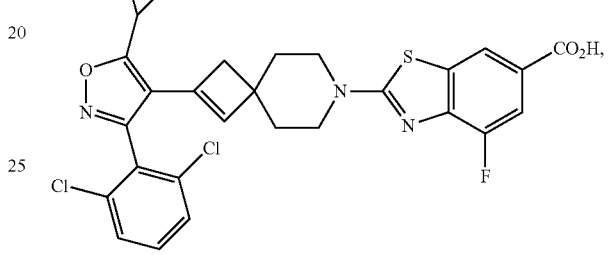
In one embodiment, the present invention provides compounds selected from:
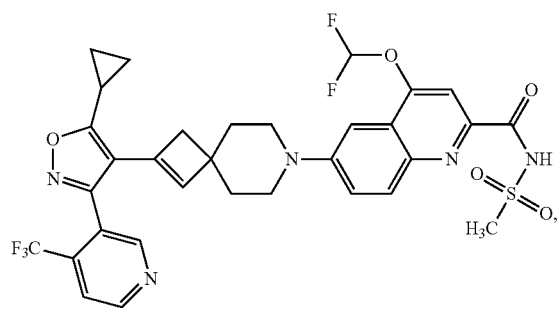
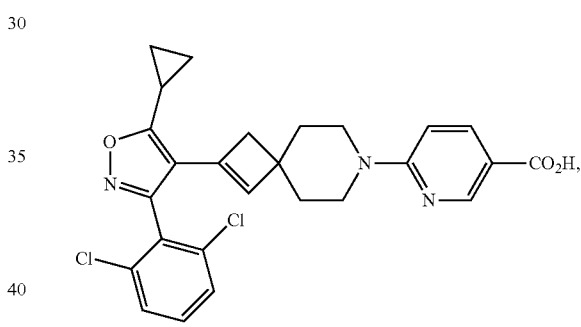
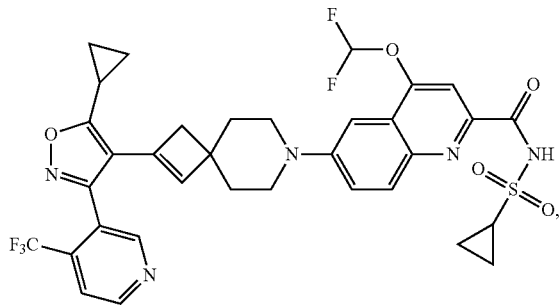
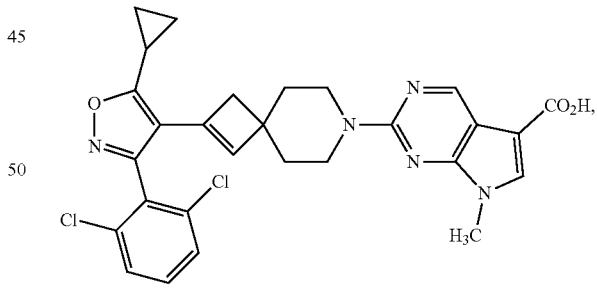
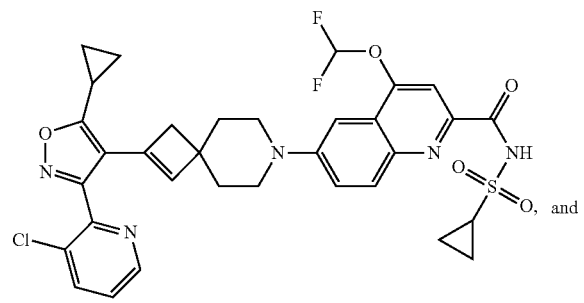
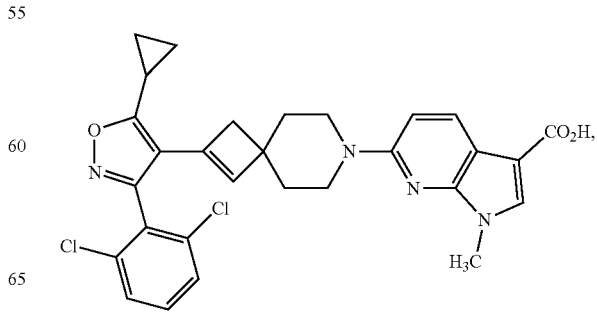

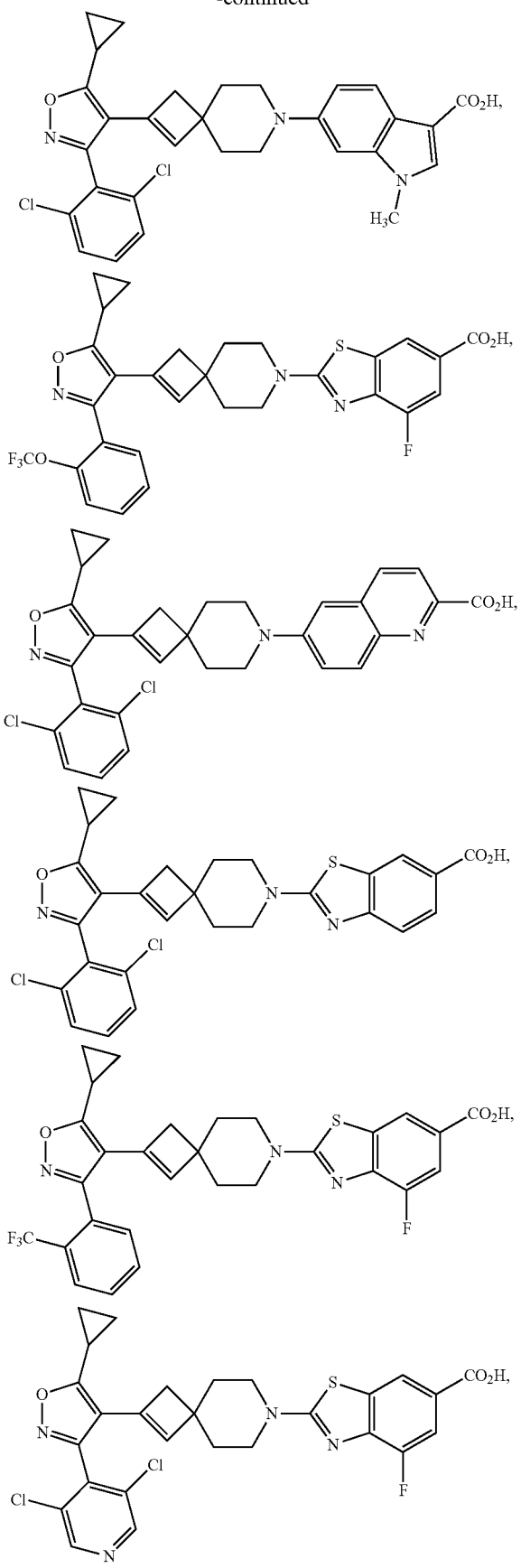
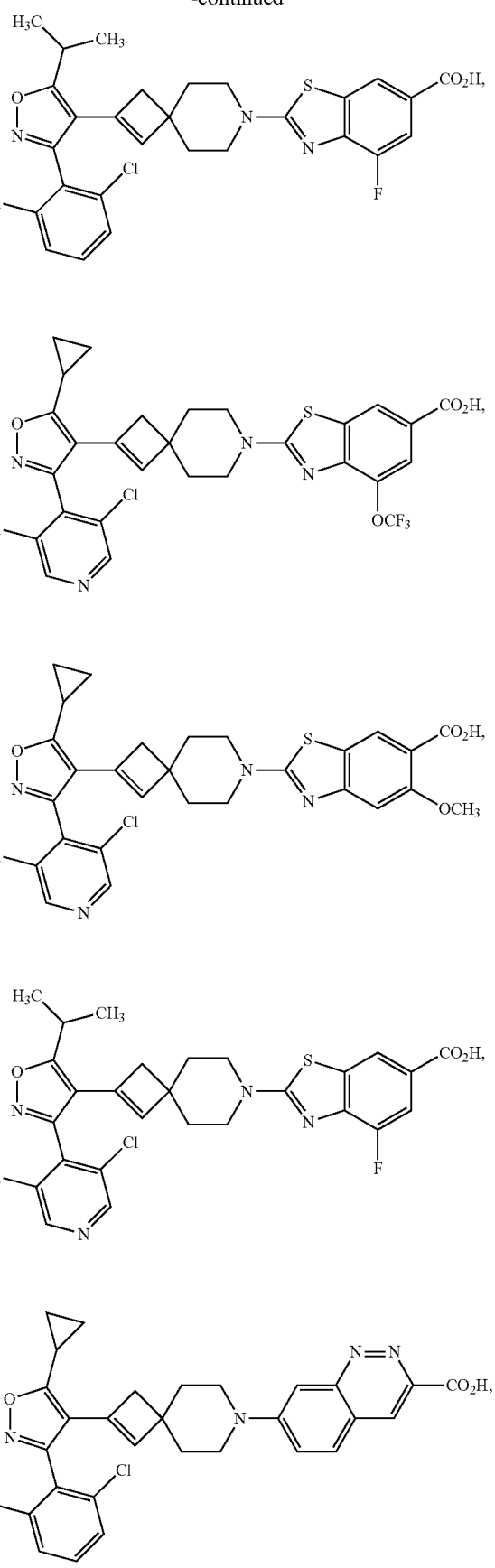

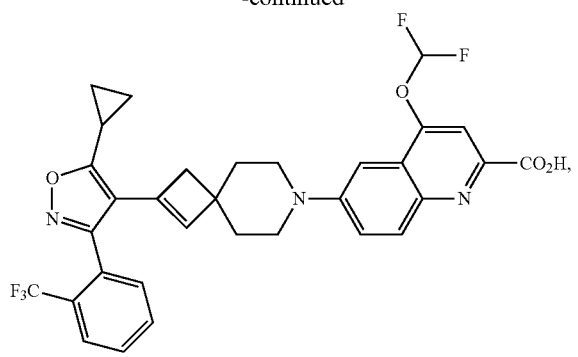
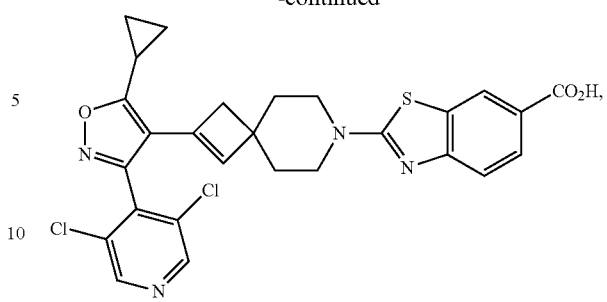
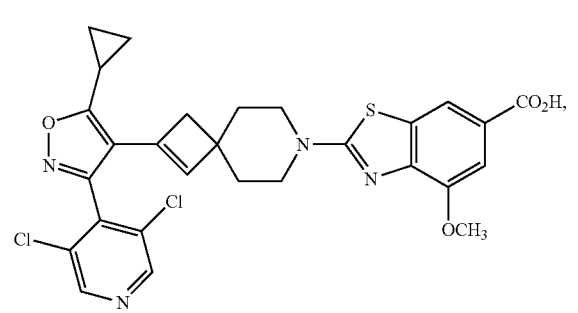
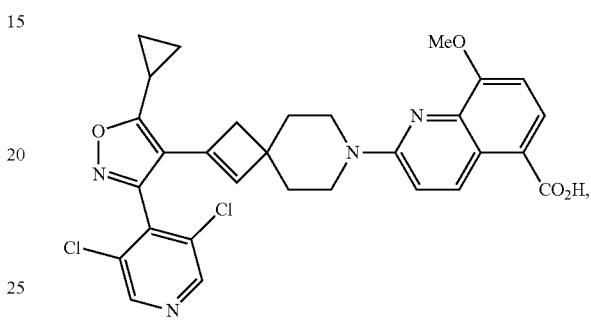
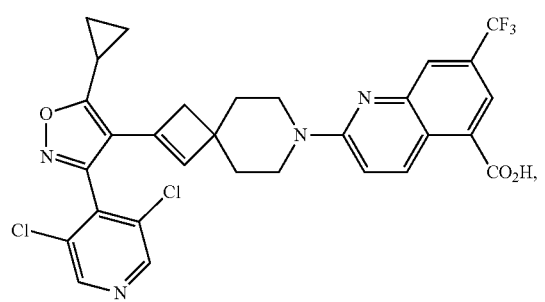
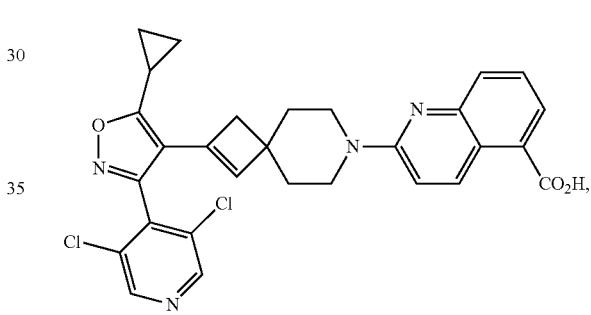
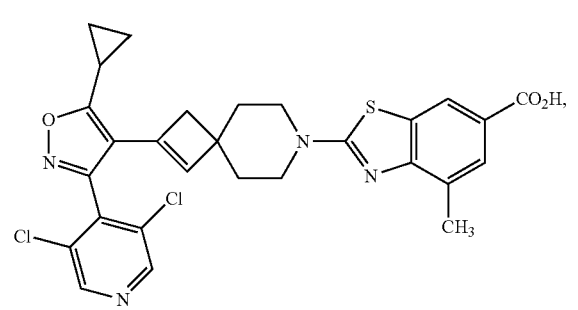
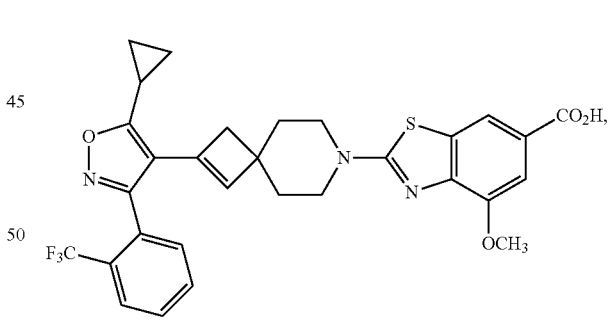
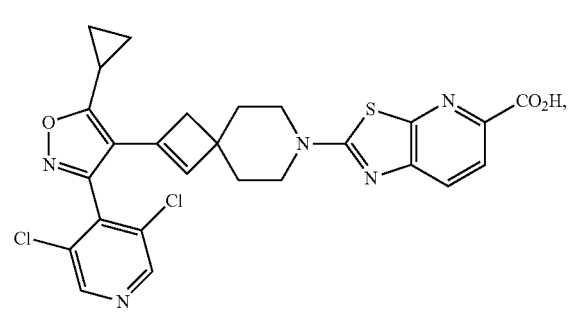
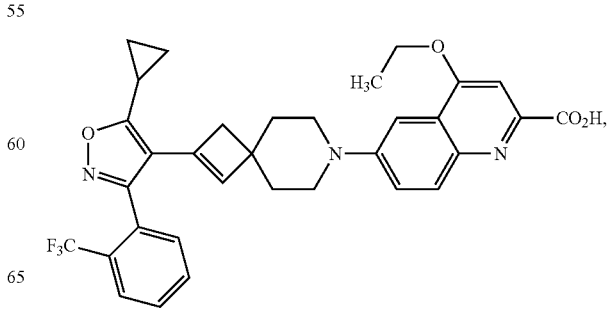

-continued
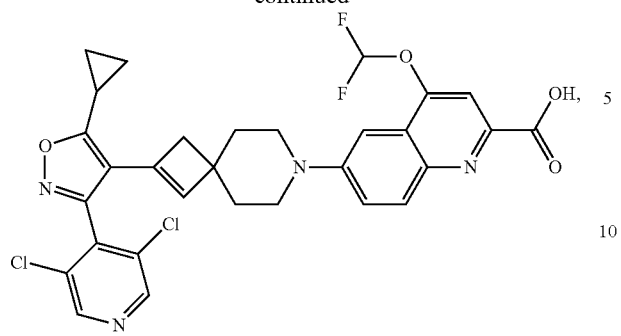
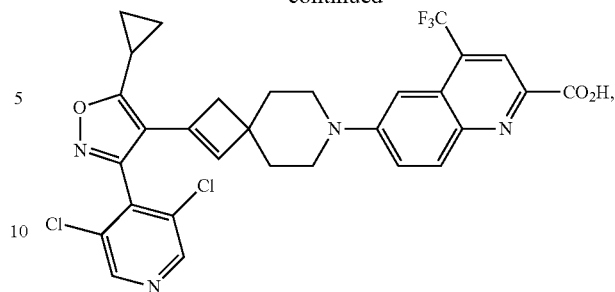
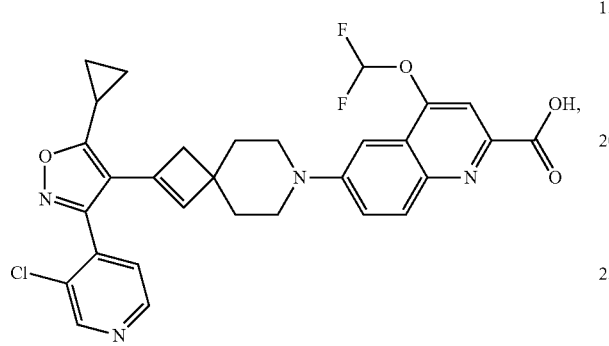
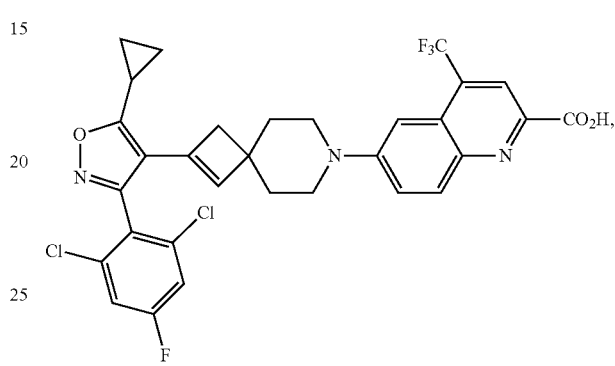
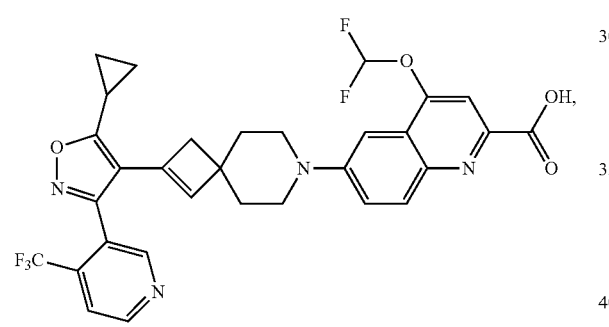
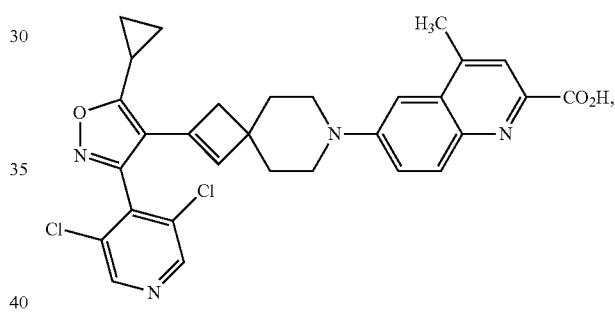
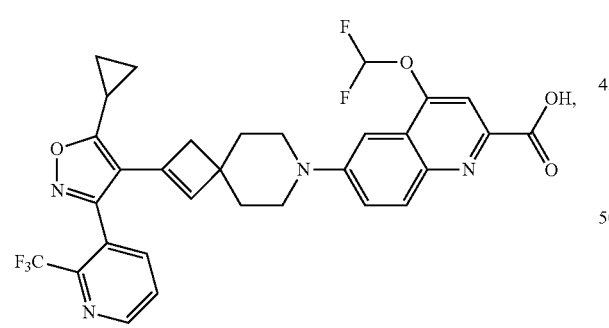
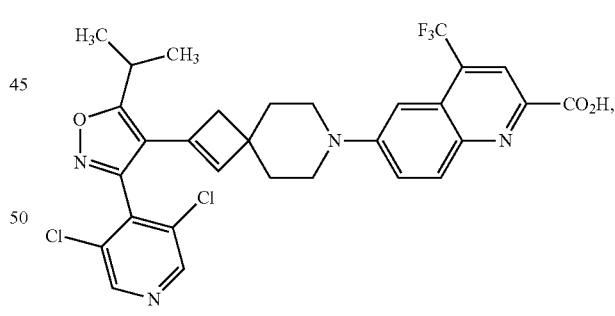
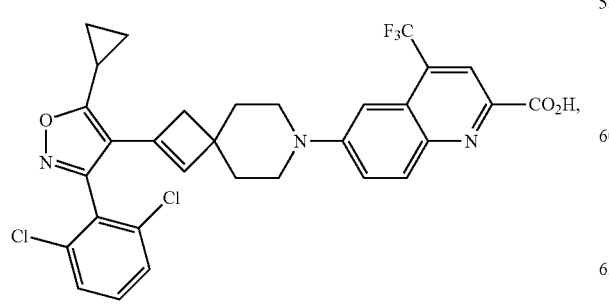
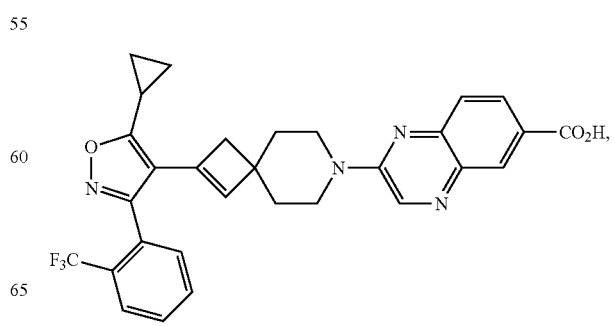

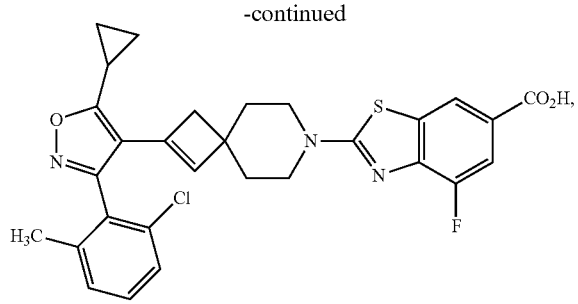
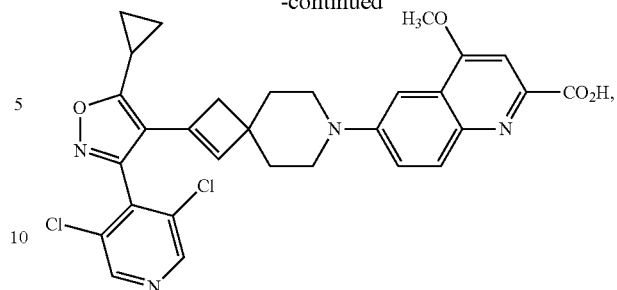
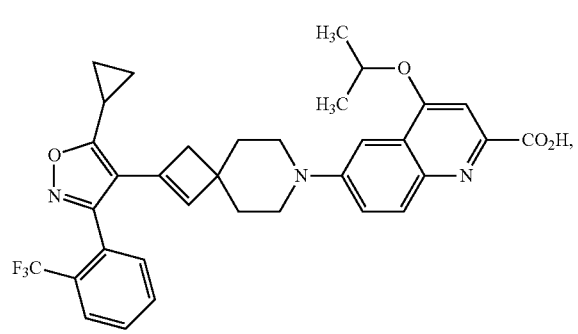
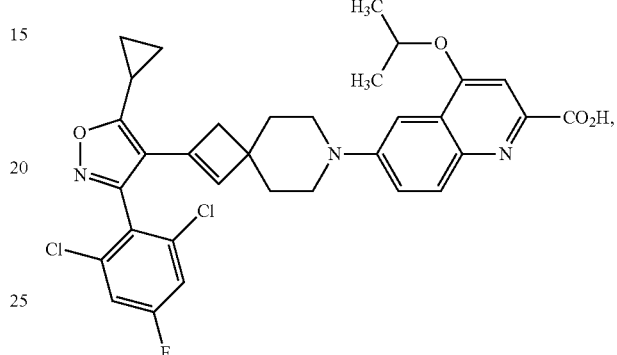
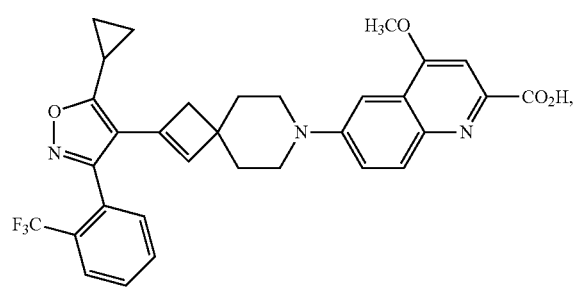
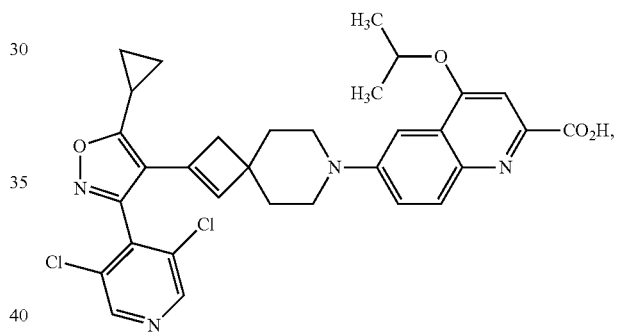
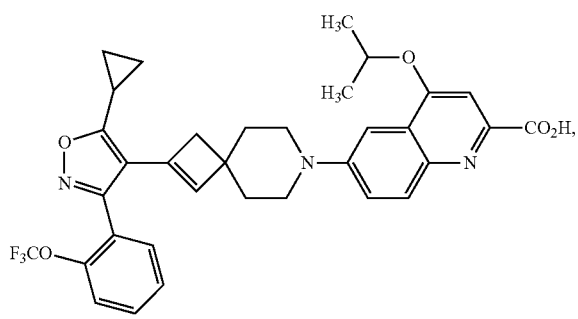
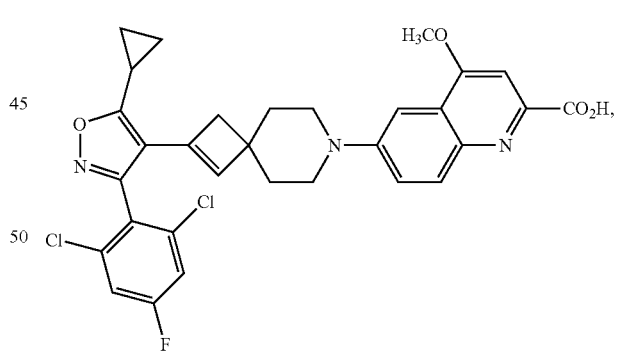
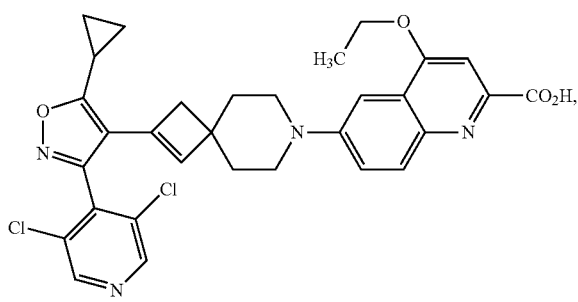
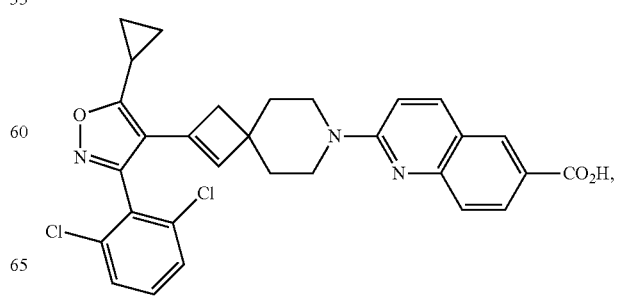

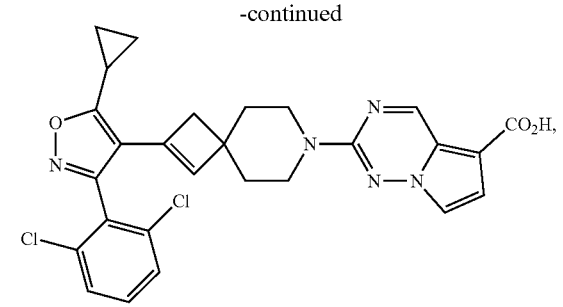
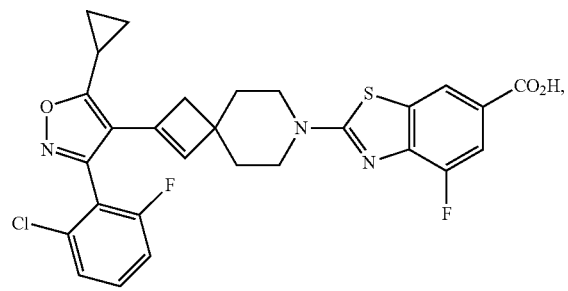
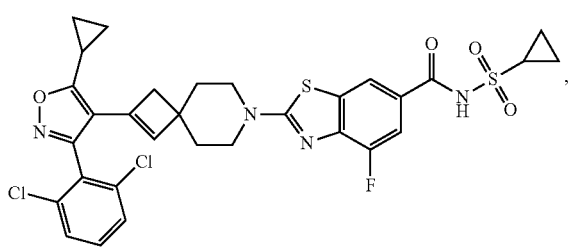
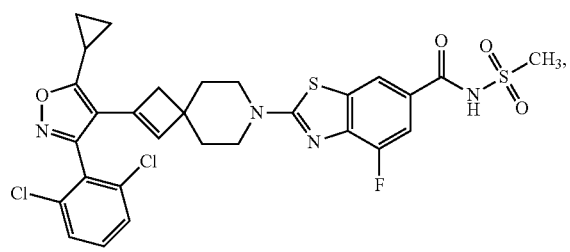
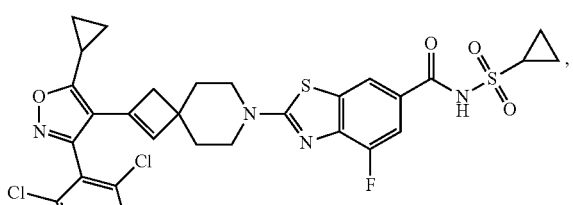
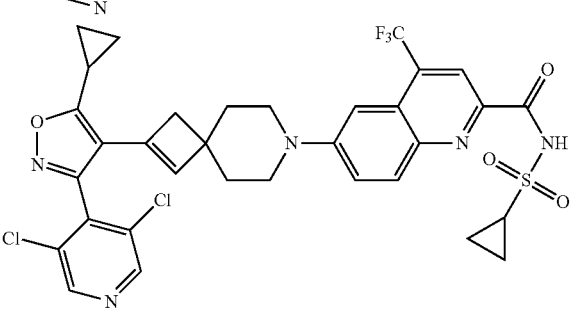
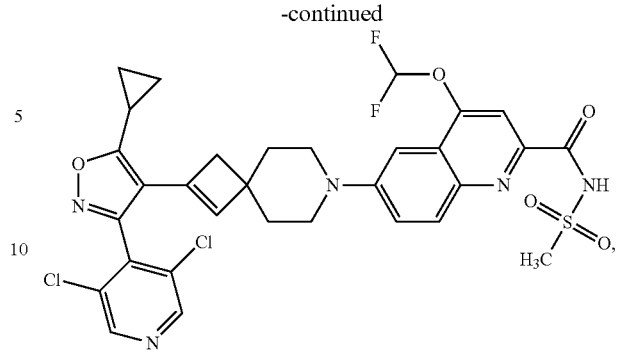
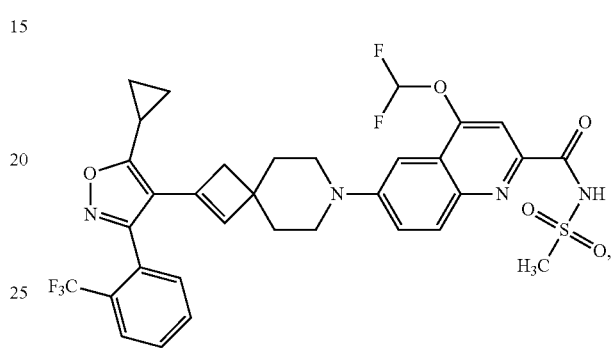
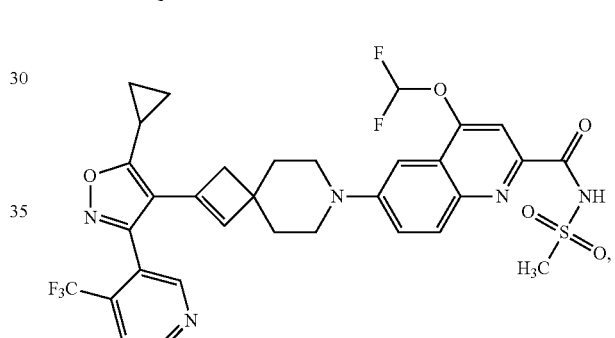
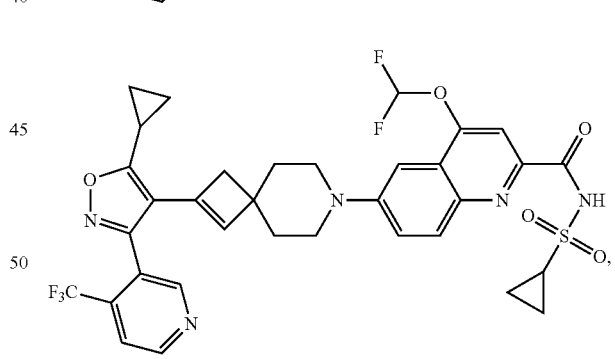
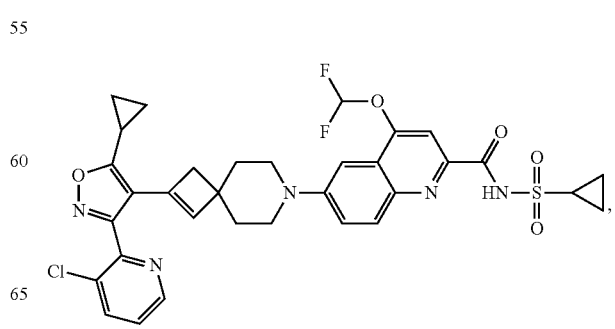

-continued
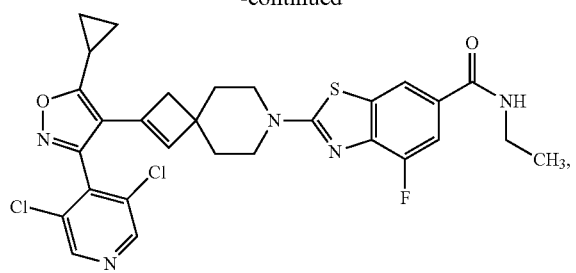
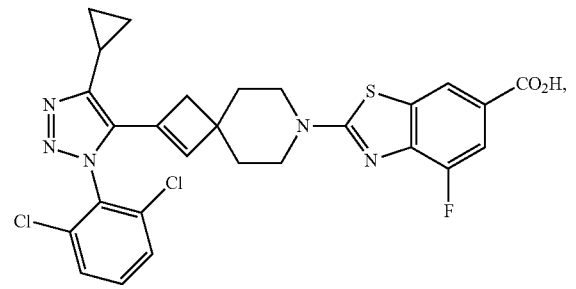
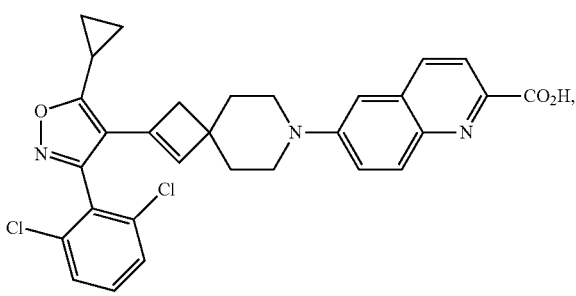
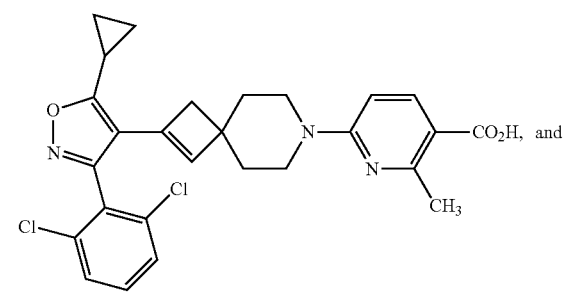
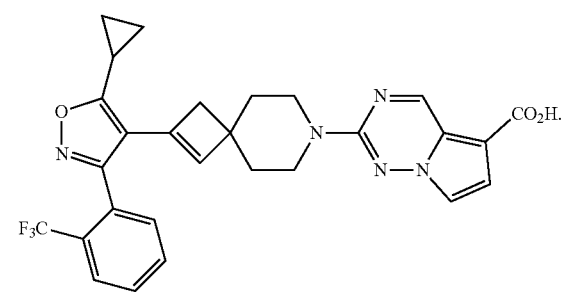
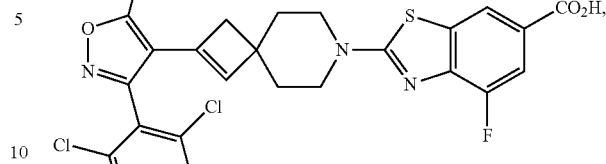
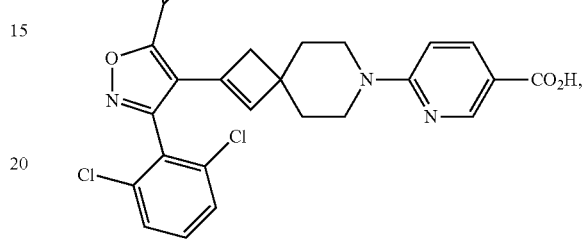
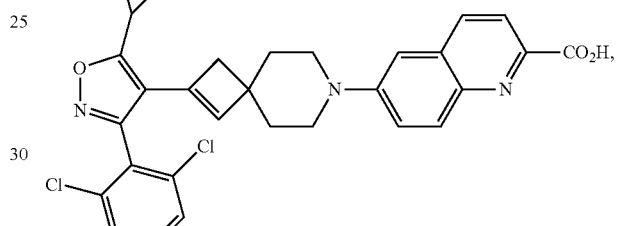
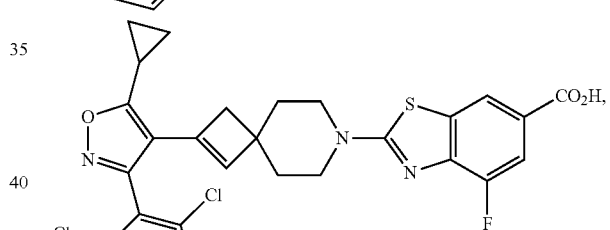
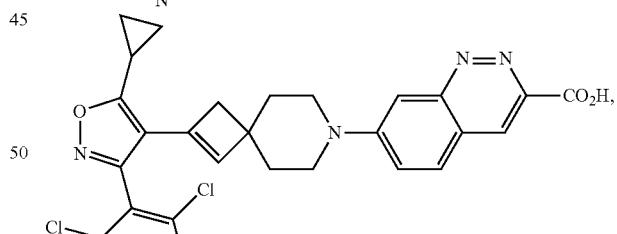
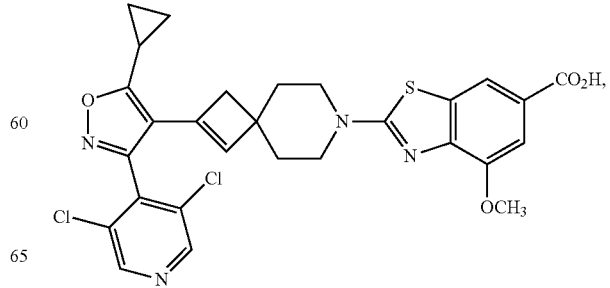
In one embodiment, the present invention provides a compound selected from:

-continued

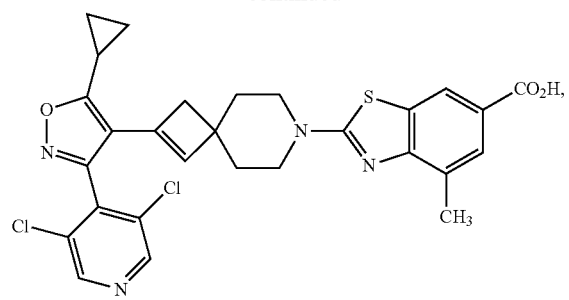
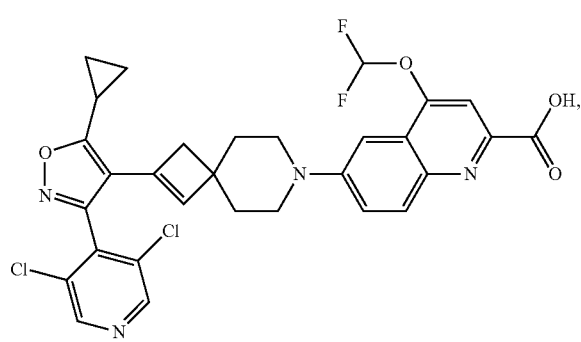
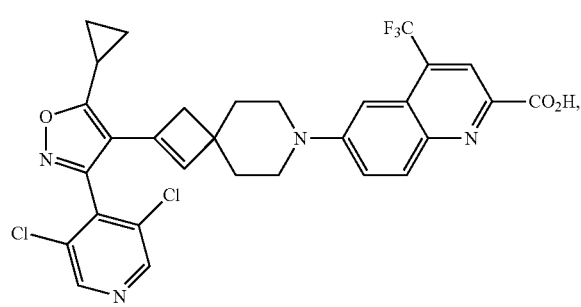
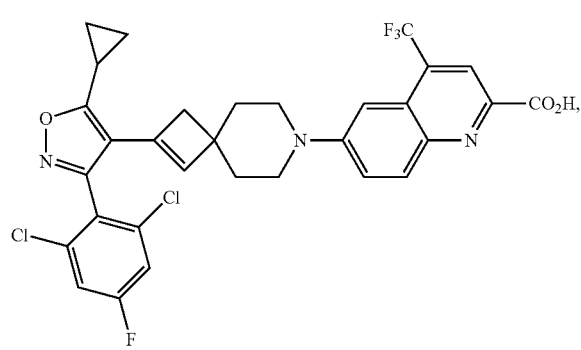
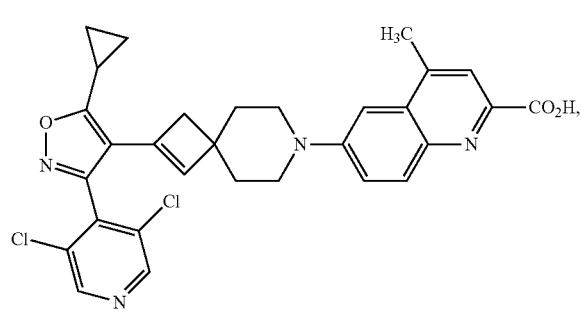

-continued

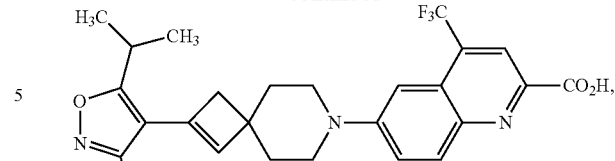
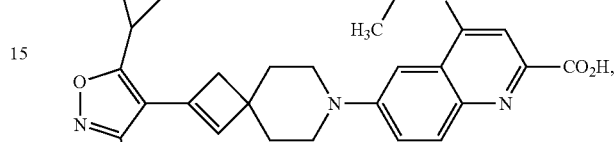
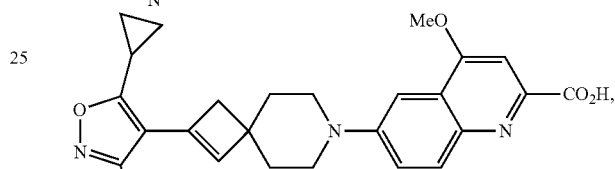
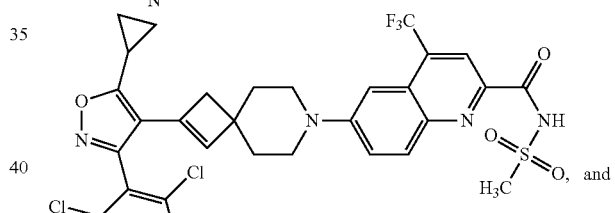
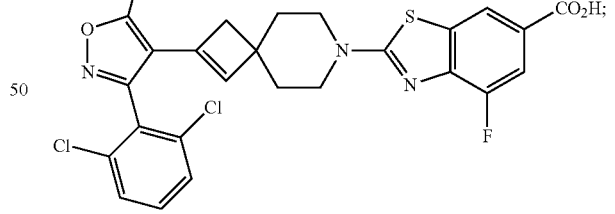

or a stereoisomer, a tautomer, or a pharmaceutically acceptable salt or solvate thereof.

In one embodiment, the present invention provides, inter alia, compounds selected from any one of the Examples as described in the specification, or a stereoisomer, a tautomer, or a pharmaceutically acceptable salt or solvate thereof.

In one embodiment, the compounds of the present invention have FXR $EC_{50}$ values ≤5000 nM, using the transient human FXR/Gal4-luciferase reporter assay; in another embodiment, the compounds of the present invention have FXR $EC_{50}$ values ≤1000 nM; in another embodiment, the compounds of the present invention have FXR $EC_{50}$ values ≤500 nM; in another embodiment, the compounds of the present invention have FXR $EC_{50}$ values ≤200 nM; in another embodiment, the compounds of the present invention have FXR $EC_{50}$ values ≤100 nM; in another embodiment, the compounds of the present invention have FXR $EC_{50}$ values ≤50 nM.

II. Pharmaceutical Compositions, Therapeutic Utilities, and Combinations

In another embodiment, the present invention provides a composition comprising at least one of the compounds of the present invention, or a stereoisomer, a tautomer, or a pharmaceutically acceptable salt or a solvate thereof.

In another embodiment, the present invention provides a pharmaceutical composition comprising a pharmaceutically acceptable carrier and at least one of the compounds of the present invention or a stereoisomer, a tautomer, or a pharmaceutically acceptable salt or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, or a pharmaceutically acceptable salt or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising one or more additional therapeutic agents.

In another embodiment, the present invention provides a method for the treatment of a disease, disorder, or condition associated with dysregulation of bile acids in a patient in need of such treatment, and the method comprises administering a therapeutically effective amount of a compound of the present invention, or a stereoisomer, a tautomer, or a pharmaceutically acceptable salt or solvate thereof, to the patient.

In another embodiment, the present invention provides a method for the treatment of a disease, disorder, or condition associated with activity of farnesoid X receptor (FXR) in a patient in need of such treatment comprising administering a therapeutically effective amount of a compound of the present invention, or a stereoisomer, a tautomer, or a pharmaceutically acceptable salt or solvate thereof, to the patient.

In another embodiment, the present invention provides a method for the treatment of the disease, disorder, or condition comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for eliciting an farnesoid X receptor (FXR) agonizing effect in a patient comprising administering a therapeutically effective amount of a compound of the present invention, or a stereoisomer, a tautomer, or a pharmaceutically acceptable salt or solvate thereof, to the patient.

In some embodiments, the disease, disorder, or condition is associated with FXR dysfunction include pathological fibrosis, cancer, inflammatory disorders, metabolic, or cholestatic disorders.

In some embodiments, the disease, disorder, or condition is associated with fibrosis, including liver, biliary, renal, cardiac, dermal, ocular, and pancreatic fibrosis.

In other embodiments, the disease, disorder, or condition is associated with cell-proliferative disorders, such as cancer. In some embodiments, the cancer includes solid tumor growth or neoplasia. In other embodiments, the cancer includes tumor metastasis. In some embodiments, the cancer is of the liver, gall bladder, small intestine, large intestine, kidney, prostate, bladder, blood, bone, brain, breast, central nervous system, cervix, colon, endometrium, esophagus, genitalia, genitourinary tract, head, larynx, lung, muscle tissue, neck, oral or nasal mucosa, ovary, pancreas, skin, spleen, stomach, testicle, or thyroid. In other embodiments, the cancer is a carcinoma, sarcoma, lymphoma, leukemia, melanoma, mesothelioma, multiple myeloma, or seminoma.

Examples of diseases, disorders, or conditions associated with the activity of FXR that can be prevented, modulated, or treated according to the present invention include, but are not limited to, transplant injection, fibrotic disorders (e.g., liver fibrosis, kidney fibrosis), inflammatory disorders (e.g., acute hepatitis, chronic hepatitis, non-alcoholic steatohepatitis (NASH), irritable bowel syndrome (IBS), inflammatory bowel disease (IBD)), as well as cell-proliferative disorders (e.g., cancer, myeloma, fibroma, hepatocellular carcinoma, colorectal cancer, prostate cancer, leukemia, Kaposi's sarcoma, solid tumors).

The fibrotic disorders, inflammatory disorders, as well as cell-proliferative disorders that are suitable to be prevented or treated by the compounds of the present invention include, but are not limited to, non-alcoholic fatty liver disease (NAFLD), alcoholic or non-alcoholic steatohepatitis (NASH), acute hepatitis, chronic hepatitis, liver cirrhosis, primary biliary cirrhosis, primary sclerosing cholangitis, drug-induced hepatitis, biliary cirrhosis, portal hypertension, regenerative failure, liver hypofunction, hepatic blood flow disorder, nephropathy, irritable bowel syndrome (IBS), inflammatory bowel disease (IBD), abnormal pancreatic secretion, benign prostatic hyperplasia, neuropathic bladder disease, diabetic nephropathy, focal segmental glomerulosclerosis, IgA nephropathy, nephropathy induced by drugs or transplantation, autoimmune nephropathy, lupus nephritis, liver fibrosis, kidney fibrosis, chronic kidney disease (CKD), diabetic kidney disease (DKD), skin fibrosis, keloids, systemic sclerosis, scleroderma, virally-induced fibrosis, idiopathic pulmonary fibrosis (IPF), interstitial lung disease, non-specific interstitial pneumonia (NSIP), usual interstitial pneumonia (UIP), radiation-induced fibrosis, familial pulmonary fibrosis, airway fibrosis, chronic obstructive pulmonary disease (COPD), spinal cord tumor, hernia of intervertebral disk, spinal canal stenosis, heart failure, cardiac fibrosis, vascular fibrosis, perivascular fibrosis, foot-and-mouth disease, cancer, myeloma, fibroma, hepatocellular carcinoma, colorectal cancer, prostate cancer, leukemia, chronic lymphocytic leukemia, Kaposi's sarcoma, solid tumors, cerebral infarction, cerebral hemorrhage, neuropathic pain, peripheral neuropathy, age-related macular degeneration (AMD), glaucoma, ocular fibrosis, corneal scarring, diabetic retinopathy, proliferative vitreoretinopathy (PVR), cicatricial pemphigoid glaucoma filtration surgery scarring, Crohn's disease or systemic lupus erythematosus; keloid formation resulting from abnormal wound healing; fibrosis occurring after organ transplantation, myelofibrosis, and fibroids. In one embodiment, the present invention provides a method for the treatment of a fibrotic disorder, an inflammatory disorder, or a cell-proliferative disorder, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of a fibrotic disorder, an inflammatory disorder, or a cell-proliferative disorder thereof.

In another embodiment, the present invention also provides the use of a compound of the present invention for the manufacture of a medicament for the treatment of a fibrotic disorder, an inflammatory disorder, or a cell-proliferative disorder thereof.

In another embodiment, the present invention provides a method for the treatment of a fibrotic disorder, an inflammatory disorder, or a cell-proliferative disorder, comprising administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of a fibrotic disorder, an inflammatory disorder, or a cell-proliferative disorder.

The compounds of the present invention may be employed in combination with additional therapeutic agent(s), such as one or more anti-fibrotic and/or anti-inflammatory therapeutic agents.

In one embodiment, additional therapeutic agent(s) used in combined pharmaceutical compositions or combined methods or combined uses, are selected from one or more, preferably one to three, of the following therapeutic agents: TGFβ receptor inhibitors (for example, galunisertib), inhibitors of TGFβ synthesis (for example, pirfenidone), inhibitors of vascular endothelial growth factor (VEGF), platelet-derived growth factor (PDGF) and fibroblast growth factor (FGF) receptor kinases (for example, nintedanib), humanized anti-αvβ6 integrin monoclonal antibody (for example, 3G9), human recombinant pentraxin-2, recombinant human Serum Amyloid P, recombinant human antibody against TGFβ-1, -2, and -3, endothelin receptor antagonists (for example, macitentan), interferon gamma, c-Jun amino-terminal kinase (JNK) inhibitor (for example, 4-[[9-[(3S)-tetrahydro-3-furanyl]-8-[(2,4,6-trifluorophenyl)amino]-9H-purin-2-yl]amino]-trans-cyclohexanol, 3-pentylbenzeneacetic acid (PBI-4050), tetra-substituted porphyrin derivative containing manganese (III), monoclonal antibody targeting eotaxin-2, interleukin-13 (IL-13) antibody (for example, lebrikizumab, tralokinumab), bispecific antibody targeting interleukin 4 (IL-4) and interleukin 13 (IL-13), NK1 tachykinin receptor agonist (for example, Sar$^9$, Met(O$_2$)$^{11}$-Substance P), Cintredekin Besudotox, human recombinant DNA-derived, IgG1 kappa monoclonal antibody to connective growth factor, and fully human IgG1 kappa antibody, selective for CC-chemokine ligand 2 (for example, carlumab, CCX140), antioxidants (for example, N-acetylcysteine), phosphodiesterase 5 (PDE5) inhibitors (for example, sildenafil), agents for treatment of obstructive airway diseases such as muscarinic antagonists (for example, tiotropium, ipatropium bromide), adrenergic β2 agonists (for example, salbutamol, salmeterol), corticosteroids (for example, triamcinolone, dexamethasone, fluticasone), immunosuppressive agents (for example, tacrolimus, rapamycin, pimecrolimus), and therapeutic agents useful for the treatment of fibrotic conditions, such as liver, biliary, and kidney fibrosis, Non-Alcoholic Fatty Liver Disease (NALFD), Non-Alcoholic Steato-Hepatitis (NASH), cardiac fibrosis, Idiopathic Pulmonary Fibrosis (IPF), and systemic sclerosis. The therapeutic agents useful for the treatment of such fibrotic conditions include, but are not limited to, FXR agonists (for example OCA, GS-9674, and LJN452), LOXL2 inhibitors (for example simtuzumab), LPA1 antagonists (for example, BMS-986020 and SAR 100842), PPAR modulators (for example, elafibrinor, pioglitazone, and saroglitazar, IVA337), SSAO/VAP-1 inhibitors (for example, PXS-4728A and SZE5302), ASK-1 inhibitors (for example GS-4997 or selonsertib), ACC inhibitors (for example, CP-640186 and NDI-010976 or GS-0976), FGF21 mimetics (for example, LY2405319 and BMS-986036), caspase inhibitors (for example, emricasan), NOX4 inhibitors (for example, GKT137831), MGAT2 inhibitor (for example, BMS-963272), αV integrin inhibitors (for example, abituzumab) and bile acid/fatty acid conjugates (for example aramchol). The FXR agonists of various embodiments of the present invention may also be used in combination with one or more therapeutic agents such as CCR2/5 inhibitors (for example, cenicriviroc), Galectin-3 inhibitors (for example, TD-139, GR-MD-02), leukotriene receptor antagonists (for example, tipelukast, montelukast), SGLT2 inhibitors (for example, dapagliflozin, remogliflozin), GLP-1 receptor agonists (for example, liraglutide and semaglutide), FAK inhibitors (for example, GSK-2256098), CB1 inverse agonists (for example, JD-5037), CB2 agonists (for example, APD-371 and JBT-101), autotaxin inhibitors (for example, GLPG1690), prolyl t-RNA synthetase inhibitors (for example, halofugenone), FPR2 agonists (for example, ZK-994), and THR agonists (for example, MGL:3196). In another embodiment, additional therapeutic agent(s) used in combined pharmaceutical compositions or combined methods or combined uses, are selected from one or more, preferably one to three, of immunoncology agents, such as Alemtuzumab, Atezolizumab, Ipilimumab, Nivolumab, Ofatumumab, Pembrolizumab, and Rituximab.

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrastemal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and nonaqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The terms "treating" or "treatment" as used herein refer to an approach for obtaining beneficial or desired results, including clinical results, by using a compound or a composition of the present invention. For purposes of this invention, beneficial or desired clinical results include, but are not limited to, one or more of the following: decreasing the severity and/or frequency one or more symptoms resulting from the disease, disorder, or condition; diminishing the extent of or causing regression of the disease, disorder, or condition; stabilizing the disease, disorder, or condition (e.g., preventing or delaying the worsening of the disease, disorder, or condition); delay or slowing the progression of the disease, disorder, or condition; ameliorating the disease, disorder, or condition state; decreasing the dose of one or more other medications required to treat the disease, disorder, or condition; and/or increasing the quality of life.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.01 to about 1000 mg per day, and most preferably between about 0.01 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 0.1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., ASK-1 inhibitors, CCR2/5 antagonists, autotaxin inhibitors, LPA1 receptor antagonists or other pharmaceutically active material.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving FXR agonists. Such compounds may be provided in a commercial kit, for example, for use in pharmaceutical research involving FXR agonist activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof; and, (c) a package insert stating that the pharmaceutical composition can be used for the treatment of dyslipidemias and the sequelae thereof. In another embodiment, the package insert states that the pharmaceutical composition can be used in combination (as defined previously) with a second therapeutic agent for the treatment of fibrosis and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

III. Definitions

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention. As used herein, "a compound of the invention" or "compounds of the invention" means one or more compounds encompassed by any one of Formula (I), (IIa), and (IIb), or stereoisomers, tautomers, or pharmaceutically acceptable salts or solvates thereof.

As used herein, the term "alkyl" or "alkylene" is intended to include both branched and straight-chain saturated aliphatic hydrocarbon groups having the specified number of carbon atoms. While "alkyl" denotes a monovalent saturated aliphatic radical (such as ethyl), "alkylene" denotes a bivalent saturated aliphatic radical (such as ethylene). For example, "$C_1$ to $C_{10}$ alkyl" or "$C_{1-10}$ alkyl" is intended to include $C_1$, $C_2$, $C_3$, $C_4$, $C_5$, $C_6$, $C_7$, $C_8$, $C_9$, and $C_{10}$ alkyl groups. "$C_1$ to $C_{10}$ alkylene" or "$C_{1-10}$ alkylene", is intended to include $C_1$, $C_2$, $C_3$, $C_4$, $C_5$, $C_6$, $C_7$, $C_8$, $C_9$, and $C_{10}$ alkylene groups. Additionally, for example, "$C_1$ to $C_6$ alkyl" or "$C_{1-6}$ alkyl" denotes alkyl having 1 to 6 carbon atoms; and "$C_1$ to $C_6$ alkylene" or "$C_{1-6}$ alkylene" denotes alkylene having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

Unless otherwise indicated, the term "lower alkyl" as employed herein alone or as part of another group includes both straight and branched chain hydrocarbons containing 1 to 8 carbons, and the terms "alkyl" and "alk" as employed herein alone or as part of another group includes both straight and branched chain hydrocarbons containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —$OCH_3$, etc.), an alkylamino (e.g., —$NHCH_3$, —$N(CH_3)_2$, etc.), or a thioalkyl group (e.g., —$SCH_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., —$CH_2CH_2$—O—$CH_3$, etc.), an alkylaminoalkyl (e.g., —$CH_2NHCH_3$, —$CH_2N(CH_3)_2$, etc.), or a thioalkyl ether (e.g., —$CH_2$—S—$CH_3$). If a terminal carbon atom of the alkyl group is replaced with a heteroatom (e.g., O, N, or S), the resulting heteroalkyl groups are, respectively, a hydroxyalkyl group (e.g., —$CH_2CH_2$—OH), an aminoalkyl group (e.g., —$CH_2NH_2$), or an alkyl thiol group (e.g., —$CH_2CH_2$—SH). A heteroalkyl group can have, for example, 1 to 20 carbon atoms, 1 to 10 carbon atoms, or 1 to 6 carbon atoms. A $C_1$-$C_6$ heteroalkyl group means a heteroalkyl group having 1 to 6 carbon atoms.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. While "alkenyl" denotes a monovalent radical, "alkenylene" denotes a bivalent radical. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. While "alkynyl" denotes a monovalent radical, "alkynylene" denotes a bivalent radical. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

As used herein, "arylalkyl" (a.k.a. aralkyl), "heteroarylalkyl" "carbocyclylalkyl" or "heterocyclylalkyl" refers to an acyclic alkyl radical in which one of the hydrogen atoms bonded to a carbon atom, typically a terminal or $sp^3$ carbon atom, is replaced with an aryl, heteroaryl, carbocyclyl, or heterocyclyl radical, respectively. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl, heteroarylalkyl, carbocyclylalkyl, or heterocyclylalkyl group can comprise 4 to 20 carbon atoms and 0 to 5 heteroatoms, e.g., the alkyl moiety may contain 1 to 6 carbon atoms.

The term "benzyl", as used herein, refers to a methyl group on which one of the hydrogen atoms is replaced by a phenyl group, wherein said phenyl group may optionally be substituted with 1 to 5 groups, preferably 1 to 3 groups, —OH, —$OCH_3$, $C_1$, F, Br, I, —CN, —$NO_2$, —$NH_2$, —NH ($CH_3$), —$N(CH_3)_2$, —$CF_3$, —$OCF_3$, —C(=O)$CH_3$, —$SCH_3$, —S(=O)$CH_3$, —S(=O)$_2CH_3$, —$CH_3$, —$CH_2CH_3$, —$CO_2H$, and —$CO_2CH_3$. "Benzyl" can also be represented by formula "Bn".

The term "lower alkoxy", "alkoxy" or "alkyloxy", "aryloxy" or "aralkoxy" refers to any of the above alkyl, aralkyl or aryl groups linked to an oxygen atom. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "lower alkylthio", "alkylthio", "thioalkoxy", "arylthio", or "aralkylthio" represents an alkyl, aryl, or aralkyl group as defined above with the indicated number of carbon atoms attached through a sulphur bridge; for example methyl-S- and ethyl-S—.

The term "alkanoyl" or "alkylcarbonyl" as used herein alone or as part of another group refers to alkyl linked to a carbonyl group. For example, alkylcarbonyl may be represented by alkyl-C(O)—. "$C_1$ to $C_6$ alkylcarbonyl" (or alkylcarbonyl), is intended to include $C_1$, $C_2$, $C_3$, $C_4$, $C_5$, and $C_6$ alkyl-C(O)— groups.

The term "alkylsulfonyl" or "sulfonamide" as used herein alone or as part of another group refers to alkyl or amino linked to a sulfonyl group. For example, alkylsulfonyl may be represented by —$S(O)_2R'$, while sulfonamide may be represented by —$S(O)_2NR^cR^d$. R' is $C_1$ to $C_6$ alkyl; and R and $R^d$ are the same as defined below for "amino".

The term "carbamate" as used herein alone or as part of another group refers to oxygen linked to an amido group. For example, carbamate may be represented by $N(R^cR^d)$—C(O)—O—, and $R^c$ and $R^d$ are the same as defined below for "amino".

The term "amido" as used herein alone or as part of another group refers to amino linked to a carbonyl group. For example, amido may be represented by $N(R^cR^d)$—C(O)—, and $R^c$ and $R^d$ are the same as defined below for "amino".

The term "amino" is defined as —$NR^{c1}R^{c2}$, wherein $R^{c1}$ and $R^{c2}$ are independently H or $C_{1-6}$ alkyl; or alternatively, $R^{c1}$ and $R^{c2}$, taken together with the atoms to which they are attached, form a 3- to 8-membered heterocyclic ring which is optionally substituted with one or more group selected from halo, cyano, hydroxyl, amino, oxo, $C_{1-6}$ alkyl, alkoxy, and aminoalkyl. When $R^{c1}$ or $R^{c2}$ (or both of them) is $C_{1-6}$ alkyl, the amino group can also be referred to as alkylamino. Examples of alkylamino group include, without limitation, —$NH_2$, methylamino, ethylamino, propylamino, isopropylamino and the like.

The term "aminoalkyl" refers to an alkyl group on which one of the hydrogen atoms is replaced by an amino group. For example, aminoalkyl may be represented by $N(R^{c1}R^{c2})$-alkylene-. "$C_1$ to $C_6$" or "$C_{1-6}$" aminoalkyl" (or aminoalkyl), is intended to include $C_1$, $C_2$, $C_3$, $C_4$, $C_5$, and $C_6$ aminoalkyl groups.

The term "halogen" or "halo" as used herein alone or as part of another group refers to chlorine, bromine, fluorine, and iodine, with chlorine or fluorine being preferred.

"Haloalkyl" is intended to include both branched and straight-chain saturated aliphatic hydrocarbon groups having the specified number of carbon atoms, substituted with one or more halogens. "$C_1$ to $C_6$ haloalkyl" or "$C_{1-6}$ haloalkyl" (or haloalkyl), is intended to include $C_1$, $C_2$, $C_3$, $C_4$, $C_5$, and $C_6$ haloalkyl groups. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms. The term "polyhaloalkyl" as used herein refers to an "alkyl" group as defined above which includes from 2 to 9, preferably from 2 to 5, halo substituents, such as F or $C_1$, preferably F, such as polyfluoroalkyl, for example, $CF_3CH_2$, $CF_3$ or $CF_3CF_2CH_2$.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Other examples of haloalkoxy also include "fluoroalkyl" which represents a fluoroalkyl group as defined above with the indicated number of carbon atoms attached through an oxygen bridge. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—. The term "polyhaloalkyloxy" as used herein refers to an "alkoxy" or "alkyloxy" group as defined above which includes from 2 to 9, preferably from 2 to 5, halo substituents, such as F or $C_1$, preferably F, such as polyfluoroalkoxy, for example, —$OCH_2CF_3$, —$OCF_3$, or —$OCH_2CF_2CF_3$.

"Hydroxyalkyl" is intended to include both branched and straight-chain saturated aliphatic hydrocarbon groups having the specified number of carbon atoms, substituted with 1 or more hydroxyl (OH). "$C_1$ to $C_6$ hydroxyalkyl" (or hydroxyalkyl), is intended to include $C_1$, $C_2$, $C_3$, $C_4$, $C_5$, and $C_6$ hydroxyalkyl groups.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbomyl. Branched cycloalkyl groups such as 1-methylcyclopropyl and 2-methylcyclopropyl are included in the definition of "cycloalkyl".

The term "cycloheteroalkyl" refers to cyclized heteroalkyl groups, including mono-, bi- or poly-cyclic ring systems. "$C_3$ to $C_7$ cycloheteroalkyl" or "$C_{3-7}$ cycloheteroalkyl" is intended to include $C_3$, $C_4$, $C_5$, $C_6$, and $C_7$ cycloheteroalkyl groups. Example cycloheteroalkyl groups include, but are not limited to, oxetanyl, tetrahydrofuranyl, tetrahydropyranyl, azetidinyl, pyrrolidinyl, piperidinyl, morpholinyl, and piperazinyl.

Branched cycloheteroalkyl groups, such as piperidinylmethyl, piperazinylmethyl, morpholinylmethyl, pyridinylmethyl, pyridizylmethyl, pyrimidylmethyl, and pyrazinylmethyl, are included in the definition of "cycloheteroalkyl".

As used herein, the term "azacyclyl" refers to a cycloheteroalkyl containing one or more nitrogen atoms in the ring. Example azacyclyl groups include, but are not limited to, pyrrolidinyl, piperidinyl, morpholinyl, and piperazinyl.

As used herein, "carbocycle", "carbocyclyl", or "carbocyclic" is intended to mean any stable 3-, 4-, 5-, 6-, 7-, or 8-membered monocyclic or 5-, 6-, 7-, 8-, 9-, 10-, 11-, 12-, or 13-membered polycyclic (including bicyclic or tricyclic) hydrocarbon ring, any of which may be saturated or partially unsaturated. That is, the term "carbocycle", "carbocyclyl", or "carbocyclic" includes, without limitation, cycloalkyl and cycloalkenyl. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, indanyl, adamantyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, indanyl, and tetrahydronaphthyl. A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

Furthermore, the term "carbocyclyl", including "cycloalkyl" and "cycloalkenyl", as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons or 3 to 6 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

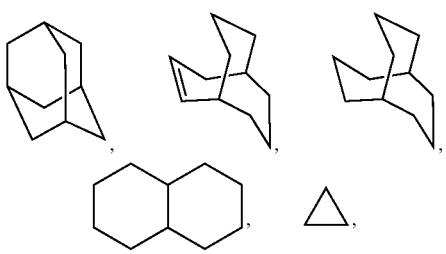

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, nitro, cyano, thiol and/or alkylthio and/or any of the alkyl substituents.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated or partially unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, 1,2-dihydronaphthyl, 1,2,3,4-tetrahydronaphthyl, and indanyl.

As used herein, the term "aryl", as employed herein alone or as part of another group, refers to monocyclic or polycyclic (including bicyclic and tricyclic) aromatic hydrocarbons, including, for example, phenyl, naphthyl, anthracenyl, and phenanthranyl. Aryl moieties are well known and described, for example, in Lewis, R. J., ed., *Hawley's Condensed Chemical Dictionary*, 13th Edition, John Wiley & Sons, Inc., New York (1997). In one embodiment, the term "aryl" denotes monocyclic and bicyclic aromatic groups containing 6 to 10 carbons in the ring portion (such as phenyl or naphthyl including 1-naphthyl and 2-naphthyl). For example, "$C_6$ or $C_{10}$ aryl" or "$C_{6-10}$ aryl" refers to phenyl and naphthyl. Unless otherwise specified, "aryl", "$C_6$ or $C_{10}$ aryl", "$C_{6-10}$ aryl", or "aromatic residue" may be unsubstituted or substituted with 1 to 5 groups, preferably 1 to 3 groups, selected from —OH, —OCH$_3$, F, C$_1$, Br, I, —CN, —NO$_2$, —NH$_2$, —N(CH$_3$)H, —N(CH$_3$)$_2$, —CF$_3$, —OCF$_3$, —C(O)CH$_3$, —SCH$_3$, —S(O)CH$_3$, —S(O)$_2$CH$_3$, —CH$_3$, —CH$_2$CH$_3$, —CO$_2$H, and —CO$_2$CH$_3$.

As used herein, the term "heterocycle", "heterocyclyl", or "heterocyclic group" is intended to mean a stable 3-, 4-, 5-, 6-, or 7-membered monocyclic or 5-, 6-, 7-, 8-, 9-, 10-, 11-, 12-, 13-, or 14-membered polycyclic (including bicyclic and tricyclic) heterocyclic ring that is saturated, or partially unsaturated, and that contains carbon atoms and 1, 2, 3 or 4 heteroatoms independently selected from the group consisting of N, O and S; and including any polycyclic group in which any of the above-defined heterocyclic rings is fused to a carbocyclic or an aryl (e.g., benzene) ring. That is, the term "heterocycle", "heterocyclyl", or "heterocyclic group" includes non-aromatic ring systems, such as heterocycloalkyl and heterocycloalkenyl. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. Examples of hetercyclyl include, without limitation, azetidinyl, piperazinyl, piperidinyl, piperidonyl, piperonyl, pyranyl, morpholinyl, tetrahydrofuranyl, tetrahydroisoquinolinyl, tetrahydroquinolinyl, morpholinyl, dihydrofuro[2,3-b]tetrahydrofuran.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1. Examples of a bicyclic heterocyclic group are, but not limited to, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

As used herein, the term "heteroaryl" is intended to mean stable monocyclic and polycyclic (including bicyclic and tricyclic) aromatic hydrocarbons that include at least one heteroatom ring member such as sulfur, oxygen, or nitrogen. Heteroaryl groups include, without limitation, pyridinyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Examples of heteroaryl include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathianyl, phenoxazinyl, phthalazinyl, pteridinyl, purinyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Examples of 5- to 10-membered heteroaryl include, but are not limited to, pyridinyl, furanyl, thienyl, pyrazolyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl. Examples of 5- to 6-membered heterocycles include, but are not limited to, pyridinyl, furanyl, thienyl, pyrrolyl, pyrazolyl, pyrazinyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, and triazolyl.

Unless otherwise indicated, "carbocyclyl" or "heterocyclyl" includes one to three additional rings fused to the carbocyclic ring or the heterocyclic ring (such as aryl, cycloalkyl, heteroaryl or cycloheteroalkyl rings, for example,

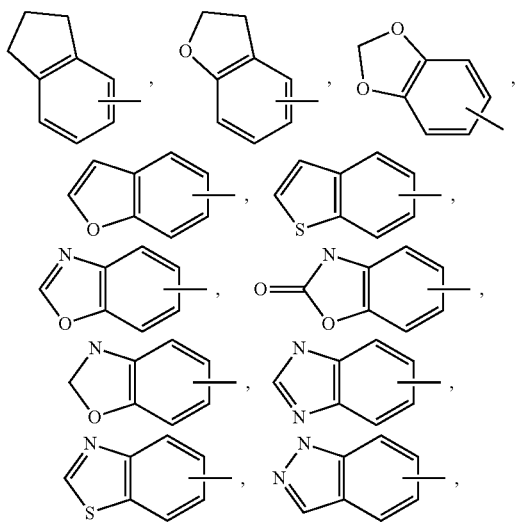

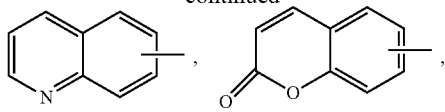

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino and arylsulfonaminocarbonyl and/or any of the alkyl substituents set out herein.

When any of the terms alkyl, alkenyl, alkynyl, cycloalkyl, carbocyclyl, heterocyclyl, aryl, and heteroaryl are used as part of another group, the number of carbon atoms and ring members are the same as those defined in the terms by themselves. For example, alkoxy, haloalkoxy, alkylamino, haloalkyl, hydroxyalkyl, aminoalkyl, haloalkoxy, alkoxyalkyl, haloalkylamino, alkoxyalkylamino, haloalkoxyalkylamino, alkylthio, and the like each independently contains the number of carbon atoms which are the same as defined for the term "alkyl", such as 1 to 4 carbon atoms, 1 to 6 carbon atoms, 1 to 10 carbon atoms, etc.

Similarly, cycloalkoxy, heterocyclyloxy, cycloalkylamino, heterocyclylamino, aralkylamino, arylamino, aryloxy, aralkyloxy, heteroaryloxy, heteroarylalkyloxy, and the like each indepdently contains ring members which are the same as defined for the terms "cycloalkyl", "heterocyclyl", "aryl", and "heteroaryl", such as 3 to 6-membered, 4 to 7-membered, 6 to 10-membered, 5 to 10-membered, 5 or 6-membered, etc.

In accordance with a convention used in the art, a bond pointing to a bold line, such as

as used in structural formulas herein, depicts the bond that is the point of attachment of the moiety or substituent to the core or backbone structure.

In accordance with a convention used in the art, a wavy or squiggly bond in a structural formula, such as

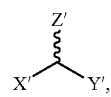

is used to depict a stereogenic center of the carbon atom to which X', Y', and Z' are attached and is intended to represent both enantiomers in a single figure. That is, a structural formula with such as wavy bond denotes each of the enantiomers individually, such as

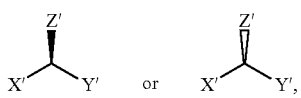

as well as a racemic mixture thereof. When a wavy or squiggly bond is attached to a double bond (such as C═C or C═N) moiety, it include cis- or trans- (or E- and Z-) geometric isomers or a mixture thereof.

It is understood herein that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the terms "pyridinyl" or "pyridyl" means 2-, 3- or 4-pyridinyl, the term "thienyl" means 2- or 3-thienyl, and so forth.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

One skilled in the art will recognize that substituents and other moieties of the compounds of the present invention should be selected in order to provide a compound which is sufficiently stable to provide a pharmaceutically useful compound which can be formulated into an acceptably stable pharmaceutical composition. Compounds of the present invention which have such stability are contemplated as falling within the scope of the present invention.

The term "counter ion" is used to represent a negatively charged species such as chloride, bromide, hydroxide, acetate, and sulfate. The term "metal ion" refers to alkali metal ions such as sodium, potassium or lithium and alkaline earth metal ions such as magnesium and calcium, as well as zinc and aluminum.

As referred to herein, the term "substituted" means that at least one hydrogen atom (attached to carbon atom or heteroatom) is replaced with a non-hydrogen group, provided that normal valencies are maintained and that the substitution results in a stable compound. When a substituent is oxo (i.e., ═O), then 2 hydrogens on the atom are replaced. Oxo substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C═C, C═N, or N═N). The term "substituted" in reference to alkyl, cycloalkyl, heteroalkyl, cycloheteroalkyl, alkylene, aryl, arylalkyl, heteroaryl, heteroarylalkyl, carbocyclyl, and heterocyclyl, means alkyl, cycloalkyl, heteroalkyl, cycloheteroalkyl, alkylene, aryl, arylalkyl, heteroaryl, heteroarylalkyl, carbocyclyl, and heterocyclyl, respectively, in which one or more hydrogen atoms, which are attached to either carbon or heteroatom, are each independently replaced with one or more non-hydrogen substituent(s).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0, 1, 2, or 3 R groups, then said group be unsubstituted when it is substituted with 0 R group, or be substituted with up to three R groups, and at each occurrence R is selected independently from the definition of R.

Also, combinations of substituents and/or variables are permissible only if such combinations result in stable compounds.

As used herein, the term "tautomer" refers to each of two or more isomers of a compound that exist together in equilibrium, and are readily interchanged by migration of an atom or group within the molecule For example, one skilled in the art would readily understand that a 1,2,3-triazole exists in two tautomeric forms as defined above:

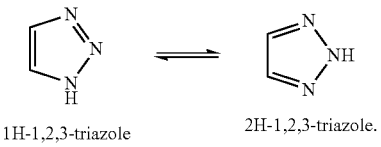

1H-1,2,3-triazole      2H-1,2,3-triazole.

Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

The compounds of the present invention can be present as salts, which are also within the scope of this invention. Pharmaceutically acceptable salts are preferred. As used herein, "pharmaceutically acceptable salts" refer to derivatives of the disclosed compounds wherein the parent compound is modified by making acid or base salts thereof. The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 18th Edition, Mack Publishing Company, Easton, Pa. (1990), the disclosure of which is hereby incorporated by reference.

If the compounds of the present invention have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of the present invention having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of Formula (I) or their pharmaceutically acceptable salts, are also included.

Preferred salts of the compounds of Formula (I) which contain a basic group include monohydrochloride, hydrogensulfate, methanesulfonate, phosphate, nitrate or acetate.

Preferred salts of the compounds of Formula (I) which contain an acid group include sodium, potassium and magnesium salts and pharmaceutically acceptable organic amines.

In addition, the compounds of the present invention may have prodrug forms. Any compound that will be converted in vivo to provide the bioactive agent is a prodrug within the scope and spirit of the invention. The term "prodrug" as used herein encompasses both the prodrugs based on the carboxylic acid residue, i.e., "prodrug esters", and the prodrugs based on the arginine mimetics moiety, i.e., "prodrugs of arginine mimetics". Such prodrugs are preferably administered orally since hydrolysis in many instances occurs principally under the influence of the digestive enzymes. Parenteral administration may be used where the esterper se is active, or in those instances where hydrolysis occurs in the blood.

The compounds of the present invention contain a carboxy group which can form physiologically hydrolyzable esters that serve as prodrugs, i.e., "prodrug esters", by being hydrolyzed in the body to yield the compounds of the present invention per se. Examples of physiologically hydrolyzable esters of compounds of the present invention include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art. The "prodrug esters" can be formed by reacting the carboxylic acid moiety of the compounds of the present invention with either alkyl or aryl alcohol, halide, or sulfonate employing procedures known to those skilled in the art. Furthermore, various forms of prodrugs are well known in the art. For examples of such prodrug derivatives, see:

Bundgaard, H., ed., *Design of Prodrugs*, Elsevier (1985), and Widder, K. et al., eds., *Methods in Enzymology*, 112:309-396, Academic Press (1985);

Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

Bundgaard, H., *Adv. Drug Deliv. Rev.*, 8:1-38 (1992);

Bundgaard, H. et al., *J. Pharm. Sci.*, 77:285 (1988); and

Kakeya, N. et al., *Chem. Pharm. Bull.*, 32:692 (1984).

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999); Rautio, J. et al., *Nature Review Drug Discovery*, 17, 559-587, (2018).

The present invention is intended to include all isotopes of atoms occurring in the present compounds. Isotopes include those atoms having the same atomic number but different mass numbers. By way of general example and without limitation, isotopes of hydrogen include deuterium (symbol D or $^2$H) and tritium (symbol T or $^3$H). Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

The term "glycosyl" means a monovalent free radical or substituent moiety obtained by removing the hemiacetal hydroxyl group from the cyclic form of a monosaccharide and, by extension, of a lower oligosaccharide. In one embodiment, the glycosyl group has the following structure:

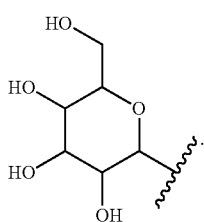

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RBF" for round bottom flask, "atm" for atmosphere, "psi" for pounds per square inch, "conc." for concentrated, "RCM" for ring-closing metathesis, "sat" or "sat'd" for saturated, "SFC" for supercritical fluid chromatography, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "¹H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Abbreviations

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RBF" for round bottom flask, "atm" for atmosphere, "psi" for pounds per square inch, "conc." for concentrated, "RCM" for ring-closing metathesis, "sat" or "sat'd" for saturated, "SFC" for supercritical fluid chromatography, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "¹H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Furthermore, the following abbreviations are employed in the Schemes, Examples and elsewhere herein:
Me methyl
Et Ethyl
Pr propyl
i-Pr isopropyl
Bu Butyl
i-Bu isobutyl
t-Bu tert-butyl
Ph phenyl
Bn benzyl
Boc or BOC tert-butyloxycarbonyl
$Boc_2O$ di-tert-butyl dicarbonate
ACN acetonitrile
AcOH or HOAc acetic acid
$AlCl_3$ aluminum chloride
AIBN Azobisisobutyronitrile
$BBr_3$ boron tribromide
$BCl_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonyl-methanimidate
CBz carbobenzyloxy
DCM or $CH_2Cl_2$ dichloromethane
$CH_3CN$ or ACN acetonitrile
$CDCl_3$ deutero-chloroform
$CHCl_3$ chloroform
mCPBA or m-CPBA meta-chloroperbenzoic acid
$Cs_2CO_3$ cesium carbonate
$Cu(OAc)_2$ copper (II) acetate
$Cy_2NMe$ N-cyclohexyl-N-methylcyclohexanamine
DBU 1,8-diazabicyclo[5.4.0]undec-7-ene
DCE 1,2 dichloroethane
DEA diethylamine
DMP or Dess-Martin Periodinane 1,1,1-tris(acetyloxy)-1,1-dihydro-1,2-beniziodoxol-3-(1H)-one
DIC or DIPCDI diisopropylcarbodiimide
DIEA, DIPEA or Hunig's base diisopropylethylamine
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylpholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
$Et_3N$ or TEA triethylamine
EtOAc ethyl acetate
$Et_2O$ diethyl ether
EtOH ethanol
GMF glass microfiber filter
Grubbs II (1,3-bis(2,4,6-trimethylphenyl)-2-imidazolidinylidene)dichloro(phenylmethylene)(triycyclohexylphosphine)ruthenium
HCl hydrochloric acid
HATU O-(7-azabenzotriazol-1-yl)-N,N,N',N'-tetramethyluronium hexafluorophosphate HEPES 4-(2-hydroxyethyl)piperaxine-1-ethanesulfonic acid
Hex hexanes
HOBt or HOBT 1-hydroxybenzotriazole
$H_2O_2$ hydrogen peroxide
IBX 2-iodoxybenzoic acid
$H_2SO_4$ sulfuric acid
Jones reagent $CrO_3$ in aqueous $H_2SO_4$, 2 M
$K_2CO_3$ potassium carbonate
$K_2HPO_4$ potassium phosphate dibasic
KOAc potassium acetate
$K_3PO_4$ potassium phosphate
LAH lithium aluminum hydride
LG leaving group
LiOH lithium hydroxide
MeOH methanol
$MgSO_4$ magnesium sulfate
MsCl methanesulfonyl chloride
MsOH or MSA methylsulfonic acid
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
NBS N-bromosuccinimide
NCS N-chlorosuccinimide
$NH_3$ ammonia
$NH_4C_1$ ammonium chloride
$NH_4OH$ ammonium hydroxide
$NH_4COOH$ ammonium formate
NMM N-methylmorpholine
OTf triflate or trifluoromethanesulfonate
$Pd_2(dba)_3$ tris(dibenzylideneacetone)dipalladium(O)
$Pd(OAc)_2$ palladium(II) acetate
Pd/C palladium on carbon
$Pd(dppf)Cl_2$ [1,1'-bis(diphenylphosphino)-ferrocene]dichloropalladium(II)
$Ph_3PCl_2$ triphenylphosphine dichloride
PG protecting group
$POCl_3$ phosphorus oxychloride
PPTS pyridinium p-toluenesulfonate
i-PrOH or IPA isopropanol
PS Polystyrene
$PtO_2$ platinum oxide
rt room temperature
RuPhos-Pd-G2 chloro(2-dicyclohexylphosphino-2',6'-diisopropoxy-1,1'-biphenyl) [2-(2'-amino-1,1'-biphenyl)]palladium(II)
SEM-Cl 2-(trimethysilyl)ethoxymethyl chloride
$SiO_2$ silica oxide
$SnCl_2$ tin(II) chloride
TBAI tetra-n-butylammonium iodide
TFA trifluoroacetic acid
THF tetrahydrofuran
$TMSCHN_2$ trimethylsilyldiazomethane
T3P propane phosphonic acid anhydride
TRIS tris(hydroxymethyl)aminomethane
pTsOH p-toluenesulfonic acid
TsCl p-tolunesulfonyl chloride IV. Methods of Preparation The compounds of the present invention can be prepared in a number of ways well known to one skilled in the art of organic synthesis using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference. The reactions are performed in a solvent or solvent mixture appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. Restrictions to the substituents that are compatible with the reaction conditions will be readily apparent to one skilled in the art and alternate methods must then be used. It will also be recognized that another major consideration in the planning of any synthetic route in this field is the judicious choice of the protecting group used for protection of the reactive functional groups present in the compounds described in this invention. A particularly useful compendium of synthetic methods which may be applicable to the preparation of compounds of the present invention may be found in Larock, R. C., Comprehensive Organic Transformations, VCH, New York (1989).

The compounds of the present invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula (I) falling into a given class may be compatible with some of the reaction conditions required in some of the methods described. Such restrictions to the substituents, which are compatible with the reaction conditions, will be readily apparent to one skilled in the art and alternate methods must be used. A particularly useful compendium of synthetic methods which may be applicable to the preparation of compounds of the present invention may be found in Larock, R. C., Comprehensive Organic Transformations, VCH, New York (1989).

Generic Schemes

Compounds of the present invention, represented by Formula (I), Formula (II), Formula (III), or any subgenera or species thereof, can be prepared according to the general routes shown in SCHEMES 1 to 13 below.

SCHEME 1

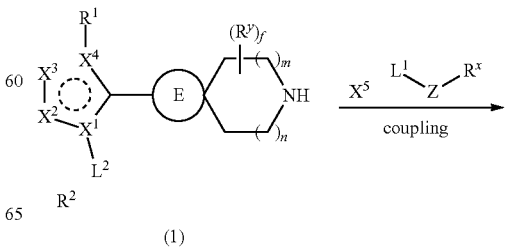

(1)

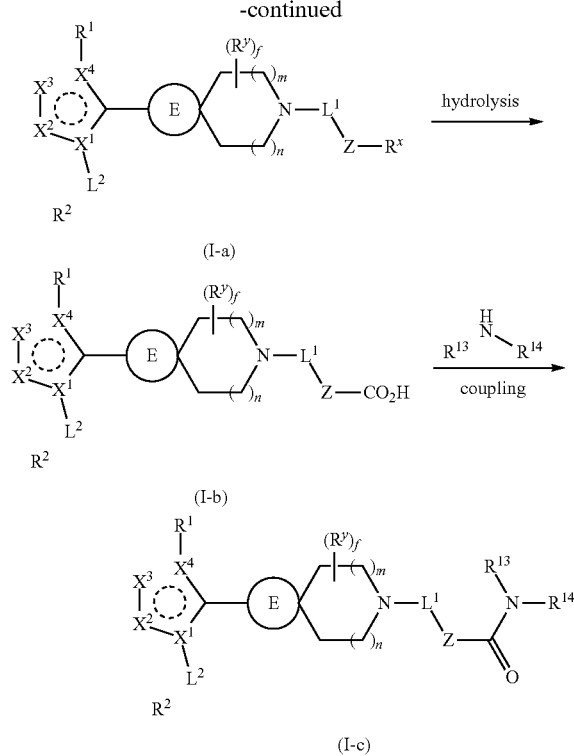

Scheme 1 describes a method of preparing compounds of Formula I-a, I-b, and I-c, a subset of Formula I. Intermediate 1 can be converted to products I-a through coupling with $X^5$-$L^1$-Z—$R^x$ ($X^5$ is a halogen, triflate or other suitable leaving group, and are commercially available or readily prepared by methods known to one skilled in the art) under conditions that are well-known to one skilled in the art. In examples where $L^1$ represents a covalent bond, products I-a can be obtained through a variety of C—N bond forming reactions between intermediate 1 and a suitable aryl halide, triflate or equivalent. Some examples include, but are not limited to, Pd-catalyzed Buchwald-Hartwig reaction, Cu-mediated Ullmann coupling, Ni-mediated amination, or nucleophilic aromatic substitution (SNAr). Alternatively, the Cu-catalyzed Chan-Evans-Lam coupling can be employed with a boronic acid or ester coupling partner. In each case, optimization of variables such as catalyst, ligand, solvent, base, additives and temperature may be required. In other examples $L^1$ represents a linker such as, but not limited to, CO or $SO_2$. In such examples products I-a can be obtained through the coupling of intermediate 1 with a suitable carboxylic acid utilizing coupling reagents such as but not limited to, T3P, EDC, DCC or CDI in the presence of a suitable base, for example triethylamine, Hunig's base, or pyridine with or without additives such as HOBT or DMAP in an appropriate solvent such as dichloromethane, ethyl acetate, DMF or THF. In some examples, carboxylic acid chlorides or sulfonyl chlorides may be reacted with intermediate 1 in order to obtain I-a by stirring in an appropriate solvent such as dichloromethane in the presence of a base such as triethylamine or Hunig's base. In each case the specific conditions utilized, including temperature, may require optimization that will be evident to one skilled in the art. If I-a contains an ester or nitrile it can be hydrolyzed to the corresponding carboxylic acid I-b under conditions such as but not limited to treatment of I-a with NaOH or LiOH in solvents consisting of MeOH, THF, and water at a temperature suitable to enable the hydrolysis. Acid-mediated hydrolysis of particular esters, such as a tert-butyl ester, may be required in some cases to obtain I-b. Examples I-c can be obtained by the coupling of I-b with $R^{13}$—NH—$R^{14}$ utilizing coupling reagents such as but not limited to, T3P, EDC, DCC or CDI in the presence of a suitable base, for example triethylamine, Hunig's base, or pyridine with or without additives such as HOBT or DMAP in an appropriate solvent such as dichloromethane, ethyl acetate, DMF or THF. In each case the specific conditions utilized to obtain I-c, including temperature and concentration, may require optimization.

SCHEME 2

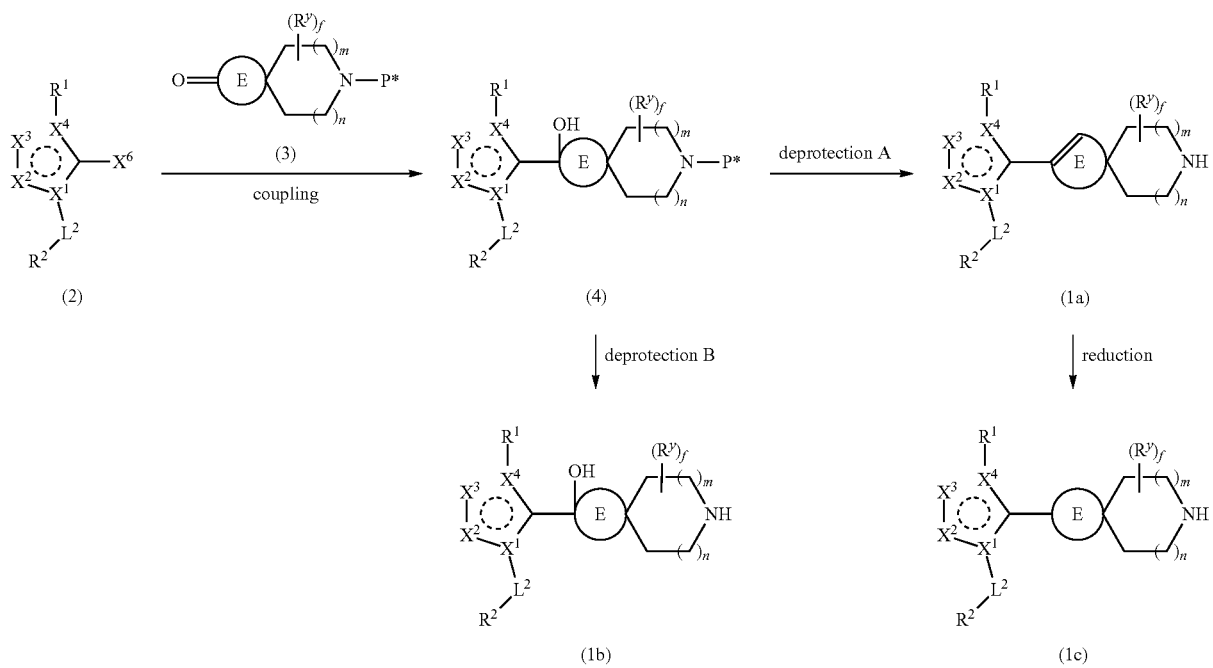

Scheme 2 describes a method for the preparation of intermediates 1a, 1b, and 1c, a subset of intermediate 1. The coupling of intermediates 2, where $X^6$ is Cl, Br or I, and ketones 3 can be accomplished through a variety of conditions such as formation of the aryl Grignard, aryl lithium, aryl zinc or other aryl metal species of 2 with subsequent addition to the ketone 3 to give tertiary alcohol products 4. Ketones 3 are commercially available or can be prepared by methods that are well-known to one skilled in the art. If appropriately acidic conditions (i.e. HCl, TFA) are employed during removal of the amino protecting group, for example where P*=Boc, alkenes 1a can be obtained as the primary isolate (deprotection A). In other cases where P*=Boc, the hydroxyl can be retained to yield intermediates 1b if dilute or weakly acidic conditions, such as TFA in DCM, are employed (deprotection B). Additionally, if P*=Cbz, palladium on carbon mediated hydrogenation can utilized to remove the protecting group without elimination of the hydroxyl to give 1b (deprotection B). Alkene intermediates 1a can be reduced under conditions such as, but not limited to, excess triethylsilane heated in TFA as solvent to give intermediates 1c. If alternative protecting groups are required for functional group compatibility, then they can be removed by methods known to one skilled in the art. Additional methods for protecting group removal may be found in Greene, T. and Wuts, P. G. M., *Protecting Groups in Organic Synthesis*, John Wiley & Sons, Inc., New York, N.Y., 2006 and references therein.

Scheme 3 describes an alternative method for the synthesis of intermediate 1a.

Ketones 3 can be converted to the corresponding boronic acid or ester in two steps consisting of enol triflate formation and subsequent Miyaura borylation. Triflate formation can be accomplished by treating 3 with a base such as LiHMDS at low temperature in THF followed by addition of Comin's reagent or another suitable triflate donor source. Typical conditions for Miyaura borylation include, but are not limited to heating the intermediate triflate with bis(pinacolato)diboron ($B_2Pin_2$), potassium acetate and a palladium catalyst such as $PdCl_2(dppf)_2$ in a suitable solvent such as THF or dioxane. Heteroaryl halide intermediate 2 can undergo Suzuki coupling with boronic acid or boronic ester 5 to yield alkene 6. Typical conditions for the Suzuki coupling include, but are not limited to, heating the intermediates 2 and 5 together with a palladium catalyst, ligand and base at a suitable temperature in a deoxygenated solvent or solvent mixture. Specific conditions include, but are not limited to $Pd(OAc)_2$, DPEPhos, $K_3PO_4$ in dioxane/water at 90° C. In each case the specific conditions utilized to obtain 6, including stoichiometry, palladium source, ligand, base, solvent, temperature, and concentration may require independent optimization. Removal of the protecting group P* can be accomplished as described in Scheme 2 to give intermediate 1a.

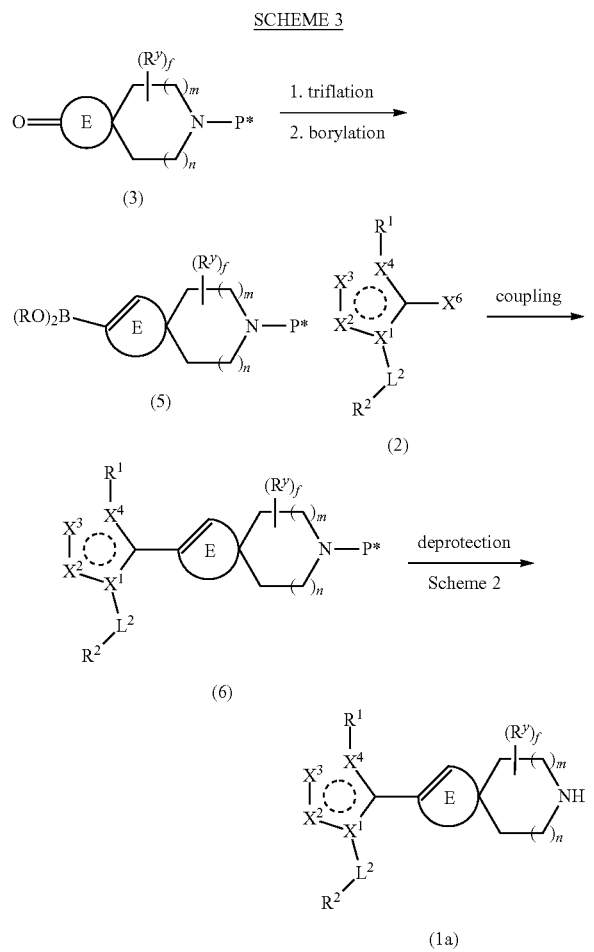

SCHEME 3

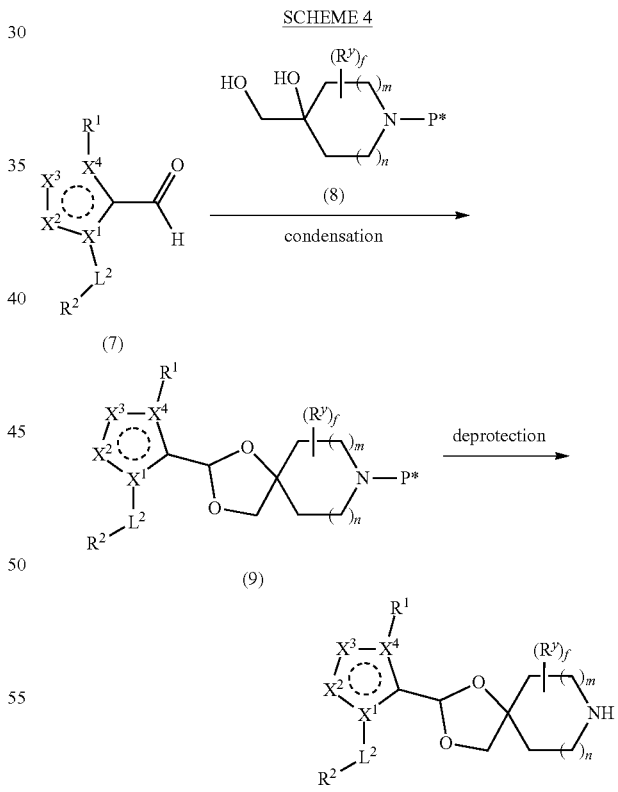

SCHEME 4

Scheme 4 describes a method for preparing intermediate 1d, a subset of intermediate 1. Intermediate 7 can undergo condensation with diol 8 (commercially available or readily prepared by methods known to one skilled in the art) under mildly-acidic dehydrating conditions to yield acetal 9. Conditions for the conversion of 7 to 9 include, but are not limited to, refluxing 7 and 8 in a solvent such as toluene in the presence of 4 Å molecular sieves and catalyticp-TSA. Removal of the protecting group P* in cases where P*=Boc, dilute or weakly acidic conditions, such as TFA in DCM, can be utilized to retain the acetal. If alternative protecting groups are required for functional group compatibility, then they can be removed by methods known to one skilled in the art. Additional methods for protecting group removal may be found in Greene, T. and Wuts, P. G. M., *Protecting Groups in Organic Synthesis*, John Wiley & Sons, Inc., New York, N.Y., 2006 and references therein.

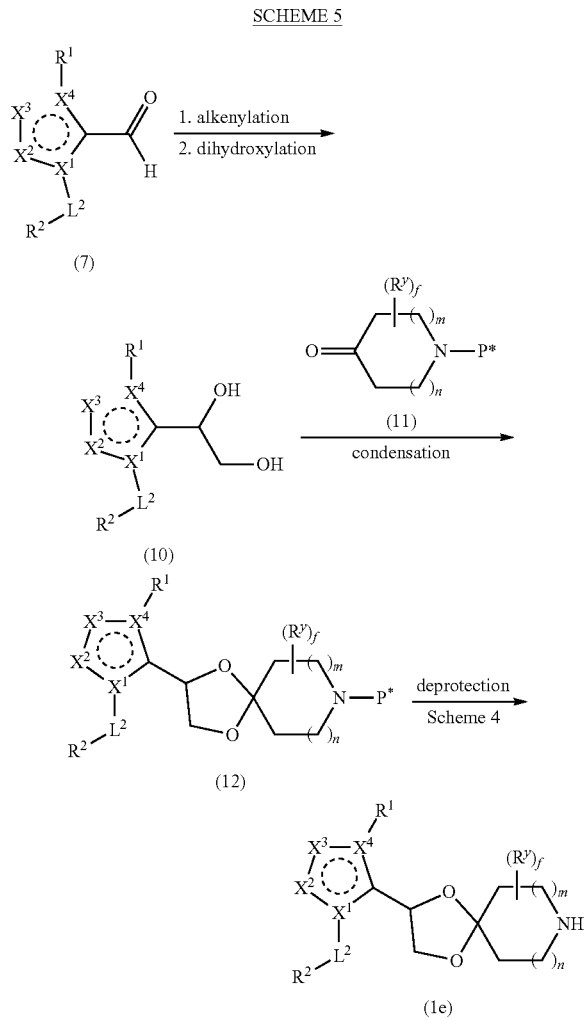

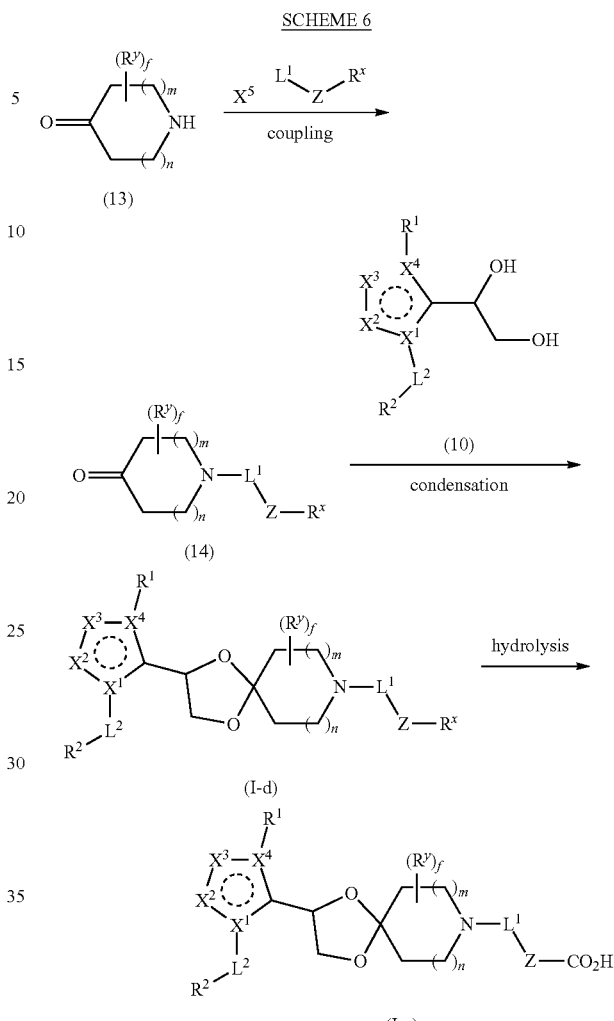

Scheme 5 describes a method for preparing intermediate 1e, a subset of intermediate 1. Intermediate aldehyde 7 can be converted to diol 10 in two steps comprising alkenylation and dihydroxylation. The alkenylation step can be accomplished with a reagent such as methyl triphenylphosphonium bromide and a suitable base such as, but not limited to KOtBu or NaHMDS in a solvent such as THF. Subjecting the resultant alkene to conditions such as but not limited to OsO$_4$ and NMO in a suitable solvent gives diol 10. Condensation of 10 with ketone 11 (commercially available or readily prepared by methods known to one skilled in the art), under conditions such as catalytic p-TSA in refluxing toluene with a drying agent such as 4 Å molecular sieves, yield ketal 12. Removal of the protecting group P* to give intermediate 1e can be carried out as described in Scheme 4.

Alternatively, scheme 6 describes a method for the preparation of compounds I-d and I-e a subset of formula I. Intermediate 14 can be obtained through a variety of coupling reactions between amino ketone 13 (commercially available or readily prepared by methods known to one skilled in the art) and a suitable aryl halide, triflate or equivalent X$^5$-L$^1$-Z—R$^x$, where X$^5$ represents the halide or triflate. Some examples of such coupling reactions include, but are not limited to, Pd-catalyzed Buchwald-Hartwig reaction, Cu-mediated Ullmann coupling, Ni-mediated amination, or nucleophilic aromatic substitution (SNAr) to give intermediate 14. Subsequent condensation between ketone 14 and diol 10 (scheme 5) under conditions that include mixing the reactants in the presence of an acid catalyst like p-TSA in a solvent such as DCE, can give products I-d. If products I-d contain an ester or nitrile they can be hydrolyzed to the corresponding carboxylic acid I-e under conditions such as but not limited to treatment of I-d with NaOH or LiOH in solvents consisting of MeOH, THF, and water at a temperature suitable to enable the hydrolysis. Acid-mediated hydrolysis of particular esters, such as a tert-butyl ester, may be required in some cases to obtain I-e.

SCHEME 7

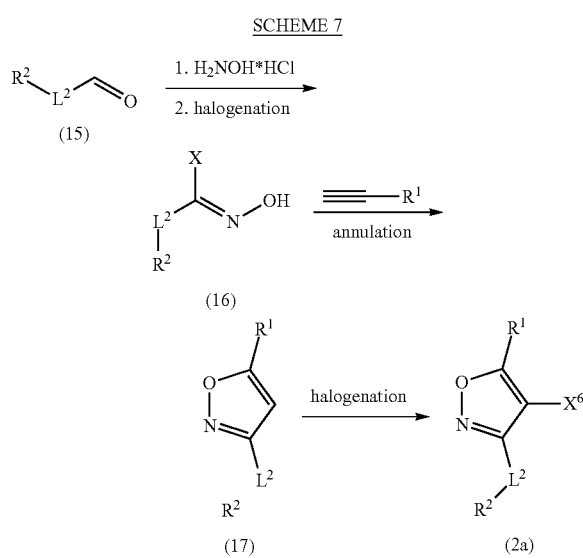

Scheme 7 describes a method for preparing intermediate 2a, a subset of intermediate 2. Aldehydes 15 (commercially available or readily prepared by methods known to one skilled in the art) can be condensed with hydroxylamine hydrochloride under a variety of conditions including, but not limited to, stirring both reactants in pyridine at room temperature, or gently heating the reactants in the presence of a base like sodium hydroxide or sodium acetate in a suitable solvent such as ethanol. The resultant oximes can be converted to the corresponding hydroximoyl halides 16 through halogenation by reagents such as but not limited to NCS or NBS in a suitable solvent such as DMF. The hydroximoyl halides 16 undergo annulation with terminal alkynes (commercially available or readily prepared by one skilled in the art) under conditions such as, but not limited to triethyl amine in dichloromethane at room temperature to afford 3,5-substituted isoxazoles 17. The 4-position of the isoxazole can be halogenated by reagents such as but not limited to NBS or NCS in a suitable solvent such as DMF to give 3,4,5-substituted isoxazole intermediates 2a.

SCHEME 8

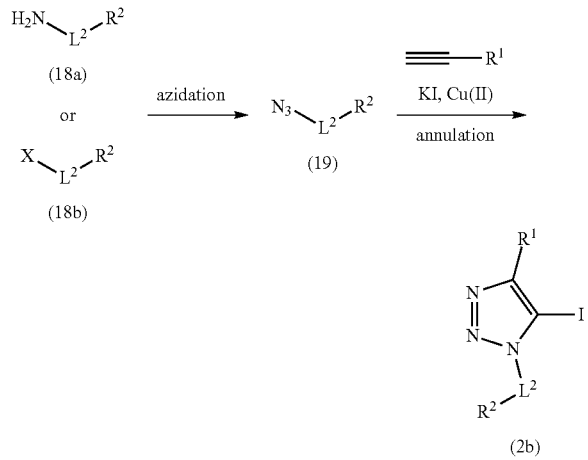

Scheme 8 describes a method of preparing intermediate 2b, a subset of intermediate 2. The synthesis can commence with azidation of amine 18a (commercially available or readily prepared by methods known to one skilled in the art) under conditions such as, but not limited to, treatment with sodium nitrite in acidic media (H$_2$O/TFA) followed by addition of sodium azide in an appropriate solvent at a suitable temperature to give azide 19. Alternatively, azide 19 can be obtained by the reaction of halide 18b (commercially available or readily prepared by methods known to one skilled in the art) with an azide salt, such as sodium azide, in a mixture of DMSO/water at an appropriate temperature. The resultant azide 19 can be annulated with a commercially available terminal alkyne to give iodotriazole intermediate 2b under conditions such as, but not limited to, copper (II) perchlorate, potassium iodide, and DBU in THF at room temperature.

SCHEME 9

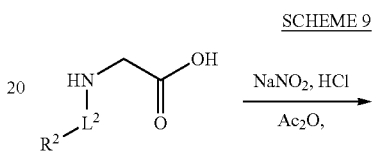

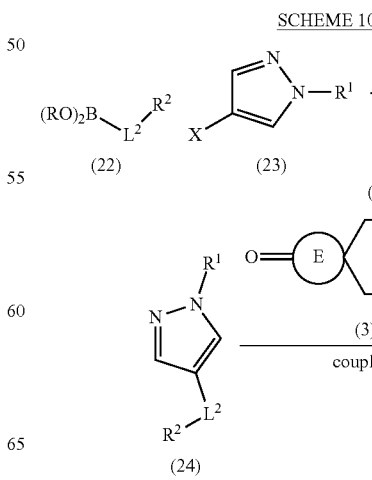

Scheme 9 describes a method of preparing intermediate 2c, a subset of intermediate 2. Commercially available or readily prepared N-substituted glycines 20 give sydnones 21 when treated with sodium nitrite, HCl and acetic anhydride under conditions that can be found in Fang, Y.; Wu, C.; Larock, R. C.; Shi, F. *J. Org. Chem.* 2011, 76, 8840. The sydnones 21 can be converted to pyrazole intermediates 2c in a two-step process involving bromination with NBS followed by copper catalyzed cycloaddition with an alkyne as described in Decuypere, E.; Specklin, S.; Gabillet, S.; Audisio, D.; Liu, H.; Plougastel, L.; Kolodych S.; Taran, F. *Org. Lett.* 2015, 17, 362.

SCHEME 10

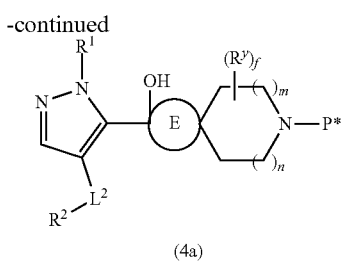

(4a)

Scheme 10 describes a method for preparing intermediate 4a, a subset of intermediate 4. An appropriately substituted boronic acid or ester 22 (commercially available or readily prepared by methods known to one skilled in the art) and a pyrazole 23 bearing a suitably reactive halogen or equivalent X, (commercially available or readily prepared by methods known to one skilled in the art) can be coupled through the Pd-catalyzed Suzuki reaction to give intermediate 24. Typical conditions for the Suzuki coupling include, but are not limited to, heating the reactants 22 and 23 together with a palladium catalyst, ligand and base at a suitable temperature in a deoxygenated solvent or solvent mixture. Specific conditions include, but are not limited to, $PdCl_2(dppf)_2$, $Na_2CO_3$ in THF/water at 120° C. In each case the specific conditions utilized to obtain 24, including stoichiometry, palladium source, ligand, base, solvent, temperature, and concentration may require independent optimization. The coupling partners 22 and 23, are either commercially available or can be readily prepared by methods known to one skilled in the art. Intermediate 24 can be deprotonated at the 5-position of the pyrazole by a sufficiently strong base such as, but not limited to, n-BuLi, or LDA in a suitable solvent such as THF or $Et_2O$. The resulting anion from deprotonation of 24 can be trapped in situ with a ketone 3 to give intermediate 2a.

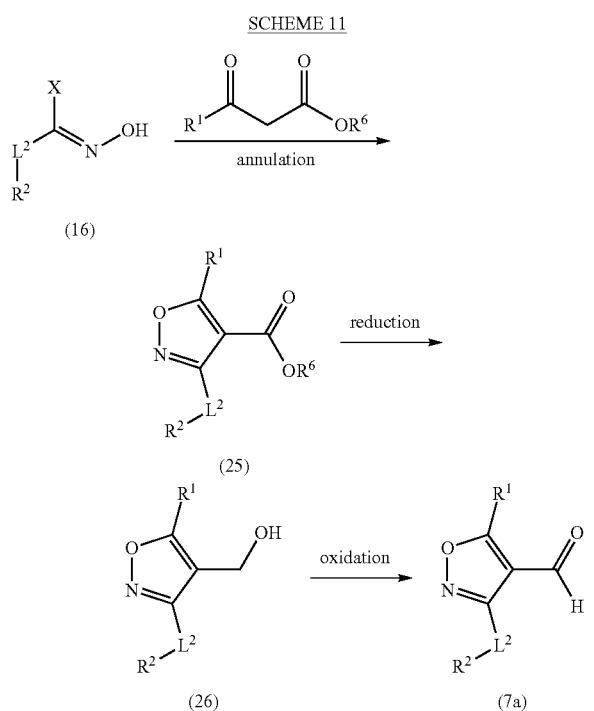

Scheme 11 describes a method of preparing intermediate 7a, a subset of intermediate 7. Hydroximoyl halides 16 (preparation described in Scheme 6) can be reacted with β-ketoesters (commercially available or readily prepared by methods known to one skilled in the art) in the presence of triethyl amine or another suitable base in a solvent such as, but not limited to, DCM to give 3,4,5-substituted isoxazole esters 25. Reduction of the ester can be accomplished by a number of reagents including, but not limited to $LiAlH_4$, DIBAL-H, or $LiBH_4$ in an appropriate solvent. The resultant hydroxyl of isoxazole 26 can be converted to aldehyde intermediates 7a under oxidative conditions including, but not limited to PCC oxidation, Dess-Martin oxidation, Swern oxidation, Ley oxidation in an appropriate solvent such as, but not limited to DCM or DCE.

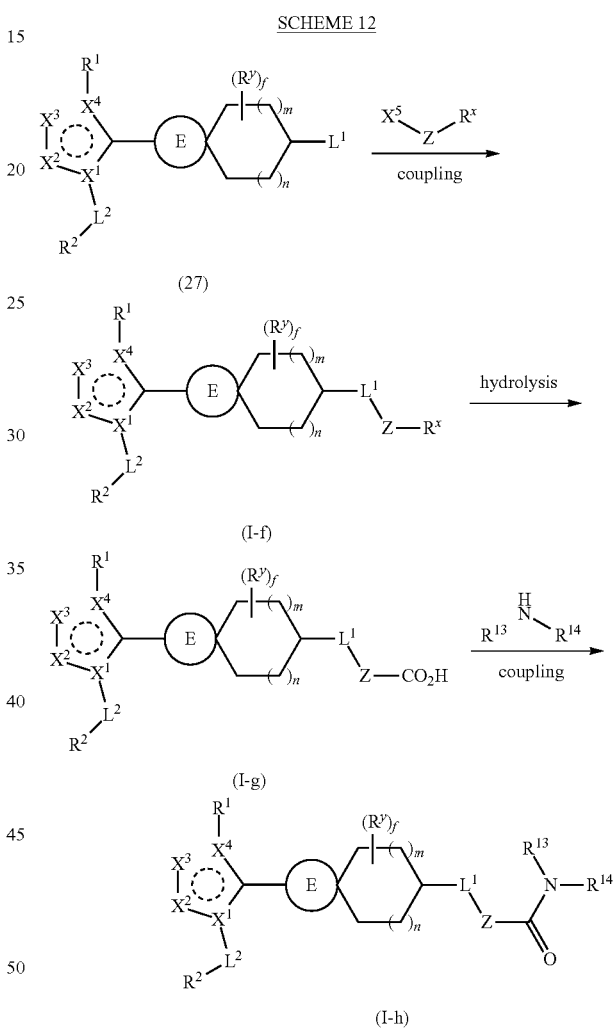

Scheme 12 describes a method of preparing compounds I-f, I-g, I-h a subset of Formula I. In some examples $L^1$ represents a linker atom such as, but not limited to, O, or N and products I-f can be obtained through the coupling of intermediate 27 with $X^5$—Z—$R^x$ ($X^5$ represents a halide or triflate) under conditions that include, but are not limited to, nucleophilic aromatic substitution (SNAr), transition metal mediated arylation (i.e. Pd, Cu, Ni), Mitsunobu coupling, reductive amination or alkylation. If I-f contains an ester or nitrile it can be hydrolyzed to the corresponding carboxylic acid I-g under conditions such as but not limited to treatment with NaOH or LiOH in solvents consisting of MeOH, THF, and water at a temperature suitable to enable the hydrolysis. Acid-mediated hydrolysis of particular esters, such as a tert-butyl ester, may be required in some cases to obtain I-g.

Examples I-h can be obtained by the coupling of I-g with $R^{13}$—NH—$R^{14}$ utilizing coupling reagents such as but not limited to, T3P, EDC, DCC or CDI in the presence of a suitable base, for example triethylamine, Hunig's base, or pyridine with or without additives such as HOBT or DMAP in an appropriate solvent such as dichloromethane, ethyl acetate, DMF or THF. In each case the specific conditions utilized to obtain I-f, I-g, and I-h including temperature and concentration, may require optimization.

SCHEME 13

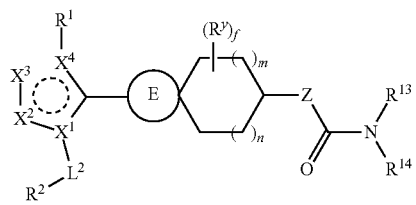
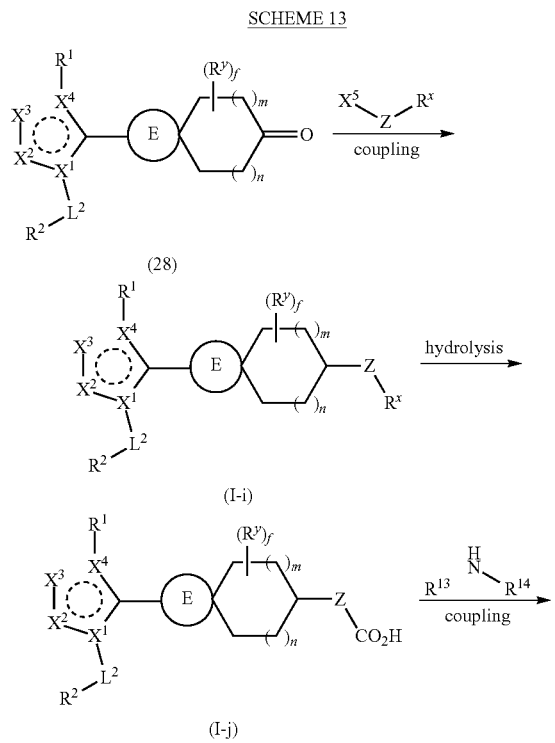

Scheme 13 describes a method of preparing compounds I-i, I-j, I-k a subset of Formula I. Products I-i can be obtained through coupling of intermediate 28 with $X^5$—Z—$R^x$ ($X^5$ represents a halide or triflate) under conditions that include, formation of the aryl Grignard, aryl lithium, aryl zinc or other aryl metal species of $X^5$—Z—$R^x$ with subsequent addition to 28. If I-i contains an ester or nitrile it can be hydrolyzed to the corresponding carboxylic acid I-j under conditions such as but not limited to treatment with NaOH or LiOH in solvents consisting of MeOH, THF, and water at a temperature suitable to enable the hydrolysis. Acid-mediated hydrolysis of particular esters, such as a tert-butyl ester, may be required in some cases to obtain I-j. Examples I-k can be obtained by the coupling of I-j with $R^{13}$—NH—$R^{15}$ utilizing coupling reagents such as but not limited to, T3P, EDC, DCC or CDI in the presence of a suitable base, for example triethylamine, Hunig's base, or pyridine with or without additives such as HOBT or DMAP in an appropriate solvent such as dichloromethane, ethyl acetate, DMF or THF. In each case the specific conditions utilized to obtain I-i, I-j, and I-k including temperature and concentration, may require optimization.

SCHEME 14

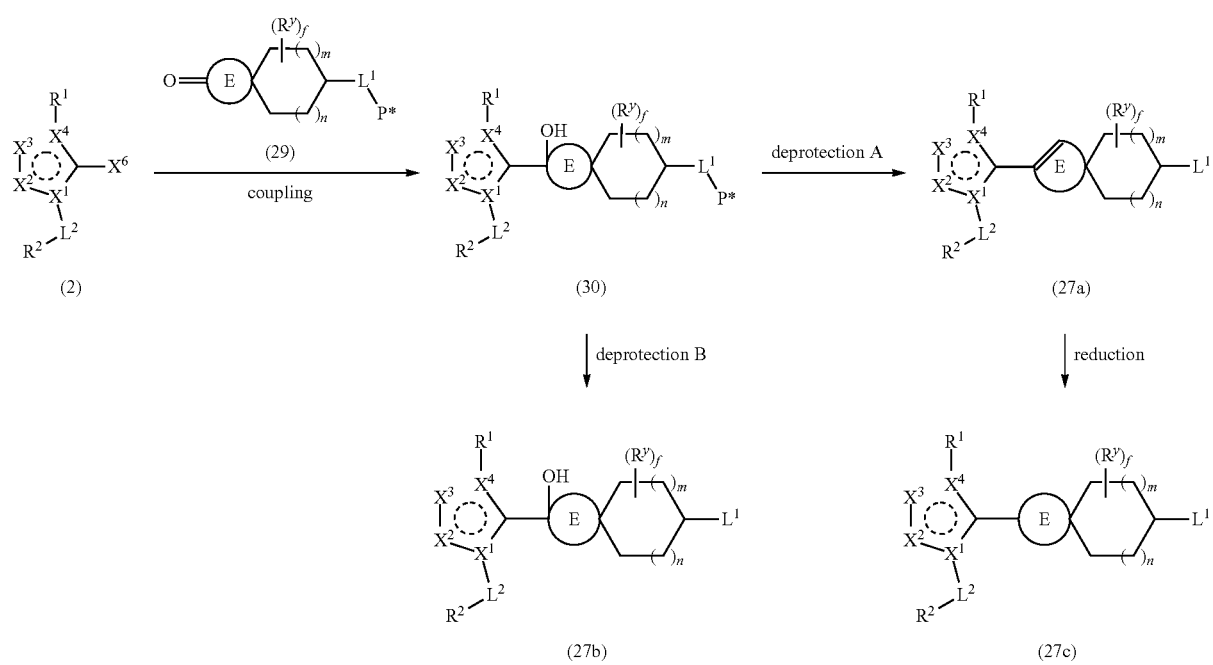

Scheme 14 describes a method for the preparation of intermediates 27a, 27b, and 27c, a subset of intermediate 27. The coupling of heteroaryl halide intermediate 2 and ketone 29 (commercially available or readily prepared by methods known to one skilled in the art) can be accomplished through a variety of conditions such as formation of the aryl Grignard, aryl lithium, aryl zinc or other aryl metal species of 2 with subsequent addition to the ketone 29 to give tertiary alcohol products 30. If appropriately acidic conditions (i.e. HCl, TFA) are employed during removal of the amino protecting group, for example where P*=Boc, alkenes 27a can be obtained as the primary isolate (deprotection A). In other cases where P*=Boc, the hydroxyl can be retained to yield intermediates 27b if dilute or weakly acidic conditions, such as TFA in DCM, are employed. Additionally, if P*=Cbz, palladium on carbon mediated hydrogenation can utilized to remove the protecting group without elimination of the hydroxyl to give 27b. Alkene intermediates 27a can be reduced under conditions such as, but not limited to, excess triethylsilane heated in TFA as solvent to give intermediates 27c. If alternative protecting groups are required for functional group compatibility, then they can be removed by methods known to one skilled in the art. Additional methods for protecting group removal may be found in Greene, T. and Wuts, P. G. M., *Protecting Groups in Organic Synthesis*, John Wiley & Sons, Inc., New York, N.Y., 2006 and references therein.

EXAMPLES

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

As appropriate, reactions were conducted under an atmosphere of dry nitrogen (or argon). For anhydrous reactions, DRISOLV® solvents from EM were employed. For other reactions, reagent grade or HPLC grade solvents were utilized. Unless otherwise stated, all commercially obtained reagents were used as received.
HPLC/MS and Preparatory/Analytical HPLC Methods Employed in Characterization or Purification of Examples NMR (nuclear magnetic resonance) spectra were typically obtained on Bruker or JEOL 400 MHz and 500 MHz instruments in the indicated solvents. All chemical shifts are reported in ppm from tetramethylsilane with the solvent resonance as the internal standard. $^1$HNMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

The term HPLC refers to a Shimadzu high performance liquid chromatography instrument with one of following methods:

General Method A

Example 1

2-(2-(5-Cyclopropyl-3-(2,6-dichlorophenyl)isoxazol-4-yl)-7-azaspiro[3.5]non-1-en-7-yl)-4-fluorobenzo[d]thiazole-6-carboxylic acid

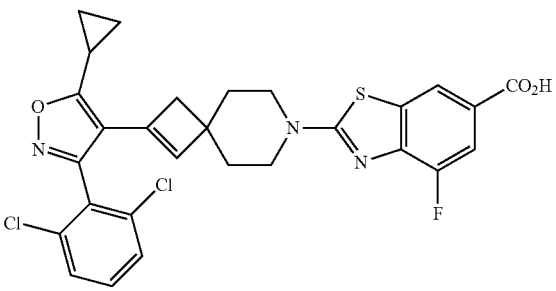

(1)

Step 1. 2,6-Dichlorobenzaldehyde oxime

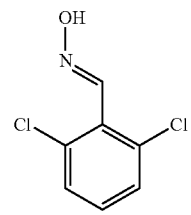 [SMILES: O/N=C/c1c(Cl)cccc1Cl]

Hydroxylamine hydrochloride (6.6 g, 95 mmol) was added to a room temperature solution of 2,6-dichlorobenzaldehyde (11.1 g, 63.4 mmol) in pyridine (31.7 mL) giving a mild exotherm. After 10 minutes the excess pyridine was removed in vacuo and the residue was partitioned between Et$_2$O and water. The organic layer was sequentially washed with saturated aqueous NH$_4$Cl, brine and the combined aqueous layers were back extracted with several small portions of Et$_2$O. The combined organic extracts were dried over Na$_2$SO$_4$, filtered and concentrated in vacuo to give a 2,6-dichlorobenzaldehyde oxime (12.4 g, 65.3 mmol, 100% yield) as a white solid. The product was carried on to the next step without further purification. $^1$H NMR (400 MHz, CDCl$_3$) δ 8.39 (s, 1H), 7.92 (s, 1H), 7.40-7.36 (m, 2H), 7.27-7.22 (m, 1H).

Step 2. 2,6-Dichloro-N-hydroxybenzimidoyl chloride

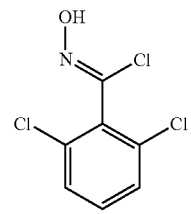 [SMILES: O/N=C(\Cl)c1c(Cl)cccc1Cl]

2,6-Dichlorobenzaldehyde oxime (12.0 g, 63.1 mmol) was dissolved in DMF (45.9 mL) and heated to 40° C. NCS (10.1 g, 76.0 mmol) dissolved in DMF (38.3 mL) was then added to the warm solution over the space of approximately 3 minutes. After stirring overnight at 40° C. the reaction mixture was cooled to room temperature, poured into ice, and extracted with Et$_2$O. The organic layer was collected and washed with brine. The combined aqueous layers were back extracted with Et$_2$O. The combined organic layers were dried over Na$_2$SO$_4$, filtered and concentrated to dryness in vacuo. The residue was purified by flash chromatography on SiO$_2$ (0-50% EtOAc/hexanes, Isco 120 g column) to give 2,6-dichloro-N-hydroxybenzimidoyl chloride (13.3 g, 59.3 mmol, 94% yield) as a waxy white solid. $^1$H NMR (500 MHz, CDCl$_3$) δ 8.02 (s, 1H), 7.43-7.37 (m, 2H), 7.37-7.30 (m, 1H).

Step 3.
5-Cyclopropyl-3-(2,6-dichlorophenyl)isoxazole

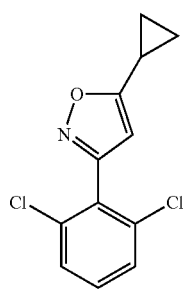 [SMILES: Clc1cccc(Cl)c1-c1cc(C2CC2)on1]

Cyclopropylacetylene (2.8 mL, 33.4 mmol) followed by Et$_3$N (3.7 mL, 26.7 mmol) were added to a room temperature solution of 2,6-dichloro-N-hydroxybenzimidoyl chloride (5.0 g, 22.3 mmol) in DCM (111 mL). The reaction mixture was stirred at room temperature overnight and was concentrated onto SiO$_2$ for purification. The resulting mixture was purified by flash chromatography on SiO$_2$ (0-45% EtOAc/hexanes, Isco 120 g column) to give 5-cyclopropyl-3-(2,6-dichlorophenyl)isoxazole (4.8 g, 18.9 mmol, 85% yield) as a white solid. $^1$H NMR (400 MHz, CDCl$_3$) δ 7.43-7.39 (m, 2H), 7.34-7.28 (m, 1H), 6.01 (s, 1H), 2.13 (tt, J=8.2, 5.3 Hz, 1H), 1.16-1.07 (m, 4H).

Step 4. 4-Bromo-5-cyclopropyl-3-(2,6-dichlorophenyl)isoxazole

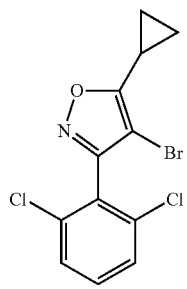 [SMILES: Clc1cccc(Cl)c1-c1noc(C2CC2)c1Br]

N-Bromosuccinimide (0.81 g, 4.6 mmol) was added to a room temperature solution of 5-cyclopropyl-3-(2,6-dichlorophenyl)isoxazole (0.93 g, 3.7 mmol) in DMF (14.6 mL). The reaction mixture was heated to 50° C. After heating overnight, additional N-bromosuccinimide (0.81 g, 4.6 mmol) was added and heating was continued. After heating for an additional 24 hours the reaction was cooled to room temperature and poured into approximately 100 mL of ice water. The resulting solid was collected by suction filtration and dried under high vacuum to give 4-bromo-5-cyclopropyl-3-(2,6-dichlorophenyl) isoxazole (1.14 g, 3.42 mmol, 94% yield) as a white powder. $^1$H NMR (400 MHz, CDCl$_3$) δ 7.49-7.36 (m, 3H), 2.19 (tt, J=8.4, 5.1 Hz, 1H), 1.36-1.29 (m, 2H), 1.24-1.16 (m, 2H).

Step 5. tert-Butyl 2-(5-cyclopropyl-3-(2,6-dichlorophenyl)isoxazol-4-yl)-2-hydroxy-7-azaspiro[3.5]nonane-7-carboxylate

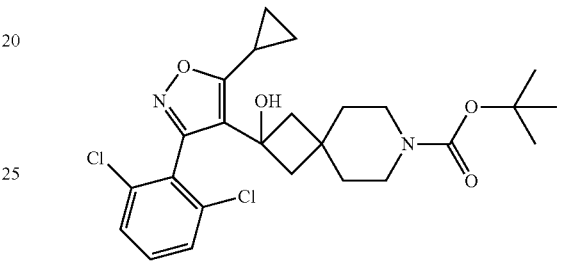

n-Butyllithium (8.1 mL, 20.3 mmol) was added slowly to a −78° C. solution of 4-bromo-5-cyclopropyl-3-(2,6-dichlorophenyl)isoxazole (5.4 g, 16.2 mmol) in THF (64.9 mL) giving a light brown solution. After 10 minutes, tert-butyl 2-oxo-7-azaspiro[3.5]nonane-7-carboxylate (3.9 g, 16.2 mmol) was added as a solution in 3 mL of THF. The temperature was maintained at −78° C. for 3 hours. The cold reaction mixture was quenched by the slow addition of 5 mL of methanol and then concentrated onto SiO$_2$ for purification by flash chromatography on SiO$_2$ (0-80% EtOAc/hexanes, Isco 120 g column) to give tert-butyl 2-(5-cyclopropyl-3-(2,6-dichlorophenyl)isoxazol-4-yl)-2-hydroxy-7-azaspiro [3.5]nonane-7-carboxylate (5.4 g, 10.9 mmol, 67% yield) as a white powder. $^1$H NMR (500 MHz, CDCl$_3$) δ 7.47-7.35 (m, 3H), 3.32-3.25 (m, 2H), 3.23-3.16 (m, 2H), 2.30 (s, 1H), 2.07-2.00 (m, 2H), 1.70 (br d, J=1.4 Hz, 2H), 1.46 (br t, J=3.0 Hz, 2H), 1.43 (s, 8H), 1.41-1.35 (m, 2H), 1.32-1.24 (m, 3H), 1.18-1.12 (m, 2H).

Step 6. 5-Cyclopropyl-3-(2,6-dichlorophenyl)-4-(7-azaspiro[3.5]non-1-en-2-yl)isoxazole

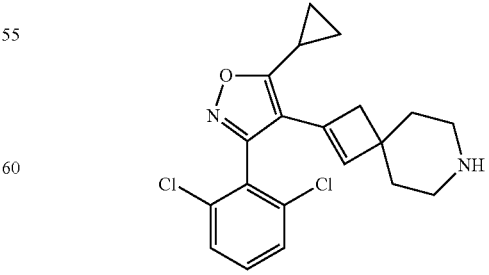

Trifluoroacetic acid (8.6 mL, 111.0 mmol) was added to a flask containing tert-butyl 2-(5-cyclopropyl-3-(2,6-dichlorophenyl)isoxazol-4-yl)-2-hydroxy-7-azaspiro[3.5]nonane-7-carboxylate (5.5 g, 11.2 mmol). The mixture was stirred at room temperature for one hour and the excess TFA was removed in vacuo. The residue was diluted with EtOAc and washed with saturated aqueous $K_2CO_3$ and then brine. The combined aqueous layers were back extracted with EtOAc and the combined organic extracts were dried over $Na_2SO_4$, filtered and concentrated in vacuo to dryness giving 5-cyclopropyl-3-(2,6-dichlorophenyl)-4-(7-azaspiro[3.5]non-1-en-2-yl)isoxazole (4.2 g, 11.2 mmol, 100% yield) as a white solid. $^1$H NMR (400 MHz, DMSO-$d_6$) δ 8.43-8.24 (m, 1H), 7.71-7.57 (m, 3H), 5.89 (s, 1H), 3.33 (br s, 2H), 3.06 (br s, 2H), 3.00-2.88 (m, 2H), 2.35 (s, 1H), 2.34-2.25 (m, 1H), 1.72-1.63 (m, 3H), 1.27-1.11 (m, 4H).

Example 1. 2-(2-(5-Cyclopropyl-3-(2,6-dichlorophenyl)isoxazol-4-yl)-7-azaspiro[3.5]non-1-en-7-yl)-4-fluorobenzo[d]thiazole-6-carboxylic acid Cesium carbonate (0.1 g, 0.33 mmol) and ethyl 2-bromo-4-fluorobenzo[d]thiazole-6-carboxylate (60.8 mg, 0.20 mmol) were added to a room temperature solution of 5-cyclopropyl-3-(2,6-dichlorophenyl)-4-(7-azaspiro[3.5]non-1-en-2-yl)isoxazole (50 mg, 0.13 mmol) in DMA (0.38 mL), and the reaction mixture was heated to 90° C. After heating for 2 hours the reaction mixture was diluted with THF (1.0 mL), water (0.2 mL) and MeOH (0.1 mL). Lithium hydroxide monohydrate (0.02 g, 0.40 mmol) was added to the mixture and the reaction vessel was sealed and heated to 90° C. overnight. The reaction was then quenched by the addition of 0.5 mL of 1.0 N HCl. The resultant mixture was loaded onto a pad of Celite in an Isco dry load cartridge for purification by C-18 reverse phase flash chromatography (10-100% B in A, A=10:90:0.1 MeCN:$H_2O$:TFA, B=90:10:0.1 MeCN:$H_2O$:TFA, 18 min linear gradient, Isco 50 g C-18 gold column) desired fractions were combined and concentrated to give 2-(2-(5-cyclopropyl-3-(2,6-dichlorophenyl)isoxazol-4-yl)-7-azaspiro[3.5]non-1-en-7-yl)-4-fluorobenzo[d]thiazole-6-carboxylic acid (69 mg, 0.1 mmol, 88% yield) as a tan solid. MS (ESI) m/z: 570.6 [M+H]$^+$; $^1$H NMR (400 MHz, CDCl$_3$) δ 8.12 (d, J=1.5 Hz, 1H), 7.74 (dd, J=11.1, 1.4 Hz, 1H), 7.47-7.40 (m, 2H), 7.39-7.33 (m, 1H), 5.78 (s, 1H), 3.78 (dt, J=13.1, 5.1 Hz, 2H), 3.63-3.51 (m, 2H), 2.43 (s, 2H), 2.18 (tt, J=8.4, 5.0 Hz, 1H), 1.80-1.74 (m, 4H), 1.38-1.28 (m, 2H), 1.21-1.11 (m, 2H); FXR EC$_{50}$=7 nM; Mouse in vivo (3 mg/kg, @ 6 h): Cyp7a1=−99%, Fgf15 =+18×; (30 mg/kg, @ 6 h): Cyp7a1=−99%, Fgf15=+31×.

Example 2

2-(2-(5-Cyclopropyl-3-(2,6-dichlorophenyl)isoxazol-4-yl)-7-azaspiro[3.5]non-1-en-7-yl)-4-fluorobenzo[d]thiazole-6-carboxylic acid

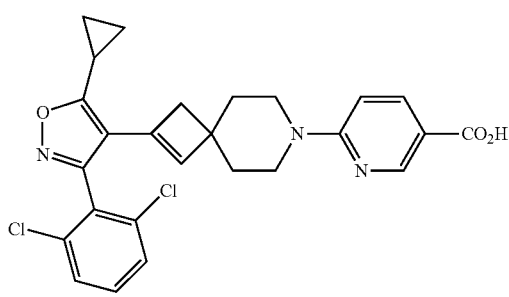

(2)

The title compound was prepared as described in General Method A for the preparation of Example 1 with replacement of ethyl 2-bromo-4-fluorobenzo[d]thiazole-6-carboxylate with methyl 6-fluoronicotinate. MS (ESI) m/z: 496.1 [M+H]$^+$; $^1$H NMR (500 MHz, DMSO-$d_6$) δ 8.57 (d, J=1.8 Hz, 1H), 7.87 (dd, J=9.0, 2.3 Hz, 1H), 7.68-7.61 (m, 2H), 7.61-7.54 (m, 1H), 6.81 (d, J=9.2 Hz, 1H), 5.85 (s, 1H), 3.86-3.75 (m, 2H), 3.42-3.30 (m, 1H), 2.38-2.25 (m, 3H), 1.58-1.46 (m, 4H), 1.27-1.16 (m, 2H), 1.15-1.07 (m, 2H); FXR EC$_{50}$=31 nM.

Example 3

2-(3-(5-Cyclopropyl-3-(2,6-dichlorophenyl)isoxazol-4-yl)-1-oxa-8-azaspiro[4.5]dec-3-en-8-yl)-4-fluorobenzo[d]thiazole-6-carboxylic acid

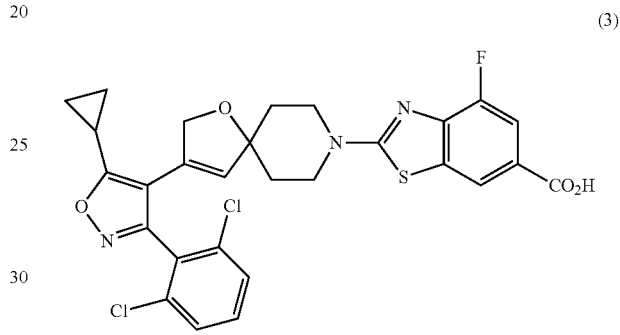

(3)

The title compound was prepared as described in General Method A for the preparation of Example 1 with replacement of tert-butyl 2-oxo-7-azaspiro[3.5]nonane-7-carboxylate with tert-butyl 3-oxo-1-oxa-8-azaspiro[4.5]decane-8-carboxylate. MS (ESI) m/z: 586.3 [M+H]$^+$; $^1$H NMR (500 MHz, DMSO-$d_6$) δ 8.14 (s, 1H), 7.70-7.51 (m, 4H), 5.67 (s, 1H), 4.57 (s, 2H), 3.74 (br s, 1H), 3.50 (br t, J=10.8 Hz, 2H), 2.34-2.23 (m, 1H), 1.78-1.66 (m, 2H), 1.59 (br d, J=13.4 Hz, 2H), 1.25-1.16 (m, 2H), 1.13-1.06 (m, 2H); FXR EC$_{50}$=240 nM.

Example 4

6-(2-(5-Cyclopropyl-3-(2,6-dichlorophenyl)isoxazol-4-yl)-7-azaspiro[3.5]non-1-en-7-yl) picolinic acid

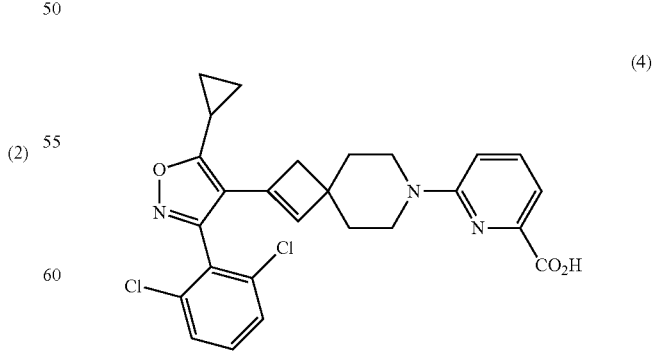

(4)

The title compound was prepared as described in General Method A for the preparation of Example 1 with replacement of ethyl 2-bromo-4-fluorobenzo[d]thiazole-6-carboxylate with methyl 6-fluoropicolinate. MS (ESI) m/z: 495.8 [M+H]$^+$; $^1$H NMR (500 MHz, DMSO-d$_6$) δ 7.70-7.57 (m, 4H), 7.24 (d, J=7.0 Hz, 1H), 7.02 (d, J=8.9 Hz, 1H), 5.85 (s, 1H), 3.85-3.69 (m, 2H), 3.41-3.23 (m, 1H), 2.38-2.27 (m, 3H), 1.54 (br s, 4H), 1.28-1.17 (m, 3H), 1.17-1.09 (m, 3H); FXR EC$_{50}$=712 nM.

Example 5

6-(2-(5-Cyclopropyl-3-(2,6-dichlorophenyl)isoxazol-4-yl)-7-azaspiro[3.5]non-1-en-7-yl)pyridazine-3-carboxylic acid (5)

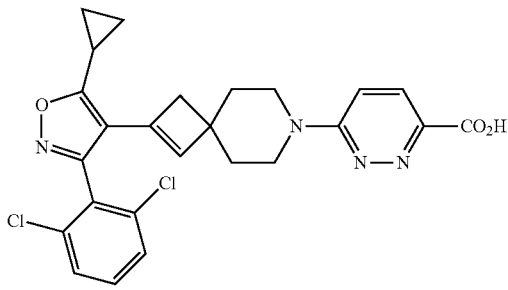

The title compound was prepared as described in General Method A for the preparation of Example 1 with replacement of ethyl 2-bromo-4-fluorobenzo[d]thiazole-6-carboxylate with methyl 6-chloropyridazine-3-carboxylate. MS (ESI) m/z: 497.2 [M+H]$^+$; $^1$H NMR (500 MHz, DMSO-d$_6$) δ 7.76 (br d, J=9.5 Hz, 1H), 7.70-7.61 (m, 2H), 7.61-7.53 (m, 1H), 7.21 (br d, J=9.8 Hz, 1H), 5.86 (s, 1H), 3.88 (br d, J=13.1 Hz, 1H), 3.44 (br d, J=4.6 Hz, 1H), 2.34 (s, 3H), 1.91 (s, 1H), 1.57 (br s, 4H), 1.29-1.16 (m, 2H), 1.13 (br d, J=2.1 Hz, 2H) FXR EC$_{50}$=313 nM.

Example 6

2-(2-(5-Cyclopropyl-3-(2,6-dichlorophenyl)isoxazol-4-yl)-7-azaspiro[3.5]non-1-en-7-yl)-7-methyl-7H-pyrrolo[2,3-d]pyrimidine-5-carboxylic acid (6)

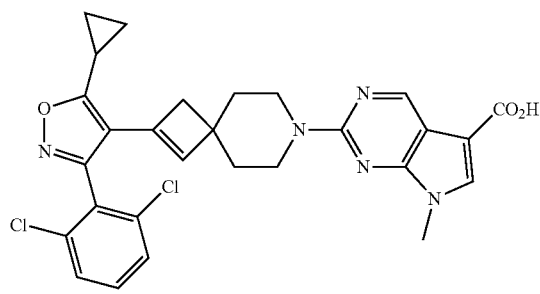

The title compound was prepared as described in General Method A for the preparation of Example 1 with replacement of ethyl 2-bromo-4-fluorobenzo[d]thiazole-6-carboxylate with methyl 2-chloro-7-methyl-7H-pyrrolo[2,3-d]pyrimidine-5-carboxylate. MS (ESI) m/z: 550.1 [M+H]$^+$; $^1$H NMR (500 MHz, DMSO-d$_6$) δ 8.78 (s, 1H), 7.75 (s, 1H), 7.67-7.60 (m, 2H), 7.61-7.53 (m, 1H), 5.85 (s, 1H), 3.99 (br d, J=13.4 Hz, 1H), 3.81-3.67 (m, 2H), 3.53-3.39 (m, 1H), 2.40-2.22 (m, 3H), 1.89 (s, 1H), 1.52 (br s, 4H), 1.29-1.16 (m, 2H), 1.11 (br d, J=2.4 Hz, 2H) additional peaks under DMSO and H$_2$O peaks; FXR EC$_{50}$=47 nM.

General Method B

Example 7

6-(2-(5-Cyclopropyl-3-(2,6-dichlorophenyl)isoxazol-4-yl)-7-azaspiro[3.5]non-1-en-7-yl)-1-methyl-1H-pyrrolo[2,3-b]pyridine-3-carboxylic acid (7)

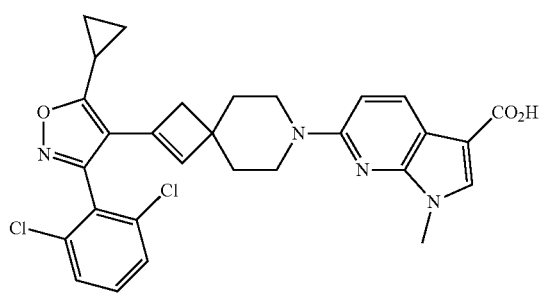

A slurry of 5-cyclopropyl-3-(2,6-dichlorophenyl)-4-(7-azaspiro[3.5]non-1-en-2-yl)isoxazole (0.13 g, 0.34 mmol, synthesis described in General Method A), methyl 6-chloro-1-methyl-1H-pyrrolo[2,3-b]pyridine-3-carboxylate (77 mg, 0.34 mmol) and Cs$_2$CO$_3$ (0.22 g, 0.69 mmol) in dioxane (3.4 mL) was degassed by bubbling nitrogen through the mixture for 5 minutes. Chloro(2-dicyclohexylphosphino-2',6'-diisopropoxy-1,1'-biphenyl)[2-(2'-amino-1,1'-biphenyl)]palladium(II) (RuPhos-Pd-G2) (13.3 mg, 0.02 mmol) was then added and the reaction mixture was sealed and heated to 90° C. After heating overnight additional RuPhos-Pd-G2 (13.3 mg, 0.02 mmol) was added, nitrogen was bubbled through the mixture and it was resealed and heated to 100° C. After 1 hour the reaction mixture was concentrated to dryness and the residue was dissolved in a mixture of THF (1.0 mL), water (0.4 mL), and MeOH (0.1 mL). Lithium hydroxide monohydrate (27.9 mg, 0.67 mmol) was added to the mixture and the reaction vessel was sealed and heated to 90° C. After heating for 2 hours the reaction was quenched with 1N HCl and then concentrated in vacuo to minimal volume. The residue was taken up in MeOH, filtered, and the crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 45-100% B over 24 minutes, then a 10-minute hold at 100% B; Flow: 20 mL/min. Fractions containing the desired product were combined and dried via centrifugal evaporation to give 6-(2-(5-Cyclopropyl-3-(2,6-dichlorophenyl)isoxazol-4-yl)-7-azaspiro[3.5]non-1-en-7-yl)-1-methyl-1H-pyrrolo[2,3-b]pyridine-3-carboxylic acid. MS (ESI) m/z: 549.2 [M+H]$^+$; $^1$H NMR (400 MHz, DMSO-d$_6$) δ 8.00 (d, J=8.8 Hz, 1H), 7.80 (s, 1H), 7.67 (d, J=1.8 Hz, 1H), 7.65 (d, J=0.7 Hz, 1H), 7.62-7.56 (m, 1H), 6.79 (d, J=8.8 Hz, 1H), 5.84 (s, 1H), 3.81-3.71 (m, 3H), 3.31 (td, J=8.5, 3.5 Hz, 2H), 2.38-2.27 (m, 5H), 1.66-1.51 (m, 5H), 1.25-1.17 (m, 2H), 1.16-1.07 (m, 3H); FXR $EC_{50}$=24 nM.

Example 8

6-(2-(5-Cyclopropyl-3-(2,6-dichlorophenyl)isoxazol-4-yl)-7-azaspiro[3.5]non-1-en-7-yl)-1-methyl-1H-indole-3-carboxylic acid (8)

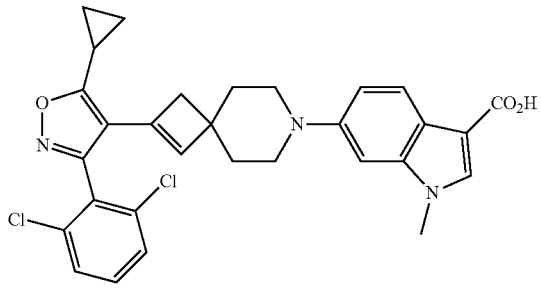

The title compound was prepared as described in General Method B for the preparation of Example 7 with replacement of methyl 6-chloro-1-methyl-1H-pyrrolo[2,3-b]pyridine-3-carboxylate with methyl 6-bromo-1-methyl-1H-indole-3-carboxylate. MS (ESI) m/z: 548.2 [M+H]$^+$; $^1$H NMR (500 MHz, DMSO-$d_6$) δ 7.86-7.75 (m, 2H), 7.71-7.63 (m, 2H), 7.63-7.55 (m, 1H), 6.97-6.86 (m, 2H), 5.87 (s, 1H), 3.75 (s, 3H), 3.30-3.20 (m, 1H), 2.96 (br t, J=9.2 Hz, 2H), 2.40-2.28 (m, 3H), 1.77-1.68 (m, 2H), 1.68-1.57 (m, 2H), 1.28-1.16 (m, 3H), 1.14 (br d, J=2.7 Hz, 2H); FXR $EC_{50}$=45 nM.

Example 9

3-(2-(5-Cyclopropyl-3-(2,6-dichlorophenyl)isoxazol-4-yl)-7-azaspiro[3.5]non-1-en-7-yl)benzoic acid (9)

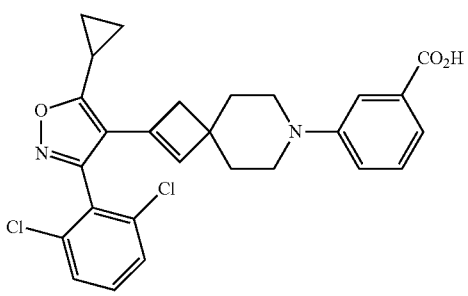

The title compound was prepared as described in General Method B for the preparation of Example 7 with replacement of methyl 6-chloro-1-methyl-1H-pyrrolo[2,3-b]pyridine-3-carboxylate with ethyl 3-bromobenzoate. MS (ESI) m/z: 495.1 [M+H]$^+$; $^1$H NMR (500 MHz, DMSO-$d_6$) δ 7.66 (d, J=7.6 Hz, 2H), 7.63-7.54 (m, 1H), 7.45 (br s, 1H), 7.38-7.26 (m, 2H), 7.19 (br d, J=7.0 Hz, 1H), 5.85 (s, 1H), 3.30 (br d, J=12.5 Hz, 1H), 3.06-2.96 (m, 1H), 2.37-2.25 (m, 3H), 1.72-1.51 (m, 4H), 1.26-1.16 (m, 2H), 1.14 (br d, J=2.7 Hz, 2H); FXR $EC_{50}$=4200 nM.

Example 10

4-(2-(5-Cyclopropyl-3-(2,6-dichlorophenyl)isoxazol-4-yl)-7-azaspiro[3.5]non-1-en-7-yl)benzoic acid (10)

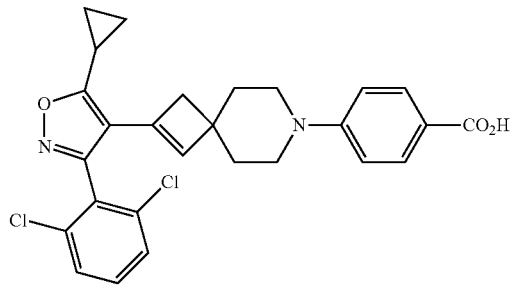

The title compound was prepared as described in General Method B for the preparation of Example 7 with replacement of methyl 6-chloro-1-methyl-1H-pyrrolo[2,3-b]pyridine-3-carboxylate with ethyl 4-bromobenzoate. MS (ESI) m/z: 495.1 [M+H]$^+$; $^1$H NMR (500 MHz, DMSO-$d_6$) δ 7.72 (br d, J=8.9 Hz, 2H), 7.68-7.52 (m, 3H), 6.91 (br d, J=8.9 Hz, 2H), 5.83 (s, 1H), 3.42 (br d, J=12.8 Hz, 1H), 3.12 (br t, J=9.2 Hz, 2H), 2.39-2.24 (m, 3H), 1.63-1.49 (m, 4H), 1.26-1.15 (m, 4H), 1.12 (br s, 2H); FXR $EC_{50}$=135 nM.

2-(3'-(5-Cyclopropyl-3-(2,6-dichlorophenyl)isoxazol-4-yl)-8-azaspiro[bicyclo[3.2.1]octane-3,1'-cyclobutan]-2'-en-8-yl)-4-fluorobenzo[d]thiazole-6-carboxylic acid (11)

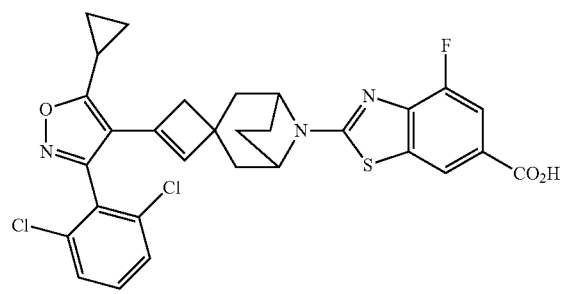

Step 1. tert-Butyl 3'-oxo-8-azaspiro[bicyclo[3.2.1]octane-3,1'-cyclobutane]-8-carboxylate

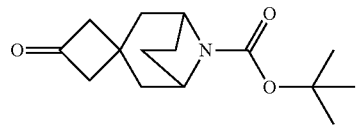 [SMILES: CC(C)(C)OC(=O)N1C2CCC1CC1(CC(=O)C1)C2]

Zinc-copper couple (28.3 g, 219 mmol) was added to a solution of tert-butyl 3-methylene-8-azabicyclo[3.2.1]octane-8-carboxylate (4.9 g, 21.9 mmol) in diethyl ether (43.0 mL). Trichloroacetyl chloride (13.6 mL, 121 mmol) in DME (21.5 mL) was added and the reaction mixture was stirred at room temperature for 36 h. The reaction was carefully quenched with 1M aqueous $K_2HPO_4$ (vigorous bubbling) and then filtered through Celite ($Et_2O$ wash). The filtrate was concentrated in vacuo and diluted with MeOH (65.6 mL). Ammonium chloride (4.49 g, 84 mmol) was added to the rapidly stirring mixture followed by zinc dust (8.0 g, 122 mmol) in two equal portions. After 40 minutes of stirring, the reaction mixture was filtered through Celite (MeOH wash) and concentrated to dryness. The residue was taken up in EtOAc and washed with water and brine. The aqueous layers were back extracted with EtOAc and the combined organics were dried over $Na_2SO_4$, filtered and concentrated to dryness onto $SiO_2$. The resulting mixture was purified by flash chromatography on $SiO_2$ (0-50% EtOAc/hex, Isco 80 g column, ELS detector used) to give tert-butyl 3'-oxo-8-azaspiro[bicyclo[3.2.1]octane-3,1'-cyclobutane]-8-carboxylate (1.1 g, 4.2 mmol, 20% yield) as a white solid. $^1H$ NMR (400 MHz, $CDCl_3$) δ 4.50-4.13 (m, 2H), 3.12 (d, J=1.8 Hz, 2H), 2.85 (br s, 2H), 2.23-1.87 (m, 4H), 1.86-1.66 (m, 4H), 1.48 (s, 9H).

Example 11. 2-(3'-(5-Cyclopropyl-3-(2,6-dichlorophenyl)isoxazol-4-yl)-8-azaspiro[bicyclo[3.2.1]octane-3,1'-cyclobutan]-2'-en-8-yl)-4-fluorobenzo[d]thiazole-6-carboxylic acid The title compound was prepared as described for the preparation of Example 1 with replacement of tert-butyl 2-oxo-7-azaspiro[3.5]nonane-7-carboxylate with tert-butyl 3'-oxo-8-azaspiro[bicyclo[3.2.1]octane-3,1'-cyclobutane]-8-carboxylate. MS (ESI) m/z: 596.5 [M+H]$^+$; ~6:4 Mixture of olefin isomers: $^1H$ NMR (400 MHz, DMSO-$d_6$) δ 8.21 (dd, J=3.6, 1.4 Hz, 1H), 7.75-7.46 (m, 5H), 6.28 (s, 1H), 5.25 (s, 1H), 4.49-4.29 (m, 2H), 2.84 (s, 1H), 2.17-1.89 (m, 7H), 1.85-1.59 (m, 3H), 1.31-1.07 (m, 5H); FXR $EC_{50}$=189 nM.

Example 12

6-(3'-(5-Cyclopropyl-3-(2,6-dichlorophenyl)isoxazol-4-yl)-8-azaspiro[bicyclo[3.2.1]octane-3,1'-cyclobutan]-2'-en-8-yl)nicotinic acid (12)

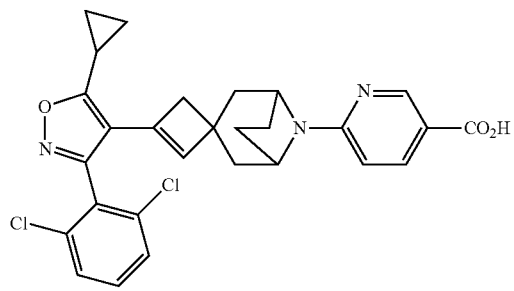

The title compound was prepared as described for the preparation of Example 11 with replacement of ethyl 2-bromo-4-fluorobenzo[d]thiazole-6-carboxylate with methyl 6-fluoronicotinate. MS (ESI) m/z: 522.6 [M+H]$^+$; $^1H$ NMR is for ~6:4 mixture of olefin isomers: $^1H$ NMR (400 MHz, DMSO-$d_6$) δ 8.66-8.51 (m, 1H), 7.99-7.78 (m, 1H), 7.71-7.48 (m, 3H), 6.71-6.64 (m, 1H), 6.24 (s, 1H), 5.18 (s, 1H), 4.57 (br d, J=3.5 Hz, 2H), 2.80 (s, 1H), 2.37-2.23 (m, 2H), 2.01-1.82 (m, 5H), 1.83-1.65 (m, 3H), 1.63-1.45 (m, 3H), 1.30-1.06 (m, 7H); FXR $EC_{50}$=182 nM.

Example 13

2-(2-(5-Cyclopropyl-3-(2,6-dichlorophenyl)isoxazol-4-yl)-7-azaspiro[3.5]nonan-7-yl)-4-fluorobenzo[d]thiazole-6-carboxylic acid (13)

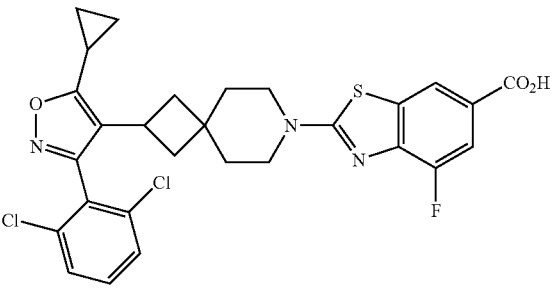

Triethylsilane (70.0 μL, 0.44 mmol) was added to a solution of 2-(2-(5-cyclopropyl-3-(2,6-dichlorophenyl)isoxazol-4-yl)-7-azaspiro[3.5]non-1-en-7-yl)-4-fluorobenzo[d]thiazole-6-carboxylic acid (Example 1) (10 mg, 0.02 mmol) in TFA (175 μL). The reaction vial was sealed and heated to 80° C. After 30 minutes the reaction mixture was concentrated to dryness and the residue was taken up in ~2 mL of 1:1 DMF and MeOH, filtered, and purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 20 minutes, then a 5-minute hold at 100% B; Flow: 20 mL/min. Fractions containing the desired product were combined and dried via centrifugal evaporation to give 2-(2-(5-Cyclopropyl-3-(2,6-dichlorophenyl) isoxazol-4-yl)-7-azaspiro[3.5] nonan-7-yl)-4-fluorobenzo[d]thiazole-6-carboxylic acid. MS (ESI) m/z: 572.0 [M+H]$^+$; $^1H$ NMR (500 MHz, DMSO-$d_6$) δ 8.16 (s, 1H), 7.71-7.52 (m, 4H), 3.45-3.34 (m, 1H), 2.28-2.17 (m, 1H), 2.12-1.99 (m, 2H), 1.78 (br t, J=10.7 Hz, 2H), 1.74-1.65 (m, 2H), 1.36-1.26 (m, 2H), 1.22 (s, 2H), 1.12 (br d, J=7.9 Hz, 3H), 1.08-0.99 (m, 3H); FXR $EC_{50}$=202 nM.

Example 14

4-(2-(3-(2-Chlorophenyl)-5-cyclopropylisoxazol-4-yl)-7-azaspiro[3.5]non-1-en-7-yl)benzoic acid (14)

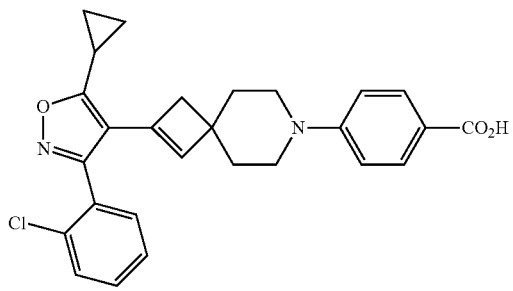

The title compound was obtained during the preparation of Example 10 from Pd-mediated dehalogenation during the Buchwald amination step. Alternatively the title compound could be prepared as described for Example 10 with the replacement of 2,6-dichlorobenzaldehyde with 2-chlorobenzaldehyde. MS (ESI) m/z: 461.1 [M+H]$^+$; $^1$H NMR (500 MHz, DMSO-$d_6$) δ 7.72 (br d, J=8.9 Hz, 2H), 7.66-7.60 (m, 1H), 7.59-7.52 (m, 1H), 7.47 (br d, J=4.0 Hz, 2H), 6.92 (br d, J=8.9 Hz, 2H), 5.86 (s, 1H), 3.49-3.38 (m, 1H), 3.21-3.06 (m, 2H), 2.92 (q, J=7.1 Hz, 1H), 2.35 (s, 2H), 2.32-2.22 (m, 1H), 1.67-1.49 (m, 4H), 1.23 (s, 3H), 1.19-1.12 (m, 4H), 1.10 (br d, J=2.4 Hz, 2H); FXR EC$_{50}$=885 nM.

Example 15

2-(3'-(5-Cyclopropyl-3-(2,6-dichlorophenyl)isoxazol-4-yl)-8-azaspiro[bicyclo[3.2.1]octane-3,1'-cyclobutan]-8-yl)-4-fluorobenzo[d]thiazole-6-carboxylic acid

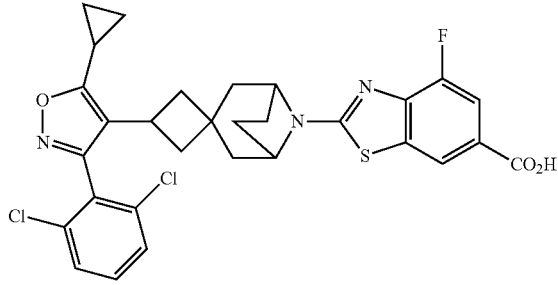

(15)

The title compound was prepared as described for the preparation of Example 13 with replacement of 2-(2-(5-cyclopropyl-3-(2,6-dichlorophenyl)isoxazol-4-yl)-7-azaspiro[3.5]non-1-en-7-yl)-4-fluorobenzo[d]thiazole-6-carboxylic acid (Example 1) with 2-(3'-(5-Cyclopropyl-3-(2,6-dichlorophenyl)isoxazol-4-yl)-8-azaspiro[bicyclo[3.2.1]octane-3,1'-cyclobutan]-2'-en-8-yl)-4-fluorobenzo[d]thiazole-6-carboxylic acid (Example 11). MS (ESI) m/z: 598.0 [M+H]$^+$; $^1$H NMR (500 MHz, DMSO-$d_6$) δ 8.17 (s, 1H), 7.68-7.52 (m, 4H), 4.48-4.12 (m, 1H), 3.89 (s, 1H), 3.58-3.34 (m, 1H), 2.23-2.13 (m, 2H), 2.11-2.03 (m, 1H), 2.03-1.86 (m, 3H), 1.83-1.72 (m, 1H), 1.72-1.54 (m, 4H), 1.33 (br d, J=13.7 Hz, 1H), 1.10 (br d, J=8.2 Hz, 2H), 1.01 (br d, J=2.4 Hz, 2H); FXR EC$_{50}$=301 nM.

Example 16

6-(3'-(5-Cyclopropyl-3-(2,6-dichlorophenyl)isoxazol-4-yl)-8-azaspiro[bicyclo[3.2.1]octane-3,1'-cyclobutan]-8-yl)nicotinic acid

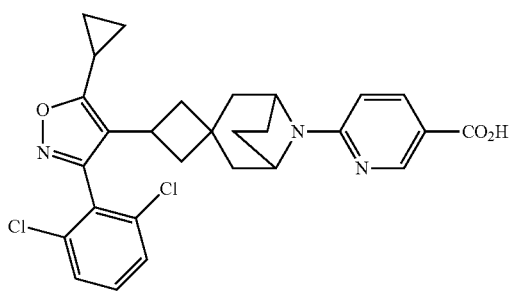

(16)

The title compound was prepared as described for the preparation of Example 15 with replacement of 2-(3'-(5-Cyclopropyl-3-(2,6-dichlorophenyl)isoxazol-4-yl)-8-azaspiro[bicyclo[3.2.1]octane-3,1'-cyclobutan]-2'-en-8-yl)-4-fluorobenzo[d]thiazole-6-carboxylic acid (Example 11) with 6-(3'-(5-Cyclopropyl-3-(2,6-dichlorophenyl)isoxazol-4-yl)-8-azaspiro[bicyclo[3.2.1]octane-3,1'-cyclobutan]-2'-en-8-yl)nicotinic acid (Example 12). MS (ESI) m/z: 523.9 [M+H]$^+$; $^1$H NMR (500 MHz, DMSO-$d_6$) δ 8.57 (d, J=1.5 Hz, 1H), 7.86 (dd, J=9.0, 2.0 Hz, 1H), 7.70-7.51 (m, 3H), 6.63 (br d, J=8.9 Hz, 1H), 4.66-4.48 (m, 1H), 4.40 (br s, 1H), 2.62-2.57 (m, 1H), 2.25-2.12 (m, 1H), 2.12-1.98 (m, 2H), 1.97-1.77 (m, 3H), 1.59 (br t, J=10.1 Hz, 4H), 1.45 (br d, J=11.6 Hz, 1H), 1.20 (br d, J=13.4 Hz, 1H), 1.10 (br d, J=8.2 Hz, 2H), 1.01 (br d, J=2.4 Hz, 2H); FXR EC$_{50}$=646 nM.

Example 17

2-(2-(5-Cyclopropyl-3-(2-(trifluoromethoxy)phenyl)isoxazol-4-yl)-7-azaspiro[3.5]non-1-en-7-yl)-4-fluorobenzo[d]thiazole-6-carboxylic acid

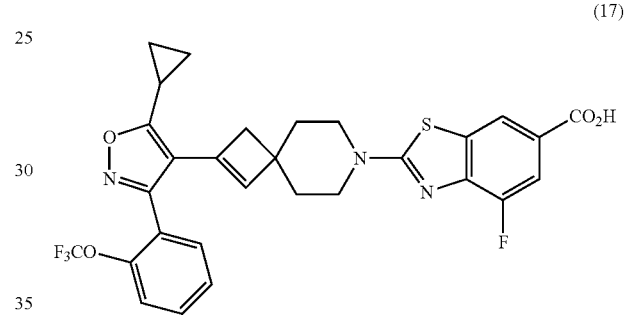

(17)

The title compound was prepared as described in General Method A for the preparation of Example 1 with replacement of 2,6-dichlorobenzaldehyde with 2-(trifluoromethoxy)benzaldehyde. MS (ESI) m/z: 585.9 [M+H]$^+$; $^1$H NMR (500 MHz, DMSO-$d_6$) δ 8.18 (br s, 1H), 7.73-7.63 (m, 1H), 7.63-7.46 (m, 4H), 5.92 (s, 1H), 3.70 (br d, J=2.2 Hz, 1H), 3.64 (br s, 2H), 3.55-3.43 (m, 1H), 2.47-2.37 (m, 2H), 2.37-2.26 (m, 1H), 1.63 (br s, 4H), 1.25-1.12 (m, 3H), 1.10 (br s, 2H); FXR EC$_{50}$=50 nM.

Example 18

6-(2-(5-Cyclopropyl-3-(2-(trifluoromethoxy)phenyl)isoxazol-4-yl)-7-azaspiro[3.5]non-1-en-7-yl)pyridazine-3-carboxylic acid

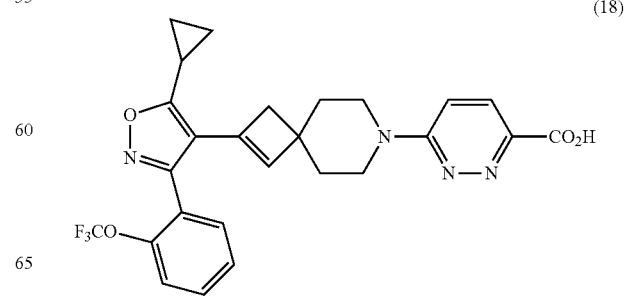

(18)

The title compound was prepared as described in General Method A for the preparation of Example 17 with replacement of ethyl 2-bromo-4-fluorobenzo[d]thiazole-6-carboxylate with methyl 6-chloropyridazine-3-carboxylate. MS (ESI) m/z: 513.2 [M+H]+; 1H NMR (500 MHz, DMSO-d6) δ 7.78 (br d, J=9.4 Hz, 1H), 7.71-7.60 (m, 1H), 7.59-7.44 (m, 3H), 7.30 (br s, 1H), 7.36-7.05 (m, 1H), 5.88 (s, 1H), 3.55-3.38 (m, 2H), 2.38 (s, 2H), 2.33-2.22 (m, 1H), 1.55 (br s, 4H), 1.25-1.10 (m, 4H), 1.06 (br s, 2H), 0.98 (d, J=6.2 Hz, 1H); FXR EC50=1500 nM.

Example 19

5-(2-(5-Cyclopropyl-3-(2,6-dichlorophenyl)isoxazol-4-yl)-7-azaspiro[3.5]non-1-en-7-yl) pyrazine-2-carboxylic acid

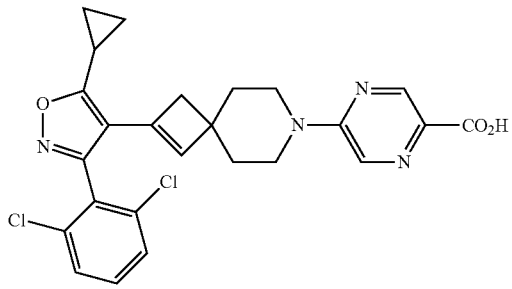

(19)

The title compound was prepared as described in General Method B for the preparation of Example 7 with replacement of methyl 6-chloro-1-methyl-1H-pyrrolo[2,3-b]pyridine-3-carboxylate with methyl 5-bromopyrazine-2-carboxylate. MS (ESI) m/z: 497.2 [M+H]+; 1H NMR (500 MHz, DMSO-d6) δ 8.59 (br s, 1H), 8.28 (br s, 1H), 7.70-7.52 (m, 3H), 5.85 (s, 1H), 4.18-3.95 (m, 4H), 3.53-3.35 (m, 2H), 2.33 (br s, 3H), 1.55 (br s, 4H), 1.21 (br d, J=5.0 Hz, 3H), 1.11 (br s, 2H), 1.00 (br d, J=6.1 Hz, 1H); FXR EC50=110 nM.

Example 20

6-(2-(5-Cyclopropyl-3-(2,6-dichlorophenyl)isoxazol-4-yl)-7-azaspiro[3.5]non-1-en-7-yl) quinoline-2-carboxylic acid

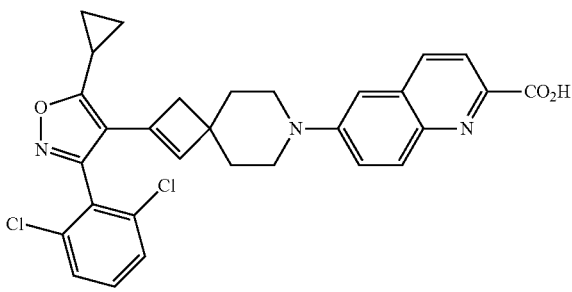

(20)

The title compound was prepared as described in General Method B for the preparation of Example 7 with replacement of methyl 6-chloro-1-methyl-1H-pyrrolo[2,3-b]pyridine-3-carboxylate with methyl 6-bromoquinoline-2-carboxylate. MS (ESI) m/z: 546.3 [M+H]+; 1H NMR (500 MHz, CDCl3) δ 8.19 (d, J=8.5 Hz, 1H), 7.95 (d, J=8.5 Hz, 1H), 7.91 (d, J=9.4 Hz, 1H), 7.72-7.65 (m, 3H), 7.63-7.55 (m, 1H), 7.22 (d, J=2.2 Hz, 1H), 5.86 (s, 1H), 3.59-3.46 (m, 2H), 3.20 (br t, J=9.4 Hz, 2H), 2.40-2.30 (m, 3H), 1.78-1.58 (m, 4H), 1.29-1.23 (m, 2H), 1.16-1.09 (m, 2H); FXR EC50=63 nM; Mouse in vivo (3 mg/kg, @6 h): Cyp7a1=−98%, Fgf15=+30×.

Example 21

6-(2-(5-Cyclopropyl-3-(2-(trifluoromethoxy)phenyl)isoxazol-4-yl)-7-azaspiro[3.5]non-1-en-7-yl) nicotinic acid

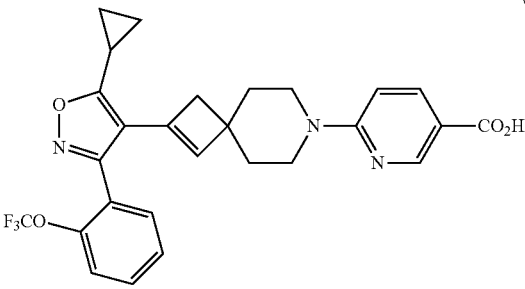

(21)

The title compound was prepared as described in General Method A for the preparation of Example 17 with replacement of ethyl 2-bromo-4-fluorobenzo[d]thiazole-6-carboxylate with methyl 6-fluoronicotinate. MS (ESI) m/z: 511.9 [M+H]+; 1H NMR (500 MHz, DMSO-d6) δ 8.54 (d, J=1.8 Hz, 1H), 7.94-7.82 (m, 1H), 7.72-7.60 (m, 1H), 7.55-7.41 (m, 3H), 6.80 (br d, J=9.2 Hz, 1H), 5.87 (s, 1H), 3.81 (br d, J=15.3 Hz, 2H), 3.46-3.27 (m, 2H), 2.36 (s, 2H), 2.31-2.20 (m, 1H), 1.60-1.42 (m, 4H), 1.23-1.11 (m, 4H), 1.10-1.00 (m, 2H); FXR EC50=770 nM.

Example 22

5-(2-(5-Cyclopropyl-3-(2,6-dichlorophenyl)isoxazol-4-yl)-7-azaspiro[3.5]non-1-en-7-yl) pyrimidine-2-carboxylic acid

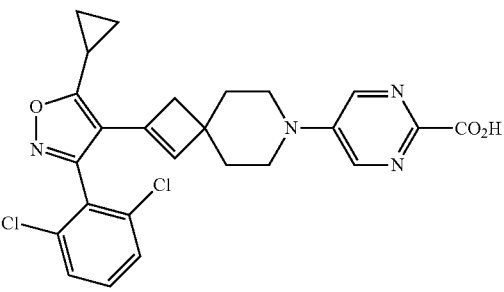

(22)

The title compound was prepared as described in General Method B for the preparation of Example 7 with replacement of methyl 6-chloro-1-methyl-1H-pyrrolo[2,3-b]pyridine-3-carboxylate with methyl 5-bromopyrimidine-2-carboxylate. MS (ESI) m/z: 497.2 [M+H]+; 1H NMR (500

MHz, DMSO-d$_6$) δ 8.46 (br s, 2H), 7.75-7.50 (m, 3H), 5.85 (s, 1H), 3.68 (br d, J=13.7 Hz, 1H), 3.51 (br s, 1H), 3.21 (br s, 2H), 2.32 (s, 3H), 1.71-1.51 (m, 4H), 1.27-1.16 (m, 2H), 1.12 (br s, 2H); FXR EC$_{50}$=1500 nM.

Example 23

5-(2-(5-Cyclopropyl-3-(2,6-dichlorophenyl)isoxazol-4-yl)-7-azaspiro[3.5]non-1-en-7-yl) picolinic acid (23)

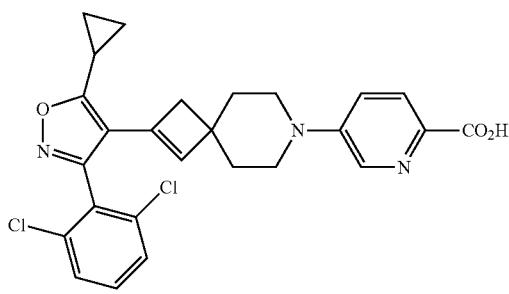

The title compound was prepared as described in General Method B for the preparation of Example 7 with replacement of methyl 6-chloro-1-methyl-1H-pyrrolo[2,3-b]pyridine-3-carboxylate with methyl 5-bromopicolinate. MS (ESI) m/z: 496.0 [M+H]$^+$; $^1$H NMR (500 MHz, DMSO-d$_6$) δ 8.29 (br s, 1H), 7.83 (d, J=8.9 Hz, 1H), 7.70-7.54 (m, 3H), 7.37-7.26 (m, 1H), 5.84 (s, 1H), 3.83-3.68 (m, 1H), 3.49 (br d, J=13.1 Hz, 1H), 3.24-3.11 (m, 2H), 2.31 (s, 3H), 1.68-1.50 (m, 4H), 1.27-1.15 (m, 2H), 1.11 (br d, J=2.1 Hz, 2H), 1.00 (d, J=6.4 Hz, 1H); FXR EC$_{50}$=340 nM.

Example 24

2-(2-(5-Cyclopropyl-3-(2,6-dichlorophenyl)isoxazol-4-yl)-7-azaspiro[3.5]non-1-en-7-yl)benzo[d]thiazole-6-carboxylic acid (24)

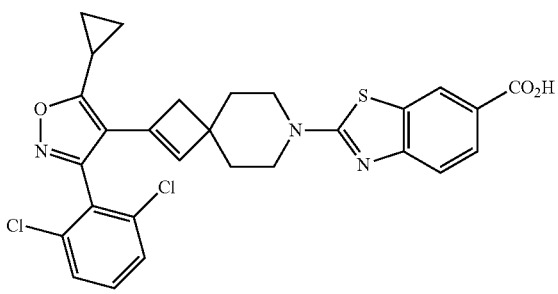

The title compound was prepared as described in General Method A for the preparation of Example 1 with replacement of ethyl 2-bromo-4-fluorobenzo[d]thiazole-6-carboxylate with ethyl 2-bromobenzo[d]thiazole-6-carboxylate. MS (ESI) m/z: 552.0 [M+H]$^+$; $^1$H NMR (500 MHz, DMSO-d$_6$) δ 8.32 (s, 1H), 7.83 (br d, J=7.9 Hz, 1H), 7.72-7.56 (m, 3H), 7.43 (br d, J=8.2 Hz, 1H), 5.89 (s, 1H), 3.90 (s, 1H), 3.71 (br d, J=11.0 Hz, 1H), 3.17 (s, 1H), 2.41-2.29 (m, 3H), 1.64 (br s, 4H), 1.30-1.17 (m, 4H), 1.14 (br d, J=2.4 Hz, 2H); FXR EC$_{50}$=17 nM.

Example 25

2-(2-(5-Cyclopropyl-3-(2,6-dichlorophenyl)isoxazol-4-yl)-7-azaspiro[3.5]non-1-en-7-yl)-1-methyl-1H-benzo[d]imidazole-5-carboxylic acid (25)

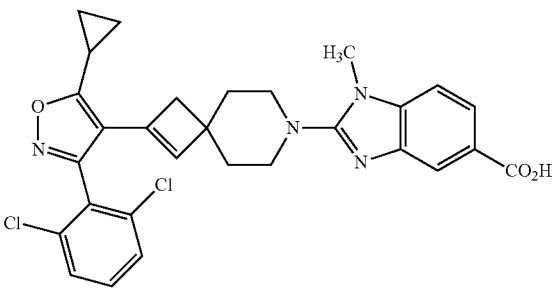

The title compound was prepared as described in General Method A for the preparation of Example 1 with replacement of ethyl 2-bromo-4-fluorobenzo[d]thiazole-6-carboxylate with methyl 2-bromo-1-methyl-1H-benzo[d]imidazole-5-carboxylate. MS (ESI) m/z: 549.2 [M+H]$^+$; $^1$H NMR (500 MHz, DMSO-d$_6$) δ 7.94 (s, 1H), 7.78 (br d, J=8.2 Hz, 1H), 7.73-7.65 (m, 2H), 7.65-7.57 (m, 1H), 7.45 (br d, J=8.5 Hz, 1H), 5.89 (s, 1H), 3.63 (s, 3H), 3.24-3.11 (m, 1H), 2.36 (s, 3H), 1.82-1.72 (m, 2H), 1.70 (br s, 2H), 1.28-1.18 (m, 4H), 1.15 (br d, J=2.1 Hz, 2H); FXR EC$_{50}$=1020 nM.

Example 26

2-(2-(5-Cyclopropyl-3-(2,6-dichlorophenyl)isoxazol-4-yl)-7-azaspiro[3.5]non-1-en-7-yl)benzo[d]oxazole-5-carboxylic acid (26)

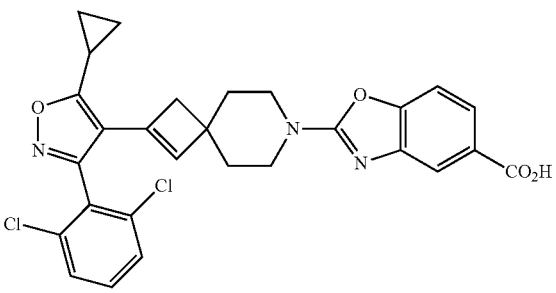

Step 1. Methyl 2-bromobenzo[d]oxazole-5-carboxylate

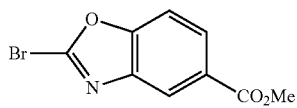

tert-Butyl nitrite (0.28 g, 2.7 mmol) was added slowly to a 0° C. suspension of copper (II) bromide (0.55 g, 2.5 mmol) in acetonitrile (11.3 mL). After 5 minutes methyl 2-aminobenzo[d]oxazole-5-carboxylate (0.43 g, 2.3 mmol) was added and the reaction mixture was brought to room temperature. After stirring overnight, the mixture was concentrated onto SiO$_2$ for purification. The residue was purified by flash chromatography on SiO$_2$ (0-60% EtOAc/hexanes, Isco 40 g column) to give methyl 2-bromobenzo[d]oxazole-5- carboxylate (0.16 g, 0.60 mmol, 27% yield) as a white solid. $^1$H NMR (400 MHz, CDCl$_3$) δ 8.44-8.35 (m, 1H), 8.13 (dd, J=8.6, 1.8 Hz, 1H), 7.58 (d, J=8.6 Hz, 1H), 3.97 (s, 3H).

Example 26. 2-(2-(5-Cyclopropyl-3-(2,6-dichlorophenyl)isoxazol-4-yl)-7-azaspiro[3.5]non-1-en-7-yl)benzo[d]oxazole-5-carboxylic acid The title compound was prepared as described in General Method A for the preparation of Example 1 with replacement of ethyl 2-bromo-4-fluorobenzo[d]thiazole-6-carboxylate with methyl 2-bromobenzo[d]oxazole-5-carboxylate. MS (ESI) m/z: 536.3 [M+H]$^+$; $^1$H NMR (500 MHz, DMSO-d$_6$) δ 7.75 (s, 1H), 7.71-7.63 (m, 3H), 7.63-7.57 (m, 1H), 7.45 (d, J=8.2 Hz, 1H), 5.89 (s, 1H), 3.82-3.66 (m, 2H), 3.47 (br d, J=8.2 Hz, 1H), 2.40-2.29 (m, 3H), 1.72-1.56 (m, 4H), 1.28-1.18 (m, 3H), 1.15 (br d, J=2.4 Hz, 2H); FXR EC$_{50}$=157 nM.

Example 27

6-(2-(5-Cyclopropyl-3-(2-(trifluoromethoxy)phenyl)isoxazol-4-yl)-7-azaspiro[3.5]non-1-en-7-yl)-5-fluoronicotinic acid

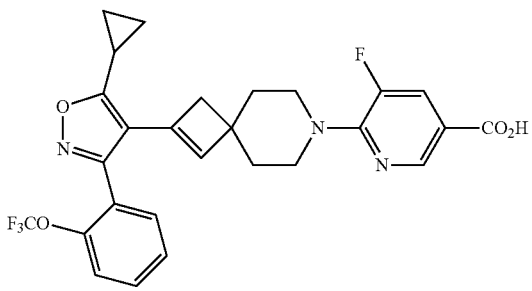

(27)

The title compound was prepared as described in General Method A for the preparation of Example 17 with replacement of ethyl 2-bromo-4-fluorobenzo[d]thiazole-6-carboxylate with methyl 6-chloro-5-fluoronicotinate. MS (ESI) m/z: 530.0 [M+H]$^+$; $^1$H NMR (500 MHz, DMSO-d$_6$) δ 8.46 (br s, 1H), 7.78-7.64 (m, 2H), 7.63-7.47 (m, 3H), 5.91 (s, 1H), 3.78 (br d, J=13.7 Hz, 2H), 2.41 (s, 2H), 2.35-2.25 (m, 1H), 1.73-1.54 (m, 4H), 1.24 (s, 1H), 1.18 (br d, J=7.6 Hz, 2H), 1.11 (br s, 2H); FXR EC$_{50}$=1100 nM.

Example 28

6-(2-(5-Cyclopropyl-3-(2,6-dichlorophenyl)isoxazol-4-yl)-7-azaspiro[3.5]non-1-en-7-yl)-5-fluoronicotinic acid

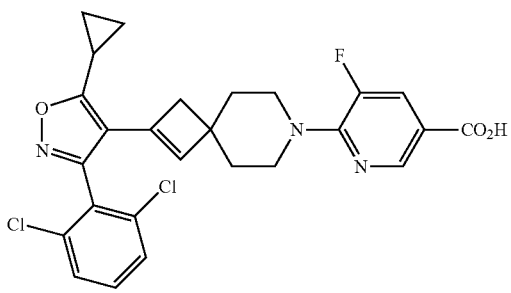

(28)

The title compound was prepared as described in General Method A for the preparation of Example 1 with replacement of ethyl 2-bromo-4-fluorobenzo[d]thiazole-6-carboxylate with methyl 6-chloro-5-fluoronicotinate. MS (ESI) m/z: 514.1 [M+H]$^+$; $^1$H NMR (500 MHz, DMSO-d$_6$) δ 8.45 (br s, 1H), 7.81-7.69 (m, 1H), 7.68-7.63 (m, 2H), 7.62-7.56 (m, 1H), 5.86 (s, 1H), 3.76 (br s, 1H), 2.34 (br s, 3H), 1.60 (br s, 4H), 1.29-1.17 (m, 3H), 1.14 (br s, 2H) additional peaks were lost due to water suppression in the $^1$H NMR experiment; FXR EC$_{50}$=453 nM.

Example 29

2-(2-(5-Cyclopropyl-3-(2,6-dichlorophenyl)isoxazol-4-yl)-7-azaspiro[3.5]non-1-en-7-yl)-4-fluorobenzo[d]thiazole-6-carboxylic acid

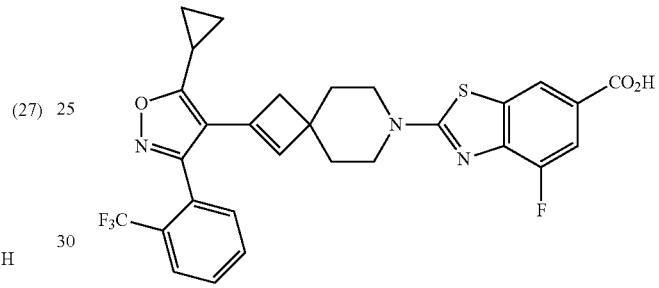

(29)

The title compound was prepared as described in General Method A for the preparation of Example 1 with replacement of 2,6-dichlorobenzaldehyde with 2-(trifluoromethyl)benzaldehyde. MS (ESI) m/z: 570.1 [M+H]$^+$; $^1$H NMR (400 MHz, DMSO-d$_6$) δ 8.20 (d, J=1.5 Hz, 1H), 7.96-7.90 (m, 1H), 7.87-7.73 (m, 2H), 7.63-7.53 (m, 2H), 5.79 (s, 1H), 3.81-3.63 (m, 3H), 2.33 (s, 4H), 1.69-1.54 (m, 4H), 1.23-1.15 (m, 3H), 1.13 (dt, J=5.4, 2.8 Hz, 2H); FXR EC$_{50}$=14 nM.

Example 30

6-(2-(5-Cyclopropyl-3-(2-(trifluoromethyl)phenyl)isoxazol-4-yl)-7-azaspiro[3.5]non-1-en-7-yl) nicotinic acid

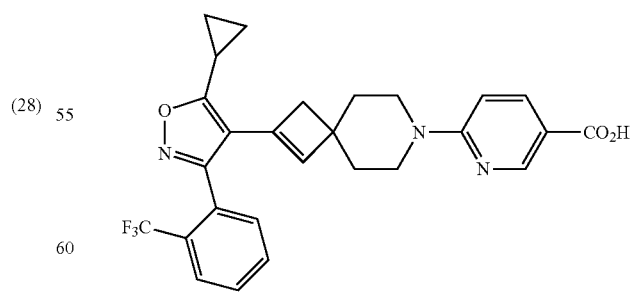

(30)

The title compound was prepared as described in General Method A for the preparation of Example 29 with replacement of ethyl 2-bromo-4-fluorobenzo[d]thiazole-6-carboxylate with methyl 6-fluoronicotinate. MS (ESI) m/z: 496.1 [M+H]$^+$; $^1$H NMR (400 MHz, DMSO-d$_6$) δ 8.58 (d, J=2.0

Hz, 1H), 7.96-7.90 (m, 1H), 7.88 (dd, J=9.0, 2.4 Hz, 1H), 7.85-7.73 (m, 2H), 7.57 (d, J=7.0 Hz, 1H), 6.83 (d, J=9.2 Hz, 1H), 5.76 (s, 1H), 3.86-3.78 (m, 2H), 3.44-3.33 (m, 2H), 2.32-2.24 (m, 3H), 1.51 (br t, J=5.5 Hz, 4H), 1.24-1.15 (m, 2H), 1.15-1.08 (m, 2H); FXR $EC_{50}$=110 nM.

Example 31

(6-(2-(5-Cyclopropyl-3-(2-(trifluoromethyl)phenyl) isoxazol-4-yl)-7-azaspiro[3.5]non-1-en-7-yl) nicotinoyl)glycine

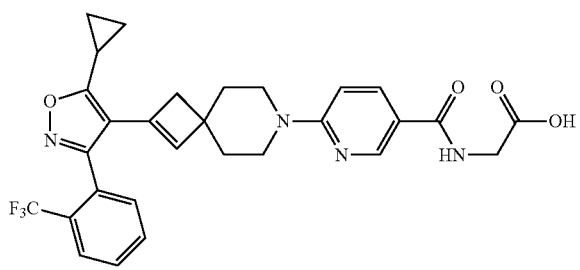

(31)

Step A. T3P (45.2 μL, 0.08 mmol) and $Et_3N$ (21.4 μL, 0.15 mmol) were added to a solution of 6-(2-(5-cyclopropyl-3-(2-(trifluoromethyl)phenyl)isoxazol-4-yl)-7-azaspiro[3.5]non-1-en-7-yl)nicotinic acid (Example 30) (19 mg, 0.04 mmol) and methyl 2-aminoacetate, HCl (9.6 mg, 0.08 mmol) in DCE (0.19 mL). The reaction mixture was stirred at room temperature for and the crude reaction mixture was loaded directly onto a $SiO_2$ cartridge for purification by flash chromatography on $SiO_2$ (0-100% EtOAc/hex, Isco 4 g column) to give methyl 2-(6-(2-(5-cyclopropyl-3-(2-(trifluoromethyl) isoxazol-4-yl)-7-azaspiro[3.5]non-1-en-7-yl)nicotinamido)acetate (10 mg, 0.018 mmol, 46.0% yield) as a white foam.

Step B. Methyl 2-(6-(2-(5-cyclopropyl-3-(2-(trifluoromethyl)phenyl)isoxazol-4-yl)-7-azaspiro[3.5]non-1-en-7-yl) nicotinamido)acetate (10 mg, 0.02 mmol) was dissolved in THF (136 μL), water (27.2 μL), MeOH (13.6 μL) and then lithium hydroxide monohydrate (3.7 mg, 0.09 mmol) was added to the mixture. The reaction vessel was sealed and heated to 60° C. After heating for 2 hours the reaction was quenched with 1N HCl and then concentrated under a stream of nitrogen to minimum volume. The residue was taken up in DMF, filtered and the crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 19 minutes, then a 5-minute hold at 100% B; Flow: 20 mL/min. Fractions containing the desired product were combined and dried via centrifugal evaporation to give (6-(2-(5-Cyclopropyl-3-(2-(trifluoromethyl)phenyl)isoxazol-4-yl)-7-azaspiro[3.5]non-1-en-7-yl)nicotinoyl)glycine (7.7 mg, 0.01 mmol, 79% yield). MS (ESI) m/z: 552.9 [M+H]$^+$; $^1$H NMR (500 MHz, DMSO-$d_6$) δ 8.78 (br d, J=1.2 Hz, 1H), 8.70 (br s, 1H), 8.13 (br t, J=6.6 Hz, 2H), 8.05-7.92 (m, 2H), 7.78 (br d, J=7.3 Hz, 1H), 7.04 (br d, J=9.2 Hz, 1H), 5.96 (s, 1H), 4.06 (br d, J=5.5 Hz, 2H), 4.02-3.90 (m, 2H), 1.71 (br s, 4H), 1.45 (s, 2H), 1.42-1.35 (m, 2H), 1.33 (br d, J=2.4 Hz, 2H), 1.21 (d, J=6.4 Hz, 2H); FXR $EC_{50}$=5300 nM.

Example 32

(2-(2-(5-Cyclopropyl-3-(2-(trifluoromethyl)phenyl) isoxazol-4-yl)-7-azaspiro[3.5]non-1-en-7-yl)-4-fluorobenzo[d]thiazole-6-carbonyl)glycine

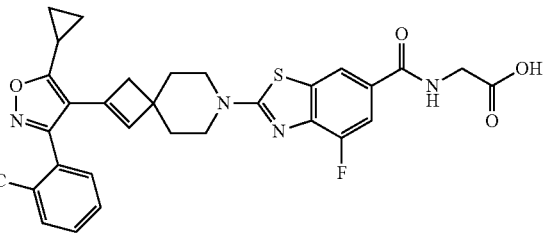

(32)

The title compound was prepared as described for the preparation of Example 31 with replacement of 6-(2-(5-cyclopropyl-3-(2-(trifluoromethyl)phenyl)isoxazol-4-yl)-7-azaspiro[3.5]non-1-en-7-yl)nicotinic acid (Example 30) with 2-(2-(5-cyclopropyl-3-(2,6-dichlorophenyl)isoxazol-4-yl)-7-azaspiro[3.5]non-1-en-7-yl)-4-fluorobenzo[d]thiazole-6-carboxylic acid (Example 29). MS (ESI) m/z: 627.1 [M+H]$^+$; $^1$H NMR (500 MHz, DMSO-$d_6$) δ 8.80 (br s, 1H), 8.11 (s, 1H), 7.93 (br d, J=7.3 Hz, 1H), 7.86-7.72 (m, 2H), 7.62 (br d, J=11.9 Hz, 1H), 7.57 (br d, J=7.3 Hz, 1H), 5.78 (s, 1H), 3.92 (br s, 1H), 3.69 (br d, J=13.7 Hz, 1H), 2.37-2.25 (m, 3H), 1.71-1.55 (m, 4H), 1.27-1.16 (m, 3H), 1.12 (br d, J=2.4 Hz, 2H); additional $^1$H NMR peaks were lost due to water suppression in the $^1$H NMR experiment; FXR $EC_{50}$=1500 nM.

Example 33

2-(2-(5-Cyclopropyl-3-(2,6-dichlorophenyl)isoxazol-4-yl)-2-hydroxy-7-azaspiro[3.5]nonan-7-yl)-4-fluorobenzo[d]thiazole-6-carboxylic acid

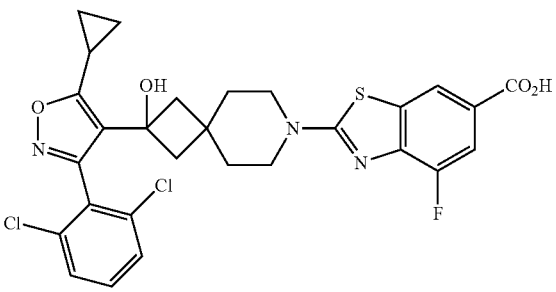

(33)

The title compound was obtained as a minor isolate during the preparation of Example 1 in General Method A and was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 25-65% B over 19 minutes, then a 5-minute hold at 100% B; Flow: 20 mL/min. Fractions containing the desired product were combined and dried via centrifugal evaporation. MS (ESI) m/z: 588.2 [M+H]+; 1H NMR (500 MHz, DMSO-d6) δ 8.18 (br s, 1H), 7.67-7.48 (m, 3H), 6.38 (s, 1H), 3.67 (br s, 1H), 3.54 (br s, 1H), 2.90 (s, 1H), 2.74 (s, 1H), 2.38 (br d, J=12.8 Hz, 2H), 2.31-2.18 (m, 1H), 1.98 (br s, 2H), 1.54 (br s, 2H), 1.18-1.06 (m, 2H), 1.01-0.90 (m, 2H); FXR EC50=4800 nM.

Example 34

2-(6-(5-cyclopropyl-3-(2-(trifluoromethyl)phenyl)isoxazol-4-yl)-2-azaspiro[3.3]hept-5-en-2-yl)-4-fluorobenzo[d]thiazole-6-carboxylic acid

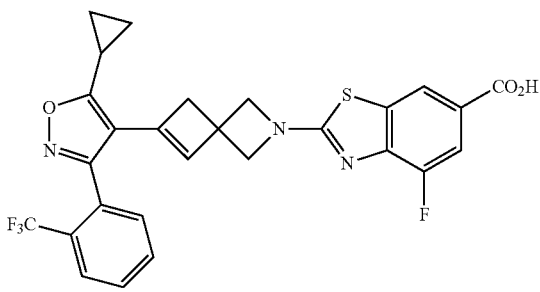

(34)

The title compound was prepared as described in General Method A for the preparation of Example 29 with replacement of tert-butyl 2-oxo-7-azaspiro[3.5]nonane-7-carboxylate with tert-butyl 6-oxo-2-azaspiro[3.3]heptane-2-carboxylate. MS (ESI) m/z: 542.6 [M+H]+; 1H NMR (400 MHz, DMSO-d6) δ 12.96 (br s, 1H), 8.23 (d, J=1.5 Hz, 1H), 7.99-7.89 (m, 1H), 7.87-7.74 (m, 2H), 7.65-7.51 (m, 2H), 5.67 (s, 1H), 4.34 (d, J=9.2 Hz, 2H), 4.24 (d, J=9.2 Hz, 2H), 2.83 (s, 2H), 2.37-2.21 (m, 1H), 1.17-1.09 (m, 2H), 0.92-0.79 (m, 2H); FXR EC50=400 nM.

Example 35

6-(6-(5-cyclopropyl-3-(2-(trifluoromethyl)phenyl)isoxazol-4-yl)-2-azaspiro[3.3]hept-5-en-2-yl)nicotinic acid

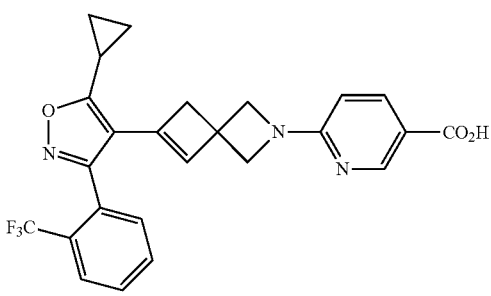

(35)

The title compound was prepared as described in General Method A for the preparation of Example 34 with replacement of ethyl 2-bromo-4-fluorobenzo[d]thiazole-6-carboxylate with methyl 6-fluoronicotinate. MS (ESI) m/z: 468.6 [M+H]+; 1H NMR (400 MHz, DMSO-d6) δ 8.56 (d, J=2.0 Hz, 1H), 7.97-7.87 (m, 2H), 7.86-7.74 (m, 2H), 7.59 (d, J=6.6 Hz, 1H), 6.35 (d, J=9.2 Hz, 1H), 5.64 (s, 1H), 4.17 (d, J=9.2 Hz, 2H), 4.06 (d, J=9.2 Hz, 2H), 2.78 (s, 2H), 2.36-2.26 (m, 1H), 1.24-1.17 (m, 2H), 1.17-1.09 (m, 2H); FXR EC50=4300 nM.

Example 36

2-(2-(5-cyclopropyl-3-(2-(trifluoromethyl)phenyl)isoxazol-4-yl)-7-azaspiro[3.5]nonan-7-yl)-4-fluorobenzo[d]thiazole-6-carboxylic acid

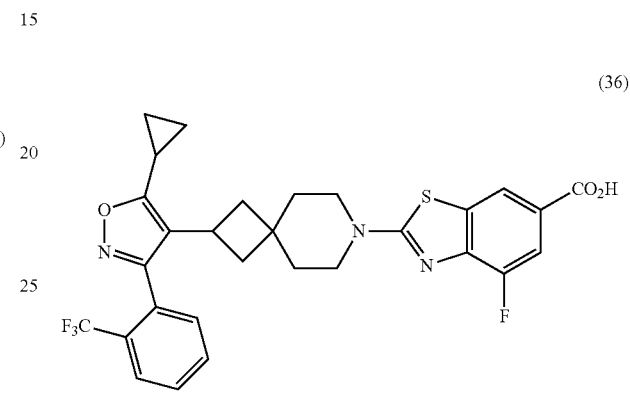

(36)

The title compound was prepared as described for the preparation of Example 13 with replacement of 2-(2-(5-cyclopropyl-3-(2,6-dichlorophenyl)isoxazol-4-yl)-7-azaspiro[3.5]non-1-en-7-yl)-4-fluorobenzo[d]thiazole-6-carboxylic acid (Example 1) with 2-(2-(5-cyclopropyl-3-(2,6-dichlorophenyl)isoxazol-4-yl)-7-azaspiro[3.5]non-1-en-7-yl)-4-fluorobenzo[d]thiazole-6-carboxylic acid (Example 29). MS (ESI) m/z: 572.4 [M+H]+; 1H NMR (500 MHz, DMSO-d6) δ 8.12 (s, 1H), 7.91 (d, J=7.6 Hz, 1H), 7.85-7.72 (m, 2H), 7.60-7.53 (m, 3H), 3.90 (s, 1H), 3.39 (br d, J=9.2 Hz, 2H), 2.27-2.14 (m, 1H), 2.09-1.96 (m, 2H), 1.91 (s, 2H), 1.77 (br t, J=10.8 Hz, 2H), 1.73-1.62 (m, 2H), 1.45-1.34 (m, 2H), 1.17-1.08 (m, 2H), 1.07-0.97 (m, 2H); FXR EC50=116 nM.

Example 37

2-(2-(5-cyclopropyl-3-(2-(trifluoromethyl)phenyl)isoxazol-4-yl)-7-azaspiro[3.5]nonan-7-yl)-4-fluorobenzo[d]thiazole-6-carboxylic acid

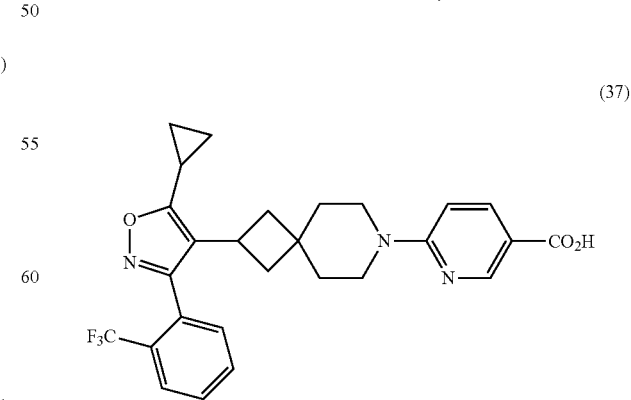

(37)

The title compound was prepared as described for the preparation of Example 36 with replacement of 2-(2-(5- cyclopropyl-3-(2-(trifluoromethyl)phenyl)isoxazol-4-yl)-7-azaspiro[3.5]non-1-en-7-yl)-4-fluorobenzo[d]thiazole-6-carboxylic acid (Example 29) with 6-(2-(5-cyclopropyl-3-(2-(trifluoromethyl)phenyl)isoxazol-4-yl)-7-azaspiro[3.5]non-1-en-7-yl)nicotinic acid (Example 30). MS (ESI) m/z: 498.4 [M+H]$^+$; $^1$H NMR (500 MHz, DMSO-d$_6$) δ 8.55 (br s, 1H), 7.90 (d, J=7.9 Hz, 1H), 7.85 (br s, 1H), 7.82-7.68 (m, 2H), 7.55 (d, J=7.3 Hz, 1H), 6.76 (br d, J=8.9 Hz, 1H), 3.65-3.50 (m, 1H), 3.46-3.29 (m, 2H), 2.26-2.15 (m, 1H), 2.04-1.93 (m, 2H), 1.90 (s, 1H), 1.72 (br t, J=10.8 Hz, 2H), 1.61-1.48 (m, 2H), 1.32-1.20 (m, 2H), 1.15-1.08 (m, 2H), 1.04-0.95 (m, 2H); FXR EC$_{50}$=1400 nM.

General Method C

Example 38

(+)-2-(2-(5-Cyclopropyl-3-(2,6-dichlorophenyl)isoxazol-4-yl)-1,3-dioxa-8-azaspiro[4.5]decan-8-yl)-4-fluorobenzo[d]thiazole-6-carboxylic acid (38)

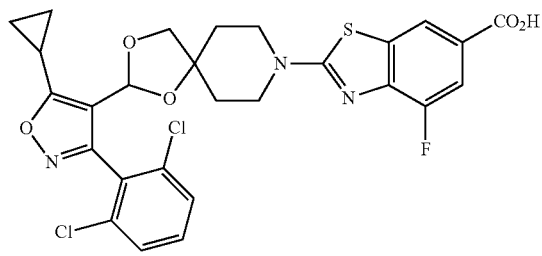

Step 1. Methyl 5-cyclopropyl-3-(2,6-dichlorophenyl)isoxazole-4-carboxylate

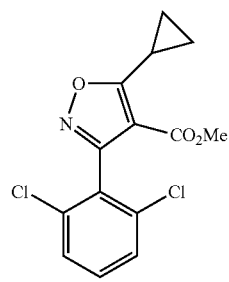 [SMILES: COC(=O)c1c(-c2c(Cl)cccc2Cl)noc1C1CC1]

To a 50 mL round bottom flask containing methyl 3-cyclopropyl-3-oxopropanoate (1.3 g, 8.9 mmol) was added triethylamine (2.5 mL, 17.8 mmol). The resulting clear solution was stirred at room temperature for 15 minutes and was cooled in an ice water bath. To the stirring solution was added a solution of 2,6-dichloro-N-hydroxybenzimidoyl chloride (2.0 g, 8.9 mmol, synthesis described in General Method A) in EtOH (4 mL) over the space of 10 minutes giving a white suspension. After addition, the resulting suspension was stirred at room temperature overnight. The reaction mixture was concentrated in vacuo and the residue was purified by flash chromatography on SiO$_2$ (0-10% EtOAc/hexanes, Isco 80 g column) to give methyl 5-cyclopropyl-3-(2,6-dichlorophenyl)isoxazole-4-carboxylate (2.4 g, 7.7 mmol, 87% yield) as a white solid. $^1$H NMR (500 MHz, CDCl$_3$) δ 7.45-7.39 (m, 2H), 7.39-7.33 (m, 1H), 3.71 (s, 3H), 2.93 (tt, J=8.5, 5.2 Hz, 1H), 1.47-1.40 (m, 2H), 1.34-1.27 (m, 2H).

Step 2. (5-Cyclopropyl-3-(2,6-dichlorophenyl)isoxazol-4-yl)methanol

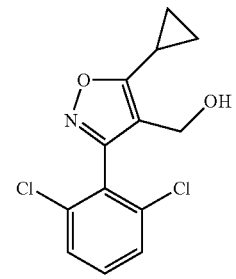 [SMILES: OCc1c(-c2c(Cl)cccc2Cl)noc1C1CC1]

To a solution of methyl 5-cyclopropyl-3-(2,6-dichlorophenyl)isoxazole-4-carboxylate (3.0 g, 9.6 mmol) in THF (11.1 mL) at 0° C. was added 1 M diisobutyl aluminum hydride (20.2 mL, 20.2 mmol) in toluene. The reaction mixture was warmed to room temperature and stirred for 2 hours. The reaction was cooled to 0° C. and quenched by the addition of MeOH (2 mL) and 1 M aq. HCl (~75 mL). The mixture was then extracted with EtOAc, and the organic layer was washed with brine. The organic layer was dried over MgSO$_4$ and concentrated to give (5-cyclopropyl-3-(2,6-dichlorophenyl)isoxazol-4-yl)methanol (2.5 g, 8.9 mmol, 92% yield) as a white solid, which was used without further purification. $^1$H NMR (500 MHz, CDCl$_3$) δ 7.46 (d, J=1.1 Hz, 1H), 7.45 (s, 1H), 7.41-7.36 (m, 1H), 4.44 (s, 2H), 2.22 (tt, J=8.5, 5.2 Hz, 1H), 1.42 (br s, 1H), 1.35-1.25 (m, 2H), 1.23-1.11 (m, 2H).

Step 3. 5-Cyclopropyl-3-(2,6-dichlorophenyl)isoxazole-4-carbaldehyde

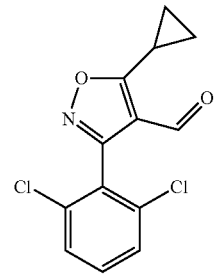 [SMILES: O=Cc1c(-c2c(Cl)cccc2Cl)noc1C1CC1]

To a solution of (5-cyclopropyl-3-(2,6-dichlorophenyl)isoxazol-4-yl)methanol (2.1 g, 7.4 mmol) in DCM (37.0 mL) was added a mixture of pyridinium chlorochromate (6.4 g, 29.6 mmol) and finely ground 3 Å molecular sieves (6.1 g). The resulting mixture was stirred at room temperature for 30 min and then filtered through a pad of Celite. The pad was washed with MeOH/DCM. The filtrate was evaporated and the residue was purified by flash chromatography on SiO$_2$ (0-100% EtOAc/hexanes, Isco 80 g column) to give 5-cyclopropyl-3-(2,6-dichlorophenyl)isoxazole-4-carbaldehyde (1.9 g, 6.8 mmol, 93% yield) as a white solid. $^1$H NMR (500

MHz, CDCl₃) δ 9.67 (s, 1H), 7.49-7.44 (m, 2H), 7.43-7.37 (m, 1H), 2.82 (tt, J=8.3, 5.2 Hz, 1H), 1.52-1.45 (m, 2H), 1.40-1.33 (m, 2H).

Step 4. (±)-tert-Butyl 2-(5-cyclopropyl-3-(2,6-dichlorophenyl)isoxazol-4-yl)-1,3-dioxa-8-azaspiro[4.5]decane-8-carboxylate

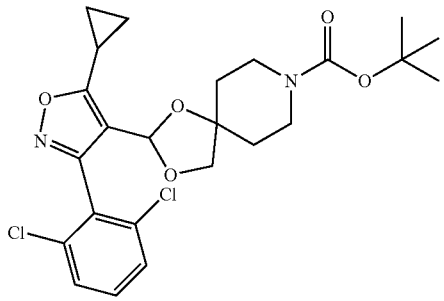 [SMILES: CC(C)(C)OC(=O)N1CCC2(CC1)COC(c1c(-c3c(Cl)cccc3Cl)noc1C1CC1)O2]

4-Methylbenzenesulfonic acid (1.7 mg, 10.0 μmol) followed by tert-butyl 4-hydroxy-4-(hydroxymethyl)piperidine-1-carboxylate (23.1 mg, 0.10 mmol) and 100 mg of oven-dried 3 Å molecular sieves were added to a room temperature suspension of 5-cyclopropyl-3-(2,6-dichlorophenyl)isoxazole-4-carbaldehyde (28.2 mg, 0.1 mmol) in toluene (0.5 mL). The resulting suspension was heated to 150° C. overnight. The solids were filtered and washed with DCM (~10 mL). The filtrate was concentrated and the residue was purified by flash chromatography on SiO₂ (0-100% EtOAc/DCM, Isco 40 g column) to give tert-butyl 2-(5-cyclopropyl-3-(2,6-dichlorophenyl)isoxazol-4-yl)-1,3-dioxa-8-azaspiro[4.5]decane-8-carboxylate (12.0 mg, 0.02 mmol, 23% yield) as a white solid. MS (ESI) m/z: 495.1 [M+H]⁺; ¹H NMR (500 MHz, CDCl₃) δ 7.45-7.37 (m, 2H), 7.36-7.30 (m, 1H), 5.95 (s, 1H), 3.76 (br. s., 1H), 3.61 (d, J=8.0 Hz, 2H), 3.47 (d, J=6.9 Hz, 1H), 3.14 (br. s., 1H), 2.94 (br. s., 1H), 2.37-2.14 (m, 1H), 1.85-1.65 (m, 1H), 1.46 (s, 10H), 1.38-1.23 (m, 3H), 1.22-1.12 (m, 2H), 1.04 (br. s., 1H); FXR EC₅₀=4.8 μM.

Step 5. (+)-2-(5-Cyclopropyl-3-(2,6-dichlorophenyl)isoxazol-4-yl)-1,3-dioxa-8-azaspiro[4.5]decane

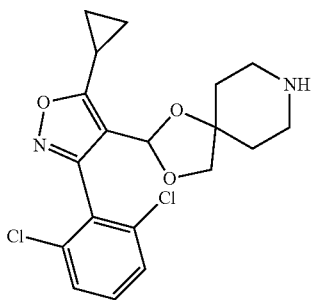 [SMILES: Clc1cccc(Cl)c1-c1noc(C2CC2)c1C1OCC2(CCNCC2)O1]

Trifluoroacetic acid (0.10 mL, 1.2 mmol) was added to a room temperature solution of (±)-tert-butyl 2-(5-cyclopropyl-3-(2,6-dichlorophenyl)isoxazol-4-yl)-1,3-dioxa-8-azaspiro[4.5]decane-8-carboxylate (60 mg, 0.12 mmol) in DCM (2 mL). The reaction mixture was stirred at room temperature overnight. The excess trifluoroacetic acid was removed in vacuo and the residue was partitioned between EtOAc (5 mL) and 1M aqueous K₂HPO₄ (5 mL). The organic layer was dried over Na₂SO₄, filtered and concentrated to dryness. The crude product was used directly in the next step.

Example 38. (+)-Ethyl 2-(2-(5-cyclopropyl-3-(2,6-dichlorophenyl)isoxazol-4-yl)-1,3-dioxa-8-azaspiro[4.5]decan-8-yl)-4-fluorobenzo[d]thiazole-6-carboxylate Cesium carbonate (74.2 mg, 0.23 mmol) and ethyl 2-bromo-4-fluorobenzo[d]thiazole-6-carboxylate (41.5 mg, 0.14 mmol) were added to a room temperature solution of 2-(5-cyclopropyl-3-(2,6-dichlorophenyl)isoxazol-4-yl)-1,3-dioxa-8-azaspiro[4.5]decane (36 mg, 0.09 mmol) in N,N-dimethylacetamide (0.26 mL). After 10 minutes of stirring at room temperature the reaction mixture was heated to 50° C. After 3 hours the reaction mixture was partially concentrated and the residue was purified by flash chromatography on SiO₂ (5-100% EtOAc/hexanes, Isco 24 g column) to yield (+)-ethyl 2-(2-(5-cyclopropyl-3-(2,6-dichlorophenyl)isoxazol-4-yl)-1,3-dioxa-8-azaspiro[4.5]decan-8-yl)-4-fluorobenzo[d]thiazole-6-carboxylate (23 mg, 0.04 mmol, 39% yield) as a white solid. MS (ESI) m/z: 618.0 [M+H]⁺; ¹H NMR (500 MHz, CDCl₃) δ 8.10 (d, J=1.4 Hz, 1H), 7.74 (dd, J=11.3, 1.4 Hz, 1H), 7.50-7.40 (m, 2H), 7.39-7.33 (m, 1H), 6.03 (s, 1H), 4.40 (q, J=7.1 Hz, 2H), 4.01 (d, J=12.4 Hz, 1H), 3.91 (d, J=11.8 Hz, 1H), 3.66 (d, J=8.3 Hz, 1H), 3.59-3.46 (m, 2H), 3.40-3.16 (m, 1H), 2.34-2.16 (m, 1H), 1.93 (dd, J=13.8, 2.5 Hz, 1H), 1.81-1.66 (m, 1H), 1.64-1.52 (m, 2H), 1.42 (t, J=7.2 Hz, 3H), 1.34 (dd, J=5.0, 2.2 Hz, 2H), 1.24-1.05 (m, 2H); FXR EC₅₀=620 nM.

Example 39

(+)-2-(2-(5-Cyclopropyl-3-(2,6-dichlorophenyl)isoxazol-4-yl)-1,3-dioxa-8-azaspiro[4.5]decan-8-yl)-4-fluorobenzo[d]thiazole-6-carboxylic acid (39)

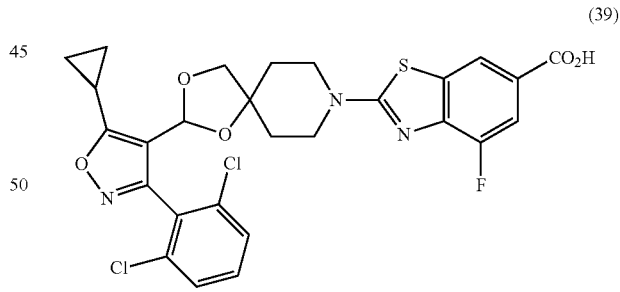

Aqueous LiOH 1.0 M (130 μL, 0.13 mmol) was added to a room temperature solution of ethyl 2-(2-(5-cyclopropyl-3-(2,6-dichlorophenyl)isoxazol-4-yl)-1,3-dioxa-8-azaspiro[4.5]decan-8-yl)-4-fluorobenzo[d]thiazole-6-carboxylate (16 mg, 0.03 mmol, Example 38) in 1:1 MeOH: THF (260 μL). The reaction mixture was stirred at room temperature overnight and then the excess solvents were removed. Acetic acid was added until ~pH 5 was achieved and the mixture was extracted with dichloromethane (10 mL). The organic layer was collected, dried over MgSO₄, filtered and concentrated in vacuo. The crude product was triturated with a 5:1 mixture of hexane: DCM to give (+)-2-(2-(5-cyclopropyl- 3-(2,6-dichlorophenyl)isoxazol-4-yl)-1,3-dioxa-8-azaspiro[4.5]decan-8-yl)-4-fluorobenzo[d]thiazole-6-carboxylic acid (12.3 mg, 0.02 mmol, 81% yield) as a white solid. MS (ESI) m/z: 590.0 [M+H]$^+$; $^1$H NMR (400 MHz, CDCl$_3$) δ 8.04 (s, 1H), 7.67 (d, J=11.0 Hz, 1H), 7.39-7.31 (m, 2H), 7.30-7.22 (m, 1H), 5.93 (s, 1H), 3.92 (d, J=11.4 Hz, 1H), 3.79 (br. s., 1H), 3.57 (d, J=8.1 Hz, 1H), 3.46 (d, J=8.1 Hz, 2H), 3.19 (t, J=11.4 Hz, 1H), 2.22-2.09 (m, 1H), 1.83 (d, J=13.0 Hz, 1H), 1.59 (td, J=12.6, 4.5 Hz, 1H), 1.53-1.41 (m, 1H), 1.31-1.20 (m, 2H), 1.15-0.95 (m, 3H); FXR EC$_{50}$=230 nM.

Example 40

Ethyl 2-((1R,3S,5S)-2'-(5-cyclopropyl-3-(2,6-dichlorophenyl)isoxazol-4-yl)-8-azaspiro[bicyclo[3.2.1]octane-3,4'-[1,3]dioxolan]-8-yl)-4-fluorobenzo[d]thiazole-6-carboxylate (40)

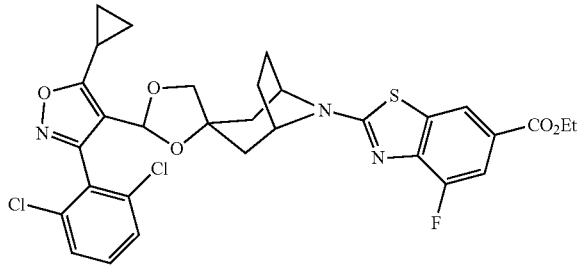

The title compound was prepared as described in General Method C for the preparation of Example 38 with replacement of tert-butyl 4-hydroxy-4-(hydroxymethyl) piperidine-1-carboxylate with tert-butyl (1R,3S,5S)-3-hydroxy-3-(hydroxymethyl)-8-azabicyclo[3.2.1]octane-8-carboxylate. MS (ESI) m/z: 644.1 [M+H]$^+$; $^1$H NMR (400 MHz, CDCl$_3$) δ 8.13 (d, J=1.54 Hz, 1H), 7.76 (dd, J=1.54, 11.22 Hz, 1H), 7.37-7.45 (m, 2H), 7.29-7.35 (m, 1H), 5.87 (s, 1H), 4.41 (q, J=7.04 Hz, 4H), 3.98 (d, J=7.70 Hz, 1H), 3.54 (d, J=7.70 Hz, 1H), 2.12-2.39 (m, 5H), 2.07 (br d, J=13.20 Hz, 1H), 1.78 (br t, J=9.35 Hz, 1H), 1.37-1.49 (m, 4H), 1.22-1.32 (m, 2H), 1.12 (dd, J=1.76, 8.36 Hz, 2H); FXR EC$_{50}$=3400 nM.

Example 41

2-((1R,5S)-2'-(5-cyclopropyl-3-(2,6-dichlorophenyl)isoxazol-4-yl)-8-azaspiro[bicyclo[3.2.1]octane-3,4'-[1,3]dioxolan]-8-yl)-4-fluorobenzo[d]thiazole-6-carboxylic acid (41)

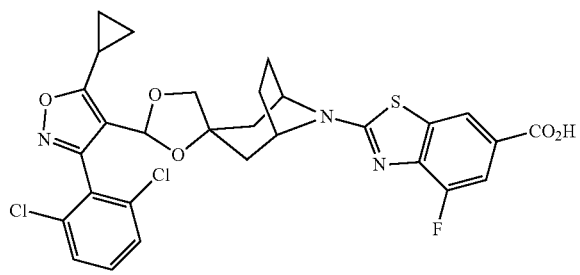

The title compound was prepared as described General Method C for the preparation of Example 39 with replacement of tert-butyl 4-hydroxy-4-(hydroxymethyl) piperidine-1-carboxylate with tert-butyl (1R,3S,5S)-3-hydroxy-3-(hydroxymethyl)-8-azabicyclo[3.2.1]octane-8-carboxylate. MS (ESI) m/z: 616.6 [M+H]$^+$; $^1$H NMR (400 MHz, CDCl$_3$) δ 8.19 (s, 1H), 7.80 (br d, J=11.00 Hz, 1H), 7.37-7.47 (m, 2H), 7.30-7.36 (m, 1H), 5.71-6.01 (m, 1H), 4.29-4.64 (m, 2H), 3.98 (d, J=7.70 Hz, 1H), 3.78 (s, 1H), 3.54 (d, J=7.70 Hz, 2H), 1.99-2.39 (m, 7H), 1.88 (s, 1H), 1.78 (s, 1H), 1.58-1.68 (m, 1H), 1.41-1.52 (m, 1H), 1.20-1.35 (m, 3H), 1.12 (dd, J=1.65, 8.47 Hz, 2H), 0.82-1.04 (m, 2H); FXR EC$_{50}$=1700 nM.

Example 42

2-(2-(5-cyclopropyl-3-(2-(trifluoromethoxy)phenyl)isoxazol-4-yl)-1,3-dioxa-8-azaspiro[4.5]decan-8-yl)-4-fluorobenzo[d]thiazole-6-carboxylic acid (42)

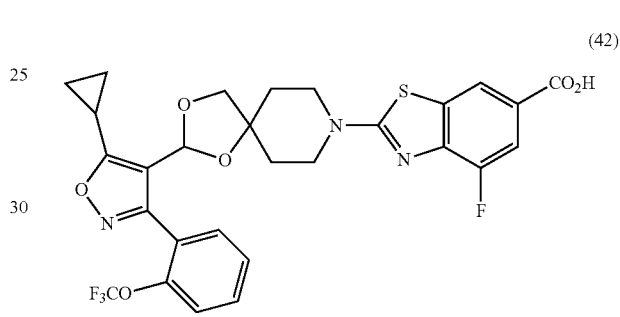

The title compound was prepared as described General Method C for the preparation of Example 39 with replacement of 2,6-dichlorobenzaldehyde with 2-(trifluoromethoxy)benzaldehyde. MS (ESI) m/z: 606.1 [M+H]$^+$; $^1$H NMR (500 MHz, DMSO-d$_6$) δ 8.11 (s, 1H), 7.70-7.62 (m, 1H), 7.59-7.48 (m, 4H), 5.94 (s, 1H), 3.84-3.67 (m, 1H), 3.64-3.37 (m, 1H), 3.24-3.15 (m, 1H), 2.94-2.89 (m, 1H), 2.46-2.39 (m, 1H), 1.90 (s, 1H), 1.85 (br d, J=13.1 Hz, 1H), 1.75-1.64 (m, 1H), 1.64-1.53 (m, 1H), 1.22-1.05 (m, 7H); FXR EC$_{50}$=1000 nM.

Example 43

6-(2-(5-Cyclopropyl-3-(2-(trifluoromethoxy)phenyl)isoxazol-4-yl)-1,3-dioxa-8-azaspiro[4.5]decan-8-yl) nicotinic acid (43)

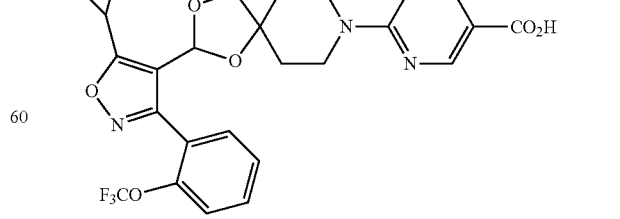

The title compound was prepared as described General Method C for the preparation of Example 42 with replacement of ethyl 2-bromo-4-fluorobenzo[d]thiazole-6-carboxylate with methyl 6-fluoronicotinate. MS (ESI) m/z: 532.4 [M+H]+; 1H NMR (500 MHz, DMSO-$d_6$) δ 8.58 (s, 1H), 7.92-7.86 (m, 2H), 7.69-7.63 (m, 2H), 7.58-7.48 (m, 7H), 6.83 (d, J=9.2 Hz, 4H), 5.94 (s, 6H), 3.96 (br d, J=14.0 Hz, 1H), 3.93-3.83 (m, 1H), 3.67-3.50 (m, 1H), 3.41-3.29 (m, 1H), 3.17 (s, 1H), 3.16-3.08 (m, 1H), 2.48-2.41 (m, 1H), 1.75 (br d, J=13.1 Hz, 1H), 1.61-1.50 (m, 1H), 1.47-1.38 (m, 1H), 1.17 (br d, J=7.0 Hz, 2H), 1.14-1.07 (m, 2H); FXR $EC_{50}$=5300 nM.

Example 44

6-(2-(5-cyclopropyl-3-(2-(trifluoromethoxy)phenyl)isoxazol-4-yl)-1,3-dioxa-8-azaspiro[4.5]decan-8-yl)picolinic acid

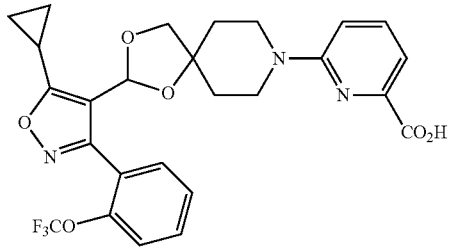

(44)

The title compound was prepared as described General Method C for the preparation of Example 42 with replacement of ethyl 2-bromo-4-fluorobenzo[d]thiazole-6-carboxylate with methyl 6-fluoropicolinate. MS (ESI) m/z: 532.4 [M+H]+; 1H NMR (500 MHz, DMSO-$d_6$) δ 7.72-7.63 (m, 1H), 7.63-7.43 (m, 5H), 7.21 (d, J=7.3 Hz, 1H), 6.96 (d, J=8.5 Hz, 1H), 5.93 (s, 1H), 3.90-3.72 (m, 2H), 3.64-3.44 (m, 2H), 3.33 (br t, J=9.9 Hz, 1H), 3.13 (br t, J=10.7 Hz, 1H), 1.74 (br d, J=13.4 Hz, 1H), 1.58 (br t, J=9.8 Hz, 1H), 1.50-1.39 (m, 1H), 1.17 (br d, J=7.0 Hz, 4H), 1.14-1.07 (m, 2H); FXR $EC_{50}$=5000 nM.

Example 45

2-(2-(5-Cyclopropyl-3-(2,6-dichlorophenyl)isoxazol-4-yl)-7-azaspiro[3.5]non-1-en-7-yl)-4-methylbenzo[d]thiazole-6-carboxylic acid

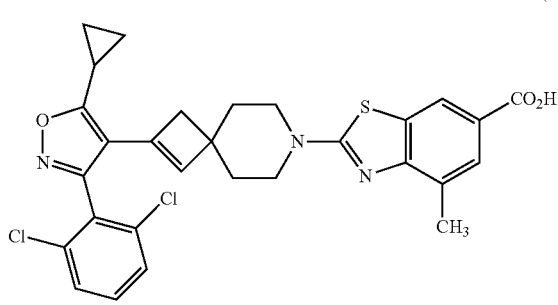

(45)

The title compound was prepared as described in General Method A for the preparation of Example 1 with replacement of ethyl 2-bromo-4-fluorobenzo[d]thiazole-6-carboxylate with methyl 2-chloro-4-methylbenzo[d]thiazole-6-carboxylate. MS (ESI) m/z: 566.1 [M+H]+; 1H NMR (500 MHz, DMSO-$d_6$) δ 8.14 (br s, 1H), 7.67 (br d, J=1.2 Hz, 2H), 7.66 (s, 1H), 7.62-7.57 (m, 1H), 5.88 (s, 1H), 3.71 (br d, J=11.9 Hz, 1H), 3.59-3.41 (m, 1H), 2.45 (s, 3H), 2.39-2.29 (m, 3H), 1.91 (s, 1H), 1.72-1.55 (m, 4H), 1.30-1.18 (m, 4H), 1.16-1.10 (m, 2H); FXR $EC_{50}$=11 nM.

Example 46

2-(2-(3-(3-Chloropyridin-2-yl)-5-cyclopropylisoxazol-4-yl)-7-azaspiro[3.5]non-1-en-7-yl)-4-fluorobenzo[d]thiazole-6-carboxylic acid

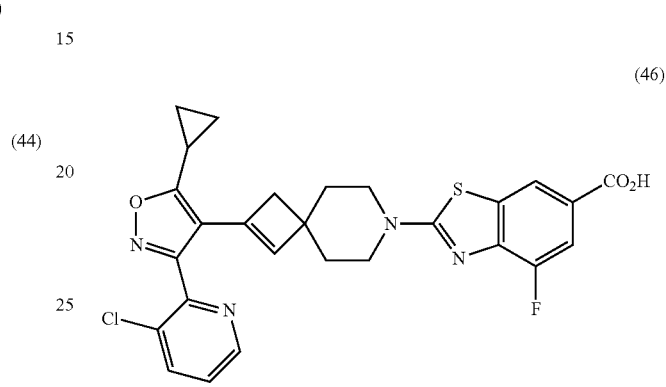

(46)

The title compound was prepared as described in General Method A for the preparation of Example 1 with replacement of 2,6-dichlorobenzaldehyde with 3-chloropicolinaldehyde. MS (ESI) m/z: 537.2 [M+H]+; 1H NMR (500 MHz, DMSO-$d_6$) δ 8.69 (d, J=4.6 Hz, 1H), 8.20 (s, 1H), 8.15 (d, J=8.2 Hz, 1H), 7.64 (dd, J=8.2, 4.6 Hz, 1H), 7.59 (d, J=11.6 Hz, 1H), 5.91 (s, 1H), 3.82-3.64 (m, 1H), 3.56-3.40 (m, 1H), 2.37 (s, 2H), 2.35-2.27 (m, 1H), 1.74-1.56 (m, 4H), 1.28-1.17 (m, 2H), 1.17-1.09 (m, 2H); FXR $EC_{50}$=200 nM.

Example 47

2-(2-(5-Cyclopropyl-3-(3,5-dichloropyridin-4-yl)isoxazol-4-yl)-7-azaspiro[3.5]non-1-en-7-yl)-4-fluorobenzo[d]thiazole-6-carboxylic acid

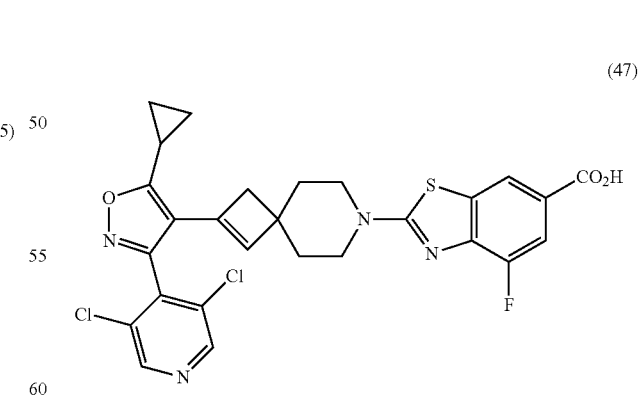

(47)

The title compound was prepared as described in General Method A for the preparation of Example 1 with replacement of 2,6-dichlorobenzaldehyde with 3,5-dichloroisonicotinaldehyde. MS (ESI) m/z: 571.1 [M+H]+; 1H NMR (500 MHz, DMSO-$d_6$) δ 8.86 (s, 2H), 8.17 (s, 1H), 7.58 (br d, J=11.4 Hz, 1H), 6.02 (s, 1H), 3.73 (br d, J=13.8 Hz, 2H), 3.66-3.44 (m, 2H), 2.42 (s, 2H), 2.40-2.28 (m, 1H), 1.69 (br s, 4H), 1.32-1.20 (m, 4H), 1.19-1.10 (m, 2H); FXR EC$_{50}$=25 nM.

Example 48

2-(2-(5-Cyclopropyl-3-(2,6-dichloro-4-fluorophenyl) isoxazol-4-yl)-7-azaspiro[3.5]non-1-en-7-yl)-4-fluorobenzo[d]thiazole-6-carboxylic acid

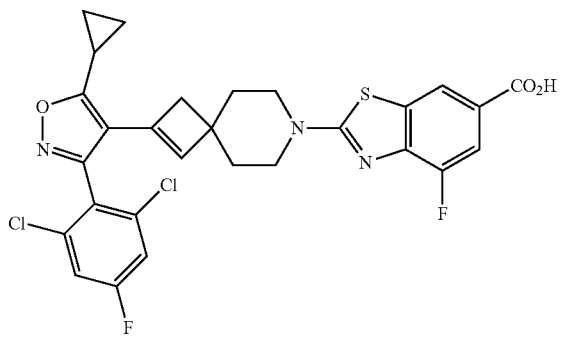

(48)

The title compound was prepared as described in General Method A for the preparation of Example 1 with replacement of 2,6-dichlorobenzaldehyde with 2,6-dichloro-4-fluorobenzaldehyde. MS (ESI) m/z: 588.1 [M+H]$^+$; $^1$H NMR (500 MHz, DMSO-d$_6$) δ 8.22 (s, 1H), 7.78 (d, J=8.5 Hz, 2H), 7.60 (br d, J=11.3 Hz, 1H), 5.96 (s, 1H), 3.74 (br s, 1H), 3.55 (br d, J=8.2 Hz, 1H), 3.33-3.14 (m, 1H), 3.04-2.95 (m, 1H), 2.41 (s, 2H), 2.39-2.29 (m, 1H), 1.68 (br s, 4H), 1.23 (br d, J=7.9 Hz, 2H), 1.16 (br d, J=2.4 Hz, 2H); FXR EC$_{50}$=115 nM.

2-(2-(3-(2,6-Dichlorophenyl)-5-isopropylisoxazol-4-yl)-7-azaspiro[3.5]non-1-en-7-yl)-4-fluorobenzo[d]thiazole-6-carboxylic acid

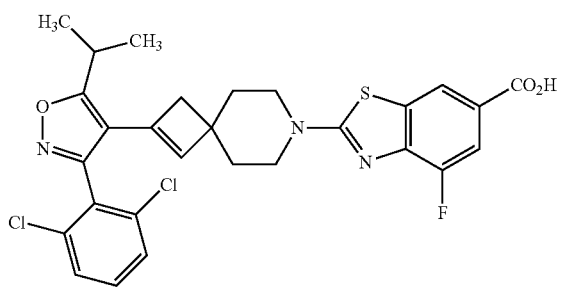

(49)

The title compound was prepared as described in General Method A for the preparation of Example 1 with replacement of cyclopropylacetylene with isopropylacetylene. MS (ESI) m/z: 572.1 [M+H]$^+$; $^1$H NMR (500 MHz, CDCl$_3$) δ 8.13 (s, 1H), 7.75 (d, J=11.1 Hz, 1H), 7.46-7.39 (m, 2H), 7.39-7.32 (m, 1H), 5.78 (s, 1H), 3.83-3.71 (m, 2H), 3.57 (ddd, J=13.0, 7.9, 4.7 Hz, 2H), 3.40-3.29 (m, 1H), 2.63 (s, 1H), 2.36 (s, 2H), 1.84-1.71 (m, 4H), 1.45 (d, J=6.9 Hz, 6H); FXR EC$_{50}$=57 nM.

Example 50

2-(2-(5-Cyclopropyl-3-(3,5-dichloropyridin-4-yl) isoxazol-4-yl)-7-azaspiro[3.5]non-1-en-7-yl)-4-(trifluoromethoxy)benzo[d]thiazole-6-carboxylic acid

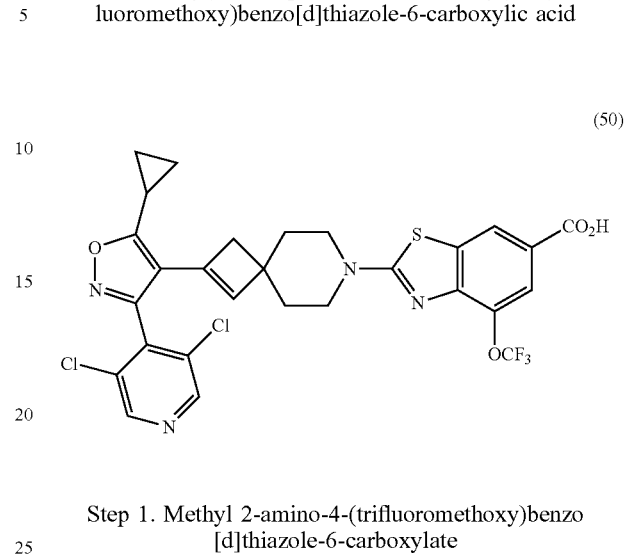

(50)

Step 1. Methyl 2-amino-4-(trifluoromethoxy)benzo[d]thiazole-6-carboxylate

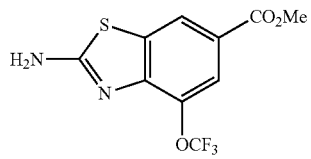 [SMILES: COC(=O)c1cc(OC(F)(F)F)c2nc(N)sc2c1]

Bromine (0.22 mL, 4.2 mmol) dissolved in acetic acid (2.8 mL) was added to a 0° C. solution of methyl 4-amino-3-(trifluoromethoxy)benzoate (1.0 g, 4.2 mmol) and sodium thiocyanate (1.4 g, 17.0 mmol) in acetic acid (5.7 mL). The reaction mixture was brought to room temperature and stirred overnight. More bromine (0.22 mL, 4.2 mmol) was added and the reaction mixture was heated to 50° C. After heating through the weekend the reaction mixture was partitioned between EtOAc and water. The organic layer was collected, dried over Na$_2$SO$_4$, filtered, and concentrated in vacuo. The residue was purified by flash chromatography on SiO$_2$ (0-100% EtOAc/hexanes, Isco 24 g column) to give methyl 2-amino-4-(trifluoromethoxy)benzo[d]thiazole-6-carboxylate (0.21 g, 0.72 mmol, 17% yield) as a yellow solid. $^1$H NMR (400 MHz, CDCl$_3$) δ 8.27 (d, J=1.5 Hz, 1H), 7.94 (t, J=1.5 Hz, 1H), 5.85 (br s, 2H), 3.96 (s, 3H).

Step 2. Methyl 2-bromo-4-(trifluoromethoxy)benzo[d]thiazole-6-carboxylate

tert-Butyl nitrite (0.11 mL, 0.86 mmol) was added to a rapidly stirring suspension of copper (II) bromide (0.18 g, 0.79 mmol) in acetonitrile (3.6 mL). After 5 minutes, the resulting dark brown mixture was added to a flask containing methyl 2-amino-4-(trifluoromethoxy)benzo[d]thiazole-6-carboxylate (0.21 g, 0.72 mmol) suspended in acetonitrile (0.5 mL). The reaction mixture was stirred at room temperature for 2.5 h and was then diluted with EtOAc and SiO$_2$ was added. The mixture was concentrated to give a free-flowing solid that was purified by flash chromatography on SiO$_2$ (0-40% EtOAc/hexanes, Isco 24 g column) to give methyl 2-bromo-4-(trifluoromethoxy)benzo[d]thiazole-6-carboxylate (0.13 g, 0.37 mmol, 51% yield) as a white solid. $^1$H NMR (400 MHz, CDCl$_3$) δ 8.50 (d, J=1.5 Hz, 1H), 8.06 (quin, J=1.4 Hz, 1H), 4.01 (s, 3H); $^{19}$F NMR (377 MHz, CDCl$_3$) δ −57.69 (s).

Example 50. 2-(2-(5-Cyclopropyl-3-(3,5-dichloropyridin-4-yl)isoxazol-4-yl)-7-azaspiro[3.5]non-1-en-7-yl)-4-(trifluoromethoxy)benzo[d]thiazole-6-carboxylic acid The title compound was prepared as described in General Method A for the preparation of Example 47 with replacement of ethyl 2-bromo-4-fluorobenzo[d]thiazole-6-carboxylate with methyl 2-bromo-4-(trifluoromethoxy)benzo[d]thiazole-6-carboxylate. MS (ESI) m/z: 637.2 [M+H]$^+$; $^1$H NMR (500 MHz, CDCl$_3$) δ 8.62 (s, 2H), 8.24 (s, 1H), 7.90 (s, 1H), 5.83 (s, 1H), 3.83-3.74 (m, 2H), 3.62-3.51 (m, 2H), 2.43 (s, 2H), 2.22-2.11 (m, 1H), 1.83-1.69 (m, 5H), 1.30 (br d, J=4.6 Hz, 2H), 1.18 (br d, J=7.6 Hz, 2H); FXR EC$_{50}$=11 nM.

Example 51

2-(2-(5-Cyclopropyl-3-(3,5-dichloropyridin-4-yl)isoxazol-4-yl)-7-azaspiro[3.5]non-1-en-7-yl)-5-methoxybenzo[d]thiazole-6-carboxylic acid (51)

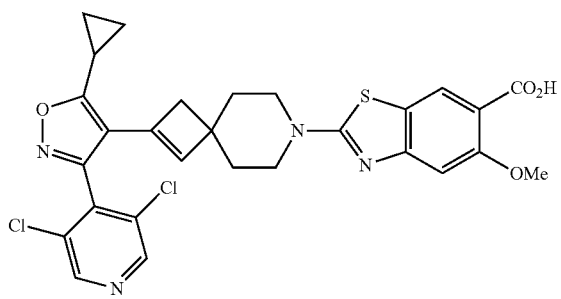

Step 1. Ethyl 2-bromo-5-methoxybenzo[d]thiazole-6-carboxylate

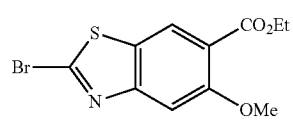 [SMILES: CCOC(=O)c1cc2sc(Br)nc2cc1OC]

The title compound can be prepared by the two-step procedure described in Example 50 for the preparation of methyl 2-bromo-4-(trifluoromethoxy)benzo[d]thiazole-6-carboxylate with the replacement of methyl 4-amino-3-(trifluoromethoxy)benzoate with ethyl 2-amino-4-methoxybenzoate. $^1$H NMR (500 MHz, CDCl$_3$) δ 8.23 (s, 1H), 7.55 (s, 1H), 4.40 (q, J=7.2 Hz, 2H), 3.98 (s, 3H), 1.41 (t, J=7.0 Hz, 3H).

Example 51. 2-(2-(5-Cyclopropyl-3-(3,5-dichloropyridin-4-yl)isoxazol-4-yl)-7-azaspiro[3.5]non-1-en-7-yl)-5-methoxybenzo[d]thiazole-6-carboxylic acid The title compound was prepared as described in General Method A for the preparation of Example 47 with replacement of ethyl 2-bromo-4-fluorobenzo[d]thiazole-6-carboxylate with ethyl 2-bromo-5-methoxybenzo[d]thiazole-6-carboxylate. MS (ESI) m/z: 583.1 [M+H]$^+$; $^1$H NMR (500 MHz, CDCl$_3$) δ 8.62 (s, 2H), 8.36 (s, 1H), 7.13 (s, 1H), 5.83 (s, 1H), 4.07 (s, 3H), 3.81-3.68 (m, 3H), 3.60-3.47 (m, 2H), 2.59 (s, 2H), 2.43 (s, 2H), 2.20-2.09 (m, 1H), 1.85-1.67 (m, 4H), 1.30 (br d, J=4.6 Hz, 2H), 1.18 (br d, J=7.7 Hz, 2H); FXR EC$_{50}$=72 nM.

Example 52

2-(2-(3-(3,5-Dichloropyridin-4-yl)-5-isopropylisoxazol-4-yl)-7-azaspiro[3.5]non-1-en-7-yl)-4-fluorobenzo[d]thiazole-6-carboxylic acid (52)

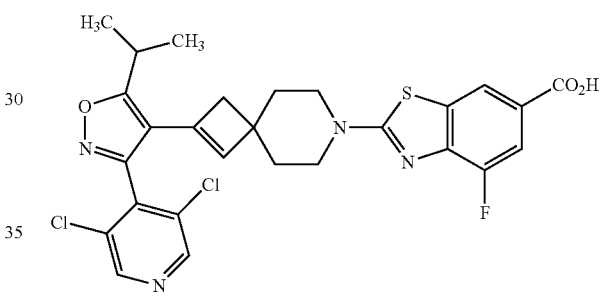

The title compound was prepared as described in General Method A for the preparation of Example 47 with replacement of cyclopropylacetylene with isopropylacetylene. MS (ESI) m/z: 573.3 [M+H]$^+$; $^1$H NMR (500 MHz, CDCl$_3$) δ 8.65 (s, 2H), 8.13 (s, 1H), 7.75 (br d, J=11.0 Hz, 1H), 5.83 (s, 1H), 3.84-3.75 (m, 2H), 3.66-3.50 (m, 2H), 3.36 (dquin, J=13.8, 6.9 Hz, 1H), 2.39 (s, 2H), 1.88-1.69 (m, 4H), 1.46 (br d, J=6.9 Hz, 6H); FXR EC$_{50}$=58 nM.

Example 53

7-(2-(5-Cyclopropyl-3-(2,6-dichlorophenyl)isoxazol-4-yl)-7-azaspiro[3.5]non-1-en-7-yl)cinnoline-3-carboxylic acid (53)

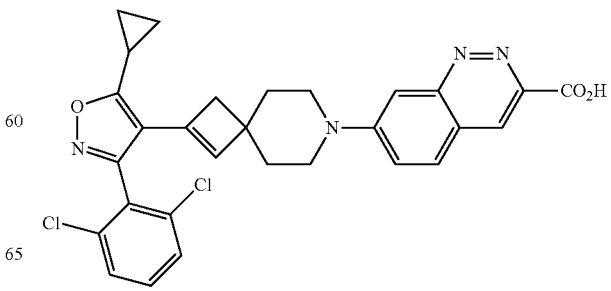

The title compound was prepared as described in General Method B for the preparation of Example 7 with replacement of methyl 6-chloro-1-methyl-1H-pyrrolo[2,3-b]pyridine-3-carboxylate with ethyl 7-chlorocinnoline-3-carboxylate, HCl. MS (ESI) m/z: 547.3 [M+H]$^+$; $^1$H NMR (500 MHz, DMSO-d$_6$) δ 8.54 (br s, 1H), 8.02 (br d, J=9.16 Hz, 1H), 7.83 (br d, J=8.85 Hz, 1H), 7.67-7.75 (m, 2H), 7.59-7.66 (m, 2H), 5.91 (s, 1H), 3.69 (br s, 2H), 3.32-3.46 (m, 1H), 3.21 (s, 1H), 2.40 (m, 3H), 1.61-1.83 (m, 4H), 1.14-1.36 (m, 4H); FXR EC$_{50}$=46 nM.

Example 54

7-(2-(5-Cyclopropyl-3-(2-(trifluoromethyl)phenyl)isoxazol-4-yl)-7-azaspiro[3.5]non-1-en-7-yl)cinnoline-3-carboxylic acid

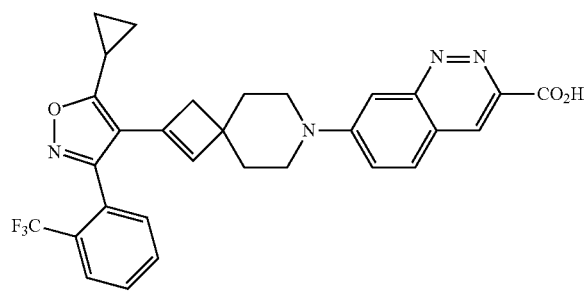

(54)

The title compound was prepared as described in General Method B for the preparation of Example 53 with replacement of 2,6-dichlorobenzaldehyde with 2-(trifluoromethyl)benzaldehyde. MS (ESI) m/z: 547.2 [M+H]$^+$; $^1$H NMR (500 MHz, DMSO-d$_6$) δ 8.52 (s, 1H), 7.99 (d, J=9.16 Hz, 1H), 7.94 (br d, J=7.63 Hz, 1H), 7.81 (br dd, J=7.63, 14.04 Hz, 3H), 7.59 (br d, J=6.41 Hz, 2H), 5.72-5.87 (m, 1H), 3.66 (br d, J=13.73 Hz, 2H), 3.33 (br t, J=8.39 Hz, 1H), 3.17 (dd, J=5.49, 10.38 Hz, 1H), 2.33 (m, 3H), 1.65 (br dd, J=3.36, 12.51 Hz, 4H), 1.08-1.30 (m, 4H); FXR EC$_{50}$=177 nM.

Example 55

7-(2-(5-Cyclopropyl-3-(3,5-dichloropyridin-4-yl)isoxazol-4-yl)-7-azaspiro[3.5]non-1-en-7-yl)cinnoline-3-carboxylic acid

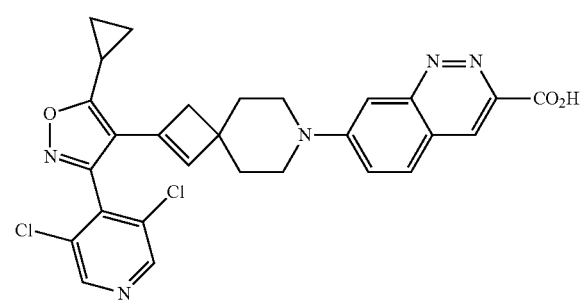

(55)

The title compound was prepared as described in General Method B for the preparation of Example 53 with replacement of 2,6-dichlorobenzaldehyde with 3,5-dichloroisonicotinaldehyde. MS (ESI) m/z: 548.0 [M+H]$^+$; $^1$H NMR (500 MHz, Methanol-d$_4$) δ 8.92 (s, 1H), 8.74 (s, 2H), 8.14 (d, J=9.63 Hz, 1H), 7.90-8.07 (m, 1H), 7.15-7.32 (m, 1H), 5.94 (s, 1H), 3.96 (br d, J=13.75 Hz, 2H), 3.53-3.76 (m, 2H), 2.56 (s, 2H), 2.36 (s, 1H), 1.84 (br t, J=4.13 Hz, 4H), 1.19-1.47 (m, 4H); FXR EC$_{50}$=191 nM.

Example 56

7-(2-(3-(2-Chloro-6-fluorophenyl)-5-cyclopropylisoxazol-4-yl)-7-azaspiro[3.5]non-1-en-7-yl)cinnoline-3-carboxylic acid (56)

The title compound was prepared as described in General Method B for the preparation of Example 53 with replacement of 2,6-dichlorobenzaldehyde with 2-chloro-6-fluorobenzaldehyde. MS (ESI) m/z: 531.0 [M+H]$^+$; $^1$H NMR (500 MHz, DMSO-d$_6$) δ 8.54 (s, 1H), 8.01 (d, J=9.2 Hz, 1H), 7.82 (d, J=9.8 Hz, 1H), 7.70-7.53 (m, 3H), 7.45 (t, J=8.7 Hz, 1H), 5.93 (s, 1H), 3.69 (br s, 2H), 2.42 (s, 2H), 2.35 (br s, 1H), 1.68 (br s, 4H), 1.27-1.08 (m, 4H), additional signals missing due to water signal suppression; FXR EC$_{50}$=194 nM.

Example 57

7-(2-(3-(2-Chloro-6-methylphenyl)-5-cyclopropylisoxazol-4-yl)-7-azaspiro[3.5]non-1-en-7-yl)cinnoline-3-carboxylic acid (57)

The title compound was prepared as described in General Method B for the preparation of Example 53 with replacement of 2,6-dichlorobenzaldehyde with 2-chloro-6-methylbenzaldehyde. MS (ESI) m/z: 527.2 [M+H]$^+$; $^1$H NMR (500 MHz, DMSO-d$_6$) δ 8.54 (s, 1H), 8.00 (d, J=9.2 Hz, 1H), 7.86-7.77 (m, 1H), 7.59 (s, 1H), 7.49-7.43 (m, 2H), 7.39-7.33 (m, 1H), 5.77 (s, 1H), 3.72-3.65 (m, 2H), 3.37-3.23 (m, 2H), 2.43-2.30 (m, 3H), 2.11 (s, 3H), 1.71-1.59 (m, 4H), 1.26-1.08 (m, 4H); FXR EC$_{50}$=227 nM.

Example 58

6-(2-(5-Cyclopropyl-3-(2-(trifluoromethyl)phenyl)isoxazol-4-yl)-7-azaspiro[3.5]non-1-en-7-yl)-4-(difluoromethoxy)quinoline-2-carboxylic acid (58)

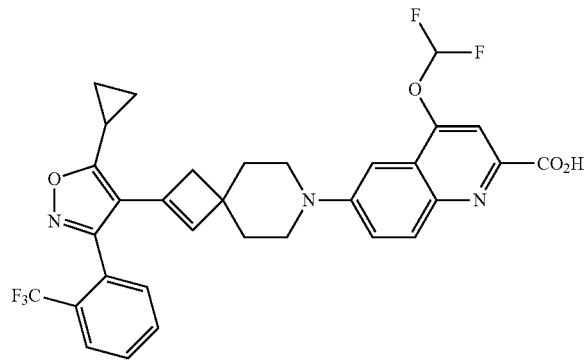

Step 1. Methyl 6-bromo-4-(difluoromethoxy)quinoline-2-carboxylate

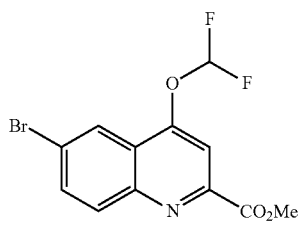 [SMILES: COC(=O)c1cc(OC(F)F)c2cc(Br)ccc2n1]

To a stirred suspension of Cs$_2$CO$_3$ (0.98 g, 3.0 mmol) in DMF (5 mL) at 0° C. was added methyl 6-bromo-4-hydroxyquinoline-2-carboxylate (0.28 g, 1.0 mmol) and sodium chlorodifluoroacetate (0.46 g, 3.0 mmol). The reaction mixture was stirred with heating at 80° C. for 30 minutes. After cooling the reaction mixture to room temperature, water (25 mL) was added, and the resulting suspension was stirred for 1 hour. The solid was collected by suction filtration and washed with water (2×5 mL). After drying under vacuum overnight, methyl 6-bromo-4-(difluoromethoxy)quinoline-2-carboxylate (0.28 g, 0.81 mmol, 81% yield) was obtained as a white solid. MS (ESI) m/z: 333.9 [M+H]$^+$; $^1$H NMR (400 MHz, CDCl$_3$) δ 8.38 (d, J=2.20 Hz, 1H), 8.16 (d, J=9.02 Hz, 1H), 7.91 (dd, J=2.20, 9.24 Hz, 1H), 7.85 (t, J=1.10 Hz, 1H), 6.61-7.17 (m, 1H), 4.09 (s, 3H).

Example 58. 6-(2-(5-Cyclopropyl-3-(2-(trifluoromethyl)phenyl)isoxazol-4-yl)-7-azaspiro[3.5]non-1-en-7-yl)-4-(difluoromethoxy)quinoline-2-carboxylic acid The title compound was prepared as described in General Method B for the preparation of Example 54 with replacement of ethyl 7-chlorocinnoline-3-carboxylate, HCl with methyl 6-bromo-4-(difluoromethoxy)quinoline-2-carboxylate. MS (ESI) m/z: 612.1 [M+H]$^+$; $^1$H NMR (400 MHz, CDCl$_3$) δ 7.95 (br d, J=9.24 Hz, 1H), 7.77-7.84 (m, 1H), 7.74 (s, 1H), 7.54-7.68 (m, 3H), 7.43 (br d, J=6.60 Hz, 1H), 7.25 (br d, J=2.20 Hz, 1H), 6.69-7.12 (m, 1H), 5.64 (s, 1H), 3.45-3.63 (m, 2H), 3.27 (ddd, J=4.18, 8.14, 12.54 Hz, 2H), 2.37 (s, 2H), 2.15 (ddd, J=3.30, 5.01, 8.42 Hz, 1H), 1.65-1.86 (m, 4H), 1.10-1.33 (m, 4H); FXR EC$_{50}$=2.3 nM.

Example 59

2-(2-(5-Cyclopropyl-3-(3,5-dichloropyridin-4-yl)isoxazol-4-yl)-7-azaspiro[3.5]non-1-en-7-yl)-4-methoxybenzo[d]thiazole-6-carboxylic acid (59)

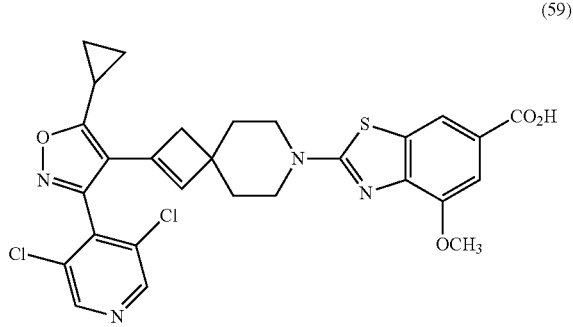 [SMILES: COc1cc(C(=O)O)cc2sc(N3CCC4(C=C(c5c(-c6c(Cl)cncc6Cl)noc5C5CC5)C4)CC3)nc12]

The title compound was prepared as described in General Method A for the preparation of Example 47 with replacement of ethyl 2-bromo-4-fluorobenzo[d]thiazole-6-carboxylate with methyl 2-bromo-4-methoxybenzo[d]thiazole-6-carboxylate. MS (ESI) m/z: 583.1 [M+H]$^+$; $^1$H NMR (400 MHz, Methanol-d$_4$) δ 8.74 (s, 2H), 7.99 (d, J=1.54 Hz, 1H), 7.55 (d, J=1.32 Hz, 1H), 5.90-6.01 (m, 1H), 4.01 (s, 3H), 3.72-3.88 (m, 2H), 3.59 (s, 2H), 2.51 (s, 2H), 2.25-2.40 (m, 1H), 1.78 (br d, J=4.18 Hz, 4H), 1.12-1.37 (m, 4H); FXR EC$_{50}$=4.1 nM.

Example 60

2-(2-(5-Cyclopropyl-3-(3,5-dichloropyridin-4-yl)isoxazol-4-yl)-7-azaspiro[3.5]non-1-en-7-yl)-7-(trifluoromethyl)quinoline-5-carboxylic acid (60)

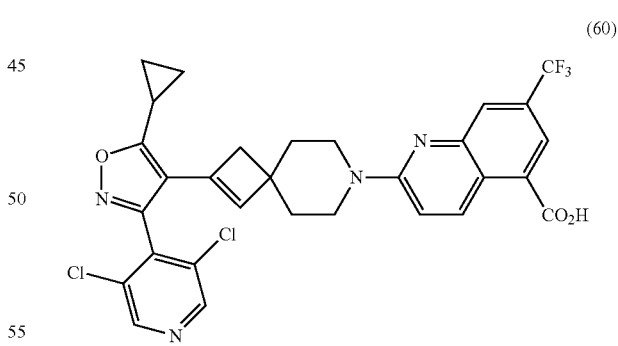

Step 1. Ethyl 7-(trifluoromethyl)quinoline-5-carboxylate

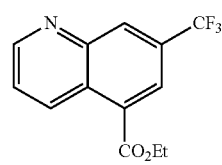 [SMILES: CCOC(=O)c1cc(C(F)(F)F)cc2ncccc12]

A solution of 3-amino-5-(trifluoromethyl)benzoic acid (0.51 g, 2.5 mmol), glycerol (0.36 mL, 5.0 mmol), and 3-nitrobenzenesulfonic acid sodium salt (1.679 g, 7.46 mmol) in 75% $H_2SO_4$ (5.9 mL) was heated to 100° C. for 1.5 h and then to 140° C. for 1 h. The reaction mixture was cooled to room temperature and then EtOH (10 mL) was added and the reaction mixture was heated to 85° C. overnight. The reaction mixture was cooled to room temperature and poured into 40 mL of ice water with 3.3 g NaOH. 1M $K_2HPO_4$ was added until the solution reached pH-7. The solution was extracted with EtOAc. The organic layer was washed with brine, dried over $Na_2SO_4$, filtered, and concentrated in vacuo. The residue was purified by flash chromatography on $SiO_2$ (0-100% EtOAc/hexanes, Isco 24 g column) to give a mixture of ethyl 7-(trifluoromethyl)quinoline-5-carboxylate and ethyl 5-(trifluoromethyl)quinoline-7-carboxylate (0.34 g, 1.3 mmol, 51% yield) as a beige solid. MS (ESI) m/z: 270.0 $[M+H]^+$.

Step 2.
5-(Ethoxycarbonyl)-7-(trifluoromethyl)quinoline 1-oxide

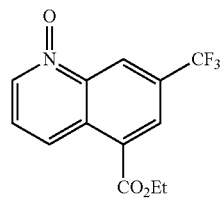 [SMILES: CCOC(=O)c1cc(C(F)(F)F)cc2c1ccc[n+]2[O-]]

m-Chloroperoxybenzoic acid (0.2 g, 0.87 mmol) was added portion wise to a solution of ethyl 7-(trifluoromethyl)quinoline-5-carboxylate (0.18 g, 0.67 mmol) in dichloromethane (5.1 mL). The reaction was stirred at room temperature overnight. The solvent volume was reduced by ~25% and the crude reaction mixture was loaded directly onto a $SiO_2$ column for purification by flash chromatography on $SiO_2$ (0-10% MeOH/DCM, Isco 24 g column) to give 5-(ethoxycarbonyl)-7-(trifluoromethyl)quinoline 1-oxide (0.20 g, 0.68 mmol, 100% yield) as a yellow solid. $^1$H NMR (400 MHz, $CDCl_3$) δ 9.36 (s, 1H), 8.97 (d, J=9.0 Hz, 1H), 8.64 (d, J=5.5 Hz, 1H), 8.53 (d, J=2.0 Hz, 1H), 7.53 (dd, J=9.1, 6.1 Hz, 1H), 4.53 (q, J=7.3 Hz, 2H), 1.50 (t, J=7.2 Hz, 3H); $^{19}$F NMR (377 MHz, $CDCl_3$) δ −62.91 (s).

Step 3. Ethyl 2-chloro-7-(trifluoromethyl)quinoline-5-carboxylate

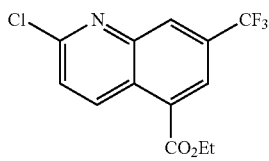 [SMILES: CCOC(=O)c1cc(C(F)(F)F)cc2nc(Cl)ccc12]

Phosphorus oxychloride (0.039 mL, 0.42 mmol) followed by DMF (0.014 mL, 0.18 mmol) were added to a 0° C. solution of 5-(ethoxycarbonyl)-7-(trifluoromethyl) quinoline 1-oxide (0.1 g, 0.35 mmol) in dichloromethane (3.5 mL). After 5 minutes the reaction mixture was brought to room temperature. After stirring at room temp for 30 h the crude reaction mixture was purified by flash chromatography on $SiO_2$ (0-70% EtOAc/hex, Isco 12 g column, product eluted around 20% EtOAc) to give a mixture of ethyl 2-chloro-7-(trifluoromethyl)quinoline-5-carboxylate and ethyl 2-chloro-5-(trifluoromethyl)quinoline-7-carboxylate as a white solid. The mixture was used in the next step.

Example 60. 2-(2-(5-Cyclopropyl-3-(3,5-dichloropyridin-4-yl)isoxazol-4-yl)-7-azaspiro[3.5]non-1-en-7-yl)-7-(trifluoromethyl)quinoline-5-carboxylic acid The title compound was prepared as described in General Method A for the preparation of Example 47 with replacement of ethyl 2-bromo-4-fluorobenzo[d]thiazole-6-carboxylate with ethyl 2-chloro-7-(trifluoromethyl)quinoline-5-carboxylate. MS (ESI) m/z: 615.1 $[M+H]^+$; $^1$H NMR (500 MHz, $CDCl_3$) δ 9.06 (br d, J=9.2 Hz, 1H), 8.64 (s, 2H), 8.18 (br s, 1H), 8.15 (br s, 1H), 7.15 (br d, J=9.6 Hz, 1H), 5.86 (s, 1H), 4.07-3.83 (m, 2H), 3.66-3.49 (m, 2H), 2.45 (s, 2H), 2.30-2.12 (m, 1H), 1.73 (br s, 4H), 1.38-1.26 (m, 2H), 1.20 (br d, J=7.9 Hz, 2H); FXR $EC_{50}$=7.2 nM.

Example 61

2-(2-(5-Cyclopropyl-3-(3,5-dichloropyridin-4-yl)isoxazol-4-yl)-7-azaspiro[3.5]non-1-en-7-yl)-4-methylbenzo[d]thiazole-6-carboxylic acid (61)

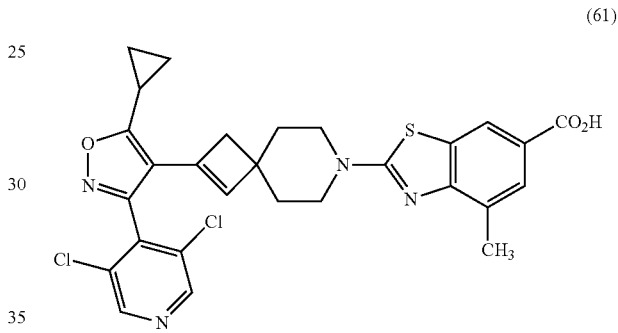

The title compound was prepared as described in General Method A for the preparation of Example 47 with replacement of ethyl 2-bromo-4-fluorobenzo[d]thiazole-6-carboxylate with methyl 2-bromo-4-methylbenzo[d]thiazole-6-carboxylate. MS (ESI) m/z: 566.9 $[M+H]^+$; $^1$H NMR (400 MHz, Methanol-$d_4$) δ 8.64 (s, 2H), 8.09 (d, J=1.10 Hz, 1H), 7.74 (d, J=0.66 Hz, 1H), 7.67 (s, 1H), 5.67-6.00 (m, 1H), 3.76 (s, 2H), 3.54 (br d, J=8.36 Hz, 2H), 2.49 (s, 3H), 2.45 (s, 2H), 2.25 (s, 1H), 2.00 (s, 1H), 1.64-1.89 (m, 4H), 1.05-1.44 (m, 5H); FXR $EC_{50}$=7.2 nM.

Example 62

2-(2-(5-Cyclopropyl-3-(3,5-dichloropyridin-4-yl)isoxazol-4-yl)-7-azaspiro[3.5]non-1-en-7-yl)thiazolo[5,4-b]pyridine-5-carboxylic acid (62)

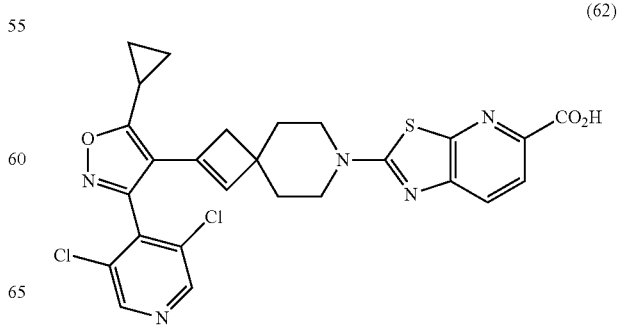

Step 1. 4-(7-(5-Chlorothiazolo[5,4-b]pyridin-2-yl)-7-azaspiro[3.5]non-1-en-2-yl)-5-cyclopropyl-3-(3,5-dichloropyridin-4-yl)isoxazole

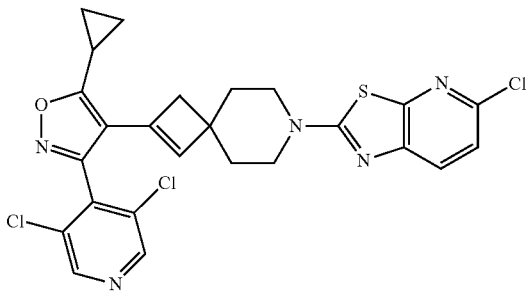 [SMILES: Clc1ccc2nc(N3CCC4(C=C(c5c(-c6c(Cl)cncc6Cl)noc5C5CC5)C4)CC3)sc2n1]

A suspension of 5-cyclopropyl-3-(3,5-dichloropyridin-4-yl)-4-(7-azaspiro[3.5]non-1-en-2-yl)isoxazole (150 mg, 0.40 mmol), 2-bromo-5-chlorothiazolo[5,4-b]pyridine (119 mg, 0.48 mmol), and cesium carbonate (325 mg, 1.0 mmol) in DMA (1.2 mL) was heated at 50° C. for 3 hours. The crude reaction mixture was purified directly by flash chromatography on SiO$_2$ (0-100% EtOAc/hexanes, Isco 40 g column) to yield 4-(7-(5-chlorothiazolo[5,4-b]pyridin-2-yl)-7-azaspiro[3.5]non-1-en-2-yl)-5-cyclopropyl-3-(3,5-dichloropyridin-4-yl)isoxazole (166 mg, 0.29 mmol, 73% yield) as a gum. MS (ESI) m/z: 543.9 [M+H]$^+$; $^1$H NMR (400 MHz, CDCl$_3$) δ 8.63 (s, 2H), 7.60 (d, J=8.36 Hz, 1H), 7.19 (d, J=8.36 Hz, 1H), 5.81 (s, 1H), 3.73 (td, J=5.06, 13.42 Hz, 2H), 3.49 (ddd, J=4.62, 8.03, 13.09 Hz, 2H), 2.44 (s, 2H), 2.10-2.25 (m, 1H), 1.70-1.81 (m, 4H), 1.13-1.36 (m, 4H).

Step 2. Methyl 2-(2-(5-cyclopropyl-3-(3,5-dichloropyridin-4-yl)isoxazol-4-yl)-7-azaspiro[3.5]non-1-en-7-yl)thiazolo[5,4-b]pyridine-5-carboxylate

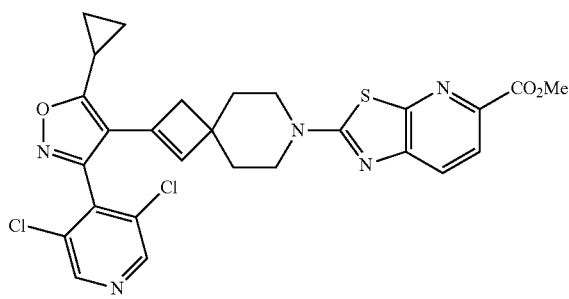 [SMILES: COC(=O)c1ccc2nc(N3CCC4(C=C(c5c(-c6c(Cl)cncc6Cl)noc5C5CC5)C4)CC3)sc2n1]

A mixture of 4-(7-(5-chlorothiazolo[5,4-b]pyridin-2-yl)-7-azaspiro[3.5]non-1-en-2-yl)-5-cyclopropyl-3-(3,5-dichloropyridin-4-yl)isoxazole (100 mg, 0.18 mmol), methanol (5 mL, 0.18 mmol), 1,3-bis(diphenylphosphanyl)propane (9.1 mg, 0.022 mmol), palladium(II) acetate (4.9 mg, 0.022 mmol), and potassium carbonate (40.6 mg, 0.29 mmol) in DMF (2.5 mL) was heated under CO (48 psi) in a pressure bottle at 85° C. for one day. The mixture was diluted with ethyl acetate (10 mL) and filtered through Celite. The filtrate was concentrated under vacuum to dryness. The residue was dissolved in ethyl acetate (20 mL) and washed with water (10 mL). The organic layer was dried over anhydrous Na$_2$SO$_4$, filtered and concentrated to dryness in vacuo. The residue was purified by flash chromatography on SiO$_2$ (0-100% EtOAc/hexanes, Isco 40 g column) to yield methyl 2-(2-(5-cyclopropyl-3-(3,5-dichloropyridin-4-yl)isoxazol-4-yl)-7-azaspiro[3.5]non-1-en-7-yl)thiazolo[5,4-b]pyridine-5-carboxylate with approximately 85% purity. The material was used for next step without further purification. MS (ESI) m/z: 568.0 [M+H]$^+$.

Example 62. 2-(2-(5-Cyclopropyl-3-(3,5-dichloropyridin-4-yl)isoxazol-4-yl)-7-azaspiro[3.5]non-1-en-7-yl)thiazolo[5,4-b]pyridine-5-carboxylic acid To a solution of methyl 2-(2-(5-cyclopropyl-3-(3,5-dichloropyridin-4-yl)isoxazol-4-yl)-7-azaspiro[3.5]non-1-en-7-yl)thiazolo[5,4-b]pyridine-5-carboxylate (20 mg, 0.04 mmol) in 1:1 methanol/THF (0.35 mL), was added 1N NaOH (0.11 mL, 0.11 mmol). The reaction mixture was heated to 60° C. for 15 minutes. The crude reaction mixture was acidified with TFA and purified directly by C-18 reverse phase flash chromatography (10-100% B in A, A =10:90:0.1 MeCN:H$_2$O:TFA, B=90:10:0.1 MeCN:H$_2$O:TFA, 18 min linear gradient, Isco 12 g C-18 gold column) to yield 2-(2-(5-cyclopropyl-3-(3,5-dichloropyridin-4-yl)isoxazol-4-yl)-7-azaspiro[3.5]non-1-en-7-yl)thiazolo[5,4-b]pyridine-5-carboxylic acid (11 mg, 0.019 mmol, 54% yield) as a red solid. MS (ESI) m/z: 554.0 [M+H]$^+$; $^1$H NMR (400 MHz, CDCl$_3$) δ 8.67 (s, 2H), 8.17 (d, J=8.36 Hz, 1H), 7.83 (s, 1H), 5.74-5.95 (m, 1H), 3.75-3.98 (m, 2H), 3.48-3.69 (m, 2H), 2.48 (s, 2H), 2.11-2.26 (m, 1H), 1.82 (br t, J=4.95 Hz, 4H), 1.14-1.51 (m, 4H); FXR EC$_{50}$=24 nM.

Example 63

2-(2-(5-Cyclopropyl-3-(3,5-dichloropyridin-4-yl)isoxazol-4-yl)-7-azaspiro[3.5]non-1-en-7-yl)benzo[d]thiazole-6-carboxylic acid (63)

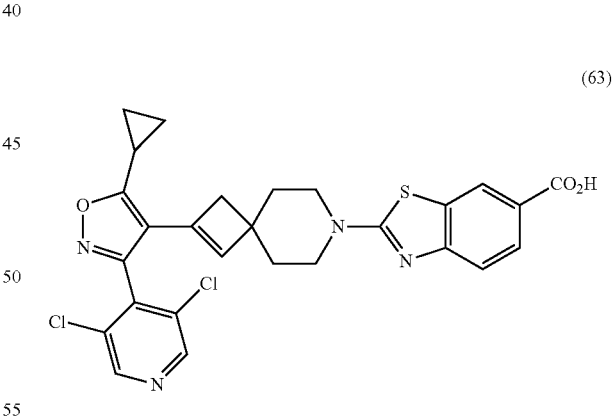

The title compound was prepared as described in General Method A for the preparation of Example 47 with replacement of ethyl 2-bromo-4-fluorobenzo[d]thiazole-6-carboxylate with ethyl 2-chlorobenzo[d]thiazole-6-carboxylate. MS (ESI) m/z: 552.9 [M+H]$^+$; $^1$H NMR (400 MHz, Methanol-d$_4$) δ 8.67 (s, 2H), 8.31 (d, J=1.54 Hz, 1H), 7.99 (dd, J=1.76, 8.58 Hz, 1H), 7.69 (s, 1H), 7.46 (d, J=8.58 Hz, 1H), 5.76-5.99 (m, 1H), 3.79 (br d, J=13.64 Hz, 2H), 3.48-3.68 (m, 2H), 2.50 (s, 2H), 2.15-2.34 (m, 1H), 2.04 (s, 1H), 1.70-1.89 (m, 4H), 1.16-1.40 (m, 4H); FXR EC$_{50}$=62 nM.

Example 64

2-(2-(5-Cyclopropyl-3-(3,5-dichloropyridin-4-yl)isoxazol-4-yl)-7-azaspiro[3.5]non-1-en-7-yl)-8-methoxyquinoline-5-carboxylic acid

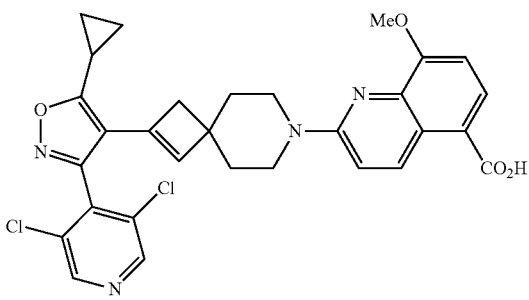

(64)

Step 1. Methyl 8-methoxyquinoline-5-carboxylate

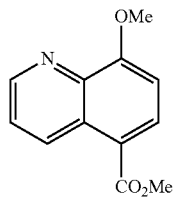 [SMILES: COC(=O)c1ccc(OC)c2ncccc12]

A solution of 3-amino-4-methoxybenzoic acid (3.3 g, 19.7 mmol), glycerol (2.9 mL, 39.5 mmol), and 3-nitrobenzenesulfonic acid sodium salt (13.3 g, 59.2 mmol) in 75% $H_2SO_4$ (47.0 mL) was heated to 100° C. for 2 h and then 140° C. for 1 h. The reaction mixture was cooled to room temperature and then MeOH (40 mL) was added and the reaction mixture was heated to 60° C. overnight. The reaction mixture was cooled to room temperature and poured into ice water and made basic with 12 M $NH_4OH$. The resulting mixture was extracted with EtOAc. The layers were separated and the aqueous layer was further extracted with EtOAc (2×). The combined organic layers were washed with brine, dried over $MgSO_4$, filtered, and concentrated in vacuo. The crude product was dry loaded onto $SiO_2$ and purified by flash chromatography on $SiO_2$ (0-100% EtOAc/hexanes) to provide methyl 8-methoxyquinoline-5-carboxylate (2.2 g, 9.9 mmol, 50% yield) as a white solid. $^1$H NMR (500 MHz, CDCl$_3$) δ 9.50 (dd, J=8.8, 1.7 Hz, 1H), 9.00 (dd, J=3.9, 1.7 Hz, 1H), 8.37 (d, J=8.3 Hz, 1H), 7.59 (dd, J=8.8, 4.1 Hz, 1H), 7.08 (d, J=8.3 Hz, 1H), 4.19 (s, 3H), 4.00 (s, 3H).

Step 2. 8-Methoxy-5-(methoxycarbonyl)quinoline 1-oxide

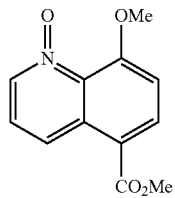 [SMILES: COC(=O)c1ccc(OC)c2c1ccc[n+]2[O-]]

m-Chloroperoxybenzoic acid (0.97 g, 4.3 mmol) was added portion wise to a solution of methyl 8-methoxyquinoline-5-carboxylate (0.72 g, 3.3 mmol) in dichloromethane (25.5 mL). The reaction was stirred at room temperature overnight. The solvent volume was reduced by ~25% and the crude reaction mixture was loaded directly onto a $SiO_2$ column for purification by flash chromatography on $SiO_2$ (0-10% MeOH/DCM, Isco 40 g column) to give 8-methoxy-5-(methoxycarbonyl)quinoline 1-oxide (0.6 g, 2.6 mmol, 78% yield) as a yellow solid. $^1$H NMR (400 MHz, CDCl$_3$) δ 9.02 (dd, J=8.9, 1.0 Hz, 1H), 8.47 (dd, J=6.2, 1.1 Hz, 1H), 8.31 (d, J=8.8 Hz, 1H), 7.34 (dd, J=8.9, 6.1 Hz, 1H), 7.07 (d, J=8.8 Hz, 1H), 4.11 (s, 3H), 3.99 (s, 3H).

Step 3. Methyl 2-chloro-8-methoxyquinoline-5-carboxylate

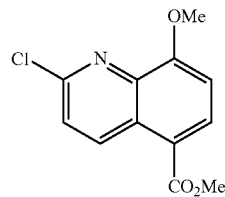 [SMILES: COC(=O)c1ccc(OC)c2nc(Cl)ccc12]

Phosphorus oxychloride (0.29 mL, 3.1 mmol) followed by DMF (0.10 mL, 1.3 mmol) were added to a 0° C. solution of 8-methoxy-5-(methoxycarbonyl)quinoline 1-oxide (0.6 g, 2.6 mmol) in dichloromethane (26 mL). After 5 minutes the reaction mixture was brought to room temperature. After 24 h the crude reaction mixture was purified by flash chromatography on $SiO_2$ (0-85% EtOAc/hexanes, followed by 0-10% DCM/MeOH, Isco 40 g column) to give methyl 2-chloro-8-methoxyquinoline-5-carboxylate (0.58 g, 2.3 mmol, 90% yield) as a white solid. $^1$H NMR (400 MHz, DMSO-d$_6$) δ 9.35 (d, J=9.0 Hz, 1H), 8.34 (d, J=8.4 Hz, 1H), 7.78 (d, J=9.0 Hz, 1H), 7.38 (d, J=8.6 Hz, 1H), 4.07 (s, 3H), 3.92 (s, 3H).

Example 64. 2-(2-(5-Cyclopropyl-3-(3,5-dichloropyridin-4-yl)isoxazol-4-yl)-7-azaspiro[3.5]non-1-en-7-yl)-8-methoxyquinoline-5-carboxylic acid The title compound was prepared as described in General Method A for the preparation of Example 47 with replacement of ethyl 2-bromo-4-fluorobenzo[d]thiazole-6-carboxylate with methyl 2-chloro-8-methoxyquinoline-5-carboxylate. MS (ESI) m/z: 577.0 [M+H]$^+$; $^1$H NMR (500 MHz, CDCl$_3$) δ 9.16 (br d, J=9.6 Hz, 1H), 8.61 (s, 2H), 8.08 (br d, J=8.3 Hz, 1H), 7.09 (br d, J=9.5 Hz, 1H), 6.92 (br d, J=8.2 Hz, 1H), 5.85 (s, 1H), 4.06 (s, 3H), 4.02-3.83 (m, 2H), 3.71 (s, 1H), 3.62-3.47 (m, 2H), 2.41 (s, 2H), 2.26-2.11 (m, 1H), 1.73 (br s, 4H), 1.29 (br d, J=4.6 Hz, 2H), 1.17 (br d, J=7.9 Hz, 2H); FXR EC$_{50}$=49 nM.

Example 65

2-(2-(5-Cyclopropyl-3-(3,5-dichloropyridin-4-yl)isoxazol-4-yl)-7-azaspiro[3.5]non-1-en-7-yl)quinoline-5-carboxylic acid

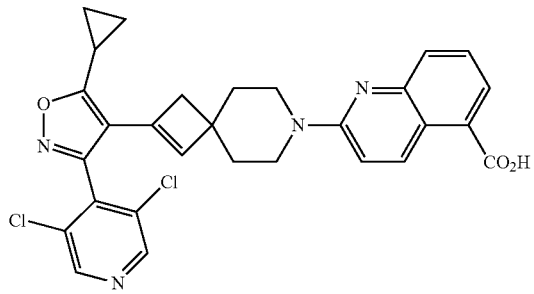
(65)

The title compound was prepared as described in General Method A for the preparation of Example 47 with replacement of ethyl 2-bromo-4-fluorobenzo[d]thiazole-6-carboxylate with methyl 2-chloroquinoline-5-carboxylate. MS (ESI) m/z: 547.2 [M+H]$^+$; $^1$H NMR (500 MHz, DMSO-d$_6$) δ 8.92-8.86 (m, 1H), 8.85 (s, 2H), 7.79 (br d, J=7.0 Hz, 1H), 7.73 (br d, J=7.9 Hz, 1H), 7.57 (br t, J=7.8 Hz, 1H), 7.31 (br d, J=9.5 Hz, 1H), 5.98 (s, 1H), 3.98-3.85 (m, 2H), 3.48 (br d, J=7.3 Hz, 1H), 2.39 (br s, 3H), 1.59 (br s, 4H), 1.33-1.19 (m, 3H), 1.16 (br s, 2H); FXR EC$_{50}$=65 nM.

Example 66

6-(2-(5-Cyclopropyl-3-(3,5-dichloropyridin-4-yl)isoxazol-4-yl)-7-azaspiro[3.5]non-1-en-7-yl)nicotinic acid

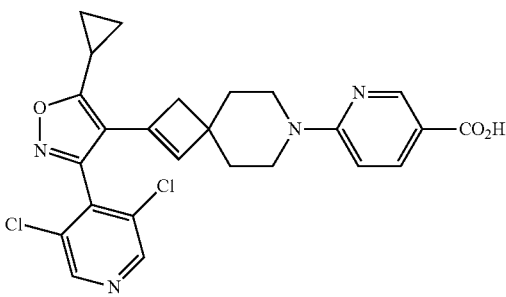
(66)

The title compound was prepared as described in General Method A for the preparation of Example 47 with replacement of ethyl 2-bromo-4-fluorobenzo[d]thiazole-6-carboxylate with methyl 6-fluoronicotinate. MS (ESI) m/z: 497.1 [M+H]$^+$; $^1$H NMR (500 MHz, DMSO-d$_6$) δ 8.88 (s, 2H), 8.60 (d, J=1.8 Hz, 1H), 7.89 (dd, J=9.2, 2.1 Hz, 1H), 6.84 (d, J=9.2 Hz, 1H), 5.98 (s, 1H), 3.93-3.74 (m, 2H), 2.44-2.30 (m, 3H), 1.56 (br s, 4H), 1.32-1.20 (m, 4H), 1.17 (br d, J=2.7 Hz, 2H); FXR EC$_{50}$=342 nM.

Example 67

6-(2-(5-Cyclopropyl-3-(2,6-dichloro-4-fluorophenyl)isoxazol-4-yl)-7-azaspiro[3.5]non-1-en-7-yl)nicotinic acid

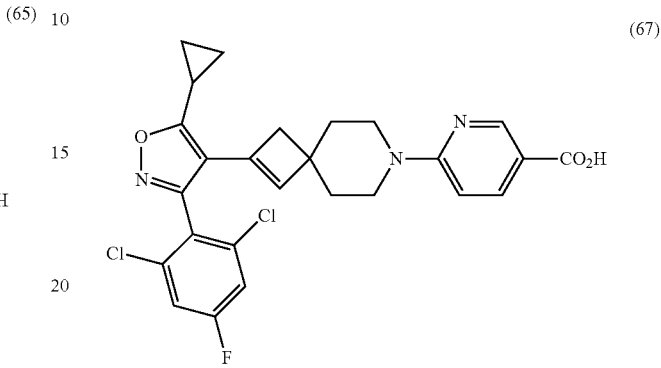
(67)

The title compound was prepared as described in General Method A for the preparation of Example 66 with replacement of 3,5-dichloroisonicotinaldehyde with 2,6-dichloro-4-fluorobenzaldehyde. MS (ESI) m/z: 514.1 [M+H]$^+$; $^1$H NMR (500 MHz, DMSO-d$_6$) δ 8.61 (s, 1H), 7.91 (br d, J=8.9 Hz, 1H), 7.78 (br d, J=8.2 Hz, 2H), 6.85 (br d, J=9.2 Hz, 1H), 5.94 (s, 1H), 3.95-3.80 (m, 2H), 2.44-2.29 (m, 3H), 1.94 (s, 2H), 1.57 (br s, 4H), 1.29-1.18 (m, 2H), 1.17 (br s, 2H) additional signals lost due to water suppression in $^1$H NMR; FXR EC$_{50}$=493 nM.

Example 68

2-(2-(5-Cyclopropyl-3-(3,5-difluoropyridin-4-yl)isoxazol-4-yl)-7-azaspiro[3.5]non-1-en-7-yl)-4-fluorobenzo[d]thiazole-6-carboxylic acid

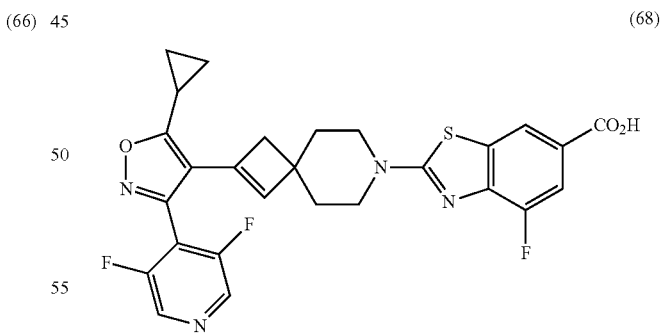
(68)

The title compound was prepared as described in General Method A for the preparation of Example 1 with replacement of 2,6-dichlorobenzaldehyde with 3,5-difluoroisonicotinaldehyde. MS (ESI) m/z: 539.0 [M+H]$^+$; $^1$H NMR (400 MHz, DMSO-d$_6$) δ 8.81 (s, 2H), 8.21 (d, J=1.5 Hz, 1H), 7.59 (dd, J=1.5, 11.5 Hz, 1H), 6.15 (s, 1H), 3.88-3.40 (m, 4H), 2.51 (s, 2H), 2.40-2.28 (m, 1H), 1.70 (dd, J=4.7, 7.0 Hz, 4H), 1.30-1.06 (m, 4H); FXR EC$_{50}$=442 nM.

Example 69

2-(2-(5-Cyclopropyl-3-(3-fluoro-5-methoxypyridin-4-yl)isoxazol-4-yl)-7-azaspiro[3.5]non-1-en-7-yl)-4-fluorobenzo[d]thiazole-6-carboxylic acid (69)

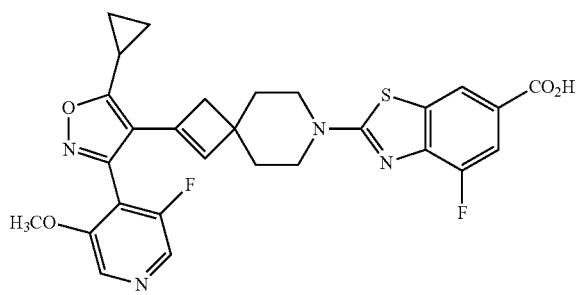

The title compound was obtained as an additional isolate during the preparation of Example 68 by displacement of one fluorine by MeOH. MS (ESI) m/z: 551.0 [M+H]+; 1H NMR (500 MHz, Methanol-d4) δ 8.40 (s, 1H), 8.34 (s, 1H), 8.15 (d, J=1.5 Hz, 1H), 7.66 (dd, J=1.5, 11.6 Hz, 1H), 5.99 (s, 1H), 4.00 (s, 3H), 3.84 (dt, J=4.9, 13.7 Hz, 2H), 3.61 (ddd, J=4.2, 8.2, 13.0 Hz, 2H), 2.53 (s, 2H), 2.32 (tt, J=5.4, 8.0 Hz, 1H), 1.79 (dt, J=5.0, 10.2 Hz, 4H), 1.22 (ddd, J=2.5, 6.3, 7.7 Hz, 4H); FXR EC$_{50}$=730 nM.

Example 70

2-(2-(5-Cyclopropyl-3-(3,5-dichloropyridin-4-yl)isoxazol-4-yl)-7-azaspiro[3.5]non-1-en-7-yl)-6-methoxybenzo[d]thiazole-4-carboxylic acid (70)

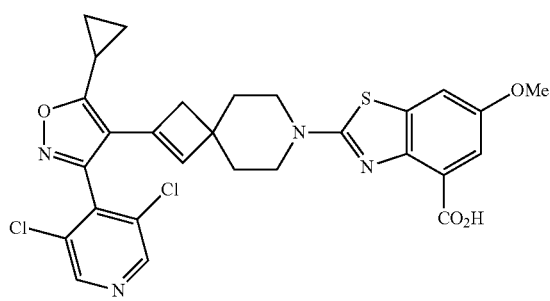

Step 1. Methyl 2-amino-6-methoxybenzo[d]thiazole-4-carboxylate

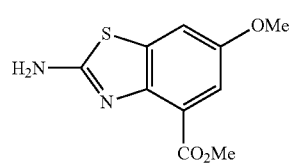 [SMILES: COC(=O)c1cc(OC)cc2sc(N)nc12]

Methyl 2-amino-5-methoxybenzoate (190 mg, 1.0 mmol) was dissolved in acetonitrile (5.2 mL). Ammonium thiocyanate (120 mg, 1.6 mmol) was added, followed by benzyltrimethylammonium tribromide (409 mg, 1.0 mmol) after 3.5 h, the reaction mixture was diluted with EtOAc, washed with saturated NaHCO3, then brine, dried over Na2SO4, filtered, and concentrated in vacuo. The crude material was purified by flash chromatography on SiO2 (0-100% EtOAc/hexanes, 17 minute gradient, Isco 12 g column) to give methyl 2-amino-6-methoxybenzo[d]thiazole-4-carboxylate (100 mg, 0.42 mmol, 40% yield). 1H NMR (400 MHz, CDCl3) δ 7.51 (d, J=2.6 Hz, 1H), 7.35 (d, J=2.6 Hz, 1H), 5.89 (br. s., 2H), 3.99 (s, 3H), 3.88 (s, 3H).

Step 2. Methyl 2-bromo-6-methoxybenzo[d]thiazole-4-carboxylate

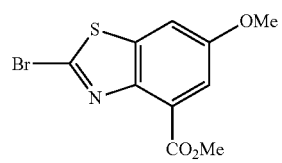

Copper (II) bromide (159 mg, 0.71 mmol) and tert-butyl nitrite (85 μL, 0.71 mmol) were dissolved in MeCN (1.7 mL) and allowed to stir 10 minutes. Methyl 2-amino-6-methoxybenzo[d]thiazole-4-carboxylate (100 mg, 0.42 mmol) was dissolved in MeCN (2.5 mL) and the copper solution was added. After 2 h, the reaction mixture was diluted with EtOAc, washed with 1 N HCl, saturated NaHCO3, then brine, dried over Na2SO4, filtered, and concentrated in vacuo to give methyl 2-bromo-6-methoxybenzo[d]thiazole-4-carboxylate. The product was used without further purification. 1H NMR (400 MHz, CDCl3) δ 7.68 (d, J=2.6 Hz, 1H), 7.46 (d, J=2.6 Hz, 1H), 4.05 (s, 3H), 3.93 (s, 3H).

Example 70. 2-(2-(5-Cyclopropyl-3-(3,5-dichloropyridin-4-yl)isoxazol-4-yl)-7-azaspiro[3.5]non-1-en-7-yl)-6-methoxybenzo[d]thiazole-4-carboxylic acid The title compound was prepared as described in General Method B for the preparation of Example 47 with replacement of ethyl 2-bromo-4-fluorobenzo[d]thiazole-6-carboxylate with 2-bromo-6-methoxybenzo[d]thiazole-4-carboxylic acid. MS (ESI) m/z: 583.0 [M+H]+; 1H NMR (500 MHz, DMSO-d6) δ 8.88 (s, 2H), 7.74 (d, J=2.7 Hz, 1H), 7.39 (d, J=2.7 Hz, 1H), 6.00 (s, 1H), 3.81 (s, 3H), 3.73-3.62 (m, 2H), 3.56-3.45 (m, 2H), 2.43 (s, 2H), 2.36 (td, J=4.3, 8.5 Hz, 1H), 1.70 (br t, J=6.2 Hz, 4H), 1.28-1.13 (m, 4H); FXR EC$_{50}$=4400 nM.

Example 71

2-(2-(5-Cyclopropyl-3-(2-(trifluoromethyl)phenyl)isoxazol-4-yl)-7-azaspiro[3.5]non-1-en-7-yl)-4-methoxybenzo[d]thiazole-6-carboxylic acid (71)

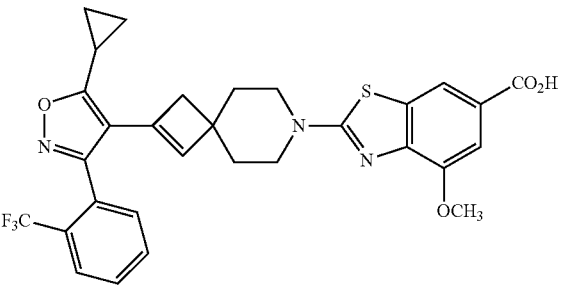

The title compound was prepared as described in General Method A for the preparation of Example 29 with replacement of ethyl 2-bromo-4-fluorobenzo[d]thiazole-6-carboxylate with methyl 2-bromo-4-methoxybenzo[d]thiazole-6-carboxylate. MS (ESI) m/z: 582.2 [M+H]+; 1H NMR (400 MHz, Methanol-$d_4$) δ 7.98 (d, J=1.54 Hz, 1H), 7.86-7.93 (m, 1H), 7.75 (br d, J=1.98 Hz, 2H), 7.54 (d, J=1.54 Hz, 1H), 7.48-7.53 (m, 1H), 5.74 (s, 1H), 4.00 (s, 3H), 3.70-3.89 (m, 2H), 3.56 (br d, J=8.36 Hz, 2H), 2.43 (s, 2H), 2.30 (s, 1H), 1.62-1.83 (m, 4H), 1.11-1.30 (m, 4H); FXR $EC_{50}$=9.4 nM.

Example 72

6-(2-(5-Cyclopropyl-3-(2-(trifluoromethyl)phenyl) isoxazol-4-yl)-7-azaspiro[3.5]non-1-en-7-yl)-4-ethoxyquinoline-2-carboxylic acid

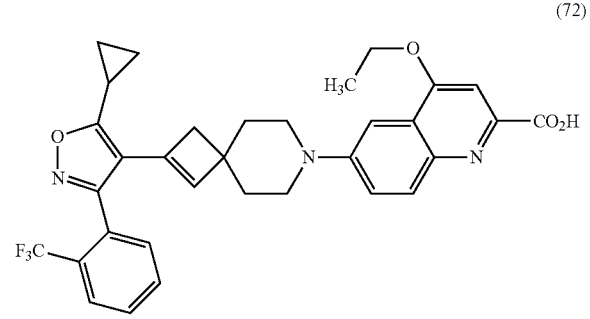 [SMILES: CCOc1cc(C(=O)O)nc2ccc(N3CCC4(C=C(c5c(-c6ccccc6C(F)(F)F)noc5C5CC5)C4)CC3)cc12]

(72)

The title compound was prepared as described in General Method B for the preparation of Example 54 with replacement of ethyl 7-chlorocinnoline-3-carboxylate, HCl with methyl 6-bromo-4-ethoxyquinoline-2-carboxylate. MS (ESI) m/z: 590.1 [M+H]+; 1H NMR (400 MHz, $CDCl_3$-d) δ 8.57-8.80 (m, 1H), 7.71-7.88 (m, 3H), 7.56-7.68 (m, 2H), 7.42-7.48 (m, 1H), 7.38 (d, J=2.64 Hz, 1H), 5.64 (s, 1H), 4.58 (d, J=7.04 Hz, 2H), 3.47-3.70 (m, 2H), 3.33 (br dd, J=4.18, 9.02 Hz, 2H), 2.38 (s, 2H), 2.09-2.21 (m, 1H), 1.76 (br t, J=4.95 Hz, 4H), 1.67 (t, J=7.04 Hz, 3H), 1.28 (dd, J=2.53, 4.95 Hz, 2H), 1.15 (dd, J=2.64, 8.36 Hz, 2H); FXR $EC_{50}$=10 nM.

Example 73

6-(2-(5-Cyclopropyl-3-(3,5-dichloropyridin-4-yl) isoxazol-4-yl)-7-azaspiro[3.5]non-1-en-7-yl)-4-(difluoromethoxy)quinoline-2-carboxylic acid

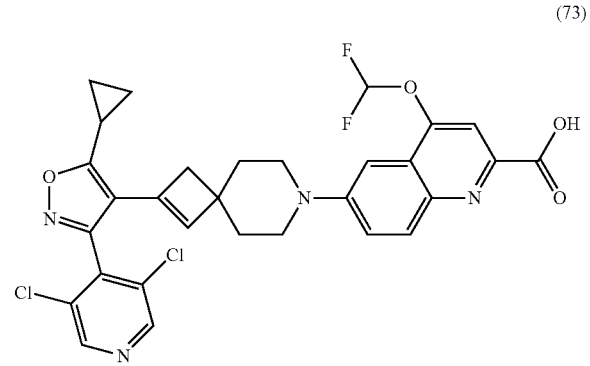 [SMILES: O=C(O)c1cc(OC(F)F)c2cc(N3CCC4(C=C(c5c(-c6c(Cl)cncc6Cl)noc5C5CC5)C4)CC3)ccc2n1]

(73)

The title compound was prepared as described in General Method B for the preparation of Example 58 with replacement of 2-(trifluoromethyl)benzaldehyde with 3,5-dichloroisonicotinaldehyde. MS (ESI) m/z: 613.0 [M+H]+; 1H NMR (400 MHz, $CDCl_3$) δ 8.63 (s, 2H), 7.95 (d, J=9.24 Hz, 1H), 7.75 (s, 1H), 7.59 (dd, J=2.75, 9.57 Hz, 1H), 7.28 (d, J=2.64 Hz, 1H), 6.90 (s, 1H), 5.83 (s, 1H), 3.44-3.64 (m, 2H), 3.29 (br s, 2H), 2.44 (s, 2H), 2.19 (ddd, J=3.30, 5.01, 8.42 Hz, 1H), 1.68-1.93 (m, 5H), 1.31-1.37 (m, 2H), 1.18 (s, 2H); FXR $EC_{50}$=16 nM.

Example 74

6-(2-(3-(3-Chloropyridin-4-yl)-5-cyclopropylisoxazol-4-yl)-7-azaspiro[3.5]non-1-en-7-yl)-4-(difluoromethoxy)quinoline-2-carboxylic acid

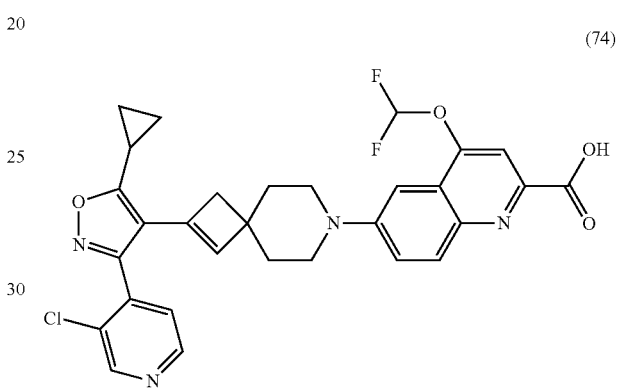

(74)

The title compound was obtained as a minor isolate from the preparation of Example 73. MS (ESI) m/z: 579.1 [M+H]+; 1H NMR (500 MHz, Methanol-$d_4$) δ 8.78 (s, 1H), 8.65 (d, J=4.95 Hz, 1H), 8.19 (d, J=9.63 Hz, 1H), 7.95 (dd, J=2.48, 9.63 Hz, 1H), 7.91 (s, 1H), 7.51-7.59 (m, 2H), 7.36-7.46 (m, 1H), 5.97 (s, 1H), 3.65-3.75 (m, 2H), 3.44 (ddd, J=3.71, 8.60, 12.72 Hz, 2H), 2.55 (s, 2H), 2.29-2.37 (m, 1H), 1.77-1.89 (m, 4H), 1.17-1.27 (m, 4H); FXR $EC_{50}$=38 nM.

Example 75

6-(2-(5-Cyclopropyl-3-(4-(trifluoromethyl)pyridin-3-yl)isoxazol-4-yl)-7-azaspiro[3.5]non-1-en-7-yl)-4-(difluoromethoxy)quinoline-2-carboxylic acid

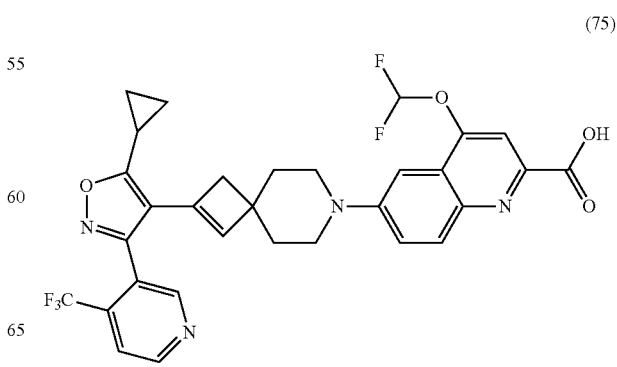

(75)

The title compound was prepared as described in General Method B for the preparation of Example 58 with replacement of 2-(trifluoromethyl)benzaldehyde with 4-(trifluoromethyl)nicotinaldehyde. MS (ESI) m/z: 613.1 [M+H]$^+$; $^1$H NMR (400 MHz, Methanol-d$_4$) δ 8.94-8.82 (m, 1H), 8.12-7.98 (m, 2H), 7.84-7.70 (m, 3H), 7.58-7.18 (m, 2H), 5.77 (s, 1H), 3.65-3.53 (m, 2H), 3.37-3.23 (m, 2H), 2.46 (s, 2H), 2.32 (tt, J=5.5, 8.0 Hz, 1H), 1.78 (dt, J=4.9, 10.3 Hz, 4H), 1.29-1.15 (m, 4H); FXR EC$_{50}$=35 nM.

Example 76

6-(2-(5-Cyclopropyl-3-(3,5-dichloropyridin-4-yl) isoxazol-4-yl)-7-azaspiro[3.5]non-1-en-7-yl)-4-methoxynicotinic acid

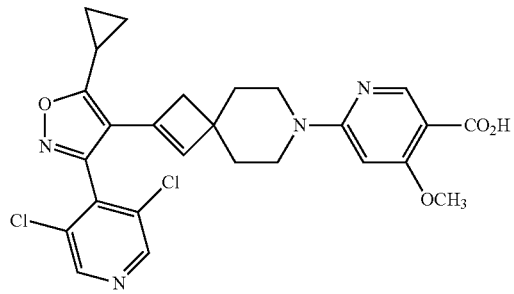

(76)

The title compound was prepared as described in General Method A for the preparation of Example 47 with replacement of ethyl 2-bromo-4-fluorobenzo[d]thiazole-6-carboxylate with methyl 6-chloro-4-methoxynicotinate. MS (ESI) m/z: 527.3 [M+H]$^+$; $^1$H NMR (500 MHz, DMSO-d$_6$) δ 8.83 (s, 2H), 8.32 (s, 1H), 6.33 (s, 1H), 5.94 (s, 1H), 3.83-3.70 (m, 6H), 3.48-3.36 (m, 2H), 2.40-2.31 (m, 3H), 1.57 (br s, 4H), 1.28-1.19 (m, 2H), 1.16-1.09 (m, 2H); FXR EC$_{50}$=2149 nM.

Example 77

6-(2-(5-Cyclopropyl-3-(2-(trifluoromethyl)pyridin-3-yl)isoxazol-4-yl)-7-azaspiro[3.5]non-1-en-7-yl)-4-(difluoromethoxy)quinoline-2-carboxylic acid

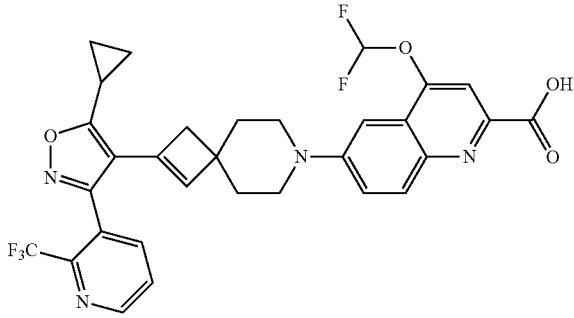 [SMILES: O=C(O)c1cc(OC(F)F)c2cc(N3CCC4(C=C(c5c(-c6cccnc6C(F)(F)F)noc5C5CC5)C4)CC3)ccc2n1]

The title compound was prepared as described in General Method B for the preparation of Example 58 with replacement of 2-(trifluoromethyl)benzaldehyde with 2-(trifluoromethyl)nicotinaldehyde. MS (ESI) m/z: 613.2 [M+H]$^+$; $^1$H NMR (400 MHz, Methanol-d$_4$) δ 9.02-8.93 (m, 1H), 8.77 (s, 1H), 8.09 (d, J=9.5 Hz, 1H), 7.91 (d, J=5.3 Hz, 1H), 7.83-7.76 (m, 2H), 7.60-7.20 (m, 2H), 5.78 (s, 1H), 3.72-3.49 (m, 2H), 3.38-3.29 (m, 2H), 2.46 (s, 2H), 2.33 (tt, J=5.6, 7.9 Hz, 1H), 1.78 (dt, J=4.8, 10.1 Hz, 4H), 1.35-1.10 (m, 4H); FXR EC$_{50}$=68 nM.

Example 78

6-(2-(3-(3-Chloropyridin-2-yl)-5-cyclopropylisoxazol-4-yl)-7-azaspiro[3.5]non-1-en-7-yl)-4-(difluoromethoxy)quinoline-2-carboxylic acid

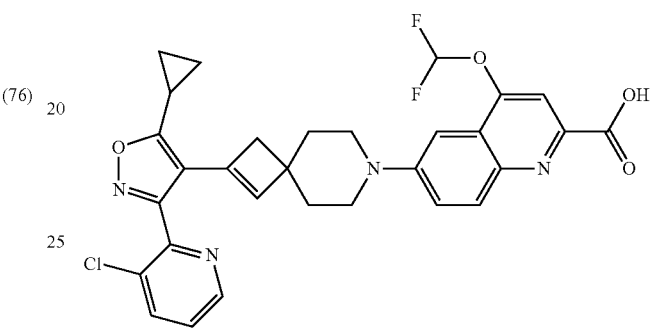

(78)

The title compound was prepared as described in General Method B for the preparation of Example 58 with replacement of 2-(trifluoromethyl)benzaldehyde with 3-chloropicolinaldehyde. MS (ESI) m/z: 579.1 [M+H]$^+$; $^1$H NMR (400 MHz, Methanol-d$_4$) δ 8.65 (dd, J=1.4, 4.8 Hz, 1H), 8.14 (d, J=9.5 Hz, 1H), 8.09 (dd, J=1.4, 8.3 Hz, 1H), 7.89-7.85 (m, 2H), 7.66-7.27 (m, 3H), 5.89 (s, 1H), 3.71-3.60 (m, 2H), 3.44-3.34 (m, 2H), 2.46 (s, 2H), 2.34 (tt, J=5.7, 7.6 Hz, 1H), 1.81 (dt, J=4.5, 9.5 Hz, 4H), 1.23 (ddq, J=2.4, 5.1, 7.3 Hz, 4H); FXR EC$_{50}$=121 nM.

Example 79

7-(2-(5-Cyclopropyl-3-(2,6-difluorophenyl)isoxazol-4-yl)-7-azaspiro[3.5]non-1-en-7-yl)cinnoline-3-carboxylic acid

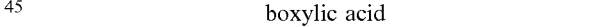

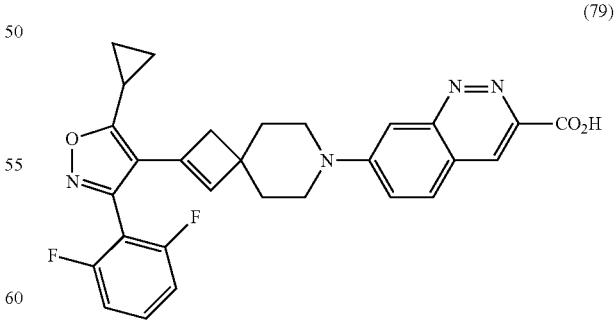

(79)

The title compound was prepared as described in General Method B for the preparation of Example 53 with replacement of 2,6-dichlorobenzaldehyde with 2,6-difluorobenzaldehyde. MS (ESI) m/z: 515.2 [M+H]$^+$; $^1$H NMR (500 MHz, DMSO-d$_6$) δ 8.56 (s, 1H), 8.02 (d, J=9.2 Hz, 1H), 7.83 (d, J=9.5 Hz, 1H), 7.69 (ddd, J=6.6, 8.4, 15.1 Hz, 1H), 7.61 (s, 1H), 7.33 (t, J=8.0 Hz, 2H), 6.00 (s, 1H), 3.76-3.67 (m, 2H), 2.48 (s, 2H), 2.35 (td, J=4.0, 8.2 Hz, 1H), 1.76-1.63 (m, 4H), 1.18 (ddt, J=2.7, 5.4, 25.3 Hz, 4H), additional signals missing due to water signal suppression; FXR EC$_{50}$=733 nM.

Example 80

7-(2-(3-(3-Chloropyridin-4-yl)-5-cyclopropylisoxazol-4-yl)-7-azaspiro[3.5]non-1-en-7-yl)cinnoline-3-carboxylic acid

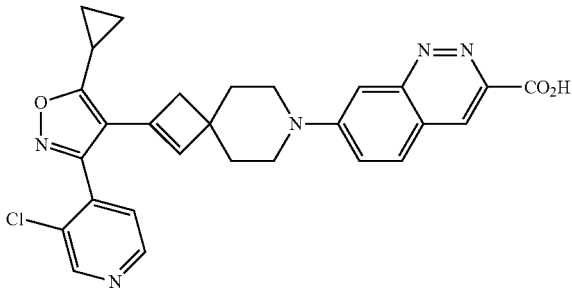

(80)

The title compound was obtained as a minor isolate during the preparation of Example 55 from reduction of one chlorine during the Pd-catalyzed Buchwald coupling step. MS (ESI) m/z: 514.0 [M+H]$^+$; $^1$H NMR (500 MHz, Methanol-d$_4$) δ 8.88 (s, 1H), 8.78 (s, 1H), 8.65 (d, J=4.95 Hz, 1H), 8.13 (d, J=9.63 Hz, 1H), 8.00 (s, 2H), 7.55 (d, J=4.95 Hz, 1H), 7.26 (d, J=1.93 Hz, 1H), 5.95-6.01 (m, 1H), 3.90-4.09 (m, 2H), 3.67 (br dd, J=5.36, 8.12 Hz, 2H), 3.02 (s, 2H), 2.34 (s, 1H), 1.85 (br s, 4H), 1.17-1.41 (m, 4H); FXR EC$_{50}$=1360 nM.

7-(2-(5-Cyclopropyl-3-(4-(trifluoromethyl)pyridin-3-yl)isoxazol-4-yl)-7-azaspiro[3.5]non-1-en-7-yl)cinnoline-3-carboxylic acid

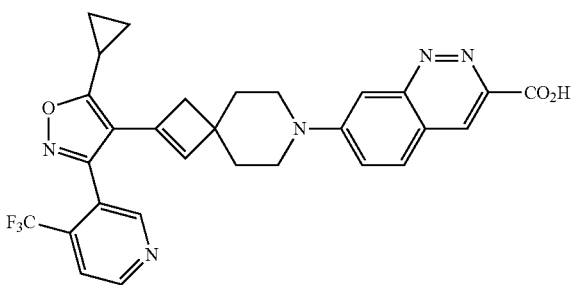

(81)

The title compound was prepared as described in General Method B for the preparation of Example 53 with replacement of 2,6-dichlorobenzaldehyde with 4-(trifluoromethyl)nicotinaldehyde. MS (ESI) m/z: 548.2 [M+H]$^+$; $^1$H NMR (500 MHz, DMSO-d$_6$) δ 9.04 (d, J=5.1 Hz, 1H), 8.86 (s, 1H), 8.50 (s, 1H), 8.02-7.94 (m, 2H), 7.78 (d, J=9.8 Hz, 1H), 7.57 (s, 1H), 5.84 (s, 1H), 3.69-3.61 (m, 2H), 2.39-2.26 (m, 3H), 1.70-1.58 (m, 4H), 1.18 (dt, J=5.1, 38.7 Hz, 4H), additional signals missing due to water signal suppression; FXR EC$_{50}$=1540 nM.

Example 82

6-(2-(5-Cyclopropyl-3-(2,6-difluorophenyl)isoxazol-4-yl)-7-azaspiro[3.5]non-1-en-7-yl)-4-(trifluoromethyl)quinoline-2-carboxylic acid

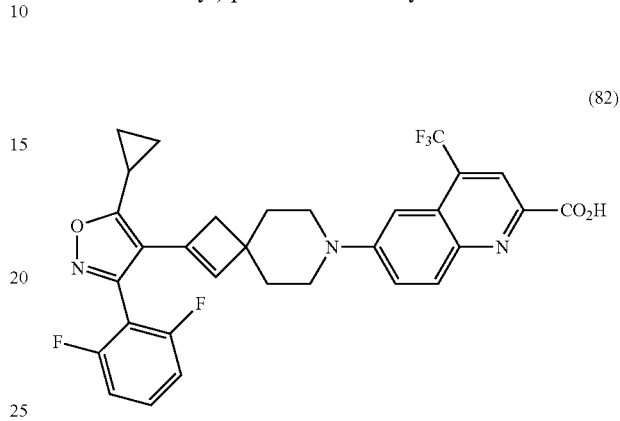

(82)

The title compound was prepared as described in General Method B for the preparation of Example 79 with replacement of ethyl 7-chlorocinnoline-3-carboxylate, HCl with ethyl 6-chloro-4-(trifluoromethyl)quinoline-2-carboxylate. MS (ESI) m/z: 582.0 [M+H]$^+$; $^1$H NMR (500 MHz, DMSO-d$_6$) δ 8.21 (s, 1H), 8.08 (d, J=9.5 Hz, 1H), 7.88 (d, J=9.5 Hz, 1H), 7.69 (q, J=7.4 Hz, 1H), 7.33 (t, J=8.1 Hz, 2H), 7.09 (s, 1H), 6.01 (s, 1H), 3.67-3.59 (m, 2H), 2.48 (s, 2H), 2.40-2.30 (m, 1H), 1.77-1.65 (m, 4H), 1.24-1.12 (m, 4H), additional signals missing due to water signal suppression; FXR EC$_{50}$=356 nM.

Example 83

6-(2-(5-Cyclopropyl-3-(2,6-dichlorophenyl)isoxazol-4-yl)-7-azaspiro[3.5]non-1-en-7-yl)-4-(trifluoromethyl)quinoline-2-carboxylic acid

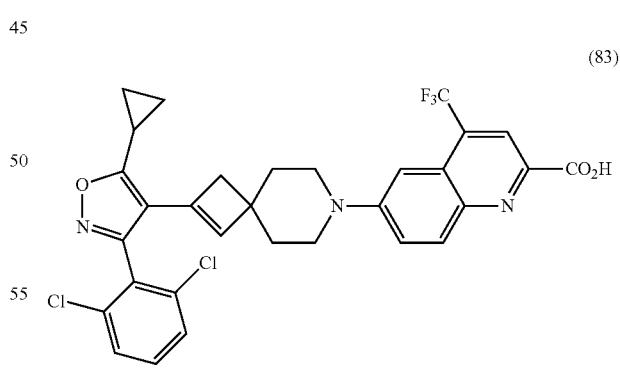

(83)

The title compound was prepared as described in General Method B for the preparation of Example 82 with replacement of 2,6-difluorobenzaldehyde with 2,6-dichlorobenzaldehyde. MS (ESI) m/z: 614.1 [M+H]$^+$; $^1$H NMR (500 MHz, DMSO-d$_6$) δ 8.22 (br s, 1H), 8.09 (br s, 1H), 7.79 (br d, J=8.85 Hz, 1H), 7.62-7.68 (m, 2H), 7.49-7.62 (m, 2H), 7.06 (br s, 1H), 5.87 (s, 1H), 3.55 (br s, 1H), 3.31-3.51 (m, 1H), 2.55 (s, 2H), 2.35 (s, 3H), 1.66 (br s, 4H), 1.17-1.25 (m, 2H), 1.13 (br s, 2H); FXR EC$_{50}$=38 nM.

Example 84

6-(2-(3-(2,6-Dichlorophenyl)-5-isopropylisoxazol-4-yl)-7-azaspiro[3.5]non-1-en-7-yl)-4-(trifluoromethyl)quinoline-2-carboxylic acid

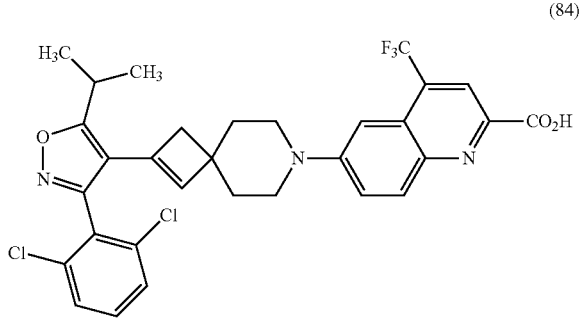 [SMILES: CC(C)c1onc(-c2c(Cl)cccc2Cl)c1C1=CC2(CCN(c3ccc4nc(C(=O)O)cc(C(F)(F)F)c4c3)CC2)C1]
(84)

The title compound was prepared as described in General Method B for the preparation of Example 83 with replacement of cyclopropylacetylene with isopropylacetylene. MS (ESI) m/z: 612.2 [M+H]$^+$; $^1$H NMR (500 MHz, CDCl$_3$) δ 8.46-8.30 (m, 1H), 8.06-7.95 (m, 1H), 7.56 (td, J=4.1, 2.6 Hz, 1H), 7.44-7.36 (m, 2H), 7.35-7.29 (m, 1H), 7.23-7.17 (m, 1H), 5.77 (s, 1H), 3.61-3.46 (m, 2H), 3.40-3.19 (m, 4H), 2.33 (br s, 3H), 1.43 (d, J=6.9 Hz, 8H), 1.26 (s, 1H); FXR EC$_{50}$=127 nM.

Example 85

6-(2-(5-Cyclopropyl-3-(3,5-dichloropyridin-4-yl)isoxazol-4-yl)-7-azaspiro[3.5]non-1-en-7-yl)-4-(trifluoromethyl)quinoline-2-carboxylic acid

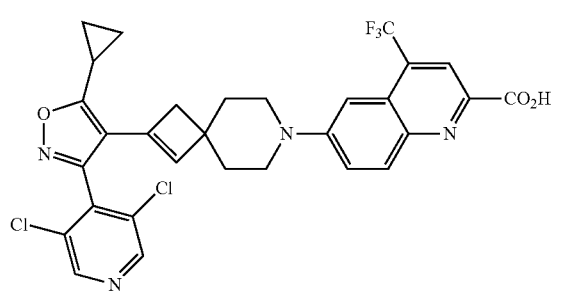
(85)

Step 1. 3,5-Dichloroisonicotinaldehyde oxime

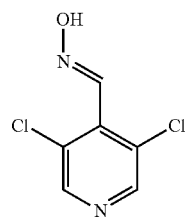 [SMILES: O/N=C/c1c(Cl)cncc1Cl]

Hydroxylamine hydrochloride (11.8 g, 170 mmol) was added to a room temperature solution of 3,5-dichloroisonicotinaldehyde (20 g, 114 mmol) in pyridine (50 mL). After 10 minutes the reaction mixture was concentrated in vacuo to remove excess pyridine. The solid was collected by suction filtration, washed with water and dried in vacuo to give 3,5-dichloroisonicotinaldehyde oxime (21.7 g, 114 mmol, 100% yield) as a white solid. $^1$H NMR (400 MHz, DMSO-d$_6$) δ 12.32 (s, 1H), 8.71 (s, 2H), 8.28 (s, 1H).

Step 2. 3,5-Dichloro-N-hydroxyisonicotinimidoyl chloride

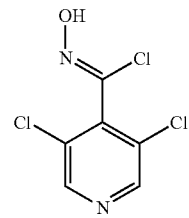 [SMILES: O/N=C(\Cl)c1c(Cl)cncc1Cl]

3,5-Dichloroisonicotinaldehyde oxime (21.7 g, 114 mmol) was suspended in DMF (114 mL). N-Chlorosuccinimide (16.7 g, 125 mmol) was added in three portions giving a clear yellow solution. After stirring for 3 hours, the reaction mixture was poured over ice and extracted with Et$_2$O. The organic layer was washed with brine and the combined aqueous layers were back extracted with Et$_2$O. The combined organics were dried over Na$_2$SO$_4$, filtered and concentrated in vacuo. The residue was purified by flash chromatography on SiO$_2$ (0-60% EtOAc/hex, Isco 120 g column) to give 3,5-dichloro-N-hydroxyisonicotinimidoyl chloride (24.8 g, 110 mmol, 97% yield) as off-white crystals. $^1$H NMR (400 MHz, CDCl$_3$) δ 8.72 (s, 1H), 8.62 (s, 2H).

Step 3. 5-Cyclopropyl-3-(3,5-dichloropyridin-4-yl)isoxazole

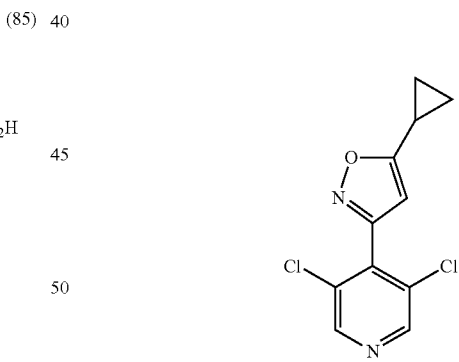

Ethynylcyclopropane (12.1 mL, 143 mmol) followed by Et$_3$N (18.4 mL, 132 mmol) were added to a room temperature solution of 3,5-dichloro-N-hydroxyisonicotinimidoyl chloride (24.8 g, 110 mmol in DCM (440 mL). After stirring overnight at room temperature, the reaction mixture was concentrated to dryness in vacuo and then taken up in EtOAc/water. The organic layer was washed with brine and the combined aqueous layers were back extracted with EtOAc. The combined organic layers were dried over Na$_2$SO$_4$, filtered and concentrated in vacuo to give 5-cyclopropyl-3-(3,5-dichloropyridin-4-yl)isoxazole (27.3 g, 107 mmol, 97% yield as a yellow solid. $^1$H NMR (400 MHz, CDCl$_3$) δ 8.63 (s, 2H), 6.09 (s, 1H), 2.24-2.11 (m, 1H), 1.23-1.07 (m, 4H).

Step 4. 4-Bromo-5-cyclopropyl-3-(3,5-dichloropyridin-4-yl)isoxazole

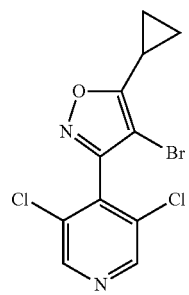 [SMILES: Clc1cncc(Cl)c1-c1noc(C2CC2)c1Br]

N-Bromosuccinimide (24.8 g, 139 mmol) was added to a room temp solution of 5-cyclopropyl-3-(3,5-dichloropyridin-4-yl)isoxazole (27.3 g, 107 mmol) in DMF (143 mL). The reaction mixture was stirred at room temp over the weekend. The reaction mixture was poured over ice and extracted with Et$_2$O. The organic layer was washed with brine and the aqueous layers were back extracted with Et$_2$O. The combined organic extracts were dried over Na$_2$SO$_4$, filtered and concentrated in vacuo to give a yellow solid. The residue was purified by flash chromatography on SiO$_2$ (0-30% EtOAc/hex, Isco 220 g column) to give 4-bromo-5-cyclopropyl-3-(3,5-dichloropyridin-4-yl)isoxazole (29.0 g, 74.9 mmol, 81% yield) as a white solid. $^1$H NMR (400 MHz, CDCl$_3$) δ 8.65 (s, 2H), 2.19 (tt, J=8.4, 5.1 Hz, 1H), 1.36-1.28 (m, 2H), 1.25-1.17 (m, 2H).

Step 5. tert-Butyl 2-(5-cyclopropyl-3-(3,5-dichloropyridin-4-yl)isoxazol-4-yl)-2-hydroxy-7-azaspiro[3.5]nonane-7-carboxylate

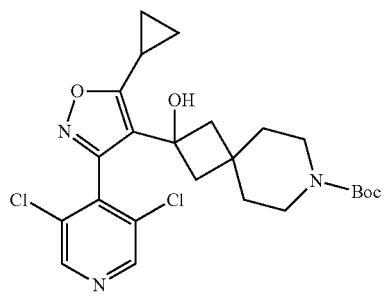 [SMILES: CC(C)(C)OC(=O)N1CCC2(CC1)CC(O)(c1c(-c3c(Cl)cncc3Cl)noc1C1CC1)C2]

n-Butyllithium (22.5 mL, 56.1 mmol) was added slowly (over the span of ~30 minutes) to a −78° C. solution of 4-bromo-5-cyclopropyl-3-(3,5-dichloropyridin-4-yl) isoxazole (15 g, 44.9 mmol) in THF (150 mL). After 10 minutes, tert-butyl 2-oxo-7-azaspiro[3.5]nonane-7-carboxylate (10.8 g, 44.9 mmol) as a solution in 8 mL of THF was added slowly to the cold stirring mixture. After 2.5 h the reaction was quenched by the slow addition of 15 mL saturated aqueous NH$_4$Cl. The mixture was extracted with EtOAc and the organic layer was washed with brine. The combined aqueous layers were further extracted with EtOAc and the combined organic extracts were dried over Na$_2$SO$_4$, filtered and concentrated in vacuo to give an orange solid residue. The residue was purified by flash chromatography on SiO$_2$ (0-100% EtOAc/DCM, Isco 220 g column, product eluted as a broad low peak) to give tert-butyl 2-(5-cyclopropyl-3-(3,5-dichloropyridin-4-yl) isoxazol-4-yl)-2-hydroxy-7-azaspiro[3.5]nonane-7-carboxylate (6.6 g, 13.4 mmol, 30% yield) as a tan foam. $^1$H NMR (400 MHz, CDCl$_3$) δ 8.65 (s, 2H), 3.34-3.25 (m, 2H), 3.24-3.17 (m, 2H), 2.25-2.11 (m, 4H), 2.09 (s, 1H), 1.78-1.65 (m, 2H), 1.49-1.42 (m, 11H), 1.42-1.35 (m, 2H), 1.34-1.28 (m, 2H), 1.22-1.11 (m, 2H).

Step 6. 5-Cyclopropyl-3-(3,5-dichloropyridin-4-yl)-4-(7-azaspiro[3.5]non-1-en-2-yl)isoxazole

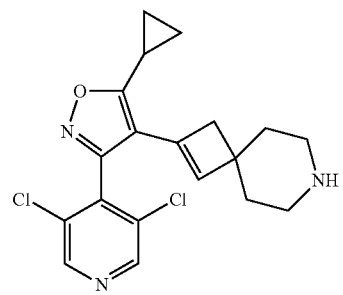 [SMILES: Clc1cncc(Cl)c1-c1noc(C2CC2)c1C1=CC2(CCNCC2)C1]

Trifluoroacetic acid (5.8 mL, 76 mmol) was added to a flask containing tert-butyl 2-(5-cyclopropyl-3-(3,5-dichloropyridin-4-yl)isoxazol-4-yl)-2-hydroxy-7-azaspiro[3.5] nonane-7-carboxylate (3.8 g, 7.6 mmol). After 3 hours the reaction mixture was concentrated to dryness. The residue was taken up in EtOAc and basified with saturated aqueous K$_2$C$_{O3}$. The organic layer was washed with brine and the combined aqueous layers were back extracted with EtOAc. The organic extracts were dried over Na$_2$SO$_4$, filtered and concentrated in vacuo to give 5-cyclopropyl-3-(3,5-dichloropyridin-4-yl)-4-(7-azaspiro[3.5]non-1-en-2-yl)isoxazole as a tan foam which was used without further purification.

Step 7. Ethyl 6-(2-(5-cyclopropyl-3-(3,5-dichloropyridin-4-yl)isoxazol-4-yl)-7-azaspiro[3.5]non-1-en-7-yl)-4-(trifluoromethyl)quinoline-2-carboxylate

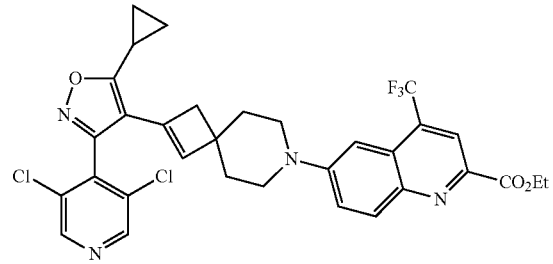 [SMILES: CCOC(=O)c1cc(C(F)(F)F)c2cc(N3CCC4(C=C(c5c(-c6c(Cl)cncc6Cl)noc5C5CC5)C4)CC3)ccc2n1]

A slurry of 5-cyclopropyl-3-(3,5-dichloropyridin-4-yl)-4-(7-azaspiro[3.5]non-1-en-2-yl)isoxazole (2.0 g, 5.3 mmol), ethyl 6-chloro-4-(trifluoromethyl)quinoline-2-carboxylate (1.9 g, 6.4 mmol) and Cs$_2$CO$_3$ (3.5 g, 10.6 mmol) in dioxane (35 mL) was degassed by bubbling N$_2$ through the stirring mixture for 10 minutes. Chloro(2-dicyclohexylphosphino-2',6'-diisopropoxy-1,1'-biphenyl)[2-(2'-amino-1,1'-biphenyl)]palladium(II) (RuPhos-Pd-G2) (0.20 g, 0.27 mmol) was added and the reaction vessel was sealed and heated to 70° C. After heating overnight the reaction mixture was diluted with EtOAc, filtered through Celite and concentrated to dryness in vacuo. The residue was purified by flash chromatography on SiO$_2$ (0-100% EtOAc/hex, Isco 80 g column) to give ethyl 6-(2-(5-cyclopropyl-3-(3,5-dichloropyridin-4-yl)isoxazol-4-yl)-7-azaspiro[3.5]non-1-en-7-yl)-4-(trifluoromethyl)quinoline-2-carboxylate (1.2 g, 1.8 mmol, 34% yield) as a yellow solid. $^1$H NMR (400 MHz, CDCl$_3$) δ 8.64 (s, 2H), 8.36 (s, 1H), 8.20 (d, J=9.5 Hz, 1H), 7.60 (dd, J=9.5, 2.6 Hz, 1H), 7.22 (s, 1H), 5.84 (s, 1H), 4.56 (q, J=7.2 Hz, 2H), 3.63-3.53 (m, 2H), 3.32 (ddd, J=12.8, 8.5, 3.9 Hz, 2H), 2.45 (s, 2H), 2.20 (tt, J=8.4, 5.1 Hz, 1H), 1.89-1.72 (m, 4H), 1.49 (t, J=7.2 Hz, 3H), 1.36-1.29 (m, 2H), 1.24-1.14 (m, 2H); $^{19}$F NMR (377 MHz, CDCl$_3$) δ −62.65 (s, 3F).

Example 85. 6-(2-(5-Cyclopropyl-3-(3,5-dichloropyridin-4-yl)isoxazol-4-yl)-7-azaspiro[3.5]non-1-en-7-yl)-4-(trifluoromethyl)quinoline-2-carboxylic acid Ethyl 6-(2-(5-cyclopropyl-3-(3,5-dichloropyridin-4-yl)isoxazol-4-yl)-7-azaspiro[3.5]non-1-en-7-yl)-4-(trifluoromethyl)quinoline-2-carboxylate (1.2 g, 1.8 mmol) was taken up in THF (12 mL), water (4.8 mL), and MeOH (1.2 mL) and then lithium hydroxide (0.43 g, 18.0 mmol) was added to the mixture. The reaction was sealed and heated to 50° C. After heating for 30 minutes the crude reaction mixture was loaded onto Celite for purification by C-18 reverse phase flash chromatography (10-100% B in A, A=10:90:0.1 MeCN:H$_2$O:TFA, B=90:10:0.1 MeCN:H$_2$O:TFA, 18 min linear gradient, Isco 100 g C-18 gold column) desired fractions were combined and concentrated to give 6-(2-(5-cyclopropyl-3-(3,5-dichloropyridin-4-yl)isoxazol-4-yl)-7-azaspiro[3.5]non-1-en-7-yl)-4-(trifluoromethyl)quinoline-2-carboxylic acid, Example 85 (1.0 g, 1.6 mmol, 89% yield) as a red solid. MS (ESI) m/z: 615.1 [M+H]$^+$; $^1$H NMR (400 MHz, CDCl$_3$) δ 8.66 (s, 2H), 8.45 (s, 1H), 8.06 (d, J=9.5 Hz, 1H), 7.65 (dd, J=9.7, 2.6 Hz, 1H), 7.27-7.24 (m, 1H), 5.86 (s, 1H), 3.65-3.58 (m, 2H), 3.41-3.32 (m, 2H), 2.47 (s, 2H), 2.25-2.16 (m, 1H), 1.89-1.76 (m, 4H), 1.37-1.31 (m, 2H), 1.25-1.17 (m, 2H); $^{19}$F NMR (377 MHz, CDCl$_3$) δ −62.85 (s, 3F); FXR EC$_{50}$=53 nM; Mouse in vivo (3 mg/kg, @ 6 h): Cyp7a1=−94%, Fgf15=+19×.

Example 86

6-(2-(5-Cyclopropyl-3-(2,6-dichloro-4-fluorophenyl)isoxazol-4-yl)-7-azaspiro[3.5]non-1-en-7-yl)-4-(trifluoromethyl)quinoline-2-carboxylic acid

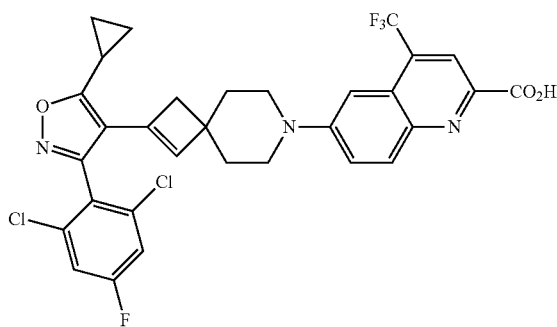

(86)

The title compound was prepared as described in General Method B for the preparation of Example 82 with replacement of 2,6-difluorobenzaldehyde with 2,6-dichloro-4-fluorobenzaldehyde. MS (ESI) m/z: 632.2 [M+H]$^+$; $^1$H NMR (500 MHz, DMSO-d$_6$) δ 8.21 (s, 1H), 8.08 (br d, J=9.5 Hz, 1H), 7.88 (br d, J=8.5 Hz, 1H), 7.77 (d, J=8.5 Hz, 2H), 7.08 (br s, 1H), 5.94 (s, 1H), 3.91 (s, 1H), 3.70-3.56 (m, 2H), 3.36-3.23 (m, 3H), 2.40 (s, 1H), 2.38-2.28 (m, 1H), 1.76-1.60 (m, 4H), 1.28-1.18 (m, 2H), 1.16 (br d, J=2.7 Hz, 2H); FXR EC$_{50}$=68 nM.

Example 87

6-(2-(5-Cyclopropyl-3-(3,5-dichloropyridin-4-yl)isoxazol-4-yl)-7-azaspiro[3.5]non-1-en-7-yl)-4-methylquinoline-2-carboxylic acid

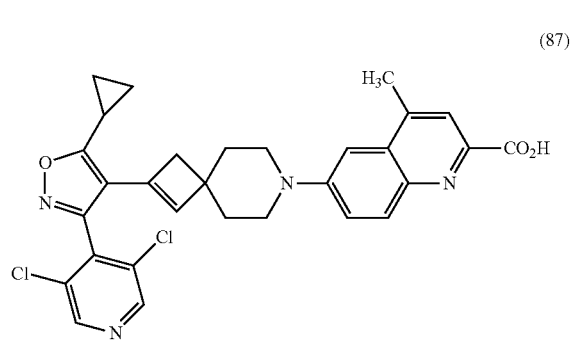 [SMILES: Cc1cc(C(=O)O)nc2ccc(N3CCC4(C=C(c5c(-c6c(Cl)cncc6Cl)noc5C5CC5)C4)CC3)cc12]

(87)

The title compound was prepared as described for the preparation of Example 85 with replacement of ethyl 6-chloro-4-(trifluoromethyl)quinoline-2-carboxylate with ethyl 6-bromo-4-methylquinoline-2-carboxylate. MS (ESI) m/z: 561.0 [M+H]$^+$; $^1$H NMR (400 MHz, CDCl$_3$) δ 8.63 (s, 2H), 7.90-8.14 (m, 2H), 7.57 (s, 1H), 7.11 (br s, 1H), 5.79-5.91 (m, 1H), 3.45-3.61 (m, 2H), 3.27 (ddd, J=3.74, 8.58, 12.54 Hz, 2H), 2.69 (s, 3H), 2.44 (s, 2H), 2.19 (s, 1H), 1.78-2.03 (m, 4H), 1.27-1.39 (m, 4H); FXR EC$_{50}$=76 nM.

Example 88

6-(2-(3-(2-Chloro-6-fluorophenyl)-5-cyclopropylisoxazol-4-yl)-7-azaspiro[3.5]non-1-en-7-yl)-4-(trifluoromethyl)quinoline-2-carboxylic acid

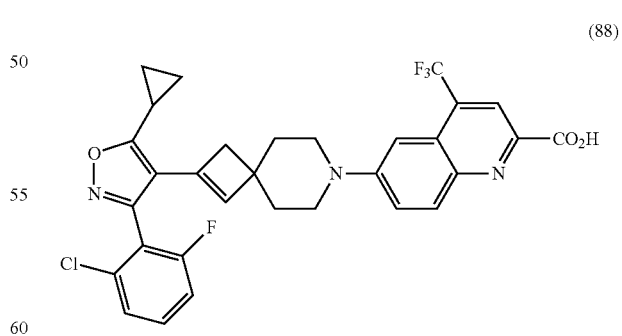

(88)

The title compound was prepared as described in General Method B for the preparation of Example 82 with replacement of 2,6-difluorobenzaldehyde with 2-chloro-6-fluorobenzaldehyde. MS (ESI) m/z: 597.9 [M+H]$^+$; $^1$H NMR (500 MHz, DMSO-d$_6$) δ 8.21 (s, 1H), 8.07 (d, J=9.4 Hz, 1H), 7.80 (d, J=9.2 Hz, 1H), 7.63 (td, J=6.1, 8.3 Hz, 1H), 7.52 (d, J=8.1 Hz, 1H), 7.41 (t, J=8.7 Hz, 1H), 7.09 (s, 1H), 5.94 (s, 1H), 3.63-3.52 (m, 2H), 3.34-3.25 (m, 2H), 2.40 (s, 2H), 2.32 (td, J=4.3, 8.5 Hz, 1H), 1.76-1.63 (m, 4H), 1.26-1.09 (m, 4H); FXR EC$_{50}$=150 nM.

Example 89

6-(2-(3-(2-Chloro-6-methylphenyl)-5-cyclopropylisoxazol-4-yl)-7-azaspiro[3.5]non-1-en-7-yl)-4-(trifluoromethyl)quinoline-2-carboxylic acid

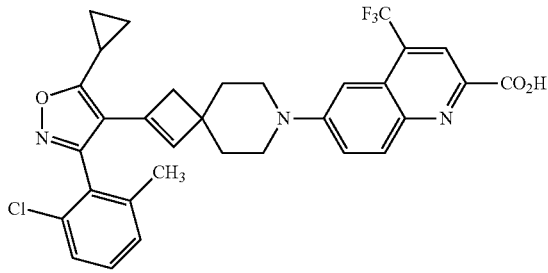

(89)

The title compound was prepared as described in General Method B for the preparation of Example 82 with replacement of 2,6-difluorobenzaldehyde with 2-chloro-6-methylbenzaldehyde. MS (ESI) m/z: 594.2 [M+H]$^+$; $^1$H NMR (500 MHz, DMSO-d$_6$) δ 8.21 (s, 1H), 8.07 (d, J=9.5 Hz, 1H), 7.83 (dd, J=2.6, 9.5 Hz, 1H), 7.50-7.40 (m, 2H), 7.36 (dd, J=2.9, 5.8 Hz, 1H), 7.07 (s, 1H), 5.78 (s, 1H), 3.63-3.55 (m, 2H), 3.31-3.22 (m, 2H), 2.42-2.31 (m, 3H), 2.11 (s, 3H), 1.74-1.59 (m, 4H), 1.25-1.10 (m, 4H); FXR EC$_{50}$=202 nM.

Example 90

6-(2-(5-Cyclopropyl-3-(4-(trifluoromethyl)pyridin-3-yl)isoxazol-4-yl)-7-azaspiro[3.5]non-1-en-7-yl)-4-(trifluoromethyl)quinoline-2-carboxylic acid

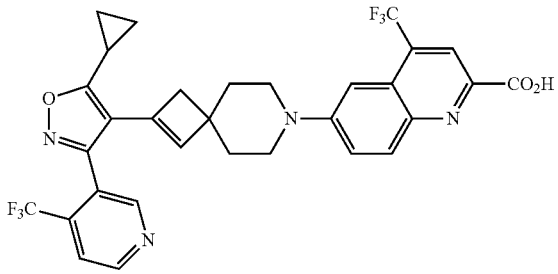

(90)

The title compound was prepared as described in General Method B for the preparation of Example 82 with replacement of 2,6-difluorobenzaldehyde with 4-(trifluoromethyl)nicotinaldehyde. MS (ESI) m/z: 615.0 [M+H]$^+$; $^1$H NMR (500 MHz, DMSO-d$_6$) δ 9.05 (d, J=5.1 Hz, 1H), 8.87 (s, 1H), 8.22 (s, 1H), 8.06 (d, J=9.5 Hz, 1H), 7.99 (d, J=5.2 Hz, 1H), 7.82-7.76 (m, 1H), 7.07 (s, 1H), 5.85 (s, 1H), 3.58-3.50 (m, 2H), 3.28-3.21 (m, 2H), 2.40-2.30 (m, 3H), 1.73-1.61 (m, 4H), 1.28-1.11 (m, 4H); FXR EC$_{50}$=195 nM.

Example 91

6-(2-(3-(3-Chloropyridin-2-yl)-5-cyclopropylisoxazol-4-yl)-7-azaspiro[3.5]non-1-en-7-yl)-4-(trifluoromethyl)quinoline-2-carboxylic acid

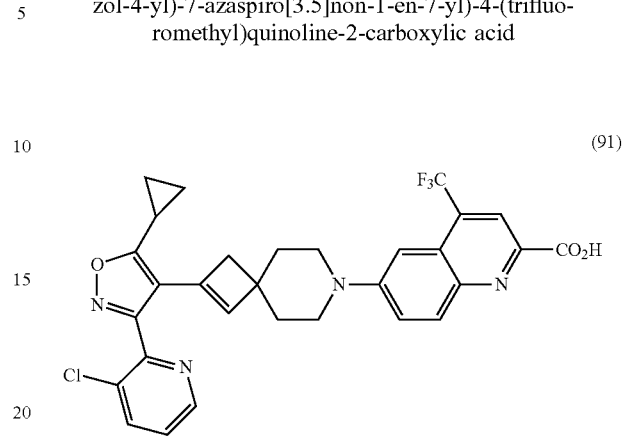

(91)

The title compound was prepared as described in General Method B for the preparation of Example 82 with replacement of 2,6-difluorobenzaldehyde with 3-chloropicolinaldehyde. MS (ESI) m/z: 581.2 [M+H]$^+$; $^1$H NMR (500 MHz, DMSO-d$_6$) δ 8.69 (d, J=4.0 Hz, 1H), 8.20 (s, 1H), 8.15 (d, J=8.2 Hz, 1H), 8.07 (br d, J=9.5 Hz, 1H), 7.86 (br d, J=8.5 Hz, 1H), 7.63 (dd, J=8.2, 4.6 Hz, 1H), 7.07 (br s, 1H), 5.89 (s, 1H), 3.70-3.52 (m, 1H), 3.31 (br t, J=8.9 Hz, 1H), 2.42-2.27 (m, 3H), 1.75-1.57 (m, 4H), 1.27-1.17 (m, 2H), 1.14 (br d, J=2.7 Hz, 2H); FXR EC$_{50}$=219 nM.

Example 92

6-(2-(5-Cyclopropyl-3-(2-(trifluoromethyl)pyridin-3-yl)isoxazol-4-yl)-7-azaspiro[3.5]non-1-en-7-yl)-4-(trifluoromethyl)quinoline-2-carboxylic acid

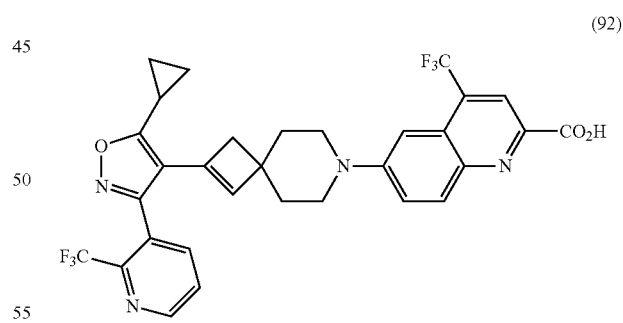

(92)

The title compound was prepared as described in General Method B for the preparation of Example 82 with replacement of 2,6-difluorobenzaldehyde with 2-(trifluoromethyl)nicotinaldehyde. MS (ESI) m/z: 615.3 [M+H]$^+$; $^1$H NMR (500 MHz, DMSO-d$_6$) δ 8.93 (dd, J=1.5, 4.8 Hz, 1H), 8.24 (s, 1H), 8.20-8.13 (m, 1H), 8.09 (d, J=9.5 Hz, 1H), 7.89 (dd, J=4.7, 7.9 Hz, 1H), 7.83-7.72 (m, 1H), 7.06 (s, 1H), 5.83 (s, 1H), 3.56-3.48 (m, 2H), 3.26-3.17 (m, 2H), 2.40-2.29 (m, 3H), 1.65 (ddd, J=6.0, 11.1, 18.2 Hz, 4H), 1.27-1.08 (m, 4H); FXR EC$_{50}$=253 nM.

Example 93

6-(2-(5-Cyclopropyl-3-(3,5-difluoropyridin-4-yl)isoxazol-4-yl)-7-azaspiro[3.5]non-1-en-7-yl)-4-(trifluoromethyl)quinoline-2-carboxylic acid

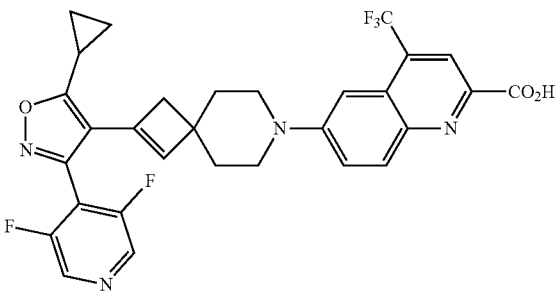

(93)

The title compound was prepared as described in General Method B for the preparation of Example 82 with replacement of 2,6-difluorobenzaldehyde with 3,5-difluoroisonicotinaldehyde. MS (ESI) m/z: 583.0 [M+H]$^+$; $^1$H NMR (400 MHz, DMSO-d$_6$) δ 8.80 (s, 2H), 8.21 (s, 1H), 8.08 (d, J=9.5 Hz, 1H), 7.89 (dd, J=2.6, 9.7 Hz, 1H), 7.08 (d, J=2.4 Hz, 1H), 6.14 (s, 1H), 3.66-3.57 (m, 2H), 3.43-3.27 (m, 2H), 2.51 (s, 2H), 2.41-2.30 (m, 1H), 1.72 (q, J=4.9, 5.4 Hz, 4H), 1.27-1.10 (m, 4H); FXR EC$_{50}$=511 nM.

Example 94

6-(2-(3-(3,5-Dichloropyridin-4-yl)-5-(1-methylcyclopropyl)isoxazol-4-yl)-7-azaspiro[3.5]non-1-en-7-yl)-4-(trifluoromethyl)quinoline-2-carboxylic acid

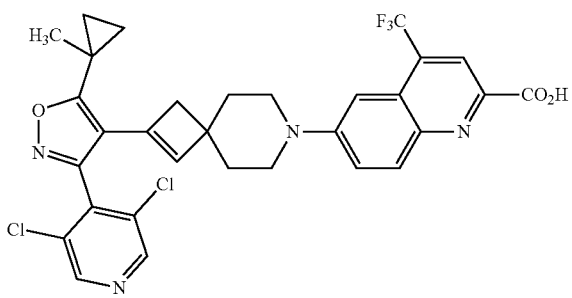

(94)

The title compound was prepared as described for the preparation of Example 85 with replacement of cyclopropylacetylene with 1-ethynyl-1-methylcyclopropane. MS (ESI) m/z: 629.2 [M+H]$^+$; $^1$H NMR (500 MHz, DMSO-d$_6$) δ 8.87 (s, 2H), 8.22 (br s, 1H), 8.08 (br d, J=9.2 Hz, 1H), 7.85 (br d, J=7.9 Hz, 1H), 7.09 (br s, 1H), 6.07 (s, 1H), 3.67-3.54 (m, 1H), 3.39-3.25 (m, 1H), 3.02-2.88 (m, 1H), 2.36 (s, 2H), 1.78-1.61 (m, 4H), 1.45 (s, 3H), 1.32-1.21 (m, 2H), 1.18 (br t, J=7.3 Hz, 2H), 1.08 (br s, 2H), 0.99 (br s, 2H); FXR EC$_{50}$=507 nM.

Example 95

6-(2-(3-(3,5-Dichloropyridin-4-yl)-5-isopropylisoxazol-4-yl)-7-azaspiro[3.5]non-1-en-7-yl)-4-(trifluoromethyl)quinoline-2-carboxylic acid

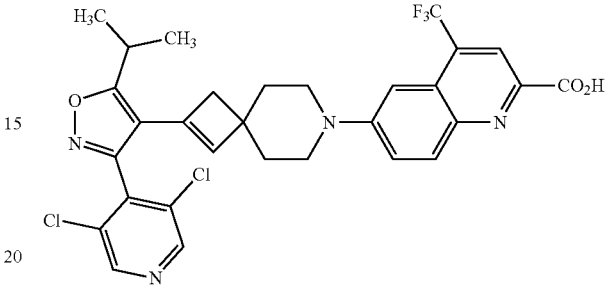

(95)

The title compound was prepared as described for the preparation of Example 85 with replacement of cyclopropylacetylene with isopropylacetylene. MS (ESI) m/z: 617.2 [M+H]$^+$; $^1$H NMR (500 MHz, CDCl$_3$) δ 8.90-8.52 (m, 2H), 8.42 (br d, J=1.0 Hz, 1H), 8.18-7.93 (m, 1H), 7.70-7.45 (m, 1H), 5.83 (s, 1H), 3.56 (br s, 2H), 3.42-3.25 (m, 3H), 2.37 (s, 2H), 1.78 (br s, 4H), 1.44 (br d, J=6.9 Hz, 6H), acid OH not observed, one quinoline C—H under CDCl$_3$ peak; FXR EC$_{50}$=37 nM.

Example 96

6-(2-(3-(2-Chloro-4-fluorophenyl)-5-cyclopropylisoxazol-4-yl)-7-azaspiro[3.5]non-1-en-7-yl)-4-(trifluoromethyl)quinoline-2-carboxylic acid

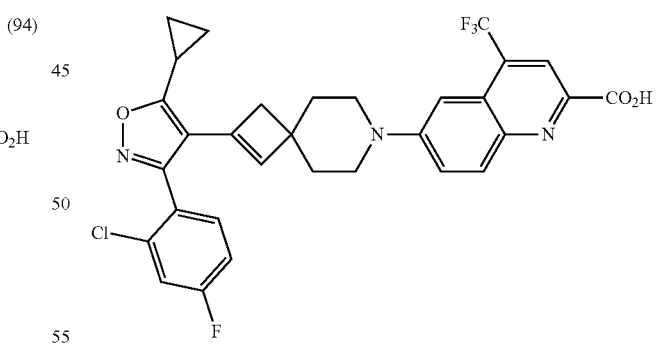

(96)

The title compound was obtained as a minor isolate during the preparation of Example 86 by reduction of one chlorine during the Pd-catalyzed Buchwald coupling step. MS (ESI) m/z: 598.2 [M+H]$^+$; $^1$H NMR (500 MHz, DMSO-d$_6$) δ 8.21 (br s, 1H), 8.08 (br s, 1H), 7.86 (br d, J=9.9 Hz, 1H), 7.63 (br d, J=8.8 Hz, 1H), 7.56 (br dd, J=8.3, 6.1 Hz, 1H), 7.42-7.31 (m, 1H), 7.11 (br s, 1H), 5.96 (s, 1H), 3.61 (br d, J=13.8 Hz, 2H), 3.44-3.24 (m, 2H), 2.43 (s, 1H), 2.37-2.24 (m, 1H), 1.83-1.63 (m, 3H), 1.35-1.05 (m, 5H) Additional signals missing due to water suppression in the $^1$H NMR experiment; FXR EC$_{50}$=869 nM.

Example 97

6-(2-(5-Cyclopropyl-3-(3-fluoro-5-methoxypyridin-4-yl)isoxazol-4-yl)-7-azaspiro[3.5]non-1-en-7-yl)-4-(trifluoromethyl)quinoline-2-carboxylic acid

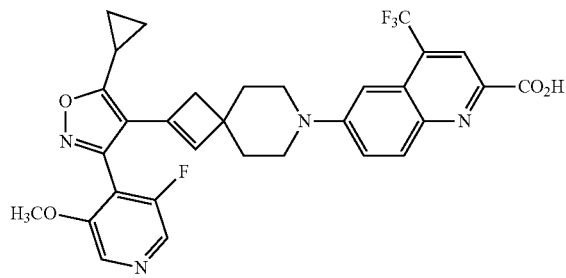

(97)

The title compound was obtained as an additional isolate during the preparation of Example 93 by displacement of one fluorine with MeOH during the hydrolysis step. MS (ESI) m/z: 595.1 [M+H]$^+$; $^1$H NMR (400 MHz, Methanol-d$_4$) δ 8.40 (d, J=3.2 Hz, 1H), 8.34 (t, J=3.2 Hz, 2H), 8.18 (br s, 1H), 7.86-7.77 (m, 1H), 7.25 (s, 1H), 5.98 (d, J=3.3 Hz, 1H), 3.99 (s, 3H), 3.72-3.62 (m, 2H), 3.45-3.36 (m, 2H), 2.52 (s, 2H), 2.37-2.28 (m, 1H), 1.88-1.72 (m, 4H), 1.21 (q, J=3.5, 6.1 Hz, 4H); FXR EC$_{50}$=1940 nM.

Example 98

6-(2-(3-Cyclohexyl-5-cyclopropylisoxazol-4-yl)-7-azaspiro[3.5]non-1-en-7-yl)-4-(trifluoromethyl)quinoline-2-carboxylic acid

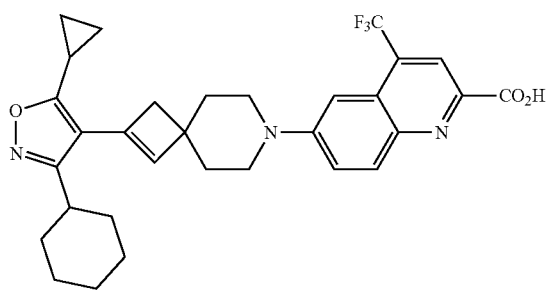

(98)

The title compound was prepared as described in General Method B for the preparation of Example 82 with replacement of 2,6-difluorobenzaldehyde with cyclohexanecarbaldehyde. MS (ESI) m/z: 552.4 [M+H]$^+$; $^1$H NMR (500 MHz, DMSO-d$_6$) δ 8.23 (s, 1H), 8.10 (d, J=9.3 Hz, 1H), 7.91 (d, J=9.9 Hz, 1H), 7.13 (s, 1H), 6.41 (s, 1H), 3.76-3.65 (m, 2H), 2.78-2.67 (m, 3H), 2.21 (dq, J=5.3, 8.6 Hz, 1H), 1.97-1.22 (m, 8H), 1.47-1.19 (m, 6H), 1.12-0.94 (m, 4H), additional signals missing due to water signal suppression; FXR EC$_{50}$=1720 nM.

Example 99

6-(2-(5-Cyclopropyl-3-(2-(trifluoromethyl)phenyl)isoxazol-4-yl)-7-azaspiro[3.5]non-1-en-7-yl)-4-(trifluoromethyl)quinoline-2-carboxylic acid

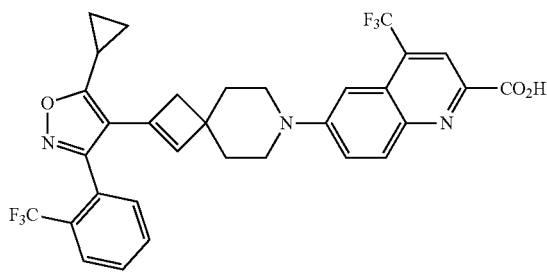

(99)

The title compound was prepared as described in General Method B for the preparation of Example 82 with replacement of 2,6-difluorobenzaldehyde with 2-(trifluoromethyl)benzaldehyde. MS (ESI) m/z: 614.1 [M+H]$^+$; $^1$H NMR (500 MHz, Methanol-d$_4$) δ 8.33 (s, 1H), 8.13 (d, J=9.35 Hz, 1H), 7.89 (d, J=7.15 Hz, 1H), 7.68-7.81 (m, 3H), 7.51 (d, J=7.15 Hz, 1H), 7.21 (br s, 1H), 5.67-5.86 (m, 1H), 3.60 (br s, 2H), 3.36 (br d, J=3.58 Hz, 2H), 2.42 (s, 2H), 2.31 (s, 1H), 1.66-1.94 (m, 4H), 1.11-1.40 (m, 4H); FXR EC$_{50}$=92 nM.

General Method D

Example 100

2-(2-(5-cyclopropyl-3-(2,6-dichlorophenyl)isoxazol-4-yl)-7-azaspiro[3.5]non-1-en-7-yl)quinoxaline-6-carboxylic acid

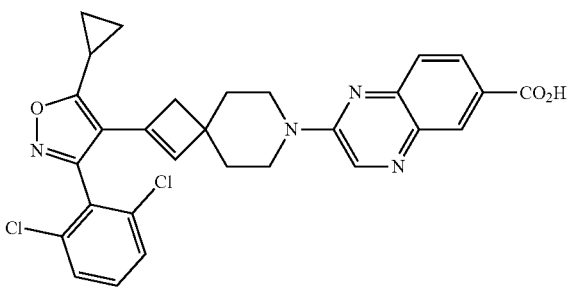

(100)

Step 1. 4-(7-(6-Bromoquinoxalin-2-yl)-7-azaspiro[3.5]non-1-en-2-yl)-5-cyclopropyl-3-(2,6-dichlorophenyl)isoxazole

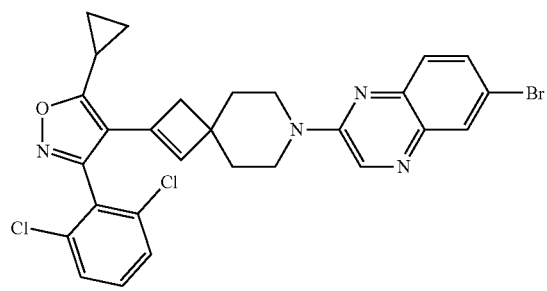 [SMILES: Clc1cccc(Cl)c1-c1noc(C2CC2)c1C1=CC2(CCN(c3cnc4cc(Br)ccc4n3)CC2)C1]

A slurry of 5-cyclopropyl-3-(2,6-dichlorophenyl)-4-(7-azaspiro[3.5]non-1-en-2-yl)isoxazole (25 mg, 0.07 mmol, synthesis described in General Method A), 6-bromo-2-chloroquinoxaline (19.5 mg, 0.08 mmol) and $Cs_2CO_3$ (43.4 mg, 0.13 mmol) in dioxane (0.3 mL) was degassed by bubbling nitrogen through the mixture for 5 minutes. Chloro(2-dicyclohexylphosphino-2',6'-diisopropoxy-1,1'-biphenyl)[2-(2'-amino-1,1'-biphenyl)]palladium(II) (RuPhos-Pd-G2) (2.59 mg, 3.33 μmol) was added and the reaction mixture was sealed and heated to 90° C. for 6 hours. The crude reaction mixture purified directly by flash chromatography on $SiO_2$ (0-100% EtOAc/hexanes, Isco 12 g column) to yield 4-(7-(6-bromoquinoxalin-2-yl)-7-azaspiro[3.5]non-1-en-2-yl)-5-cyclopropyl-3-(2,6-dichlorophenyl)isoxazole (26 mg, 0.04 mmol, 64% yield) as a gum. $^1$H NMR (400 MHz, $CDCl_3$) δ 8.57 (s, 1H), 8.03 (d, J=2.2 Hz, 1H), 7.64 (dd, J=8.8, 2.2 Hz, 1H), 7.53 (d, J=8.8 Hz, 1H), 7.46-7.42 (m, 2H), 7.40-7.34 (m, 1H), 5.80 (s, 1H), 3.94 (dt, J=13.5, 5.1 Hz, 2H), 3.66-3.50 (m, 2H), 2.44 (s, 2H), 2.21 (tt, J=8.4, 5.1 Hz, 1H), 1.76 (t, J=5.6 Hz, 4H), 1.36-1.30 (m, 2H), 1.22-1.15 (m, 2H).

Step 2. 2-(2-(5-Cyclopropyl-3-(2,6-dichlorophenyl)isoxazol-4-yl)-7-azaspiro[3.5]non-1-en-7-yl)quinoxaline-6-carbonitrile

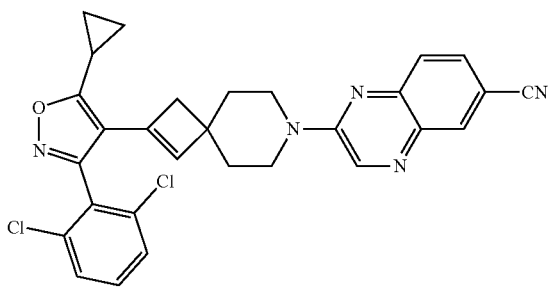 [SMILES: N#Cc1ccc2nc(N3CCC4(C=C(c5c(-c6c(Cl)cccc6Cl)noc5C5CC5)C4)CC3)cnc2c1]

A microwave vial containing 4-(7-(6-bromoquinoxalin-2-yl)-7-azaspiro[3.5]non-1-en-2-yl)-5-cyclopropyl-3-(2,6-dichlorophenyl)isoxazole (20 mg, 0.03 mmol), Xantphos (4.0 mg, 6.9 μmol), $Pd_2(dba)_3$ (6.3 mg, 6.9 μmol), and zinc cyanide (4.0 mg, 0.03 mmol) was purged three times with nitrogen and anhydrous DMF (0.5 mL) was added. The reaction mixture was heated under microwave irradiation at 110° C. for 1.5 h. The reaction mixture was diluted with EtOAc (10 mL) and washed with brine (10 mL). The organic layer was dried over $Na_2SO_4$, filtered and concentrated to dryness in vacuo. The crude product was purified by flash chromatography on $SiO_2$ (0 to 100% EtOAc/hexanes, Isco 12 g column) to yield 2-(2-(5-cyclopropyl-3-(2,6-dichlorophenyl)isoxazol-4-yl)-7-azaspiro[3.5]non-1-en-7-yl)quinoxaline-6-carbonitrile (11.5 mg, 0.02 mmol, 60% yield) as a gum. $^1$H NMR (400 MHz, $CDCl_3$) δ 8.65 (s, 1H), 8.19 (d, J=1.8 Hz, 1H), 7.74-7.68 (m, 1H), 7.67-7.62 (m, 1H), 7.48-7.42 (m, 2H), 7.40-7.34 (m, 1H), 5.79 (s, 1H), 4.02 (dt, J=13.5, 5.0 Hz, 2H), 3.68-3.59 (m, 2H), 2.46 (s, 2H), 2.20 (tt, J=8.4, 5.1 Hz, 1H), 1.77 (t, J=5.6 Hz, 4H), 1.37-1.31 (m, 2H), 1.24-1.15 (m, 2H).

Example 100. 2-(2-(5-cyclopropyl-3-(2,6-dichlorophenyl)isoxazol-4-yl)-7-azaspiro[3.5]non-1-en-7-yl)quinoxaline-6-carboxylic acid To a solution of 2-(2-(5-cyclopropyl-3-(2,6-dichlorophenyl)isoxazol-4-yl)-7-azaspiro[3.5]non-1-en-7-yl)quinoxaline-6-carbonitrile (11.5 mg, 0.02 mmol) in EtOH (72.5 μL), was added NaOH (21.8 μL, 0.11 mmol). The reaction mixture was sealed and heated to 90° C. for 2 h. The crude reaction mixture was purified by C-18 reverse phase flash chromatography (10-100% B in A, A=10:90:0.1 MeCN:$H_2O$:TFA, B=90:10:0.1 MeCN:$H_2O$:TFA, 18 min linear gradient, Isco 24 g C-18 gold column) desired fractions were combined and concentrated to give 2-(2-(5-cyclopropyl-3-(2,6-dichlorophenyl) isoxazol-4-yl)-7-azaspiro[3.5]non-1-en-7-yl)quinoxaline-6-carboxylic acid (9.6 mg, 0.017 mmol, 79% yield) as a yellow solid. MS (ESI) m/z: 546.9 [M+H]$^+$; $^1$H NMR (400 MHz, Methanol-$d_4$) δ 8.69 (s, 1H), 8.44 (d, J=1.98 Hz, 1H), 8.11 (dd, J=1.87, 8.69 Hz, 1H), 7.59 (d, J=8.58 Hz, 1H), 7.37-7.52 (m, 3H), 5.80 (s, 1H), 4.03 (td, J=4.98, 13.59 Hz, 2H), 3.52-3.73 (m, 2H), 2.43 (s, 2H), 2.18-2.32 (m, 1H), 1.72 (br t, J=5.50 Hz, 4H), 1.07-1.40 (m, 6H); FXR $EC_{50}$=33 nM.

Example 101

2-(2-(5-Cyclopropyl-3-(2-(trifluoromethyl)phenyl)isoxazol-4-yl)-7-azaspiro[3.5]non-1-en-7-yl)quinoxaline-6-carboxylic acid (101)

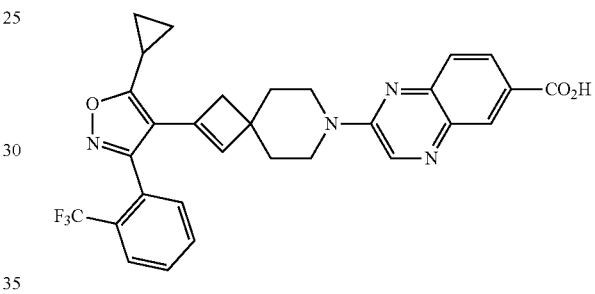

The title compound was prepared as described for the preparation of Example 100 with replacement of 2,6-dichlorobenzaldehyde with 2-(trifluoromethyl)benzaldehyde. MS (ESI) m/z: 547.0 [M+H]$^+$; $^1$H NMR (400 MHz, Methanol-$d_4$) δ 8.81-8.91 (m, 1H), 8.50 (d, J=1.76 Hz, 1H), 8.20 (dd, J=1.98, 8.80 Hz, 1H), 7.85-7.99 (m, 1H), 7.71-7.80 (m, 2H), 7.68 (d, J=8.80 Hz, 1H), 7.46-7.57 (m, 1H), 5.75 (s, 1H), 3.96-4.35 (m, 2H), 3.60-3.89 (m, 2H), 2.46 (s, 1H), 2.31 (s, 1H), 1.63-1.90 (m, 4H), 1.10-1.44 (m, 4H); FXR $EC_{50}$=17 nM.

Example 102

2-(2-(5-Cyclopropyl-3-(2-(trifluoromethyl)phenyl)isoxazol-4-yl)-7-azaspiro[3.5]non-1-en-7-yl)thiazolo[5,4-b]pyridine-5-carboxylic acid (102)

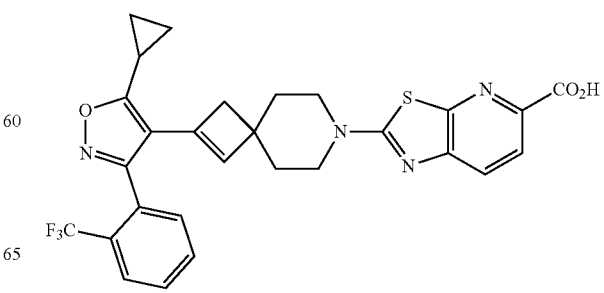

The title compound was prepared as described for the preparation of Example 62 with replacement of 3,5-dichloroisonicotinaldehyde with 2-(trifluoromethyl)benzaldehyde. MS (ESI) m/z: 553.2 [M+H]+; 1H NMR (500 MHz, CDCl3) δ 8.15 (br d, J=8.25 Hz, 1H), 7.83 (br d, J=7.43 Hz, 1H), 7.76 (br d, J=8.25 Hz, 1H), 7.62-7.73 (m, 2H), 7.46 (br d, J=6.60 Hz, 1H), 5.57-5.82 (m, 1H), 3.78 (br d, J=11.55 Hz, 2H), 3.46-3.65 (m, 2H), 2.42 (s, 2H), 2.15 (br d, J=4.68 Hz, 1H), 1.24-1.38 (m, 4H), 1.18 (m, 4H); FXR EC50=18 nM.

Example 103

2-(2-(3-(2-Chloro-6-methylphenyl)-5-cyclopropylisoxazol-4-yl)-7-azaspiro[3.5]non-1-en-7-yl)-4-fluorobenzo[d]thiazole-6-carboxylic acid

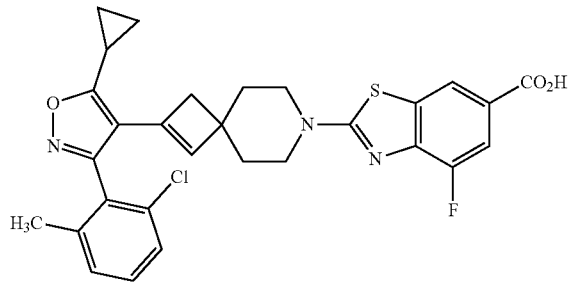

(103)

The title compound was prepared as described in General Method A for the preparation of Example 1 with replacement of 2,6-dichlorobenzaldehyde with 2-chloro-6-methylbenzaldehyde. MS (ESI) m/z: 549.9 [M+H]+; 1H NMR (500 MHz, DMSO-d6) δ 8.21 (s, 1H), 7.60 (d, J=11.5 Hz, 1H), 7.48-7.42 (m, 2H), 7.40-7.33 (m, 1H), 5.80 (s, 1H), 3.78-3.69 (m, 2H), 3.53-3.45 (m, 2H), 2.43-2.29 (m, 3H), 2.12 (s, 3H), 1.66 (br s, 4H), 1.24-1.10 (m, 4H); FXR EC50=19 nM.

Example 104

6-(2-(5-Cyclopropyl-3-(2-(trifluoromethyl)phenyl)isoxazol-4-yl)-7-azaspiro[3.5]non-1-en-7-yl)-4-isopropoxyquinoline-2-carboxylic acid

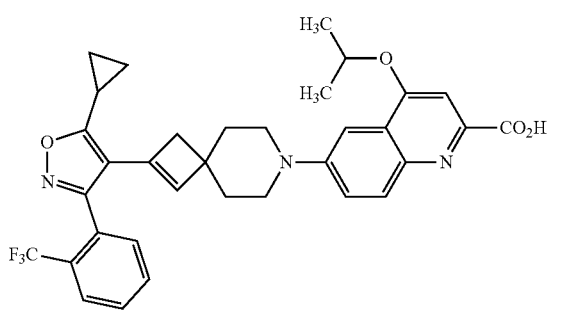

(104)

The title compound was prepared as described in General Method B for the preparation of Example 99 with replacement of ethyl 6-chloro-4-(trifluoromethyl) quinoline-2-carboxylate with methyl 6-bromo-4-isopropoxyquinoline-2-carboxylate. MS (ESI) m/z: 604.2 [M+H]+; 1H NMR (500 MHz, Methanol-d4) δ 8.08-8.36 (m, 1H), 7.83-8.03 (m, 2H), 7.64-7.82 (m, 3H), 7.51 (br d, J=6.60 Hz, 1H), 7.43 (br s, 1H), 5.63-5.84 (m, 1H), 5.20-5.46 (m, 1H), 3.62 (br s, 4H), 2.42 (br s, 2H), 2.29 (br d, J=4.40 Hz, 1H), 1.75 (br s, 4H), 1.60 (br s, 6H), 1.20 (br s, 4H); FXR EC50=59 nM.

Example 105

6-(2-(5-Cyclopropyl-3-(2-(trifluoromethyl)phenyl)isoxazol-4-yl)-7-azaspiro[3.5]non-1-en-7-yl)-4-methoxyquinoline-2-carboxylic acid

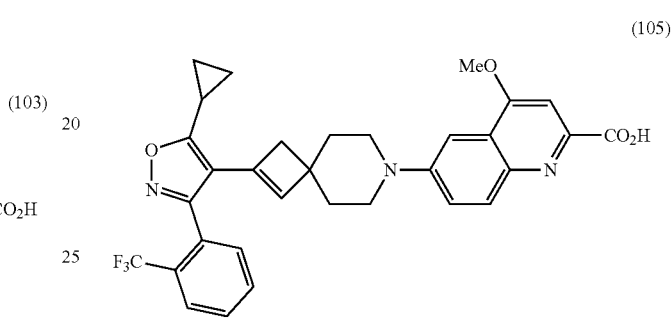

(105)

The title compound was prepared as described in General Method B for the preparation of Example 99 with replacement of ethyl 6-chloro-4-(trifluoromethyl) quinoline-2-carboxylate with methyl 6-bromo-4-methoxyquinoline-2-carboxylate. MS (ESI) m/z: 576.1 [M+H]+; 1H NMR (400 MHz, Methanol-d4) δ 8.10 (d, J=9.46 Hz, 1H), 7.86-7.93 (m, 1H), 7.72-7.85 (m, 3H), 7.71 (s, 1H), 7.47-7.60 (m, 1H), 7.43 (d, J=2.64 Hz, 1H), 5.61-5.86 (m, 1H), 4.31 (s, 3H), 3.51-3.68 (m, 2H), 3.21-3.31 (m, 2H), 2.41 (s, 2H), 2.23-2.36 (m, 1H), 1.72-1.89 (m, 4H), 1.11-1.22 (m, 4H); FXR EC50=62 nM.

Example 106

6-(2-(5-Cyclopropyl-3-(2-(trifluoromethoxy)phenyl)isoxazol-4-yl)-7-azaspiro[3.5]non-1-en-7-yl)-4-isopropoxyquinoline-2-carboxylic acid

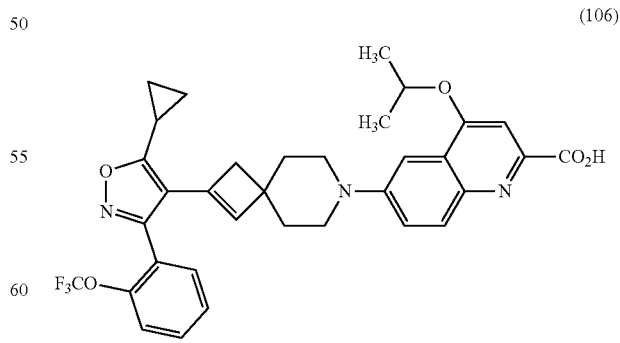

(106)

The title compound was prepared as described in General Method B for the preparation of Example 104 with replacement of 2-(trifluoromethyl)benzaldehyde with 2-(trifluoromethoxy)benzaldehyde. MS (ESI) m/z: 620.2 [M+H]+; 1H NMR (500 MHz, CDCl$_3$) δ 8.65 (br d, J=9.63 Hz, 1H), 7.83 (br d, J=7.70 Hz, 1H), 7.77 (s, 1H), 7.54-7.59 (m, 1H), 7.52 (dd, J=1.38, 7.70 Hz, 1H), 7.42 (br d, J=7.15 Hz, 3H), 5.87 (s, 1H), 5.16-5.27 (m, 1H), 3.53-3.66 (m, 2H), 3.39 (td, J=3.78, 12.52 Hz, 2H), 2.52 (s, 2H), 2.19 (br t, J=4.95 Hz, 1H), 1.79-1.93 (m, 4H), 1.62 (d, J=6.05 Hz, 6H), 1.30 (dd, J=2.34, 4.81 Hz, 2H), 1.17 (dd, J=2.61, 8.39 Hz, 2H); FXR EC$_{50}$=21 nM.

Example 107

6-(2-(5-Cyclopropyl-3-(3,5-dichloropyridin-4-yl)isoxazol-4-yl)-7-azaspiro[3.5]non-1-en-7-yl)-4-ethoxyquinoline-2-carboxylic acid

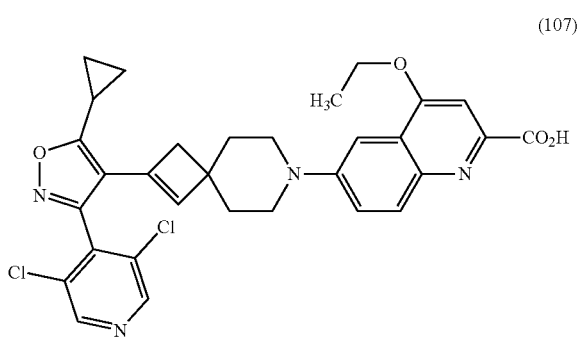 [SMILES: CCOc1cc(C(=O)O)nc2ccc(N3CCC4(C=C(c5c(-c6c(Cl)cncc6Cl)noc5C5CC5)C4)CC3)cc12]

(107)

The title compound was prepared as described in General Method B for the preparation of Example 72 with replacement of 2-(trifluoromethyl)benzaldehyde with 3,5-dichloroisonicotinaldehyde. MS (ESI) m/z: 591.1 [M+H]$^+$; $^1$H NMR (400 MHz, CDCl$_3$) δ 8.68 (br d, J=9.46 Hz, 1H), 8.65 (s, 1H), 7.79-7.87 (m, 1H), 7.76 (s, 1H), 7.39 (d, J=2.42 Hz, 1H), 5.84 (s, 1H), 4.59 (d, J=7.04 Hz, 2H), 3.57 (br s, 2H), 3.35 (br s, 2H), 2.45 (s, 2H), 2.14-2.27 (m, 1H), 1.82 (br s, 4H), 1.67 (t, J=7.04 Hz, 3H), 1.06-1.50 (m, 4H); FXR EC$_{50}$=31 nM.

Example 108

6-(2-(5-Cyclopropyl-3-(3,5-dichloropyridin-4-yl)isoxazol-4-yl)-7-azaspiro[3.5]non-1-en-7-yl)-4-methoxyquinoline-2-carboxylic acid

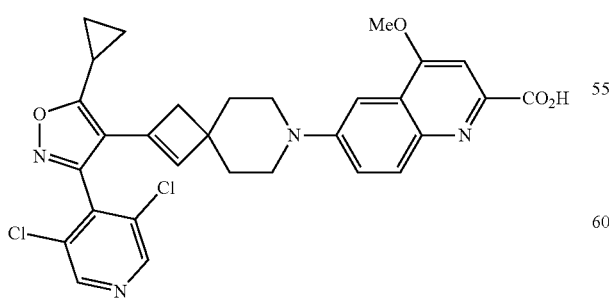

(108)

The title compound was prepared as described in General Method B for the preparation of Example 107 with replacement of methyl 6-bromo-4-ethoxyquinoline-2-carboxylate with methyl 6-bromo-4-methoxyquinoline-2-carboxylate. MS (ESI) m/z: 577.0 [M+H]$^+$; $^1$H NMR (400 MHz, Methanol-d$_4$) δ 8.68 (s, 2H), 8.11 (d, J=9.46 Hz, 1H), 7.78 (dd, J=2.53, 9.57 Hz, 1H), 7.72 (d, J=2.64 Hz, 1H), 7.44 (d, J=2.42 Hz, 1H), 5.89 (s, 1H), 4.30 (s, 3H), 3.57 (br s, 2H), 3.22-3.32 (m, 2H), 2.48 (s, 2H), 2.13-2.36 (m, 1H), 1.81 (br d, J=4.18 Hz, 4H), 1.17-1.34 (m, 4H); FXR EC$_{50}$=32 nM; Mouse in vivo (3 mg/kg, @ 6 h): Cyp7a1=−97%, Fgf15=+14×.

Example 109

6-(2-(3-(3-Chloropyridin-4-yl)-5-cyclopropylisoxazol-4-yl)-7-azaspiro[3.5]non-1-en-7-yl)-4-methoxyquinoline-2-carboxylic acid

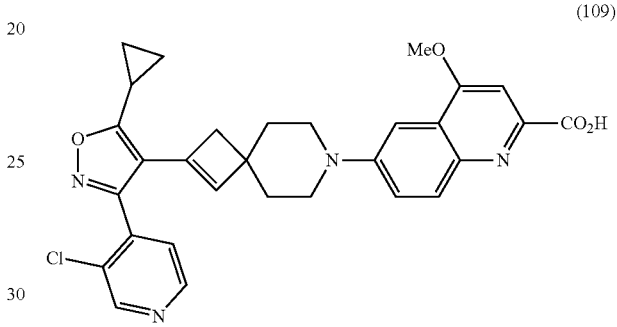

(109)

The title compound was obtained as a minor isolate during the preparation of Example 108 by reduction of one chlorine during the Pd-catalyzed Buchwald coupling step. MS (ESI) m/z: 543.1 [M+H]$^+$; $^1$H NMR (400 MHz, CDCl$_3$) δ 8.65 (s, 2H), 8.03 (d, J=9.24 Hz, 1H), 7.61 (s, 2H), 7.40 (d, J=2.64 Hz, 1H), 5.86 (s, 1H), 4.16 (s, 3H), 3.44-3.59 (m, 2H), 3.12-3.37 (m, 2H), 2.45 (s, 2H), 1.82 (br d, J=2.42 Hz, 7H), 1.13-1.44 (m, 8H), 0.91 (s, 3H); FXR EC$_{50}$=140 nM.

Example 110

6-(2-(5-Cyclopropyl-3-(2,6-dichloro-4-fluorophenyl)isoxazol-4-yl)-7-azaspiro[3.5]non-1-en-7-yl)-4-isopropoxyquinoline-2-carboxylic acid

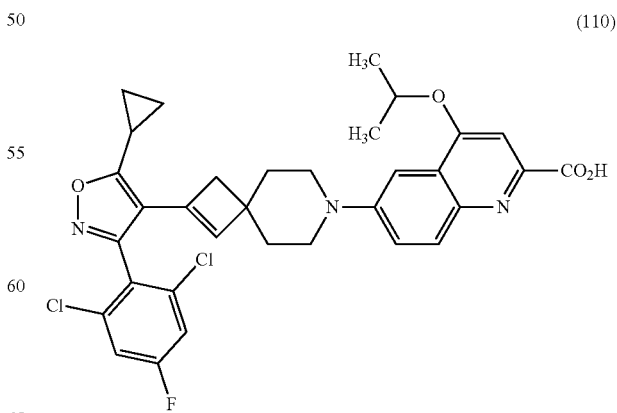

(110)

The title compound was prepared as described in General Method B for the preparation of Example 104 with replacement of 2-(trifluoromethyl)benzaldehyde with 2,6-dichloro-4-fluorobenzaldehyde. MS (ESI) m/z: 622.0 [M+H]⁺; ¹H NMR (500 MHz, CDCl₃) δ 7.96 (br d, J=8.9 Hz, 1H), 7.53 (br s, 2H), 7.43-7.27 (m, 1H), 7.24-7.16 (m, 2H), 5.84 (s, 1H), 5.02-4.88 (m, 1H), 3.46 (br s, 3H), 3.36-3.15 (m, 2H), 2.40 (s, 2H), 2.21-2.12 (m, 1H), 1.81 (br d, J=10.2 Hz, 4H), 1.50 (br s, 6H), 1.28 (br s, 2H), 1.14 (br d, J=7.4 Hz, 2H); FXR EC₅₀=37 nM.

Example 111

6-(2-(5-Cyclopropyl-3-(3,5-dichloropyridin-4-yl)isoxazol-4-yl)-7-azaspiro[3.5]non-1-en-7-yl)-4-isopropoxyquinoline-2-carboxylic acid

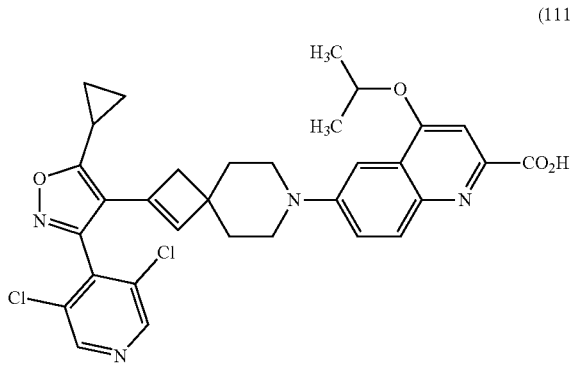
(111)

The title compound was prepared as described in General Method B for the preparation of Example 104 with replacement of 2-(trifluoromethyl)benzaldehyde with 2,6-dichloro-4-fluorobenzaldehyde. MS (ESI) m/z: 605.1 [M+H]⁺; ¹H NMR (500 MHz, Methanol-d₄) δ 8.73 (s, 2H), 8.18 (d, J=9.63 Hz, 1H), 7.98 (br d, J=2.75 Hz, 1H), 7.77 (s, 1H), 7.46 (d, J=2.75 Hz, 1H), 5.87-6.03 (m, 1H), 5.28-5.46 (m, 1H), 3.56-3.78 (m, 2H), 3.40 (td, J=4.47, 8.67 Hz, 2H), 2.51 (s, 2H), 2.25-2.36 (m, 1H), 1.71-1.94 (m, 4H), 1.61 (d, J=6.05 Hz, 6H), 1.03-1.34 (m, 4H); FXR EC₅₀=47 nM.

Example 112

6-(2-(5-Cyclopropyl-3-(2,6-dichloro-4-fluorophenyl)isoxazol-4-yl)-7-azaspiro[3.5]non-1-en-7-yl)-4-methoxyquinoline-2-carboxylic acid

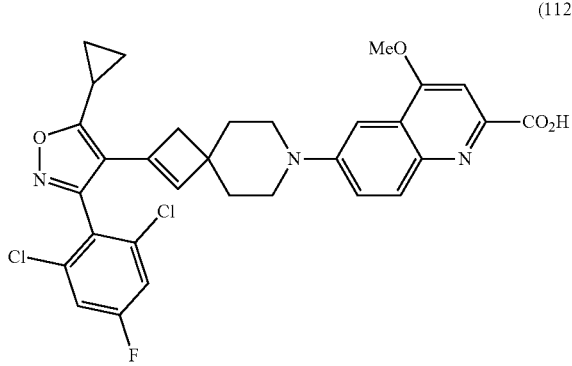 [SMILES: COc1cc(C(=O)O)nc2ccc(N3CCC4(C=C(c5c(-c6c(Cl)cc(F)cc6Cl)noc5C5CC5)C4)CC3)cc12]
(112)

The title compound was prepared as described in General Method B for the preparation of Example 108 with replacement of 3,5-dichloroisonicotinaldehyde with 2,6-dichloro-4-fluorobenzaldehyde. MS (ESI) m/z: 594.2 [M+H]⁺; ¹H NMR (500 MHz, CDCl₃) δ 7.96 (br d, J=9.2 Hz, 1H), 7.58 (s, 1H), 7.54 (br d, J=9.1 Hz, 1H), 7.40 (br s, 1H), 7.21 (br d, J=8.0 Hz, 2H), 5.85 (s, 1H), 4.14 (s, 3H), 3.74 (s, 1H), 3.61-3.39 (m, 2H), 3.39-3.19 (m, 2H), 2.42 (s, 2H), 2.18 (br d, J=4.6 Hz, 1H), 1.83 (br d, J=12.4 Hz, 4H), 1.30 (br d, J=3.7 Hz, 2H), 1.17 (br d, J=7.0 Hz, 2H); FXR EC₅₀=54 nM.

Example 113

6-(2-(5-Cyclopropyl-3-(2-(trifluoromethoxy)phenyl)isoxazol-4-yl)-7-azaspiro[3.5]non-1-en-7-yl)-4-ethoxyquinoline-2-carboxylic acid

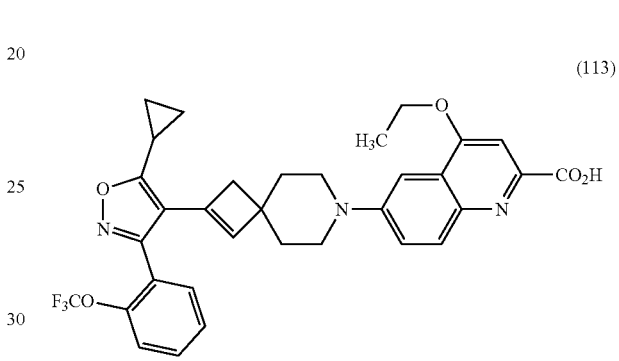
(113)

The title compound was prepared as described in General Method B for the preparation of Example 72 with replacement of 2-(trifluoromethyl)benzaldehyde with 2-(trifluoromethoxy)benzaldehyde. MS (ESI) m/z: 606.2 [M+H]⁺; ¹H NMR (500 MHz, CDCl₃) δ 8.68 (br d, J=9.35 Hz, 1H), 7.72-8.01 (m, 2H), 7.47-7.66 (m, 2H), 7.35-7.44 (m, 3H), 5.70-5.99 (m, 1H), 4.60 (q, J=6.97 Hz, 2H), 3.53-3.77 (m, 3H), 3.37-3.43 (m, 2H), 2.51 (s, 2H), 2.13-2.23 (m, 1H), 1.78-1.88 (m, 4H), 1.66-1.78 (m, 3H), 1.25-1.35 (m, 2H), 1.11-1.23 (m, 2H); FXR EC₅₀=116 nM.

Example 114

2-(2-(5-Cyclopropyl-3-(2,6-dichlorophenyl)isoxazol-4-yl)-7-azaspiro[3.5]non-1-en-7-yl)benzo[d]oxazole-6-carboxylic acid

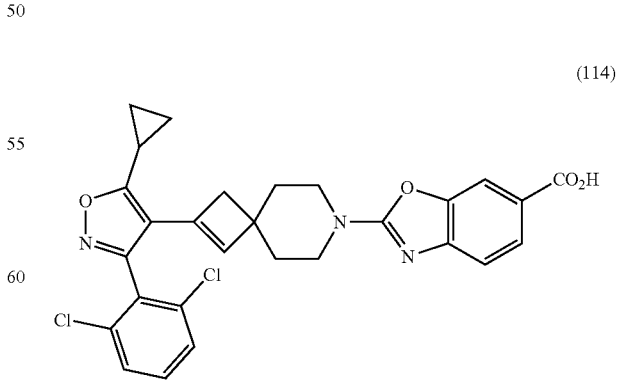
(114)

The title compound was prepared as described in General Method A for the preparation of Example 1 with replacement of ethyl 2-bromo-4-fluorobenzo[d]thiazole-6-carboxylate with methyl 2-chlorobenzo[d]oxazole-6-carboxylate. MS (ESI) m/z: 536.1 [M+H]$^+$; $^1$H NMR (500 MHz, DMSO-d$_6$) δ 7.78-7.92 (m, 2H), 7.63-7.67 (m, 2H), 7.53-7.63 (m, 1H), 7.28 (d, J=8.16 Hz, 1H), 5.91 (s, 1H), 3.65-3.81 (m, 2H), 3.46-3.57 (m, 2H), 2.37 (s, 2H), 2.23-2.36 (m, 1H), 1.59-1.71 (m, 4H), 1.11-1.29 (m, 4H); FXR EC$_{50}$=127 nM.

Example 115

6-(2-(5-Cyclopropyl-3-(2,6-dichlorophenyl)isoxazol-4-yl)-7-azaspiro[3.5]non-1-en-7-yl)-4-methylnicotinic acid

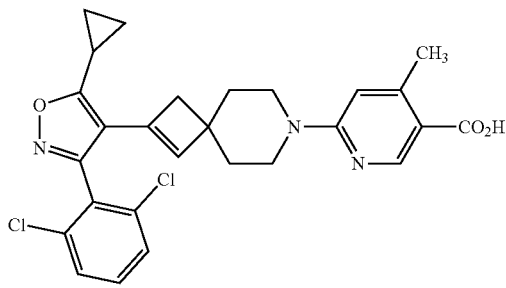

(115)

The title compound was prepared as described in General Method A for the preparation of Example 1 with replacement of ethyl 2-bromo-4-fluorobenzo[d]thiazole-6-carboxylate with methyl 6-fluoro-4-methylnicotinate. MS (ESI) m/z: 510.0 [M+H]$^+$; $^1$H NMR (500 MHz, DMSO-d$_6$) δ 8.55 (s, 1H), 7.63-7.70 (m, 2H), 7.61 (s, 1H), 6.65 (s, 1H), 5.71-6.02 (m, 1H), 3.81 (br d, J=13.43 Hz, 2H), 3.26-3.40 (m, 2H), 2.43 (s, 3H), 2.32 (s, 3H), 1.52 (br s, 4H), 1.08-1.34 (m, 4H); FXR EC$_{50}$=132 nM.

Example 116

6-(2-(5-Cyclopropyl-3-(2,6-dichlorophenyl)isoxazol-4-yl)-7-azaspiro[3.5]non-1-en-7-yl)-4-(trifluoromethyl)nicotinic acid

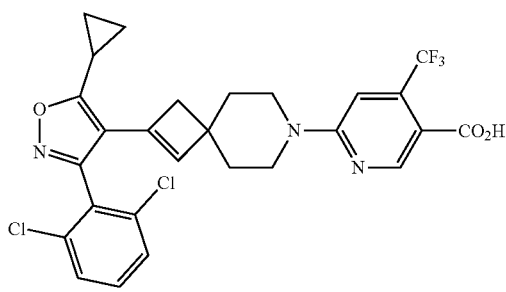

(116)

The title compound was prepared as described in General Method A for the preparation of Example 1 with replacement of ethyl 2-bromo-4-fluorobenzo[d]thiazole-6-carboxylate with methyl 6-chloro-4-(trifluoromethyl)nicotinate. MS (ESI) m/z: 564.2 [M+H]$^+$; $^1$H NMR (500 MHz, DMSO-d$_6$) δ 8.63 (s, 1H), 7.64-7.68 (m, 2H), 7.60 (dd, J=7.02, 8.85 Hz, 1H), 7.03 (s, 1H), 5.77-6.14 (m, 1H), 3.88 (br d, J=13.43 Hz, 2H), 2.55 (s, 3H), 2.35 (s, 2H), 1.56 (br s, 4H), 1.21 (br d, J=8.24 Hz, 2H), 1.11-1.17 (m, 2H); FXR EC$_{50}$=135 nM.

Example 117

6-(2-(5-Cyclopropyl-3-(2,6-dichlorophenyl)isoxazol-4-yl)-7-azaspiro[3.5]non-1-en-7-yl)-1-methyl-1H-pyrrolo[3,2-c]pyridine-3-carboxylic acid

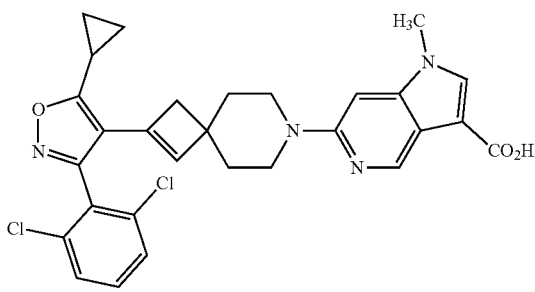

(117)

The title compound was prepared as described in General Method B for the preparation of Example 7 with replacement of methyl 6-chloro-1-methyl-1H-pyrrolo[2,3-b]pyridine-3-carboxylate with methyl 6-chloro-1-methyl-1H-pyrrolo[3,2-c]pyridine-3-carboxylate. MS (ESI) m/z: 549.1 [M+H]$^+$; $^1$H NMR (500 MHz, DMSO-d$_6$) δ 8.64 (s, 1H), 8.00 (s, 1H), 7.64-7.70 (m, 2H), 7.60 (br d, J=7.02 Hz, 1H), 7.14-7.34 (m, 1H), 6.97-7.09 (m, 1H), 5.74-5.99 (m, 1H), 3.75 (s, 3H), 3.67 (br s, 1H), 3.29 (br s, 1H), 2.89 (s, 1H), 2.73 (s, 1H), 2.35 (s, 3H), 1.64 (br d, J=16.48 Hz, 4H), 1.05-1.36 (m, 4H); FXR EC$_{50}$=139 nM.

Example 118

2-(2-(5-Cyclopropyl-3-(2,6-dichlorophenyl)isoxazol-4-yl)-7-azaspiro[3.5]non-1-en-7-yl)pyrimidine-5-carboxylic acid

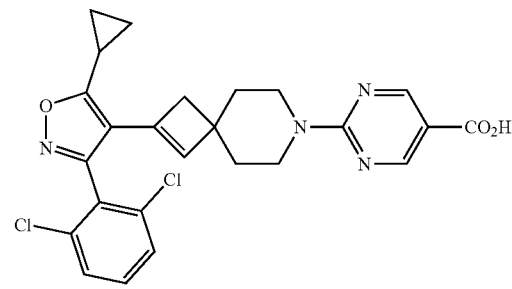

(118)

The title compound was prepared as described in General Method A for the preparation of Example 1 with replacement of ethyl 2-bromo-4-fluorobenzo[d]thiazole-6-carboxylate with methyl 2-chloropyrimidine-5-carboxylate. MS (ESI) m/z: 497.1 [M+H]$^+$; $^1$H NMR (500 MHz, DMSO-d$_6$) δ 8.73 (s, 2H), 7.64-7.71 (m, 2H), 7.62 (s, 1H), 5.80-5.92 (m, 1H), 3.94-4.27 (m, 2H), 2.35 (m, 3H), 1.54 (br s, 4H), 1.08-1.30 (m, 4H), additional signals missing due to water signal suppression; FXR EC$_{50}$=171 nM.

Example 119

2-(2-(5-Cyclopropyl-3-(2,6-dichlorophenyl)isoxazol-4-yl)-7-azaspiro[3.5]non-1-en-7-yl)-4-(trifluoromethyl)pyrimidine-5-carboxylic acid

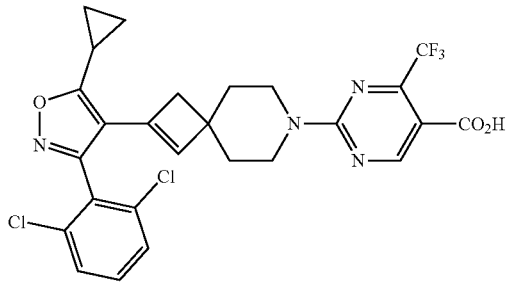

(119)

The title compound was prepared as described in General Method A for the preparation of Example 1 with replacement of ethyl 2-bromo-4-fluorobenzo[d]thiazole-6-carboxylate with ethyl 2-chloro-4-(trifluoromethyl)pyrimidine-5-carboxylate. MS (ESI) m/z: 565.2 [M+H]$^+$; $^1$H NMR (500 MHz, DMSO-d$_6$) δ 8.80 (s, 1H), 7.64 (s, 2H), 7.60 (br d, J=7.02 Hz, 1H), 5.79-5.92 (m, 1H), 4.01 (br s, 2H), 2.34 (m, 3H), 1.55 (m, 4H), 1.09-1.30 (m, 4H), additional signals missing due to water signal suppression; FXR EC$_{50}$=316 nM.

Example 120

2-(2-(5-Cyclopropyl-3-(2,6-dichlorophenyl)isoxazol-4-yl)-7-azaspiro[3.5]non-1-en-7-yl)-6-methylpyrimidine-4-carboxylic acid

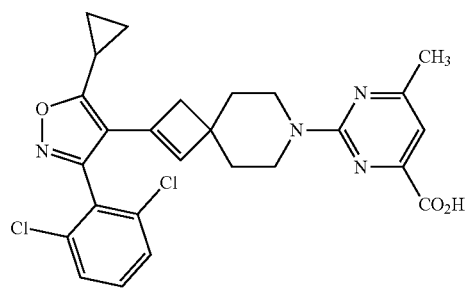

(120)

The title compound was prepared as described in General Method A for the preparation of Example 1 with replacement of ethyl 2-bromo-4-fluorobenzo[d]thiazole-6-carboxylate with methyl 2-chloro-6-methylpyrimidine-4-carboxylate. MS (ESI) m/z: 511.4 [M+H]$^+$; $^1$H NMR (500 MHz, DMSO-d$_6$) δ 7.63-7.71 (m, 2H), 7.60 (br d, J=7.32 Hz, 1H), 6.84 (s, 1H), 5.84-5.90 (m, 1H), 3.99 (br d, J=12.82 Hz, 2H), 2.32 (m, 3H), 2.29 (s, 3H), 1.50 (br s, 4H), 1.07-1.26 (m, 4H), additional signals missing due to water signal suppression; FXR EC$_{50}$=1390 nM.

Example 121

6-(2-(5-Cyclopropyl-3-(2,6-dichlorophenyl)isoxazol-4-yl)-7-azaspiro[3.5]non-1-en-7-yl)-5-methylnicotinic acid

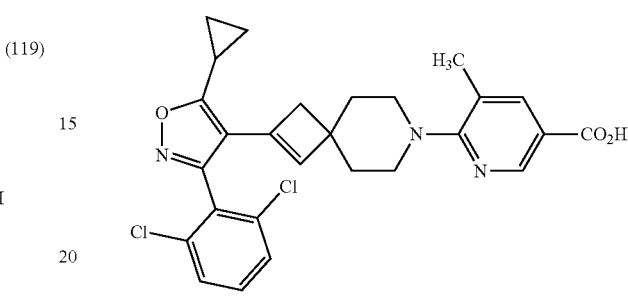

(121)

The title compound was prepared as described in General Method A for the preparation of Example 1 with replacement of ethyl 2-bromo-4-fluorobenzo[d]thiazole-6-carboxylate with methyl 6-fluoro-5-methylnicotinate. MS (ESI) m/z: 510.2 [M+H]$^+$; $^1$H NMR (500 MHz, DMSO-d$_6$) δ 8.55 (br s, 1H), 7.87 (br s, 1H), 7.52-7.76 (m, 3H), 5.74-5.94 (m, 1H), 3.08-3.45 (m, 2H), 3.02 (m, 2H), 2.32 (m, 3H), 2.23 (s, 3H), 1.52-1.85 (m, 4H), 1.18-1.35 (m, 4H); FXR EC$_{50}$=2590 nM.

Example 122

2-(2-(5-Cyclopropyl-3-(2,6-dichlorophenyl)isoxazol-4-yl)-7-azaspiro[3.5]non-1-en-7-yl)quinoline-6-carboxylic acid

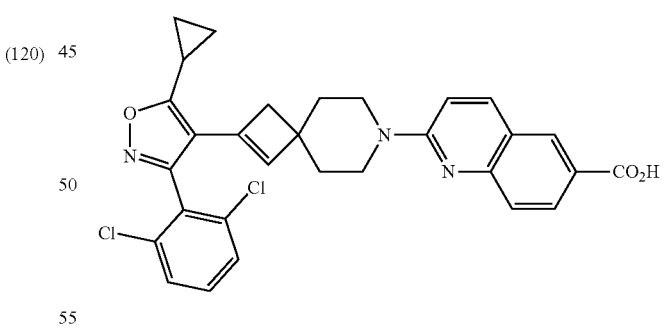

(122)

The title compound was prepared as described in General Method B for the preparation of Example 7 with replacement of methyl 6-chloro-1-methyl-1H-pyrrolo[2,3-b]pyridine-3-carboxylate with methyl 2-chloroquinoline-6-carboxylate. MS (ESI) m/z: 546.1 [M+H]$^+$; $^1$H NMR (500 MHz, Methanol-d$_4$) δ 8.52-8.61 (m, 1H), 8.45 (d, J=9.63 Hz, 1H), 8.38 (dd, J=1.51, 8.67 Hz, 1H), 7.93 (d, J=8.80 Hz, 1H), 7.55-7.62 (m, 3H), 7.50-7.55 (m, 1H), 5.87 (s, 1H), 4.11 (br d, J=14.03 Hz, 2H), 3.65-3.90 (m, 2H), 2.56 (s, 2H), 2.34 (s, 1H), 2.06 (s, 1H), 1.90 (br t, J=4.26 Hz, 4H), 1.14-1.33 (m, 4H); FXR EC$_{50}$=40 nM.

163

2-(2-(5-Cyclopropyl-3-(2,6-dichlorophenyl)isoxazol-4-yl)-7-azaspiro[3.5]non-1-en-7-yl)pyrrolo[2,1-f][1,2,4]triazine-5-carboxylic acid (123)

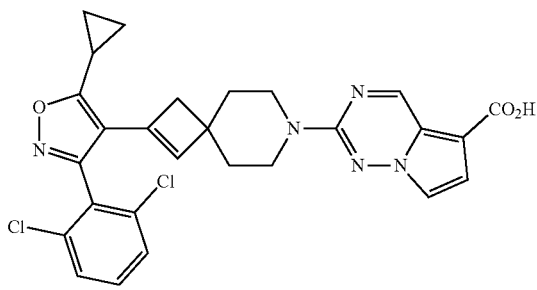

Step 1. Ethyl 2-chloropyrrolo[2,1-f][1,2,4]triazine-5-carboxylate

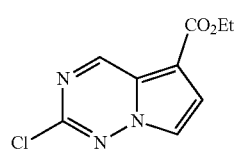 [SMILES: CCOC(=O)c1ccn2nc(Cl)ncc12]

A mixture of ethyl 2,4-dichloropyrrolo[2,1-f][1,2,4]triazine-5-carboxylate (1.3 g, 3.4 mmol), and sodium acetate (3.8 g, 45.9 mmol) in a mixture of EtOAc (80 mL) and 2-propanol (16 mL) was stirred at room temperature under hydrogen atmosphere (balloon pressure). After 2.5 h, the resulting mixture was filtered through a pad of Celite, and the filtrate was evaporated under reduced pressure. The crude residue was purified by flash chromatography on $SiO_2$ (0-100% EtOAc/hexanes, Isco 80 g column) to give ethyl 2-chloropyrrolo[2,1-f][1,2,4]triazine-5-carboxylate (470 mg, 2.1 mmol, 61% yield) as a yellow solid. MS (ESI) m/z: 226.1 [M+H]$^+$; $^1$H NMR (600 MHz, CDCl$_3$) δ 9.46 (s, 1H), 7.77 (d, J=2.6 Hz, 1H), 7.45 (d, J=2.8 Hz, 1H), 4.43 (d, J=7.2 Hz, 2H), 1.44 (t, J=7.1 Hz, 3H).

Example 123. 2-(2-(5-Cyclopropyl-3-(2,6-dichlorophenyl)isoxazol-4-yl)-7-azaspiro[3.5]non-1-en-7-yl)pyrrolo[2,1-f][1,2,4]triazine-5-carboxylic acid The title compound was prepared as described in General Method A for the preparation of Example 1 with replacement of ethyl 2-bromo-4-fluorobenzo[d]thiazole-6-carboxylate with ethyl 2-chloropyrrolo[2,1-f][1,2,4]triazine-5-carboxylate. MS (ESI) m/z: 535.9 [M+H]$^+$; $^1$H NMR (500 MHz, DMSO-d$_6$) δ 9.19 (br s, 1H), 7.57-7.69 (m, 4H), 7.04 (br s, 1H), 5.87 (s, 1H), 3.75-3.96 (m, 2H), 2.34 (m, 3H), 1.56 (br s, 4H), 1.17-1.27 (m, 2H), 1.09-1.17 (m, 2H), additional signals missing due to water signal suppression; FXR EC$_{50}$=40 nM.

164

6-(2-(5-Cyclopropyl-3-(2,6-dichlorophenyl)isoxazol-4-yl)-7-azaspiro[3.5]non-1-en-7-yl)-2-methylnicotinic acid (124)

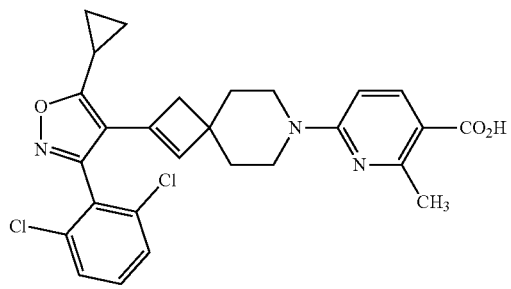

The title compound was prepared as described in General Method A for the preparation of Example 1 with replacement of ethyl 2-bromo-4-fluorobenzo[d]thiazole-6-carboxylate with methyl 6-chloro-2-methylnicotinate. MS (ESI) m/z: 510.1 [M+H]$^+$; $^1$H NMR (500 MHz, DMSO-d$_6$) δ 7.90 (br d, J=9.00 Hz, 1H), 7.64-7.72 (m, 2H), 7.54-7.63 (m, 1H), 6.65 (br d, J=8.92 Hz, 1H), 5.76-5.97 (m, 1H), 3.78-3.96 (m, 2H), 3.34 (br s, 1H), 2.55 (m, 3H), 2.33 (br s, 3H), 1.52 (br s, 4H), 1.10-1.25 (m, 4H), additional signals missing due to water signal suppression; FXR EC$_{50}$=78 nM.

Example 125

6-(2-(5-Cyclopropyl-3-(2,6-dichlorophenyl)isoxazol-4-yl)-7-azaspiro[3.5]non-1-en-7-yl)-1-methyl-1H-indazole-3-carboxylic acid (125)

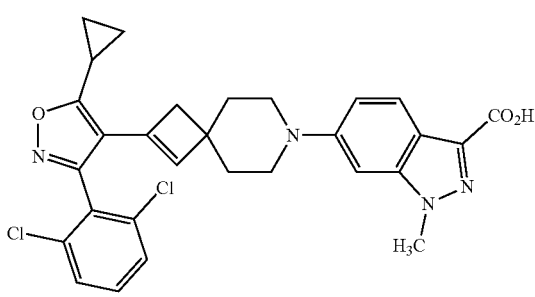

The title compound was prepared as described in General Method B for the preparation of Example 7 with replacement of methyl 6-chloro-1-methyl-1H-pyrrolo[2,3-b]pyridine-3-carboxylate with methyl 6-bromo-1-methyl-3a,7a-dihydro-1H-indazole-3-carboxylate. MS (ESI) m/z: 549.0 [M+H]$^+$; $^1$H NMR (500 MHz, Methanol-d$_4$) δ 8.19-8.31 (m, 1H), 7.95 (d, J=1.38 Hz, 1H), 7.53-7.70 (m, 3H), 7.49 (d, J=9.35 Hz, 1H), 5.97 (s, 1H), 4.53 (s, 3H), 3.52-3.85 (m, 5H), 2.61 (s, 2H), 2.36 (s, 1H), 1.97-2.22 (m, 5H), 1.09-1.51 (m, 5H); FXR EC$_{50}$=96 nM.

Example 126

6-(2-(5-Cyclopropyl-3-(2,6-dichlorophenyl)isoxazol-4-yl)-7-azaspiro[3.5]non-1-en-7-yl)-3-(trifluoromethyl)imidazo[1,5-a]pyridine-1-carboxylic acid (126)

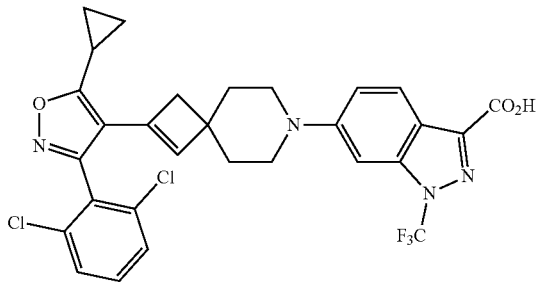

Step 1. Ethyl 2-(5-bromopyridin-2-yl)-2-(hydroxyimino)acetate

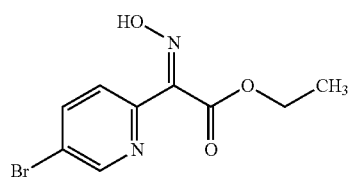

Sodium nitrite (28.3 mg, 0.41 mmol) in water (0.5 mL) was added to the mixture of ethyl 2-(5-bromopyridin-2-yl)acetate (100 mg, 0.41 mmol) in AcOH (0.5 mL) at 0° C. The reaction mixture was stirred at room temperature for 1 h and water (0.5 mL) was added. Stirring was maintained for 1 h and the reaction mixture was basified with 1M aqueous $K_2HPO_4$, to pH 8-9. The aqueous layer was extracted with EtOAc, and the organic layer was dried over $MgSO_4$, filtered, and concentrated in vacuo. The crude product was used directly in next step.

Step 2. Ethyl 6-bromo-3-(trifluoromethyl)imidazo[1,5-a]pyridine-1-carboxylate

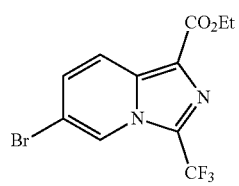 [SMILES: CCOC(=O)c1nc(C(F)(F)F)n2cc(Br)ccc12]

Ethyl 2-(5-bromopyridin-2-yl)-2-(hydroxyimino)acetate (4.5 g, 16.5 mmol) was suspended in THF (50 mL). TFA (6.2 mL) was added followed by portion wise addition of zinc dust (2.2 g, 33.0 mmol). Trifluoroacetic anhydride (4.7 mL, 33.0 mmol) was added and the reaction mixture was stirred for 1 hour. The mixture was filtered through Celite and concentrated in vacuo. Pyridine (25 mL) was added to the residue followed by slow addition of trifluoroacetic anhydride (4.7 mL, 33.0 mmol). After 1 h the reaction mixture was concentrated in vacuo and purified by flash chromatography on $SiO_2$ (0-100% EtOAc/hexanes, Isco 80 g column) to give ethyl 6-bromo-3-(trifluoromethyl) imidazo[1,5-a]pyridine-1-carboxylate (5 g, 14.8 mmol, 90% yield) as a yellow solid. $^1$H NMR (400 MHz, $CDCl_3$) δ 8.38 (s, 1H), 8.24 (dd, J=9.7, 0.9 Hz, 1H), 7.36 (dd, J=9.6, 1.4 Hz, 1H), 4.50 (q, J=7.3 Hz, 2H), 1.46 (t, J=7.2 Hz, 3H).

Example 126. 6-(2-(5-Cyclopropyl-3-(2,6-dichlorophenyl)isoxazol-4-yl)-7-azaspiro[3.5]non-1-en-7-yl)-3-(trifluoromethyl)imidazo[1,5-a]pyridine-1-carboxylic acid The title compound was prepared as described in General Method B for the preparation of Example 7 with replacement of methyl 6-chloro-1-methyl-1H-pyrrolo[2,3-b]pyridine-3-carboxylate with ethyl 6-bromo-3-(trifluoromethyl) imidazo[1,5-a]pyridine-1-carboxylate. MS (ESI) m/z: 603.2 [M+H]$^+$; $^1$H NMR (500 MHz, Methanol-$d_4$) δ 8.11-8.18 (m, 1H), 7.61 (s, 1H), 7.50-7.59 (m, 3H), 7.46 (dd, J=1.79, 10.04 Hz, 1H), 5.85 (s, 1H), 3.06 (ddd, J=3.30, 8.60, 12.04 Hz, 2H), 2.43 (s, 2H), 2.33 (s, 1H), 2.06 (s, 1H), 1.59-1.91 (m, 4H), 1.05-1.37 (m, 5H); FXR $EC_{50}$=102 nM.

Example 127

6-(2-(5-Cyclopropyl-3-(2,6-dichlorophenyl)isoxazol-4-yl)-7-azaspiro[3.5]non-1-en-7-yl)-3-methylimidazo[1,5-a]pyridine-1-carboxylic acid (127)

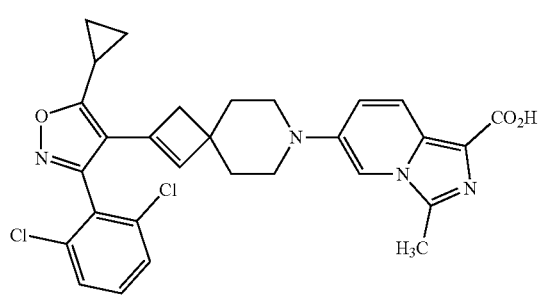

Step 1. Methyl 6-bromo-3-methylimidazo[1,5-a]pyridine-1-carboxylate

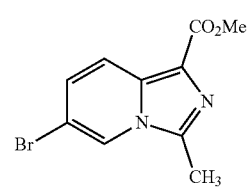

Potassium carbonate (0.14 g, 0.98 mmol) was added to a solution of 6-bromo-3-methylimidazo[1,5-a]pyridine-1-carboxylic acid (0.1 g, 0.39 mmol) in DMF (0.78 mL). After 5 minutes, iodomethane (0.04 mL, 0.59 mmol) was added to the thick slurry and the reaction mixture was stirred at room temperature overnight. The reaction mixture was diluted with Et$_2$O and water. The organic layer was washed with brine and the combined aqueous layers were back extracted with Et$_2$O. The combined organic extracts were dried over Na$_2$SO$_4$, filtered and concentrated in vacuo to give white crystals of a suitable purity to carry on to the next step. $^1$H NMR (400 MHz, CDCl$_3$) δ 8.08 (dd, J=9.6, 1.0 Hz, 1H), 8.00-7.97 (m, 1H), 7.14 (dd, J=9.7, 1.5 Hz, 1H), 3.98 (s, 3H), 2.70 (s, 3H).

Example 127. 6-(2-(5-Cyclopropyl-3-(2,6-dichlorophenyl)isoxazol-4-yl)-7-azaspiro[3.5]non-1-en-7-yl)-3-methylimidazo[1,5-a]pyridine-1-carboxylic acid The title compound was prepared as described in General Method B for the preparation of Example 126 with replacement of ethyl 6-bromo-3-(trifluoromethyl) imidazo[1,5-a]pyridine-1-carboxylate with methyl 6-bromo-3-methylimidazo[1,5-a]pyridine-1-carboxylate. MS (ESI) m/z: 549.2 [M+H]$^+$; $^1$H NMR (500 MHz, Methanol-d$_4$) δ 7.96-8.14 (m, 1H), 7.41-7.70 (m, 5H), 5.86 (s, 1H), 3.35-3.49 (m, 2H), 3.13 (ddd, J=3.58, 8.73, 12.17 Hz, 2H), 2.86 (s, 3H), 2.44 (s, 2H), 2.25-2.37 (m, 1H), 2.06 (s, 2H), 1.66-1.90 (m, 4H); FXR EC$_{50}$=267 nM.

Example 128

6-(2-(5-Cyclopropyl-3-(2,6-dichlorophenyl)isoxazol-4-yl)-7-azaspiro[3.5]non-1-en-7-yl)-1-methyl-1H-indole-2-carboxylic acid (128)

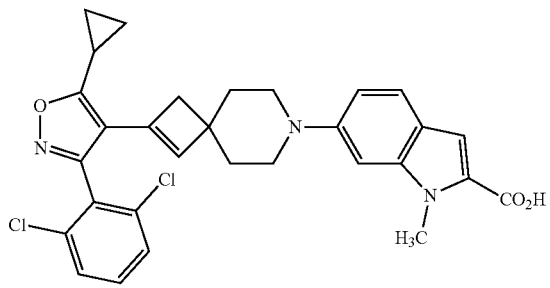

The title compound was prepared as described in General Method B for the preparation of Example 7 with replacement of methyl 6-chloro-1-methyl-1H-pyrrolo[2,3-b]pyridine-3-carboxylate with methyl 6-bromo-1-methyl-1H-indole-2-carboxylate. MS (ESI) m/z: 548.2 [M+H]$^+$; $^1$H NMR (500 MHz, Methanol-d$_4$) δ 8.10-8.23 (m, 1H), 8.04 (d, J=8.53 Hz, 1H), 7.93 (d, J=9.35 Hz, 1H), 7.44-7.67 (m, 3H), 7.18 (d, J=2.20 Hz, 1H), 5.85 (s, 1H), 4.87 (s, 3H), 3.48 (br dd, J=5.09, 11.97 Hz, 2H), 3.33 (br s, 2H), 3.04-3.25 (m, 2H), 2.42 (s, 2H), 2.18-2.35 (m, 1H), 1.61-1.97 (m, 4H), 1.04-1.36 (m, 4H); FXR EC$_{50}$=287 nM.

Example 129

7-(2-(5-Cyclopropyl-3-(2,6-dichlorophenyl)isoxazol-4-yl)-7-azaspiro[3.5]non-1-en-7-yl)isoquinoline-3-carboxylic acid (129)

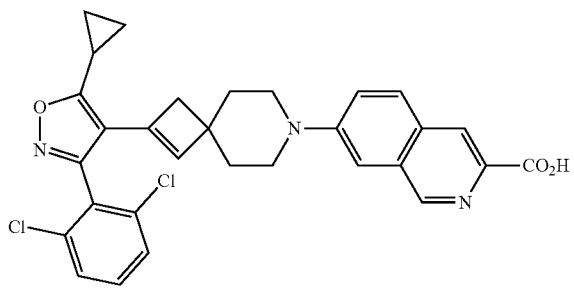

The title compound was prepared as described in General Method B for the preparation of Example 7 with replacement of methyl 6-chloro-1-methyl-1H-pyrrolo[2,3-b]pyridine-3-carboxylate with methyl 7-chloroisoquinoline-3-carboxylate. MS (ESI) m/z: 546.3 [M+H]$^+$; $^1$H NMR (400 MHz, CDCl$_3$) δ 9.19-8.84 (m, 1H), 8.66-8.34 (m, 1H), 8.05-7.69 (m, 1H), 7.66-7.50 (m, 1H), 7.49-7.29 (m, 3H), 5.78 (s, 1H), 3.52 (br d, J=2.6 Hz, 3H), 3.39-3.21 (m, 2H), 2.99 (s, 1H), 2.47-2.32 (m, 2H), 2.26-2.10 (m, 1H), 1.78 (br s, 4H), 1.38-1.23 (m, 2H), 1.22-1.09 (m, 2H); FXR EC$_{50}$=341 nM.

Example 130

2-((7-(2-(5-Cyclopropyl-3-(2,6-dichlorophenyl)isoxazol-4-yl)-7-azaspiro[3.5]non-1-en-7-yl)quinoxalin-2-yl)oxy)acetic acid (130)

Step 1. tert-Butyl 2-((7-bromoquinoxalin-2-yl)oxy)acetate

Potassium carbonate (0.10 g, 0.75 mmol) was added to a room temperature solution of 7-bromoquinoxalin-2-ol (11 g, 0.5 mmol) in acetone (5 mL). After 5 minutes, tert-butyl 2-bromoacetate (0.15 g, 0.75 mmol) was added, and the reaction mixture was stirred at 25° C. overnight. Saturated aqueous $NH_4C_1$ (20 mL) was added and the resulting mixture was extracted with $Et_2O$ (3×10 mL). The combined organic layers were dried over $MgSO_4$, filtered, and concentrated in vacuo. The crude product was purified by flash chromatography on $SiO_2$ (0-100% EtOAc/hexanes, Isco 40 g column) to yield tert-butyl 2-((7-bromoquinoxalin-2-yl)oxy)acetate (26 mg, 0.07 mmol, 15% yield). MS (ESI) m/z: 340.9 [M+H]$^+$; $^1$H NMR (400 MHz, CDCl$_3$) δ 8.48-8.67 (m, 1H), 7.98 (d, J=1.98 Hz, 1H), 7.91 (d, J=8.80 Hz, 1H), 7.68 (dd, J=2.20, 8.80 Hz, 1H), 4.94 (s, 2H), 1.51 (s, 9H).

Example 130. 2-((7-(2-(5-Cyclopropyl-3-(2,6-dichlorophenyl)isoxazol-4-yl)-7-azaspiro[3.5]non-1-en-7-yl)quinoxalin-2-yl)oxy)acetic acid The title compound was prepared as described in General Method B for the preparation of Example 7 with replacement of methyl 6-chloro-1-methyl-1H-pyrrolo[2,3-b]pyridine-3-carboxylate with tert-butyl 2-((7-bromoquinoxalin-2-yl)oxy)acetate and hydrolysis of the tert-butyl ester with TFA instead of LiOH. MS (ESI) m/z: 577.0 [M+H]$^+$; $^1$H NMR (400 MHz, Methanol-d$_4$) δ 8.37 (s, 1H), 7.90 (d, J=9.02 Hz, 1H), 7.48-7.61 (m, 4H), 7.37 (d, J=2.64 Hz, 1H), 5.88 (s, 1H), 5.08 (s, 2H), 3.50-3.65 (m, 2H), 3.39 (dt, J=4.29, 8.53 Hz, 2H), 2.48 (s, 2H), 2.34 (s, 1H), 1.76-1.96 (m, 4H), 1.16-1.30 (m, 4H); FXR EC$_{50}$=373 nM.

Example 131

6-(2-(5-Cyclopropyl-3-(2,6-dichlorophenyl)isoxazol-4-yl)-7-azaspiro[3.5]non-1-en-7-yl)-1-((2-(trimethylsilyl)ethoxy)methyl)-1H-indole-3-carboxylic acid (131)

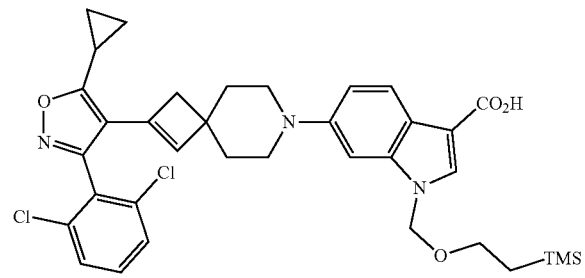

Step 1. Methyl 6-bromo-1-((2-(trimethylsilyl)ethoxy)methyl)-1H-indole-3-carboxylate

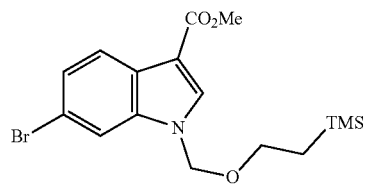 [SMILES: COC(=O)c1cn(COCC[Si](C)(C)C)c2cc(Br)ccc12]

Sodium hydride (48.0 mg, 1.2 mmol) was added to a room temp solution of methyl 6-bromo-1H-indole-3-carboxylate (0.25 g, 1.0 mmol) in THF (50 mL). After stirring for 15 minutes, SEM-C$_1$ (0.21 mL, 1.2 mmol) was added and the resulting suspension was stirred at 25° C. overnight. Water (50 mL) was added to the reaction mixture giving a sticky precipitate. The solvent was decanted and the residue was purified by flash chromatography on $SiO_2$ (0-30% EtOAc/hexanes, Isco 24 g column) to yield methyl 6-bromo-1-((2-(trimethylsilyl)ethoxy)methyl)-1H-indole-3-carboxylate (0.36 g, 0.83 mmol) as a gum. MS (ESI) m/z: 384.0 [M+H]$^+$; $^1$H NMR (500 MHz, CDCl$_3$) δ 8.06 (d, J=8.53 Hz, 1H), 7.86 (s, 1H), 7.72 (d, J=1.65 Hz, 1H), 7.43 (dd, J=1.65, 8.53 Hz, 1H), 5.48 (s, 2H), 4.80 (s, 1H), 3.94 (s, 3H), 1.29 (br t, J=7.15 Hz, 3H), −0.23-0.22 (m, 11H).

Example 131. 6-(2-(5-Cyclopropyl-3-(2,6-dichlorophenyl)isoxazol-4-yl)-7-azaspiro[3.5]non-1-en-7-yl)-1-((2-(trimethylsilyl)ethoxy)methyl)-1H-indole-3-carboxylic acid The title compound was prepared as described in General Method B for the preparation of Example 7 with replacement of methyl 6-chloro-1-methyl-1H-pyrrolo[2,3-b]pyridine-3-carboxylate with methyl 6-bromo-1-((2-(trimethylsilyl)ethoxy)methyl)-1H-indole-3-carboxylate. MS (ESI) m/z: 664.2 [M+H]$^+$; $^1$H NMR (500 MHz, Methanol-d$_4$) δ 8.10-8.23 (m, 1H), 8.04 (d, J=8.53 Hz, 1H), 7.93 (d, J=9.35 Hz, 1H), 7.44-7.67 (m, 3H), 7.18 (d, J=2.20 Hz, 1H), 5.85 (s, 1H), 4.87 (s, 3H), 3.48 (br dd, J=5.09, 11.97 Hz, 2H), 3.33 (br s, 2H), 3.04-3.25 (m, 2H), 2.42 (s, 2H), 2.18-2.35 (m, 1H), 1.61-1.97 (m, 4H), 1.04-1.36 (m, 4H); FXR EC$_{50}$=445 nM.

Example 132

7-(2-(5-Cyclopropyl-3-(2,6-dichlorophenyl)isoxazol-4-yl)-7-azaspiro[3.5]non-1-en-7-yl)-8-methylquinoline-3-carboxylic acid (132)

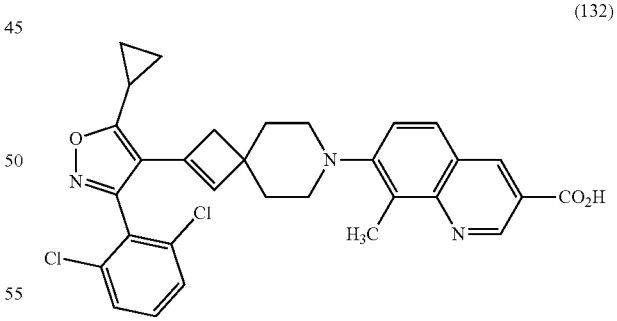

The title compound was prepared as described in General Method B for the preparation of Example 7 with replacement of methyl 6-chloro-1-methyl-1H-pyrrolo[2,3-b]pyridine-3-carboxylate with methyl 7-bromo-8-methylquinoline-3-carboxylate. MS (ESI) m/z: 560.0 [M+H]$^+$; $^1$H NMR (500 MHz, Methanol-d$_4$) δ 9.11-9.45 (m, 2H), 8.14 (d, J=9.08 Hz, 1H), 7.76 (d, J=9.08 Hz, 1H), 7.42-7.65 (m, 3H), 5.83-6.00 (m, 1H), 3.35-3.45 (m, 2H), 3.10-3.30 (m, 2H), 2.66 (s, 3H), 2.48 (s, 2H), 2.34 (s, 1H), 1.66-1.94 (m, 4H), 1.18-1.43 (m, 4H); FXR EC$_{50}$=958 nM.

Example 133

3-(2-(5-Cyclopropyl-3-(2,6-dichlorophenyl)isoxazol-4-yl)-7-azaspiro[3.5]non-1-en-7-yl)-1-methyl-1H-indazole-6-carboxylic acid

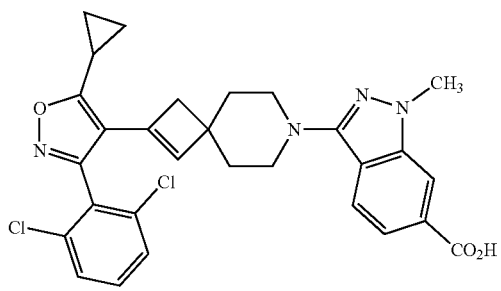

(133)

The title compound was prepared as described in General Method B for the preparation of Example 7 with replacement of methyl 6-chloro-1-methyl-1H-pyrrolo[2,3-b]pyridine-3-carboxylate with methyl 3-bromo-1-methyl-1H-indazole-6-carboxylate. MS (ESI) m/z: 549.0 [M+H]+; $^1$H NMR (500 MHz, Methanol-$d_4$) δ 8.19-8.31 (m, 1H), 7.95 (d, J=1.38 Hz, 1H), 7.53-7.70 (m, 3H), 7.49 (d, J=9.35 Hz, 1H), 5.97 (s, 1H), 4.53 (s, 3H), 3.52-3.85 (m, 5H), 2.61 (s, 2H), 2.36 (s, 1H), 1.97-2.22 (m, 5H), 1.09-1.51 (m, 5H); FXR EC$_{50}$=1175 nM.

Example 134

3-(2-(5-Cyclopropyl-3-(2-(trifluoromethyl)phenyl)isoxazol-4-yl)-7-azaspiro[3.5]non-1-en-7-yl)-1-methyl-1H-indazole-6-carboxylic acid

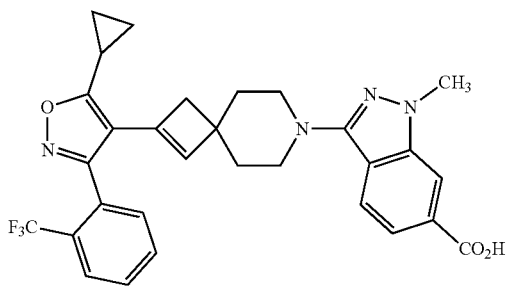

(134)

The title compound was prepared as described in General Method B for the preparation of Example 133 with replacement of 2,6-dichlorobenzaldehyde with 2-(trifluoromethyl)benzaldehyde. MS (ESI) m/z: 549.1 [M+H]+; $^1$H NMR (500 MHz, Methanol-$d_4$) δ 8.07-8.17 (m, 1H), 7.86-7.96 (m, 1H), 7.72-7.85 (m, 3H), 7.69 (br d, J=8.80 Hz, 1H), 7.52 (d, J=6.88 Hz, 1H), 5.74 (s, 1H), 3.95 (s, 3H), 3.43-3.71 (m, 4H), 3.12-3.28 (m, 2H), 2.41 (s, 2H), 2.31 (s, 1H), 1.58-1.97 (m, 5H), 1.06-1.33 (m, 5H); FXR EC$_{50}$=3314 nM.

Example 135

2-(2-(5-Cyclopropyl-3-(2-(trifluoromethyl)phenyl)isoxazol-4-yl)-7-azaspiro[3.5]non-1-en-7-yl)pyrrolo[2,1-f][1,2,4]triazine-5-carboxylic acid

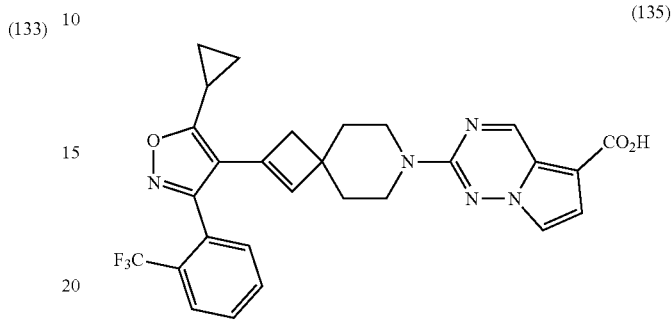

(135)

The title compound was prepared as described in General Method A for the preparation of Example 123 with replacement of 2,6-dichlorobenzaldehyde with 2-(trifluoromethyl)benzaldehyde. MS (ESI) m/z: 536.1 [M+H]+; $^1$H NMR (400 MHz, Methanol-$d_4$) δ 9.00-9.33 (m, 2H), 8.10 (d, J=9.46 Hz, 1H), 7.87 (d, J=1.76 Hz, 1H), 7.67-7.83 (m, 3H), 7.51 (dd, J=1.65, 7.15 Hz, 1H), 7.14 (d, J=2.20 Hz, 1H), 5.73 (s, 1H), 3.76-4.07 (m, 2H), 3.58 (br dd, J=6.05, 13.75 Hz, 2H), 2.46 (s, 2H), 2.31 (s, 1H), 2.05 (s, 1H), 1.76 (t, J=5.61 Hz, 4H), 1.10-1.38 (m, 5H); FXR EC$_{50}$=87 nM.

Example 136

2-(2-(3-(2-Chloro-6-fluorophenyl)-5-cyclopropylisoxazol-4-yl)-7-azaspiro[3.5]non-1-en-7-yl)-4-fluorobenzo[d]thiazole-6-carboxylic acid

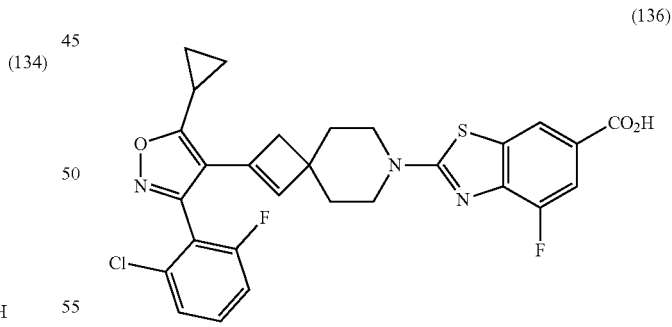

(136)

The title compound was prepared as described in General Method A for the preparation of Example 1 with replacement of 2,6-dichlorobenzaldehyde with 2-chloro-6-fluorobenzaldehyde. MS (ESI) m/z: 554.2 [M+H]+; $^1$H NMR (500 MHz, DMSO-$d_6$) δ 8.18 (d, J=1.5 Hz, 1H), 7.68-7.61 (m, 1H), 7.58 (d, J=11.5 Hz, 1H), 7.53 (d, J=8.2 Hz, 1H), 7.42 (t, J=8.7 Hz, 1H), 5.93 (s, 1H), 3.54-3.45 (m, 2H), 2.40 (s, 2H), 2.33 (dt, J=3.4, 8.3 Hz, 1H), 1.65 (q, J=4.8, 5.3 Hz, 4H), 1.25-1.08 (m, 4H), additional signals missing due to water signal suppression; FXR EC$_{50}$=37 nM.

Example 137

2-(2-(5-Cyclopropyl-3-(2,6-difluorophenyl)isoxazol-4-yl)-7-azaspiro[3.5]non-1-en-7-yl)-4-fluorobenzo[d]thiazole-6-carboxylic acid

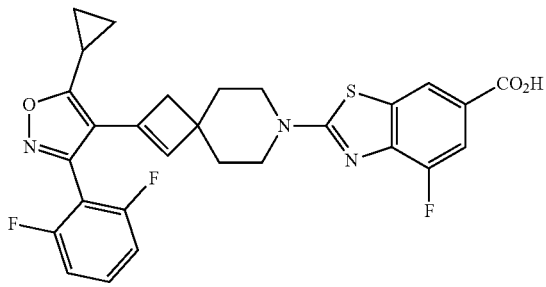

(137)

The title compound was prepared as described in General Method A for the preparation of Example 1 with replacement of 2,6-dichlorobenzaldehyde with 2,6-difluorobenzaldehyde. MS (ESI) m/z: 538.1 [M+H]$^+$; $^1$H NMR (500 MHz, DMSO-d$_6$) δ 8.20 (br s, 1H), 7.75-7.50 (m, 2H), 7.33 (t, J=8.1 Hz, 2H), 6.02 (s, 1H), 3.79-3.67 (m, 2H), 2.47 (s, 2H), 2.38-2.27 (m, 1H), 1.71-1.65 (m, 1H), 1.18 (dtd, J=3.6, 6.5, 29.1 Hz, 4H), additional signals missing due to water signal suppression; FXR EC$_{50}$=155 nM.

Example 138

2-(2-(5-Cyclopropyl-3-(2-(trifluoromethyl)pyridin-3-yl)isoxazol-4-yl)-7-azaspiro[3.5]non-1-en-7-yl)-4-fluorobenzo[d]thiazole-6-carboxylic acid

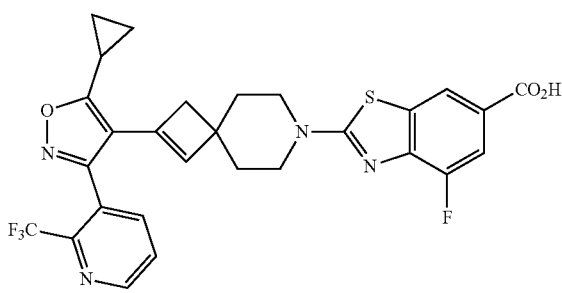

(138)

The title compound was prepared as described in General Method A for the preparation of Example 1 with replacement of 2,6-dichlorobenzaldehyde with 2-(trifluoromethyl) nicotinaldehyde. MS (ESI) m/z: 571.3 [M+H]$^+$; $^1$H NMR (500 MHz, DMSO-d$_6$) δ 8.92 (d, J=4.8 Hz, 1H), 8.17 (d, J=1.5 Hz, 1H), 8.12 (d, J=7.9 Hz, 1H), 7.87 (dd, J=4.8, 7.9 Hz, 1H), 7.57 (dd, J=1.5, 11.4 Hz, 1H), 5.83 (s, 1H), 3.69 (br s, 2H), 3.54-3.40 (m, 2H), 2.38-2.26 (m, 3H), 1.64-1.57 (m, 4H), 1.28-1.06 (m, 4H); FXR EC$_{50}$=319 nM.

Example 139

2-(2-(5-Cyclopropyl-3-(4-(trifluoromethyl)pyridin-3-yl)isoxazol-4-yl)-7-azaspiro[3.5]non-1-en-7-yl)-4-fluorobenzo[d]thiazole-6-carboxylic acid

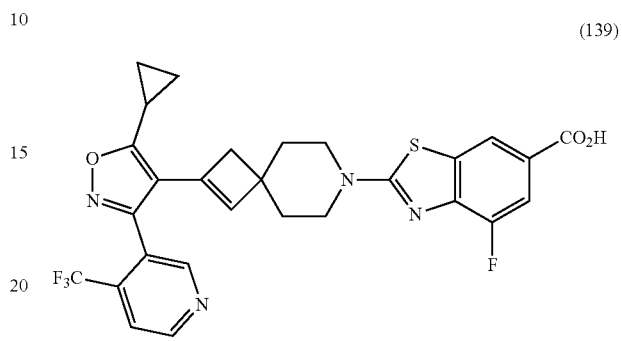

(139)

The title compound was prepared as described in General Method A for the preparation of Example 1 with replacement of 2,6-dichlorobenzaldehyde with 4-(trifluoromethyl) nicotinaldehyde. MS (ESI) m/z: 571.1 [M+H]$^+$; $^1$H NMR (500 MHz, DMSO-d$_6$) δ 9.01 (d, J=5.2 Hz, 1H), 8.79 (s, 1H), 8.14 (d, J=1.6 Hz, 1H), 7.94 (d, J=5.2 Hz, 1H), 7.61-7.51 (m, 1H), 5.84 (s, 1H), 3.76-3.65 (m, 2H), 2.33 (s, 2H), 2.32-2.26 (m, 1H), 1.63 (br s, 4H), 1.25-1.08 (m, 4H), additional signals missing due to water signal suppression; FXR EC$_{50}$=482 nM.

Example 140

2-(2-(5-Cyclopropyl-3-(2-(trifluoromethoxy)phenyl)isoxazol-4-yl)-7-azaspiro[3.5]non-1-en-7-yl)quinoline-6-carboxylic acid

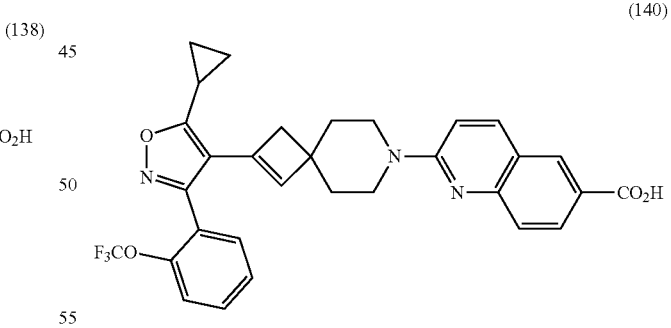

(140)

The title compound was prepared as described in General Method B for the preparation of Example 122 with replacement of 2,6-dichlorobenzaldehyde with 2-(trifluoromethoxy)benzaldehyde. MS (ESI) m/z: 562.1 [M+H]$^+$; $^1$H NMR (500 MHz, DMSO-d$_6$) δ 8.30 (s, 1H), 8.09 (d, J=9.34 Hz, 1H), 7.88-8.05 (m, 1H), 7.68 (br t, J=7.70 Hz, 1H), 7.49-7.57 (m, 4H), 7.25 (br d, J=9.34 Hz, 1H), 5.79-6.01 (m, 1H), 3.95 (br d, J=12.79 Hz, 2H), 3.75 (br s, 2H), 3.43-3.64 (m, 1H), 2.40 (s, 2H), 2.21-2.37 (m, 1H), 1.57 (br s, 4H), 1.12-1.27 (m, 4H); FXR EC$_{50}$=133 nM.

Example 141

6-(2-(5-Cyclopropyl-3-(2-(trifluoromethyl)phenyl)isoxazol-4-yl)-7-azaspiro[3.5]non-1-en-7-yl)-1-methyl-1H-indole-3-carboxylic acid

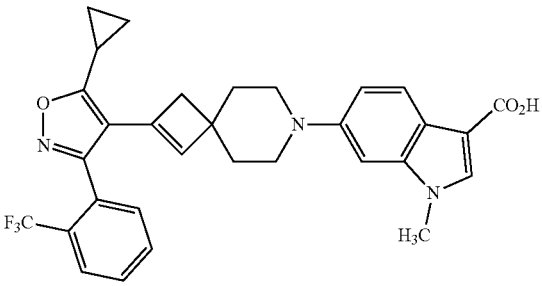
(141)

The title compound was prepared as described in General Method B for the preparation of Example 8 with replacement of 2,6-dichlorobenzaldehyde with 2-(trifluoromethyl)benzaldehyde. MS (ESI) m/z: 548.1 [M+H]⁺; H NMR (400 MHz, Methanol-$d_4$) δ 8.27 (d, J=8.58 Hz, 1H), 8.12 (s, 1H), 7.89-7.96 (m, 1H), 7.87 (d, J=1.98 Hz, 1H), 7.75-7.82 (m, 2H), 7.51-7.58 (m, 1H), 7.46 (dd, J=2.20, 8.80 Hz, 1H), 5.55-6.26 (m, 1H), 3.95 (s, 3H), 3.59-3.82 (m, 4H), 2.59 (s, 2H), 2.34 (s, 1H), 2.01-2.21 (m, 5H), 1.01-1.45 (m, 4H); FXR $EC_{50}$=142 nM.

Example 142

6-(2-(5-Cyclopropyl-3-(3,5-dichloropyridin-4-yl)isoxazol-4-yl)-7-azaspiro[3.5]non-1-en-7-yl)-4-(2-hydroxyethoxy)quinoline-2-carboxylic acid

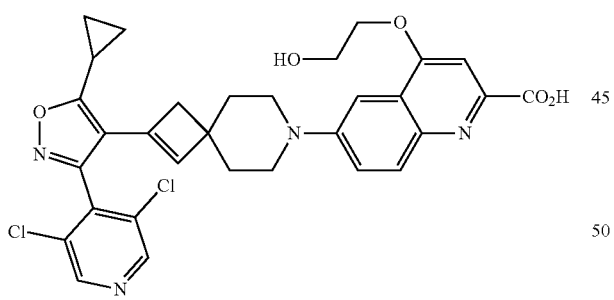
(142)

Step 1. Methyl 6-bromo-4-(2-hydroxyethoxy)quinoline-2-carboxylate

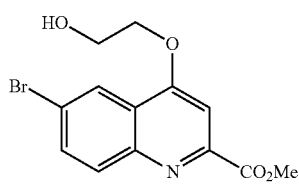

Methyl 6-bromo-4-hydroxyquinoline-2-carboxylate (0.25 g, 0.87 mmol), 2-bromoethan-1-ol (0.19 mL, 2.7 mmol) and potassium carbonate (0.37 g, 2.7 mmol) in acetonitrile (15 mL) were heated to 80° C. After 16 hours, additional 2-bromoethan-1-ol (0.19 mL, 2.7 mmol) was added. After 16 hours, the reaction mixture was diluted with water (25 mL), extracted with ethyl acetate (2×25 mL). The organic layer was dried over $Na_2SO_4$, filtered, and concentrated in vacuo. The residue was purified using silica gel chromatography to isolate methyl 6-bromo-4-(2-hydroxyethoxy)quinoline-2-carboxylate (0.25 g, 0.78 mmol, 88% yield). ¹H NMR (400 MHz, DMSO-$d_6$) δ 8.51 (d, J=2.2 Hz, 1H), 8.06-8.01 (m, 1H), 8.00-7.93 (m, 1H), 7.58 (s, 1H), 4.48 (s, 1H), 4.35 (t, J=4.5 Hz, 2H), 3.95 (s, 3H), 3.91-3.84 (m, 2H).

Example 142. 6-(2-(5-Cyclopropyl-3-(3,5-dichloropyridin-4-yl)isoxazol-4-yl)-7-azaspiro[3.5]non-1-en-7-yl)-4-(2-hydroxyethoxy)quinoline-2-carboxylic acid The title compound was prepared as described for the preparation of Example 85 with replacement of ethyl 6-chloro-4-(trifluoromethyl)quinoline-2-carboxylate with methyl 6-bromo-4-(2-hydroxyethoxy)quinoline-2-carboxylate. MS (ESI) m/z: 606.2 [M+H]⁺; ¹H NMR (500 MHz, Methanol-$d_4$) δ 8.74 (s, 2H), 8.13 (d, J=9.63 Hz, 1H), 7.83-7.93 (m, 1H), 7.73 (s, 1H), 7.56-7.65 (m, 1H), 5.89-5.97 (m, 1H), 4.52-4.66 (m, 2H), 4.11 (br d, J=3.85 Hz, 2H), 3.66 (s, 2H), 3.41 (s, 2H), 2.50 (s, 2H), 2.30-2.38 (m, 1H), 1.73-1.91 (m, 4H), 1.28-1.55 (m, 4H); FXR $EC_{50}$=147 nM.

Example 143

6-(2-(5-Cyclopropyl-3-(2-(trifluoromethyl)phenyl)isoxazol-4-yl)-7-azaspiro[3.5]non-1-en-7-yl)-4-(2-hydroxyethoxy)quinoline-2-carboxylic acid

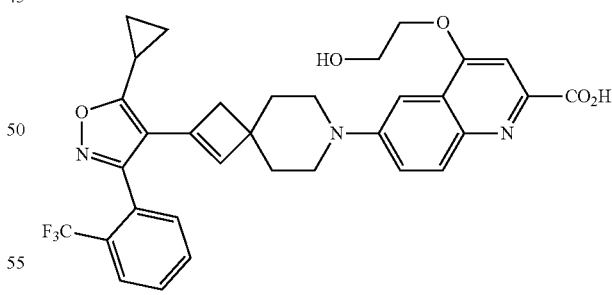
(143)

The title compound was prepared as described in General Method B for the preparation of Example 142 with replacement of 3,5-dichloroisonicotinaldehyde with 2-(trifluoromethyl)benzaldehyde. MS (ESI) m/z: 606.2 [M+H]⁺; ¹H NMR (500 MHz, Methanol-$d_4$) δ 7.84-7.99 (m, 2H), 7.76 (t, J=8.12 Hz, 2H), 7.48-7.58 (m, 4H), 5.65-5.90 (m, 1H), 4.36 (t, J=4.54 Hz, 2H), 3.97-4.14 (m, 2H), 3.42-3.48 (m, 2H), 3.12-3.19 (m, 2H), 2.39 (s, 2H), 2.24-2.36 (m, 1H), 1.63-1.89 (m, 4H), 1.00-1.33 (m, 4H); FXR $EC_{50}$=159 nM.

Example 144

6-(2-(5-Cyclopropyl-3-(2-(trifluoromethyl)pyridin-3-yl)isoxazol-4-yl)-7-azaspiro[3.5]non-1-en-7-yl)-4-methoxyquinoline-2-carboxylic acid

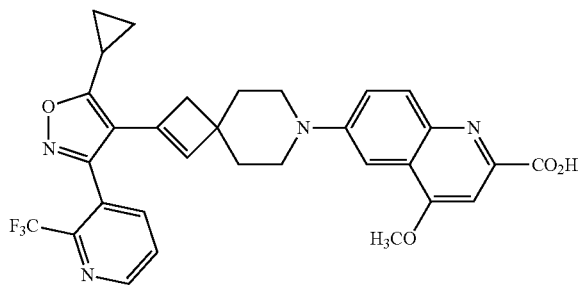 [SMILES: COc1cc(C(=O)O)nc2ccc(N3CCC4(C=C(c5c(-c6cccnc6C(F)(F)F)noc5C5CC5)C4)CC3)cc12]

The title compound was prepared as described in General Method B for the preparation of Example 108 with replacement of 3,5-dichloroisonicotinaldehyde with 2-(trifluoromethyl)nicotinaldehyde. MS (ESI) m/z: 577.3 [M+H]$^+$; $^1$H NMR (500 MHz, DMSO-$d_6$) δ 8.88 (d, J=4.7 Hz, 1H), 8.13-7.96 (m, 2H), 7.85 (dd, J=4.7, 7.9 Hz, 1H), 7.67 (br s, 1H), 7.49 (s, 1H), 7.22 (br s, 1H), 5.76 (s, 1H), 4.08 (s, 3H), 3.42 (br s, 2H), 3.13 (br s, 2H), 2.29 (br s, 3H), 1.59 (br s, 4H), 1.23-1.05 (m, 4H); FXR EC$_{50}$=156 nM.

Example 145

6-(2-(3-(3-Chloropyridin-2-yl)-5-cyclopropylisoxazol-4-yl)-7-azaspiro[3.5]non-1-en-7-yl)-4-methoxyquinoline-2-carboxylic acid (145)

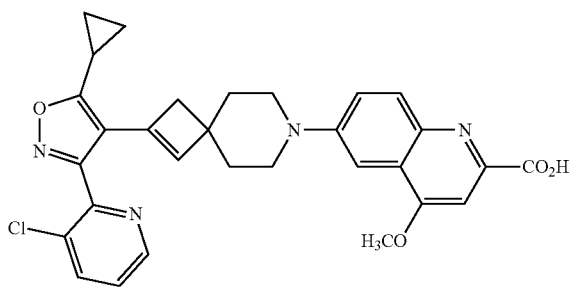

The title compound was prepared as described in General Method B for the preparation of Example 108 with replacement of 3,5-dichloroisonicotinaldehyde with 3-chloropicolinaldehyde. MS (ESI) m/z: 543.1 [M+H]$^+$; $^1$H NMR (500 MHz, DMSO-$d_6$) δ 8.69 (d, J=4.6 Hz, 1H), 8.15 (d, J=8.2 Hz, 1H), 7.95 (d, J=9.4 Hz, 1H), 7.68 (dd, J=2.8, 9.4 Hz, 1H), 7.63 (dd, J=4.7, 8.3 Hz, 1H), 7.47 (s, 1H), 7.26 (d, J=2.7 Hz, 1H), 5.87 (s, 1H), 4.09 (s, 3H), 3.18 (br t, J=9.4 Hz, 2H), 2.34 (br s, 3H), 1.74-1.59 (m, 4H), 1.24-1.09 (m, 4H), additional signals missing due to water signal suppression; FXR EC$_{50}$=160 nM.

Example 146

6-(2-(5-Cyclopropyl-3-(4-(trifluoromethyl)pyridin-3-yl)isoxazol-4-yl)-7-azaspiro[3.5]non-1-en-7-yl)-4-methoxyquinoline-2-carboxylic acid (146)

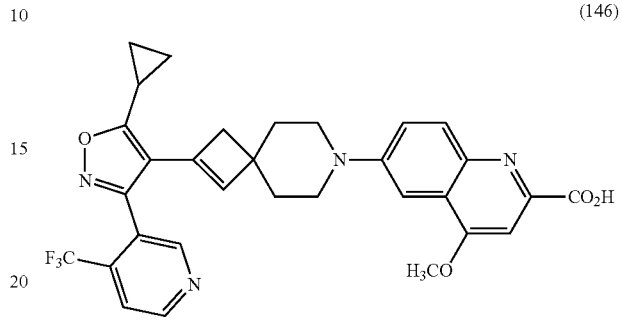

The title compound was prepared as described in General Method B for the preparation of Example 108 with replacement of 3,5-dichloroisonicotinaldehyde with 4-(trifluoromethyl)nicotinaldehyde. MS (ESI) m/z: 577.2 [M+H]$^+$; $^1$H NMR (500 MHz, DMSO-$d_6$) δ 9.02 (d, J=5.2 Hz, 1H), 8.82 (s, 1H), 8.02-7.87 (m, 2H), 7.63 (dd, J=2.8, 9.4 Hz, 1H), 7.46 (s, 1H), 7.27 (d, J=2.8 Hz, 1H), 5.83 (s, 1H), 4.08 (s, 3H), 2.32 (br s, 3H), 1.71-1.59 (m, 4H), δ 1.25-1.08 (m, 4H), additional signals missing due to water signal suppression; FXR EC$_{50}$=185 nM.

Example 147

6-(2-(3-Cyclohexyl-5-cyclopropylisoxazol-4-yl)-7-azaspiro[3.5]non-1-en-7-yl)-4-methoxyquinoline-2-carboxylic acid (147)

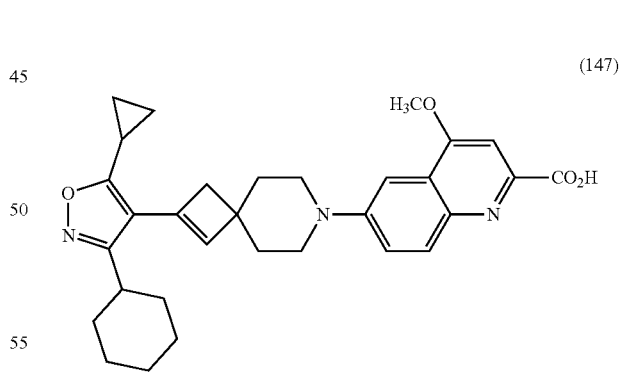

The title compound was prepared as described in General Method B for the preparation of Example 108 with replacement of 3,5-dichloroisonicotinaldehyde with cyclohexanecarbaldehyde. MS (ESI) m/z: 514.1 [M+H]$^+$; $^1$H NMR (500 MHz, DMSO-$d_6$) δ 7.97 (d, J=9.2 Hz, 1H), 7.78-7.68 (m, 1H), 7.49 (s, 1H), 7.33 (d, J=2.8 Hz, 1H), 6.41 (s, 1H), 4.12 (s, 3H), 3.58-3.66 (m, 2H), 3.34-3.26 (m, 2H), 2.73 (br s, 3H), 2.24-2.17 (m, 1H), 2.00-1.62 (m, 8H), 1.48-1.18 (m, 6H), 1.11-0.95 (m, 4H); FXR EC$_{50}$=1063 nM.

Example 148

7-(2-(3-(2,6-Dichlorophenyl)-5-isopropylisoxazol-4-yl)-7-azaspiro[3.5]non-1-en-7-yl) cinnoline-3-carboxylic acid

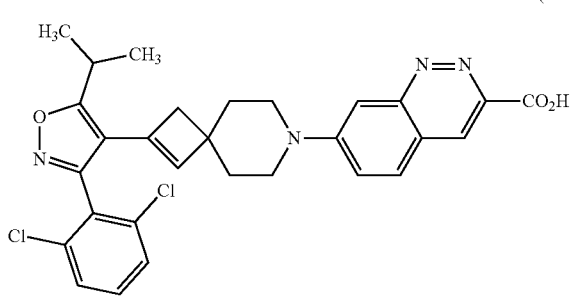

(148)

The title compound was prepared as described in General Method B for the preparation of Example 53 with replacement of cyclopropylacetylene with isopropylacetylene. MS (ESI) m/z: 549.1 [M+H]+; 1H NMR (500 MHz, CDCl3) δ 8.52 (br dd, J=4.8, 1.3 Hz, 1H), 7.85-7.74 (m, 1H), 7.72-7.62 (m, 1H), 7.62-7.52 (m, 1H), 7.49-7.37 (m, 2H), 7.37-7.28 (m, 1H), 5.77 (s, 1H), 3.69-3.58 (m, 1H), 3.46-3.37 (m, 1H), 3.37-3.25 (m, 2H), 2.59 (s, 2H), 2.35 (s, 1H), 1.78 (br s, 4H), 1.43 (br d, J=6.9 Hz, 6H); FXR EC50=548 nM.

Example 149

6-(2-(5-Cyclopropyl-3-(3,5-dichloropyridin-4-yl)isoxazol-4-yl)-7-azaspiro[3.5]non-1-en-7-yl)quinoline-2-carboxylic acid

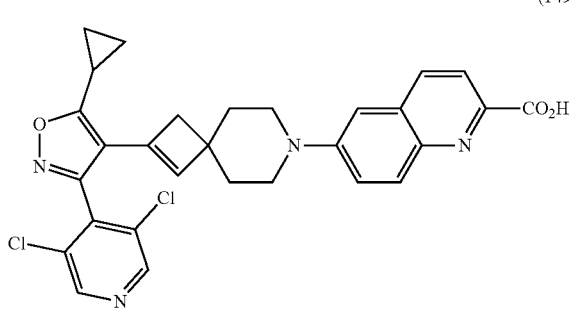

(149)

The title compound was prepared as described in General Method B for the preparation of Example 20 with replacement of 2,6-dichlorobenzaldehyde with 3,5-dichloroisonicotinaldehyde. MS (ESI) m/z: 547.3 [M+H]+; 1H NMR (500 MHz, DMSO-d6) δ 8.86 (s, 2H), 8.18 (d, J=8.5 Hz, 1H), 7.94 (dd, J=12.7, 9.0 Hz, 2H), 7.75-7.57 (m, 1H), 7.21 (br d, J=1.5 Hz, 1H), 6.00 (s, 1H), 3.63-3.46 (m, 2H), 3.00 (s, 1H), 2.40 (s, 2H), 2.39-2.31 (m, 1H), 1.79-1.61 (m, 4H), 1.31-1.21 (m, 4H), 1.17 (br d, J=2.6 Hz, 2H); FXR EC50=205 nM.

Example 150

6-(2-(3-(3-Chloropyridin-4-yl)-5-cyclopropylisoxazol-4-yl)-7-azaspiro[3.5]non-1-en-7-yl)quinoline-2-carboxylic acid

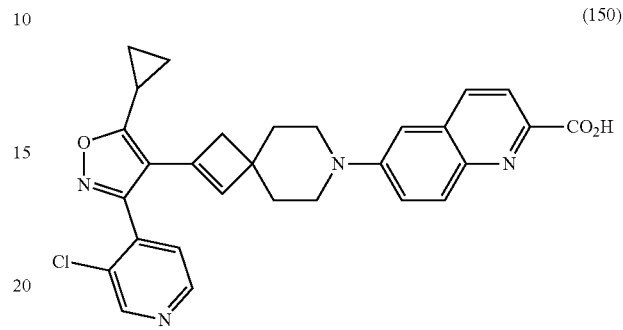

(150)

The title compound was obtained as a minor isolate during the preparation of Example 149 from reduction of one chlorine during the Pd-catalyzed Buchwald coupling step. MS (ESI) m/z: 513.3 [M+H]+; 1H NMR (500 MHz, DMSO-d6) δ 8.84 (s, 1H), 8.69 (br d, J=4.9 Hz, 1H), 8.20 (br d, J=8.4 Hz, 1H), 7.94 (br dd, J=12.1, 9.0 Hz, 2H), 7.68 (br d, J=6.9 Hz, 1H), 7.60 (d, J=4.8 Hz, 1H), 7.22 (br s, 1H), 7.14 (br s, 2H), 6.01 (s, 1H), 3.65-3.44 (m, 3H), 2.46-2.39 (m, 2H), 2.39-2.27 (m, 2H), 1.80-1.61 (m, 3H), 1.28-1.17 (m, 2H), 1.19-1.09 (m, 2H); FXR EC50=4345 nM.

Example 151

6-(2-(5-Cyclopropyl-3-(2,6-difluorophenyl)isoxazol-4-yl)-7-azaspiro[3.5]non-1-en-7-yl)quinoline-2-carboxylic acid (151)

The title compound was prepared as described in General Method B for the preparation of Example 20 with replacement of 2,6-dichlorobenzaldehyde with 2,6-difluorobenzaldehyde. MS (ESI) m/z: 514.1 [M+H]+; 1H NMR (500 MHz, DMSO-d6) δ 8.22 (d, J=8.6 Hz, 1H), 7.95 (dd, J=9.0, 13.8 Hz, 2H), 7.74-7.63 (m, 2H), 7.33 (t, J=8.1 Hz, 2H), 7.23 (d, J=2.6 Hz, 1H), 6.00 (s, 1H), 3.59-3.51 (m, 2H), 3.22 (dd, J=12.1, 22.7 Hz, 2H), 2.46 (s, 2H), 2.35 (ddd, J=5.2, 8.5, 13.2 Hz, 1H), 1.80-1.60 (m, 4H), 1.28-1.09 (m, 4H); FXR EC50=1991 nM.

Example 152

6-(2-(3-(3-Chloropyridin-2-yl)-5-cyclopropylisoxazol-4-yl)-7-azaspiro[3.5]non-1-en-7-yl)quinoline-2-carboxylic acid

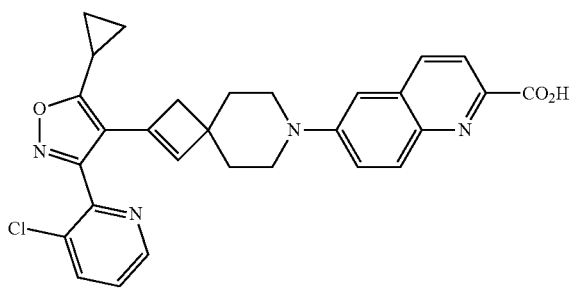

(152)

The title compound was prepared as described in General Method B for the preparation of Example 20 with replacement of 2,6-dichlorobenzaldehyde with 3-chloropicolinaldehyde. MS (ESI) m/z: 513.2 [M+H]$^+$; $^1$H NMR (500 MHz, DMSO-d$_6$) δ 8.68 (br d, J=4.0 Hz, 1H), 8.21 (br s, 1H), 8.13 (br d, J=8.0 Hz, 1H), 7.95 (br s, 1H), 7.68 (br d, J=5.7 Hz, 1H), 7.62 (dd, J=8.0, 4.6 Hz, 1H), 7.22 (br s, 1H), 5.91 (br s, 1H), 3.51 (br s, 1H), 3.26 (br d, J=5.7 Hz, 2H), 2.41-2.25 (m, 3H), 1.69 (br s, 4H), 1.20 (br d, J=7.7 Hz, 2H), 1.14 (br d, J=2.0 Hz, 2H) additional peaks lost under DMSO signal; FXR EC$_{50}$=1633 nM.

Example 153

6-(2-(5-Cyclopropyl-3-(2-(trifluoromethyl)pyridin-3-yl)isoxazol-4-yl)-7-azaspiro[3.5]non-1-en-7-yl)quinoline-2-carboxylic acid

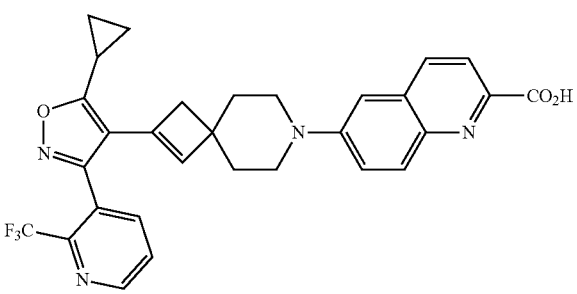

(153)

The title compound was prepared as described in General Method B for the preparation of Example 20 with replacement of 2,6-dichlorobenzaldehyde with 2-(trifluoromethyl)nicotinaldehyde. MS (ESI) m/z: 547.3 [M+H]$^+$; $^1$H NMR (500 MHz, DMSO-d$_6$) δ 8.89 (d, J=4.8 Hz, 1H), 8.19 (d, J=8.6 Hz, 1H), 8.09 (d, J=7.9 Hz, 1H), 7.94 (d, J=8.7 Hz, 2H), 7.85 (dd, J=4.8, 7.9 Hz, 1H), 7.65 (d, J=9.4 Hz, 1H), 7.17 (s, 1H), 5.78 (s, 1H), 3.52-3.42 (m, 2H), 3.20-3.12 (m, 2H), 2.29 (br s, 3H), 1.67-1.53 (m, 4H), 1.26-1.06 (m, 4H); FXR EC$_{50}$=1282 nM.

Example 154

6-(2-(5-Cyclopropyl-3-(4-(trifluoromethyl)pyridin-3-yl)isoxazol-4-yl)-7-azaspiro[3.5]non-1-en-7-yl)quinoline-2-carboxylic acid

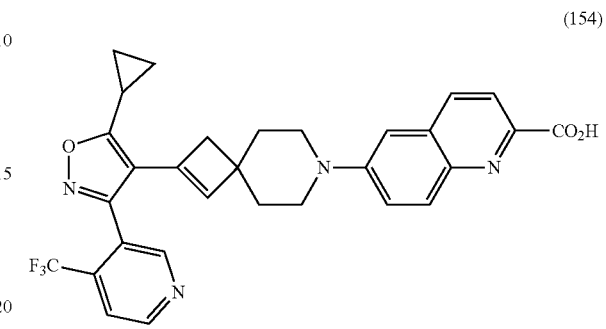

(154)

The title compound was prepared as described in General Method B for the preparation of Example 20 with replacement of 2,6-dichlorobenzaldehyde with 4-(trifluoromethyl)nicotinaldehyde. MS (ESI) m/z: 547.3 [M+H]$^+$; $^1$H NMR (500 MHz, DMSO-d$_6$) δ 9.03 (d, J=5.1 Hz, 1H), 8.85 (s, 1H), 8.18 (d, J=8.6 Hz, 1H), 7.99-7.88 (m, 3H), 7.66 (dd, J=2.5, 9.4 Hz, 1H), 7.19 (d, J=2.7 Hz, 1H), 5.82 (s, 1H), 3.22-3.16 (m, 2H), 2.36-2.19 (m, 3H), 1.70-1.58 (m, 4H), 1.24-1.11 (m, 4H), additional signals missing due to water signal suppression; FXR EC$_{50}$=554 nM.

Example 155

6-(2-(5-Cyclopropyl-3-(2,6-dichloro-4-fluorophenyl)isoxazol-4-yl)-7-azaspiro[3.5]non-1-en-7-yl)quinoline-2-carboxylic acid

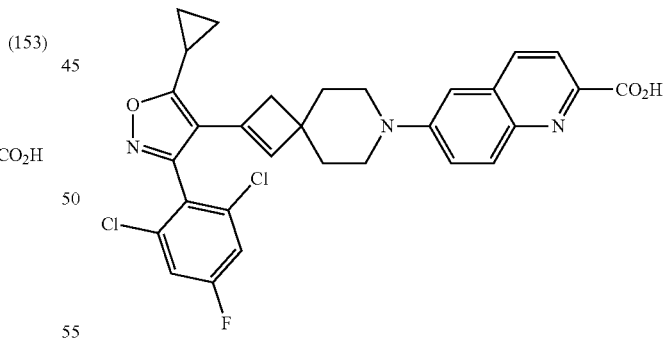

(155)

The title compound was prepared as described in General Method B for the preparation of Example 20 with replacement of 2,6-dichlorobenzaldehyde with 2,6-dichloro-4-fluorobenzaldehyde. MS (ESI) m/z: 564.1 [M+H]$^+$; $^1$H NMR (500 MHz, DMSO-d$_6$) δ 8.20 (br d, J=8.5 Hz, 1H), 7.96 (br t, J=9.6 Hz, 2H), 7.77 (d, J=8.5 Hz, 2H), 7.69 (br d, J=9.8 Hz, 1H), 7.22 (br s, 1H), 5.93 (s, 1H), 3.91 (s, 1H), 3.54 (br d, J=8.2 Hz, 1H), 3.35-3.07 (m, 2H), 2.42-2.28 (m, 3H), 1.81-1.61 (m, 4H), 1.22 (br d, J=7.9 Hz, 2H), 1.15 (br d, J=2.7 Hz, 2H) additional signals lost due to water suppression in $^1$H NMR experiment; FXR EC$_{50}$=523 nM.

Example 156

6-(2-(3-(2-Chloro-6-fluorophenyl)-5-cyclopropylisoxazol-4-yl)-7-azaspiro[3.5]non-1-en-7-yl)quinoline-2-carboxylic acid

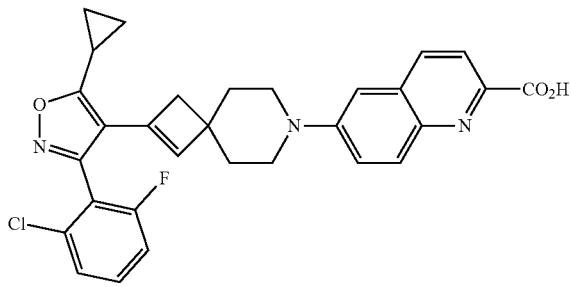

(156)

The title compound was prepared as described in General Method B for the preparation of Example 20 with replacement of 2,6-dichlorobenzaldehyde with 2-chloro-6-fluorobenzaldehyde. MS (ESI) m/z: 530.4 [M+H]$^+$; $^1$H NMR (500 MHz, DMSO-$d_6$) δ 8.20 (d, J=8.6 Hz, 1H), 7.95 (dd, J=9.0, 15.1 Hz, 2H), 7.66 (q, J=7.4, 10.2 Hz, 2H), 7.55 (d, J=8.1 Hz, 1H), 7.45 (t, J=8.7 Hz, 1H), 7.22 (s, 1H), 5.92 (s, 1H), 3.57-3.48 (m, 2H), 3.21 (br s, 2H), 2.40 (s, 2H), 2.39-2.28 (m, 1H), 1.76-1.60 (m, 4H), 1.26-1.08 (m, 4H); FXR EC$_{50}$=326 nM.

Example 157

6-(2-(3-(2-Chloro-6-methylphenyl)-5-cyclopropylisoxazol-4-yl)-7-azaspiro[3.5]non-1-en-7-yl)quinoline-2-carboxylic acid

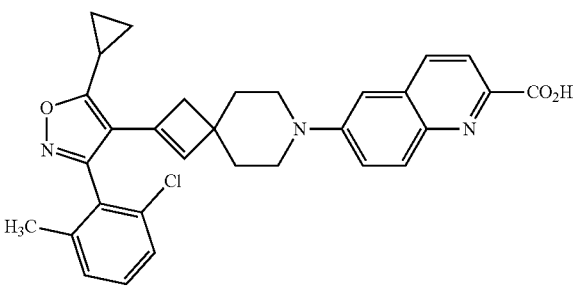

(157)

The title compound was prepared as described in General Method B for the preparation of Example 20 with replacement of 2,6-dichlorobenzaldehyde with 2-chloro-6-methylbenzaldehyde. MS (ESI) m/z: 526.4 [M+H]$^+$; $^1$H NMR (500 MHz, DMSO-$d_6$) δ 8.21 (d, J=8.7 Hz, 1H), 8.01-7.88 (m, 2H), 7.68 (d, J=9.4 Hz, 1H), 7.47-7.41 (m, 2H), 7.35 (t, J=4.5 Hz, 1H), 7.21 (s, 1H), 5.76 (s, 1H), 3.24-3.14 (m, 2H), 2.35 (q, J=12.5 Hz, 3H), 2.10 (s, 3H), 1.72-1.58 (m, 4H), 1.25-1.08 (m, 4H), additional signals missing due to water signal suppression; FXR EC$_{50}$=223 nM.

Example 158

7-(2-(3-(2-Chloro-6-fluorophenyl)-5-cyclopropylisoxazol-4-yl)-7-azaspiro[3.5]non-1-en-7-yl)isoquinoline-3-carboxylic acid

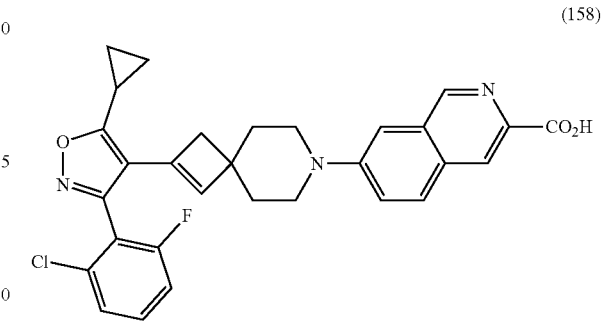

(158)

The title compound was prepared as described in General Method B for the preparation of Example 129 with replacement of 2,6-dichlorobenzaldehyde with 2-chloro-6-fluorobenzaldehyde. MS (ESI) m/z: 530.2 [M+H]$^+$; $^1$H NMR (500 MHz, DMSO-$d_6$) δ 9.09 (s, 1H), 8.40 (s, 1H), 7.96 (d, J=9.1 Hz, 1H), 7.73-7.59 (m, 2H), 7.54 (d, J=8.2 Hz, 1H), 7.50-7.36 (m, 2H), 5.91 (s, 1H), 3.28-3.20 (m, 2H), 2.40 (s, 2H), 2.34 (tt, J=5.0, 8.2 Hz, 1H), 1.73-1.59 (m, 4H), 1.27-1.09 (m, 4H), additional signals missing due to water signal suppression; FXR EC$_{50}$=459 nM.

Example 159

7-(2-(5-Cyclopropyl-3-(2-(trifluoromethyl)phenyl)isoxazol-4-yl)-7-azaspiro[3.5]non-1-en-7-yl)isoquinoline-3-carboxylic acid

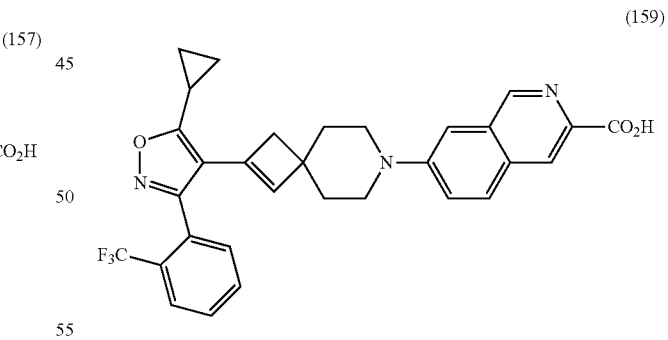

(159)

The title compound was prepared as described in General Method B for the preparation of Example 129 with replacement of 2,6-dichlorobenzaldehyde with 2-(trifluoromethyl)benzaldehyde. MS (ESI) m/z: 546.1 [M+H]$^+$; $^1$H NMR (500 MHz, DMSO-$d_6$) δ 9.09 (s, 1H), 8.39 (s, 1H), 7.93 (dd, J=13.4, 8.4 Hz, 2H), 7.85-7.73 (m, 2H), 7.66 (dd, J=9.2, 2.3 Hz, 1H), 7.56 (d, J=7.3 Hz, 1H), 7.39 (d, J=1.7 Hz, 1H), 5.78 (s, 1H), 3.52 (br dd, J=12.6, 5.2 Hz, 2H), 2.36-2.20 (m, 3H), 1.75-1.56 (m, 4H), 1.26-1.17 (m, 2H), 1.16-1.08 (m, 2H), 1.02 (d, J=6.2 Hz, 1H) additional proton signals were lost due to water suppression; FXR EC$_{50}$=254 nM.

Example 160

7-(2-(5-Cyclopropyl-3-(4-(trifluoromethyl)pyridin-3-yl)isoxazol-4-yl)-7-azaspiro[3.5]non-1-en-7-yl)isoquinoline-3-carboxylic acid

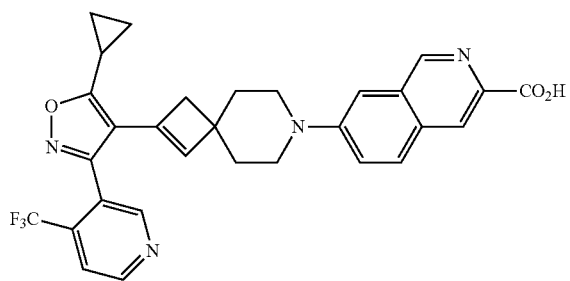

(160)

The title compound was prepared as described in General Method B for the preparation of Example 129 with replacement of 2,6-dichlorobenzaldehyde with 4-(trifluoromethyl)nicotinaldehyde. MS (ESI) m/z: 547.2 [M+H]$^+$; $^1$H NMR (500 MHz, DMSO-d$_6$) δ 9.08 (s, 1H), 9.03 (d, J=5.2 Hz, 1H), 8.85 (s, 1H), 8.38 (s, 1H), 7.97 (d, J=5.2 Hz, 1H), 7.94 (d, J=9.2 Hz, 1H), 7.70-7.64 (m, 1H), 7.39 (s, 1H), 5.82 (s, 1H), 3.26-3.18 (m, 2H), 2.37-2.29 (m, 3H), 1.72-1.57 (m, 4H), 1.25-1.10 (m, 4H), additional signals missing due to water signal suppression; FXR EC$_{50}$=1608 nM.

Example 161

7-(2-(3-(3-Chloropyridin-2-yl)-5-cyclopropylisoxazol-4-yl)-7-azaspiro[3.5]non-1-en-7-yl) isoquinoline-3-carboxylic acid

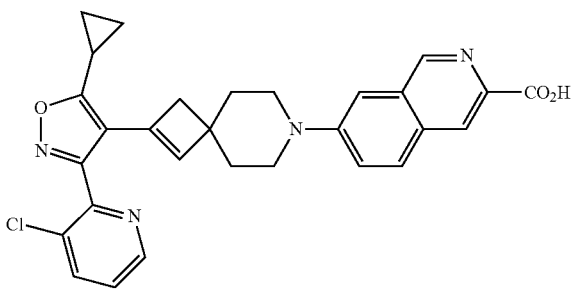

(161)

The title compound was prepared as described in General Method B for the preparation of Example 129 with replacement of 2,6-dichlorobenzaldehyde with 4-(trifluoromethyl)nicotinaldehyde. MS (ESI) m/z: 513.2 [M+H]$^+$; $^1$H NMR (500 MHz, DMSO-d$_6$) δ 9.10 (s, 1H), 8.69 (br d, J=4.6 Hz, 1H), 8.40 (s, 1H), 8.15 (br d, J=7.9 Hz, 1H), 7.96 (br d, J=9.2 Hz, 1H), 7.69 (br d, J=8.2 Hz, 1H), 7.63 (dd, J=8.2, 4.6 Hz, 1H), 7.41 (s, 1H), 5.88 (s, 1H), 3.67-3.41 (m, 5H), 3.37-3.12 (m, 2H), 2.41-2.22 (m, 3H), 1.81-1.55 (m, 5H), 1.21 (br d, J=7.9 Hz, 2H), 1.14 (br d, J=2.4 Hz, 2H); FXR EC$_{50}$=2324 nM.

Example 162

7-(2-(5-Cyclopropyl-3-(2,6-difluorophenyl)isoxazol-4-yl)-7-azaspiro[3.5]non-1-en-7-yl)isoquinoline-3-carboxylic acid

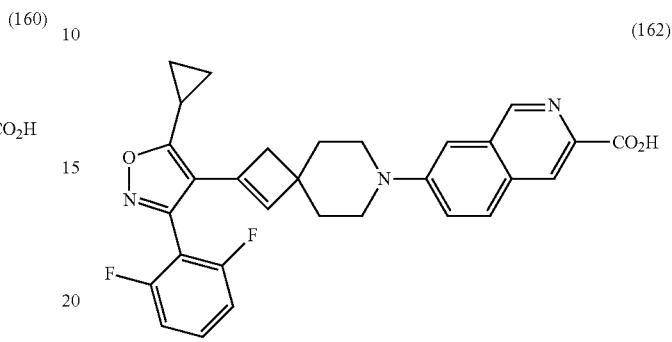

(162)

The title compound was prepared as described in General Method B for the preparation of Example 129 with replacement of 2,6-dichlorobenzaldehyde with 2,6-difluorobenzaldehyde. MS (ESI) m/z: 514.1 [M+H]$^+$; $^1$H NMR (500 MHz, DMSO-d$_6$) δ 9.10 (s, 1H), 8.41 (s, 1H), 7.96 (d, J=9.1 Hz, 1H), 7.70 (q, J=6.7, 7.3 Hz, 2H), 7.42 (s, 1H), 7.33 (t, J=8.2 Hz, 2H), 6.00 (s, 1H), 3.61-3.53 (m, 2H), 3.29-3.21 (m, 2H), 2.46 (s, 2H), 2.39-2.28 (m, 1H), 1.77-1.57 (m, 4H), 1.28-1.08 (m, 4H); FXR EC$_{50}$=2824 nM.

Example 163

6-(2-(5-Cyclopropyl-3-(2-(trifluoromethyl)phenyl)isoxazol-4-yl)-7-azaspiro[3.5]non-1-en-7-yl)-4-(trifluoromethyl)nicotinic acid

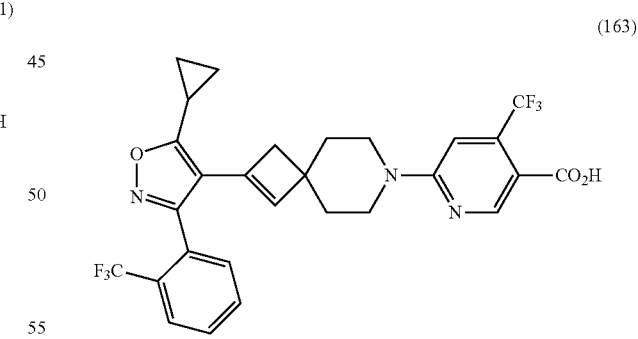

(163)

The title compound was prepared as described in General Method A for the preparation of Example 116 with replacement of 2,6-dichlorobenzaldehyde with 2-(trifluoromethyl)benzaldehyde. MS (ESI) m/z: 564.4 [M+H]$^+$; $^1$H NMR (500 MHz, DMSO-d$_6$) δ 8.63 (s, 1H), 7.92 (br d, J=7.93 Hz, 1H), 7.79 (br dd, J=7.63, 11.90 Hz, 2H), 7.56 (br d, J=7.02 Hz, 1H), 7.02 (s, 1H), 5.75 (s, 1H), 3.72-4.11 (m, 2H), 2.55 (s, 2H), 2.29 (s, 1H), 1.41-1.64 (m, 4H), 1.15-1.24 (m, 2H), 1.11 (br d, J=2.44 Hz, 2H), additional signals missing due to water signal suppression; FXR EC$_{50}$=344 nM.

Example 164

6-(2-(5-Cyclopropyl-3-(2-(trifluoromethyl)phenyl)isoxazol-4-yl)-7-azaspiro[3.5]non-1-en-7-yl)-1-methyl-1H-indazole-3-carboxylic acid

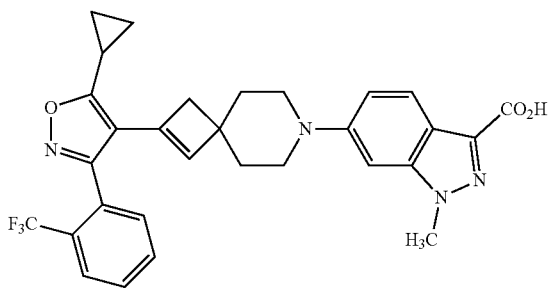

(164)

The title compound was prepared as described in General Method B for the preparation of Example 125 with replacement of 2,6-dichlorobenzaldehyde with 2-(trifluoromethyl)benzaldehyde. MS (ESI) m/z: 549.1 [M+H]+; 1H NMR (400 MHz, Methanol-$d_4$) δ 8.27 (d, J=8.58 Hz, 1H), 8.12 (s, 1H), 7.89-7.96 (m, 1H), 7.87 (d, J=1.98 Hz, 1H), 7.75-7.82 (m, 2H), 7.51-7.58 (m, 1H), 7.46 (dd, J=2.20, 8.80 Hz, 1H), 5.55-6.26 (m, 1H), 3.95 (s, 3H), 3.59-3.82 (m, 4H), 2.59 (s, 2H), 2.34 (s, 1H), 2.01-2.21 (m, 5H), 1.01-1.45 (m, 4H); FXR $EC_{50}$=392 nM.

Example 165

6-(2-(5-Cyclopropyl-3-(2-(trifluoromethoxy)phenyl)isoxazol-4-yl)-7-azaspiro[3.5]non-1-en-7-yl)-1-methyl-1H-indazole-3-carboxylic acid

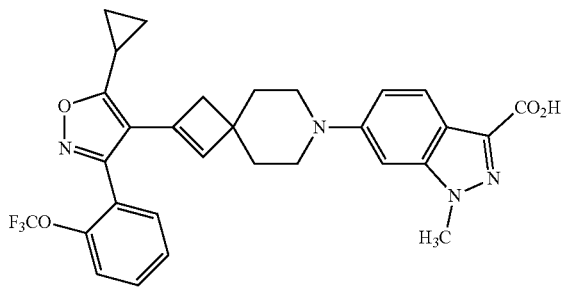

(165)

The title compound was prepared as described in General Method B for the preparation of Example 125 with replacement of 2,6-dichlorobenzaldehyde with 2-(trifluoromethoxy)benzaldehyde. MS (ESI) m/z: 565.3 [M+H]+; 1H NMR (500 MHz, DMSO-$d_6$) δ 7.74-7.67 (m, 1H), 7.65 (br d, J=9.2 Hz, 1H), 7.62-7.47 (m, 4H), 7.38 (br d, J=8.5 Hz, 1H), 5.95 (s, 1H), 4.09 (s, 3H), 3.27 (br d, J=4.6 Hz, 1H), 3.03 (br s, 1H), 2.41 (s, 2H), 2.37-2.27 (m, 1H), 1.82-1.64 (m, 4H), 1.24 (s, 2H), 1.21-1.15 (m, 2H), 1.12 (br d, J=2.4 Hz, 2H); FXR $EC_{50}$=2975 nM.

Example 166

6-(2-(5-Cyclopropyl-3-(2-(trifluoromethoxy)phenyl)isoxazol-4-yl)-7-azaspiro[3.5]non-1-en-7-yl)-3-(trifluoromethyl)imidazo[1,5-a]pyridine-1-carboxylic acid

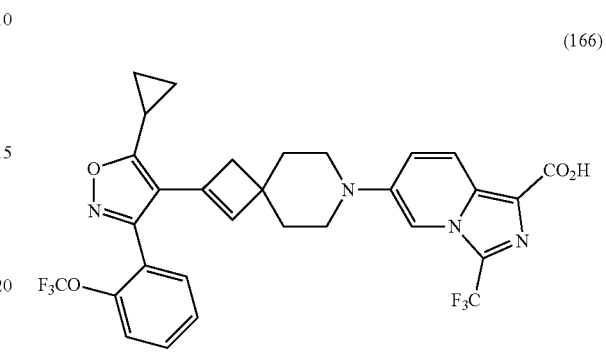

(166)

The title compound was prepared as described in General Method B for the preparation of Example 126 with replacement of 2,6-dichlorobenzaldehyde with 2-(trifluoromethoxy)benzaldehyde. MS (ESI) m/z: 619.1 [M+H]+; 1H NMR (500 MHz, DMSO-$d_6$) δ 8.04 (d, J=9.77 Hz, 1H), 7.70 (s, 1H), 7.47-7.61 (m, 5H), 5.82-5.99 (m, 1H), 3.20-3.50 (m, 2H), 3.00 (br s, 2H), 2.39 (s, 2H), 2.23-2.35 (m, 1H), 1.56-1.86 (m, 4H), 1.05-1.33 (m, 4H); FXR $EC_{50}$=494 nM.

Example 167

6-(2-(3-Cyclohexyl-5-cyclopropylisoxazol-4-yl)-7-azaspiro[3.5]non-1-en-7-yl)-4-ethoxyquinoline-2-carboxylic acid

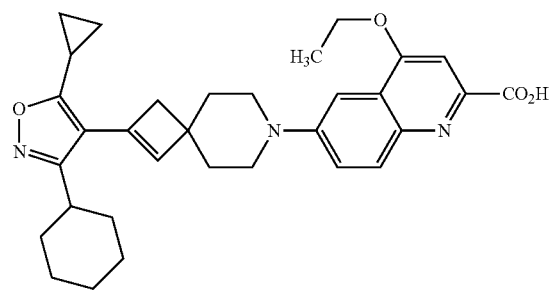

(167)

The title compound was prepared as described in General Method B for the preparation of Example 72 with replacement of 2-(trifluoromethyl)benzaldehyde with cyclohexanecarbaldehyde. MS (ESI) m/z: 528.4 [M+H]+; 1H NMR (500 MHz, DMSO-$d_6$) δ 7.99 (d, J=9.3 Hz, 1H), 7.76 (d, J=9.2 Hz, 1H), 7.48 (s, 1H), 7.34 (d, J=2.8 Hz, 1H), 6.41 (s, 1H), 4.41 (q, J=6.9 Hz, 2H), 3.66-3.55 (m, 2H), 3.33-3.23 (m, 2H), 2.73 (br s, 3H), 2.24-2.16 (m, 1H), 1.17-1.61 (m, 8H), 1.51 (t, J=6.9 Hz, 3H), 1.47-1.16 (m, 6H), 1.11-0.94 (m, 4H); FXR $EC_{50}$=3096 nM.

Example 168

6-(2-(3-Cyclohexyl-5-cyclopropylisoxazol-4-yl)-7-azaspiro[3.5]non-1-en-7-yl)-1-methyl-1H-indole-3-carboxylic acid

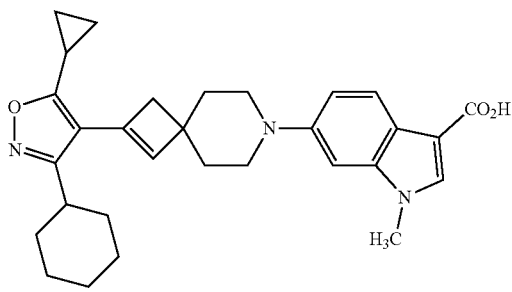
(168)

The title compound was prepared as described in General Method B for the preparation of Example 8 with replacement of 2,6-dichlorobenzaldehyde with cyclohexanecarbaldehyde. MS (ESI) m/z: 486.4 [M+H]$^+$; $^1$H NMR (500 MHz, DMSO-d$_6$) δ 7.94 (d, J=7.4 Hz, 2H), 7.31 br (s, 1H), 7.19 (br s, 1H), 6.43 (s, 1H), 3.83 (s, 3H), 3.50 (br s, 2H), 2.77-2.69 (m, 3H), 2.20 (tt, J=5.1, 8.7 Hz, 1H), 2.04-1.64 (m, 8H), 1.52-1.19 (m, 6H), 1.12-0.94 (m, 4H), additional signals missing due to water signal suppression; FXR EC$_{50}$=3972 nM.

Example 169

2-(2-(5-Cyclopropyl-3-(2-(trifluoromethyl)phenyl)isoxazol-4-yl)-7-azaspiro[3.5]non-1-en-7-yl)-6-methylpyrimidine-4-carboxylic acid

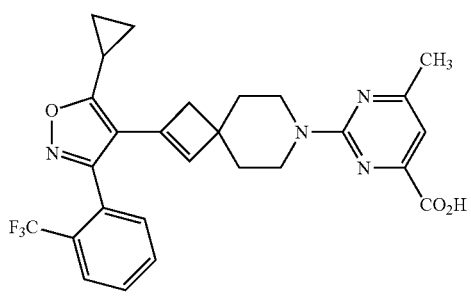
(169)

The title compound was prepared as described in General Method A for the preparation of Example 120 with replacement of 2,6-dichlorobenzaldehyde with 2-(trifluoromethyl)benzaldehyde. MS (ESI) m/z: 511.3 [M+H]$^+$; $^1$H NMR (500 MHz, DMSO-d$_6$) δ 7.92 (br d, J=7.63 Hz, 1H), 7.70-7.87 (m, 2H), 7.56 (br d, J=7.32 Hz, 1H), 6.82 (s, 1H), 5.64-5.92 (m, 1H), 3.97 (br d, J=13.12 Hz, 2H), 2.55 (m, 2H), 2.28 (s, 3H), 1.91 (s, 1H), 1.47 (br s, 4H), 1.15-1.26 (m, 2H), 1.11 (br d, J=2.14 Hz, 2H), additional signals missing due to water signal suppression; FXR EC$_{50}$=1300 nM.

Example 170

7-(2-(5-Cyclopropyl-3-(2-(trifluoromethyl)phenyl)isoxazol-4-yl)-7-azaspiro[3.5]non-1-en-7-yl)-8-methylquinoline-3-carboxylic acid

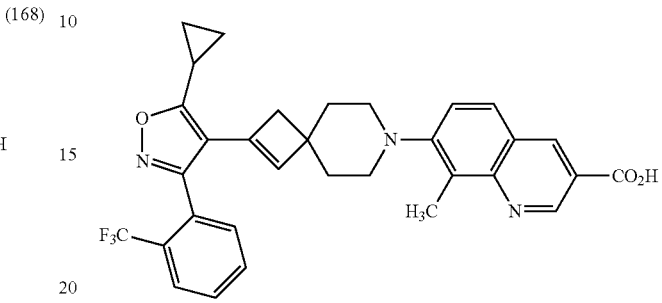

The title compound was prepared as described in General Method B for the preparation of Example 132 with replacement of 2,6-dichlorobenzaldehyde with 2-(trifluoromethyl)benzaldehyde. MS (ESI) m/z: 560.0 [M+H]$^+$; $^1$H NMR (500 MHz, Methanol-d$_4$) δ 8.10-8.23 (m, 1H), 8.04 (d, J=8.53 Hz, 1H), 7.93 (d, J=9.35 Hz, 1H), 7.44-7.67 (m, 3H), 7.18 (d, J=2.20 Hz, 1H), 5.85 (s, 1H), 4.87 (s, 3H), 3.48 (br dd, J=5.09, 11.97 Hz, 2H), 3.33 (br s, 2H), 3.04-3.25 (m, 2H), 2.42 (s, 2H), 2.18-2.35 (m, 1H), 1.61-1.97 (m, 4H), 1.04-1.36 (m, 4H); FXR EC$_{50}$=1747 nM.

Example 171

6-(2-(3-(3-Chloropyridin-2-yl)-5-cyclopropylisoxazol-4-yl)-7-azaspiro[3.5]non-1-en-7-yl)nicotinic acid

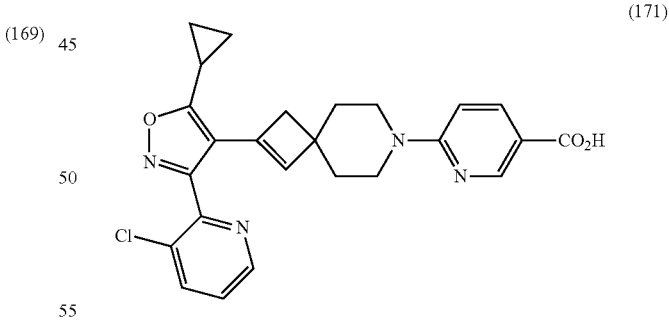
(171)

The title compound was prepared as described in General Method A for the preparation of Example 2 with replacement of 2,6-dichlorobenzaldehyde with 3-chloropicolinaldehyde. MS (ESI) m/z: 463.2 [M+H]$^+$; $^1$H NMR (500 MHz, DMSO-d$_6$) δ 8.68 (d, J=4.6 Hz, 1H), 8.58 (d, J=1.5 Hz, 1H), 8.13 (d, J=8.2 Hz, 1H), 7.89 (dd, J=9.2, 1.8 Hz, 1H), 7.62 (dd, J=8.2, 4.9 Hz, 1H), 6.82 (d, J=9.2 Hz, 1H), 5.86 (s, 1H), 3.88-3.76 (m, 1H), 3.45-3.33 (m, 1H), 3.27 (dd, J=10.5, 6.0 Hz, 1H), 3.21-3.11 (m, 1H), 2.41-2.24 (m, 3H), 1.53 (br t, J=5.2 Hz, 4H), 1.29-1.16 (m, 2H), 1.16-1.08 (m, 2H), 1.01 (d, J=6.1 Hz, 1H); FXR EC$_{50}$=1871 nM.

Example 172

5-(2-(5-Cyclopropyl-3-(2-(trifluoromethoxy)phenyl)isoxazol-4-yl)-7-azaspiro[3.5]non-1-en-7-yl)-1-methyl-1H-pyrrolo[2,3-c]pyridine-2-carboxylic acid

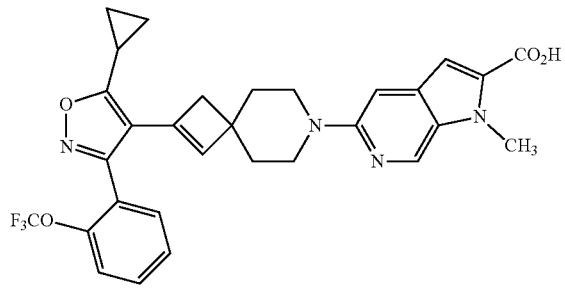

(172)

The title compound was prepared as described in General Method A for the preparation of Example 17 with replacement of ethyl 2-bromo-4-fluorobenzo[d]thiazole-6-carboxylate with ethyl 5-chloro-1-methyl-1H-pyrrolo[2,3-c]pyridine-2-carboxylate. MS (ESI) m/z: 565.9 [M+H]$^+$; $^1$H NMR (500 MHz, DMSO-$d_6$) δ 8.46 (s, 1H), 7.66-7.77 (m, 1H), 7.47-7.64 (m, 3H), 6.78 (s, 1H), 6.62 (s, 1H), 5.91 (s, 1H), 4.02 (s, 3H), 3.52-3.68 (m, 2H), 3.15 (br d, J=9.16 Hz, 2H), 2.38 (m, 3H), 1.52-1.78 (m, 4H), 1.09-1.37 (m, 4H); FXR EC$_{50}$=2366 nM.

Example 173

3-(2-(5-Cyclopropyl-3-(2-(trifluoromethoxy)phenyl)isoxazol-4-yl)-7-azaspiro[3.5]non-1-en-7-yl)-1-methyl-1H-pyrazolo[4,3-b]pyridine-6-carboxylic acid

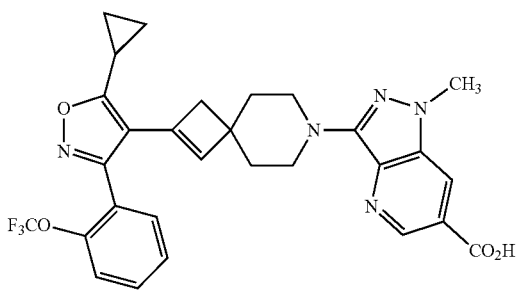

(173)

The title compound was prepared as described in General Method B for the preparation of Example 113 with replacement of methyl 6-bromo-4-ethoxyquinoline-2-carboxylate with methyl 3-bromo-1-methyl-1H-pyrazolo[4,3-b]pyridine-6-carboxylate. MS (ESI) m/z: 566.2 [M+H]$^+$; $^1$H NMR (500 MHz, DMSO-$d_6$) δ 8.78 (s, 1H), 8.40 (s, 1H), 7.65-7.74 (m, 2H), 7.40-7.63 (m, 3H), 5.91 (s, 1H), 3.83-3.84 (m, 2H), 3.88 (s, 3H), 2.36-2.44 (m, 2H), 2.32 (br s, 1H), 1.59-1.77 (m, 4H), 1.15-1.23 (m, 2H), 1.11 (br d, J=2.44 Hz, 2H); additional signals missing due to water signal suppression; FXR EC$_{50}$=2791 nM.

Example 174

5-(2-(5-Cyclopropyl-3-(2-(trifluoromethoxy)phenyl)isoxazol-4-yl)-7-azaspiro[3.5]non-1-en-7-yl)-1-methyl-1H-indazole-3-carboxylic acid

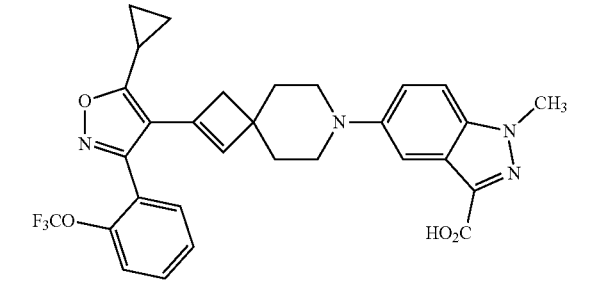

(174)

The title compound was obtained via hydrolysis of 5-(2-(5-cyclopropyl-3-(2-(trifluoromethoxy)phenyl)isoxazol-4-yl)-7-azaspiro[3.5]non-1-en-7-yl)-1-methyl-1H-indazole-3-carbonitrile under the conditions described in General Method D for the preparation of Example 100. MS (ESI) m/z: 565.1 [M+H]$^+$; $^1$H NMR (500 MHz, DMSO-$d_6$) δ 7.67-7.76 (m, 1H), 7.65 (br d, J=9.16 Hz, 1H), 7.48-7.61 (m, 3H), 7.38 (br d, J=8.54 Hz, 1H), 7.02-7.31 (m, 1H), 5.95 (s, 1H), 3.27 (br d, J=4.58 Hz, 2H), 3.03 (br s, 2H), 2.55 (s, 3H), 2.37-2.45 (m, 2H), 2.33 (br s, 1H), 1.59-1.89 (m, 4H), 1.05-1.21 (m, 4H); FXR EC$_{50}$=236 nM.

Example 175

6-(2-(5-Cyclopropyl-3-(2-(trifluoromethoxy)phenyl)isoxazol-4-yl)-7-azaspiro[3.5]non-1-en-7-yl)-1-methyl-1H-indazole-3-carbonitrile

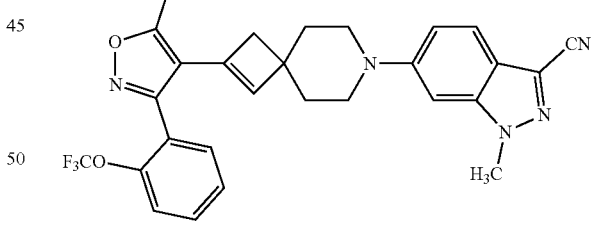

(175)

A slurry of 5-cyclopropyl-4-(7-azaspiro[3.5]non-1-en-2-yl)-3-(2-(trifluoromethoxy)phenyl)isoxazole (18 mg, 0.046 mmol), 6-bromo-1-methyl-1H-indazole-3-carbonitrile (16.3 mg, 0.069 mmol) and Cs$_2$CO$_3$ (30.0 mg, 0.092 mmol) in dioxane (154 L) was degassed by bubbling nitrogen through the mixture for 5 min. Chloro(2-dicyclohexylphosphino-2',6'-diisopropoxy-1,1'-biphenyl)[2-(2'-amino-1,1'-biphenyl)]palladium(II) (RuPhos-Pd-G2) (1.791 mg, 2.305 μmol) was added and the reaction mixture was sealed and heated to 90° C. After 24 h, 2 mL of methanol was added, the solids were filtered, and the filtrate was purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 35-75% B over 25 minutes, then a 5-minute hold at 100% B; Flow: 20 mL/min. Fractions containing the desired product were combined and dried to give 6-(2-(5-cyclopropyl-3-(2-(trifluoromethoxy)phenyl)isoxazol-4-yl)-7-azaspiro[3.5]non-1-en-7-yl)-1-methyl-1H-indazole-3-carbonitrile (11.1 mg, 0.019 mmol, 42% yield). MS (ESI) m/z: 545.9 [M+H]$^+$; $^1$H NMR (500 MHz, DMSO-d$_6$) δ 7.63-7.80 (m, 4H), 7.48-7.62 (m, 3H), 7.32 (br d, J=9.77 Hz, 1H), 6.85 (s, 1H), 5.80-6.18 (m, 1H), 4.23 (s, 3H), 3.19-3.51 (m, 2H), 3.04 (br t, J=9.16 Hz, 2H), 2.35-2.42 (m, 2H), 2.31 (br s, 1H), 1.54-1.81 (m, 4H), 1.03-1.33 (m, 4H); FXR EC$_{50}$=3244 nM.

Example 176

6-(2-(5-Cyclopropyl-3-(2-(trifluoromethoxy)phenyl)isoxazol-4-yl)-7-azaspiro[3.5]non-1-en-7-yl)-1-methyl-1H-indazole-3-carboxylic acid

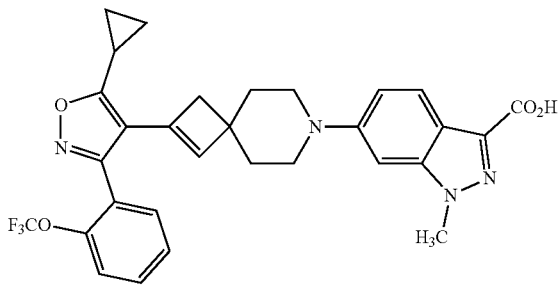
(176)

The title compound was obtained via hydrolysis of 6-(2-(5-cyclopropyl-3-(2-(trifluoromethoxy)phenyl)isoxazol-4-yl)-7-azaspiro[3.5]non-1-en-7-yl)-1-methyl-1H-indazole-3-carbonitrile (Example 175) under the conditions described in General Method D for the preparation of Example 100. MS (ESI) m/z: 565.3 [M+H]$^+$; $^1$H NMR (500 MHz, DMSO-d$_6$) δ 7.82 (br d, J=8.85 Hz, 1H), 7.64-7.75 (m, 1H), 7.49-7.62 (m, 4H), 7.08 (br d, J=8.54 Hz, 1H), 6.94 (br s, 1H), 5.80-6.02 (m, 1H), 4.01 (br s, 3H), 3.08 (br t, J=9.16 Hz, 2H), 2.39 (s, 2H), 2.22-2.35 (m, 1H), 1.59-1.74 (m, 4H), 1.18 (br d, J=7.93 Hz, 2H), 1.11 (br d, J=2.14 Hz, 2H), additional signals missing due to water signal suppression; FXR EC$_{50}$=2975 nM.

Example 177

2-(2-(5-Cyclopropyl-3-(2,6-dichlorophenyl)isoxazol-4-yl)-7-azaspiro[3.5]non-1-en-7-yl) thiazolo[4,5-b]pyridine-6-carboxylic acid

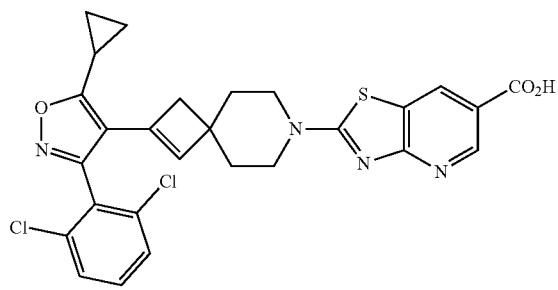
(177)

Step 1. 4-(7-(6-Bromothiazolo[4,5-b]pyridin-2-yl)-7-azaspiro[3.5]non-1-en-2-yl)-5-cyclopropyl-3-(2,6-dichlorophenyl)isoxazole

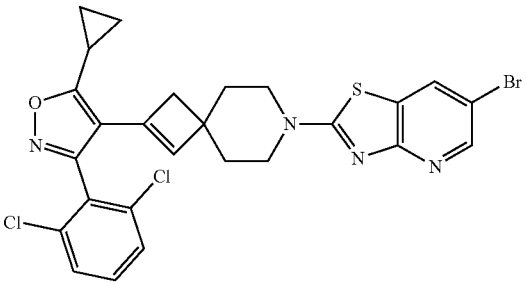 [SMILES: Clc1cccc(Cl)c1-c1noc(C2CC2)c1C1=CC2(CCN(c3nc4ncc(Br)cc4s3)CC2)C1]

Cesium carbonate (83 mg, 0.26 mmol) was added to a room temp solution of 5-cyclopropyl-3-(2,6-dichlorophenyl)-4-(7-azaspiro[3.5]non-1-en-2-yl)isoxazole (50 mg, 0.102 mmol, synthesis described in General Method A) and 6-bromo-2-chlorothiazolo[4,5-b]pyridine (38.2 mg, 0.15 mmol) in DMA (0.25 mL). The reaction mixture was heated to 50° C. for 4 h and the crude reaction mixture was purified by flash chromatography on SiO$_2$ (0-100% EtOAc/hexanes, Isco 12 g column) to give 4-(7-(6-bromothiazolo[4,5-b]pyridin-2-yl)-7-azaspiro[3.5]non-1-en-2-yl)-5-cyclopropyl-3-(2,6-dichlorophenyl)isoxazole (51 mg, 0.082 mmol, 81% yield). $^1$H NMR (500 MHz, CDCl$_3$) δ 8.40 (d, J=2.20 Hz, 1H), 7.93 (d, J=1.93 Hz, 1H), 7.41-7.50 (m, 2H), 7.33-7.39 (m, 1H), 5.78 (s, 1H), 3.68-3.94 (m, 2H), 3.40-3.63 (m, 2H), 2.42 (s, 2H), 2.14-2.28 (m, 1H), 1.67-1.85 (m, 5H), 1.28-1.39 (m, 3H), 1.10-1.22 (m, 2H).

Step 2. 2-(2-(5-Cyclopropyl-3-(2,6-dichlorophenyl)isoxazol-4-yl)-7-azaspiro[3.5]non-1-en-7-yl)thiazolo[4,5-b]pyridine-6-carbonitrile

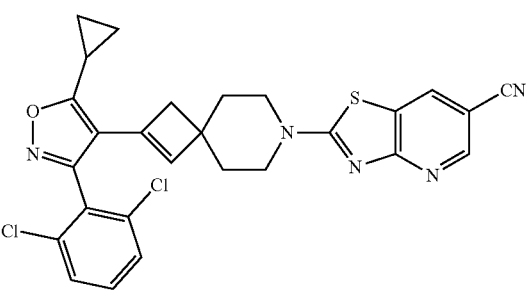 [SMILES: N#Cc1cnc2nc(N3CCC4(C=C(c5c(-c6c(Cl)cccc6Cl)noc5C5CC5)C4)CC3)sc2c1]

A microwave vial containing 4-(7-(6-bromothiazolo[4,5-b]pyridin-2-yl)-7-azaspiro[3.5]non-1-en-2-yl)-5-cyclopropyl-3-(2,6-dichlorophenyl)isoxazole (30 mg, 0.051 mmol), Xantphos (5.9 mg, 10.2 µmol), Pd$_2$(dba)$_3$ (9.3 mg, 10.2 µmol), and zinc cyanide (6.0 mg, 0.051 mmol) was purged three times with nitrogen and then anhydrous DMF (0.5 mL) was added. The reaction mixture was heated under microwave irradiation at 110° C. for 1.5 h. The reaction mixture was diluted with EtOAc and washed with brine. The organic layer was dried over Na$_2$SO$_4$, filtered and concentrated in vacuo to dryness. The residue was purified by flash chromatography on SiO$_2$ (0-100% EtOAc/hexanes, Isco 12 g column) to yield 2-(2-(5-cyclopropyl-3-(2,6-dichlorophenyl)isoxazol-4-yl)-7-azaspiro[3.5]non-1-en-7-yl)thiazolo[4, 5-b]pyridine-6-carbonitrile (15.5 mg, 0.028 mmol, 54% yield) as a gum. $^1$H NMR (400 MHz, CDCl$_3$) δ 8.54-8.79 (m, 1H), 7.87-8.19 (m, 1H), 7.42-7.49 (m, 2H), 7.29-7.41 (m, 2H), 5.71-5.87 (m, 1H), 3.75-4.02 (m, 2H), 3.63 (br d, J=3.96 Hz, 2H), 2.44 (s, 2H), 2.12-2.36 (m, 2H), 1.79 (t, J=5.72 Hz, 4H), 1.62 (br s, 3H), 1.29-1.38 (m, 2H), 1.09-1.25 (m, 3H), 0.88 (dd, J=3.30, 7.92 Hz, 1H).

Example 177. 2-(2-(5-Cyclopropyl-3-(2,6-dichlorophenyl)isoxazol-4-yl)-7-azaspiro[3.5]non-1-en-7-yl)thiazolo[4,5-b]pyridine-6-carboxylic acid The title compound was obtained via hydrolysis of 2-(2-(5-Cyclopropyl-3-(2,6-dichlorophenyl)isoxazol-4-yl)-7-azaspiro[3.5]non-1-en-7-yl)thiazolo[4,5-b]pyridine-6-carbonitrile under the conditions described in General Method D for the preparation of Example 100. MS (ESI) m/z: 552.9 [M+H]$^+$; $^1$H NMR (400 MHz, Methanol-d$_4$) δ 8.93 (d, J=1.76 Hz, 1H), 8.81 (d, J=1.76 Hz, 1H), 7.45-7.70 (m, 4H), 5.87 (s, 1H), 3.58-4.43 (m, 5H), 2.52 (s, 2H), 2.33 (s, 1H), 1.83 (t, J=5.72 Hz, 4H), 1.10-1.43 (m, 5H); FXR EC$_{50}$=121 nM.

6-(2-(5-Cyclopropyl-3-(2-(trifluoromethyl)phenyl)isoxazol-4-yl)-7-azaspiro[3.5]non-1-en-7-yl)quinoxaline-2-carboxylic acid (178)

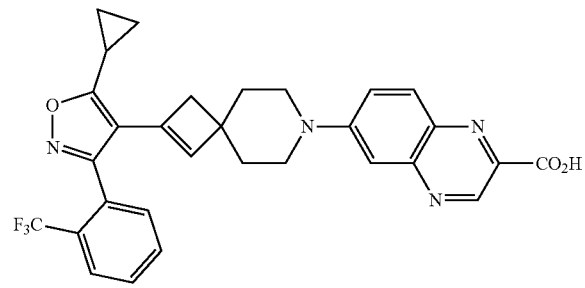

Step 1. 6-(2-(5-Cyclopropyl-3-(2-(trifluoromethyl)phenyl)isoxazol-4-yl)-7-azaspiro[3.5]non-1-en-7-yl)quinoxaline-2-carbonitrile

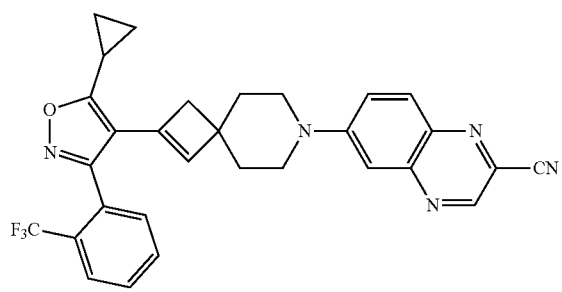 [SMILES: N#Cc1cnc2cc(N3CCC4(C=C(c5c(-c6ccccc6C(F)(F)F)noc5C5CC5)C4)CC3)ccc2n1]

A slurry of 5-cyclopropyl-4-(7-azaspiro[3.5]non-1-en-2-yl)-3-(2-(trifluoromethyl)phenyl)isoxazole (30 mg, 0.08 mmol, synthesis described in General method A), 6-chloroquinoxaline-2-carbonitrile (18.7 mg, 0.10 mmol) and Cs$_2$CO$_3$ (52.2 mg, 0.16 mmol) in dioxane (0.40 mL) was degassed by bubbling nitrogen through the mixture for 5 min. Chloro(2-dicyclohexylphosphino-2',6'-diisopropoxy-1,1'-biphenyl)[2-(2'-amino-1,1'-biphenyl)]palladium(II) (RuPhos-Pd-G2) (3.11 mg, 4.01 µmol) was then added and the reaction mixture was sealed and heated to 90° C. for 6 h. The crude mixture purified directly by flash chromatography on SiO$_2$ (0-100% EtOAc/hexanes, Isco 12 g column) to yield 6-(2-(5-cyclopropyl-3-(2-(trifluoromethyl)phenyl)isoxazol-4-yl)-7-azaspiro[3.5]non-1-en-7-yl)quinoxaline-2-carbonitrile (31 mg, 0.056 mmol, 70% yield) as a gum. MS (ESI) m/z: 528.1 [M+H]$^+$; $^1$H NMR (400 MHz, CDCl$_3$) δ 8.83 (s, 1H), 7.89 (d, J=9.7 Hz, 1H), 7.84-7.77 (m, 1H), 7.68-7.60 (m, 2H), 7.58 (dd, J=9.6, 2.8 Hz, 1H), 7.44 (dd, J=7.0, 1.8 Hz, 1H), 7.18 (d, J=2.9 Hz, 1H), 5.63 (s, 1H), 3.61 (dt, J=13.4, 5.0 Hz, 2H), 3.38 (ddd, J=13.0, 8.1, 4.4 Hz, 2H), 2.39 (s, 2H), 2.15 (tt, J=8.4, 5.1 Hz, 1H), 1.80-1.69 (m, 4H), 1.32-1.26 (m, 2H), 1.19-1.12 (m, 2H).

Example 178. 6-(2-(5-Cyclopropyl-3-(2-(trifluoromethyl)phenyl)isoxazol-4-yl)-7-azaspiro[3.5]non-1-en-7-yl)quinoxaline-2-carboxylic acid The title compound was obtained via hydrolysis of 6-(2-(5-cyclopropyl-3-(2-(trifluoromethyl)phenyl)isoxazol-4-yl)-7-azaspiro[3.5]non-1-en-7-yl)quinoxaline-2-carbonitrile under the conditions described in General Method D for the preparation of Example 100. MS (ESI) m/z: 547.1 [M+H]$^+$; $^1$H NMR (500 MHz, CDCl$_3$) δ 9.45 (s, 1H), 7.93 (d, J=9.35 Hz, 1H), 7.82 (br d, J=7.43 Hz, 1H), 7.55-7.74 (m, 3H), 7.39-7.55 (m, 1H), 7.31 (d, J=1.93 Hz, 1H), 5.65 (s, 1H), 3.51-3.66 (m, 2H), 3.31-3.51 (m, 2H), 2.41 (s, 2H), 1.98-2.20 (m, 1H), 1.62-1.81 (m, 4H), 1.24-1.37 (m, 2H), 1.09-1.24 (m, 2H); FXR EC$_{50}$=172 nM.

General Method E

Example 179

2-(2-(5-Cyclopropyl-3-(2,6-dichlorophenyl)isoxazol-4-yl)-7-azaspiro[3.5]non-1-en-7-yl)-N-(cyclopropylsulfonyl)-4-fluorobenzo[d]thiazole-6-carboxamide (179)

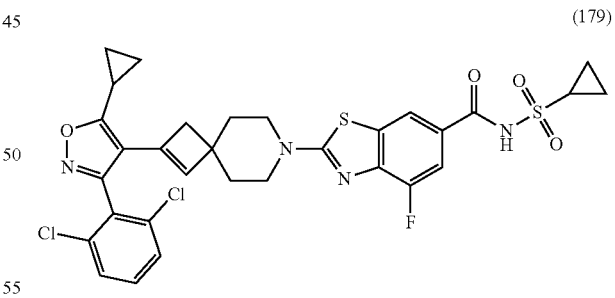

2-(2-(5-Cyclopropyl-3-(2,6-dichlorophenyl)isoxazol-4-yl)-7-azaspiro[3.5]non-1-en-7-yl)-4-fluorobenzo[d]thiazole-6-carboxylic acid (Example 1, 15 mg, 0.03 mmol, synthesis described in General Method A) was dissolved in THF (0.26 mL) in a 5 mL round bottom flask that was equipped with a magnetic stirrer under nitrogen. CDI (12.8 mg, 0.08 mmol) was added and the mixture was heated at 60° C. for 1 h followed by addition of cyclopropanesulfonamide (12.7 mg, 0.10 mmol) and DBU (11.9 µL, 0.08 mmol). The reaction mixture was stirred at room temperature for 6 h. The crude mixture was purified via preparative LC/MS with the following conditions: Column: XBridge C18, 19×200 mm, 5-μm particles; Mobile Phase A: 5:95 acetonitrile: water with 0.1% TFA; Mobile Phase B: 95:5 acetonitrile: water with 0.1% TFA; Gradient: 5-100% B over 20 minutes, then a hold at 100% B; Flow: 20 mL/min. Fractions containing the desired product were combined and dried to give 2-(2-(5-cyclopropyl-3-(2,6-dichlorophenyl) isoxazol-4-yl)-7-azaspiro[3.5]non-1-en-7-yl)-N-(cyclopropylsulfonyl)-4-fluorobenzo[d]thiazole-6-carboxamide (12.0 mg, 0.02 mmol, 64% yield). MS (ESI) m/z: 673.0 [M+H]+; 1H NMR (400 MHz, CDCl3) δ 8.11 (d, J=1.54 Hz, 1H), 7.65 (dd, J=1.43, 11.99 Hz, 1H), 7.36 (d, J=1.76 Hz, 1H), 7.34 (d, J=0.66 Hz, 1H), 7.30 (s, 1H), 5.69 (s, 1H), 3.64-3.74 (m, 2H), 3.27-3.35 (m, 2H), 2.06-2.18 (s, 2H), 1.88-1.93 (m, 2H), 1.04-1.16 (m, 4H), 0.64-0.92 (m, 8H); FXR EC$_{50}$=13 nM.

Example 180

2-(2-(5-Cyclopropyl-3-(2,6-dichlorophenyl)isoxazol-4-yl)-7-azaspiro[3.5]non-1-en-7-yl)-4-fluoro-N-(methylsulfonyl)benzo[d]thiazole-6-carboxamide

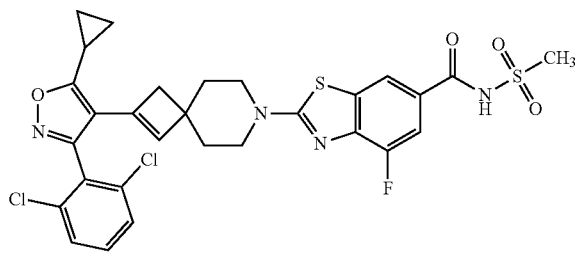

(180)

The title compound was prepared as described in General Method E for the preparation of Example 179 with replacement of cyclopropanesulfonamide with methanesulfonamide. MS (ESI) m/z: 646.9 [M+H]+; 1H NMR (500 MHz, DMSO-d$_6$) δ 8.11 (s, 1H), 7.67 (s, 2H), 7.54-7.65 (m, 2H), 6.94-7.35 (m, 1H), 5.91 (s, 1H), 2.90 (s, 2H), 2.55 (s, 3H), 2.28-2.44 (s, 2H), 1.92 (m, 1H), 1.60-1.71 (m, 4H), 1.22 (br d, J=7.93 Hz, 2H), 1.12-1.18 (m, 2H), additional signals missing due to water signal suppression; FXR EC$_{50}$=35 nM.

Example 181

2-(2-(5-Cyclopropyl-3-(3,5-dichloropyridin-4-yl) isoxazol-4-yl)-7-azaspiro[3.5]non-1-en-7-yl)-N-(cyclopropylsulfonyl)-4-fluorobenzo[d]thiazole-6-carboxamide

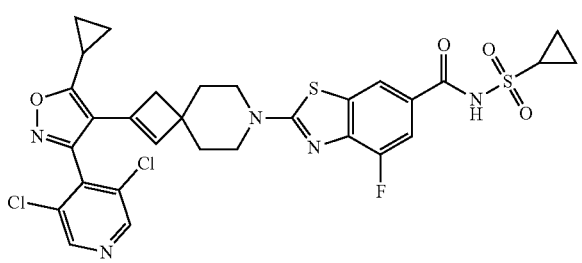

(181)

The title compound was prepared as described in General Method E for the preparation of Example 179 with replacement of 2,6-dichlorobenzaldehyde with 3,5-dichloroisonicotinaldehyde. MS (ESI) m/z: 674.0 [M+H]+; 1H NMR (500 MHz, CDCl3) δ 8.68 (br s, 1H), 8.66 (s, 2H), 7.92 (d, J=1.38 Hz, 1H), 7.53 (dd, J=1.24, 10.87 Hz, 1H), 5.84 (s, 1H), 3.71-3.94 (m, 2H), 3.58 (ddd, J=4.54, 7.84, 12.93 Hz, 2H), 2.47 (s, 2H), 2.07-2.30 (m, 2H), 1.73-1.88 (m, 4H), 1.47 (dd, J=1.93, 4.68 Hz, 2H), 1.34 (dd, J=2.34, 4.81 Hz, 2H), 1.10-1.29 (m, 4H); FXR EC$_{50}$=60 nM.

2-(2-(5-Cyclopropyl-3-(3,5-dichloropyridin-4-yl) isoxazol-4-yl)-7-azaspiro[3.5]non-1-en-7-yl)-4-fluoro-N-(methylsulfonyl)benzo[d]thiazole-6-carboxamide

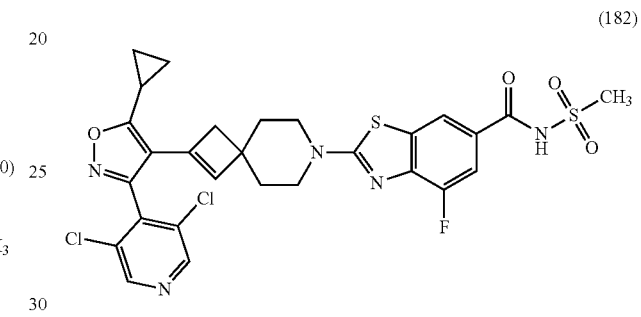

(182)

The title compound was prepared as described in General Method E for the preparation of Example 181 with replacement of cyclopropanesulfonamide with methanesulfonamide. MS (ESI) m/z: 648.0 [M+H]+; 1H NMR (400 MHz, CDCl3) δ 8.65 (s, 2H), 8.03 (d, J=9.24 Hz, 1H), 7.61 (s, 2H), 7.40 (d, J=2.64 Hz, 1H), 5.86 (s, 1H), 4.16 (s, 3H), 3.44-3.59 (m, 2H), 3.12-3.37 (m, 2H), 2.45 (s, 2H), 1.82 (br d, J=2.42 Hz, 7H), 1.13-1.44 (m, 8H), 0.91 (s, 3H); FXR EC$_{50}$=688 nM.

Example 183

6-(2-(5-Cyclopropyl-3-(3,5-dichloropyridin-4-yl) isoxazol-4-yl)-7-azaspiro[3.5]non-1-en-7-yl)-N-(cyclopropylsulfonyl)-4-(trifluoromethyl)quinoline-2-carboxamide

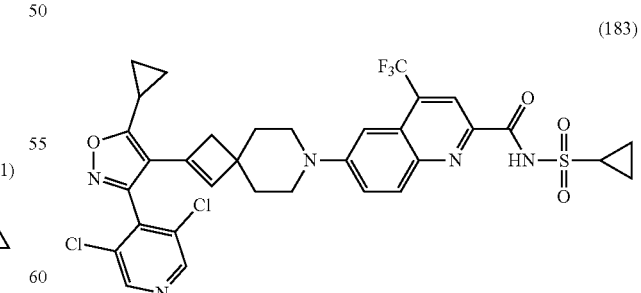

(183)

The title compound was prepared as described in General Method E for the preparation of Example 179 with replacement of 2-(2-(5-Cyclopropyl-3-(2,6-dichlorophenyl)isoxazol-4-yl)-7-azaspiro[3.5]non-1-en-7-yl)-4-fluorobenzo[d] thiazole-6-carboxylic acid (Example 1) with 6-(2-(5-

Cyclopropyl-3-(3,5-dichloropyridin-4-yl)isoxazol-4-yl)-7-azaspiro[3.5]non-1-en-7-yl)-4-(trifluoromethyl)quinoline-2-carboxylic acid (Example 85). MS (ESI) m/z: 718.2 [M+H]+; 1H NMR (400 MHz, Acetone-d6) δ 8.62-8.83 (m, 1H), 8.43 (br d, J=1.76 Hz, 1H), 8.11 (br dd, J=1.87, 8.69 Hz, 1H), 7.88 (s, 2H), 7.32-7.69 (m, 2H), 3.89-4.29 (m, 2H), 3.47-3.80 (m, 2H), 2.38-2.62 (m, 2H), 2.13-2.28 (m, 1H), 1.65-1.78 (m, 1H), 0.95-1.34 (m, 5H); FXR EC50=55 nM.

6-(2-(5-Cyclopropyl-3-(3,5-dichloropyridin-4-yl)isoxazol-4-yl)-7-azaspiro[3.5]non-1-en-7-yl)-N-(methylsulfonyl)-4-(trifluoromethyl)quinoline-2-carboxamide

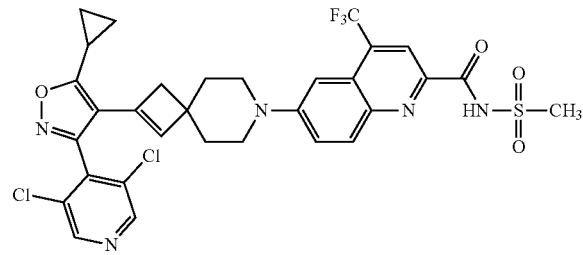

(184)

The title compound was prepared as described in General Method E for the preparation of Example 183 with replacement of cyclopropanesulfonamide with methanesulfonamide. MS (ESI) m/z: 691.1 [M+H]+; 1H NMR (400 MHz, Acetone-d6) δ 8.62-8.83 (m, 1H), 8.43 (br d, J=1.76 Hz, 1H), 8.11 (br dd, J=1.87, 8.69 Hz, 1H), 7.88 (s, 2H), 7.32-7.69 (m, 2H), 3.89-4.29 (m, 2H), 3.47-3.80 (m, 2H), 2.38-2.62 (m, 2H), 2.13-2.28 (m, 1H), 1.65-1.78 (m, 1H), 0.95-1.34 (m, 5H); FXR EC50=73 nM; Mouse in vivo (3 mg/kg, @ 6 h): Cyp7a1=−99%, Fgf15=+28×.

Example 185

6-(2-(5-Cyclopropyl-3-(3,5-dichloropyridin-4-yl)isoxazol-4-yl)-7-azaspiro[3.5]non-1-en-7-yl)-4-(difluoromethoxy)-N-(methylsulfonyl)quinoline-2-carboxamide

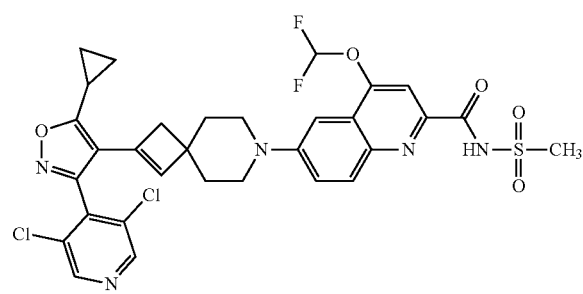

(185)

The title compound was prepared as described in General Method E for the preparation of Example 184 with replacement of ethyl 6-chloro-4-(trifluoromethyl)quinoline-2-carboxylate with methyl 6-bromo-4-(difluoromethoxy)quinoline-2-carboxylate. MS (ESI) m/z: 690.0 [M+H]+; 1H NMR (500 MHz, Methanol-d4) δ 8.75 (br s, 2H), 8.14 (br d, J=8.53 Hz, 1H), 7.83 (br s, 2H), 7.10-7.65 (m, 2H), 5.81-6.14 (m, 1H), 3.67 (br d, J=5.50 Hz, 2H), 3.42 (br s, 2H), 2.68 (br s, 2H), 2.54 (br s, 3H), 2.23-2.48 (m, 1H), 1.70-1.93 (m, 4H), 1.11-1.56 (m, 4H); FXR EC50=16 nM.

6-(2-(5-Cyclopropyl-3-(2-(trifluoromethyl)phenyl)isoxazol-4-yl)-7-azaspiro[3.5]non-1-en-7-yl)-4-(difluoromethoxy)-N-(methylsulfonyl)quinoline-2-carboxamide

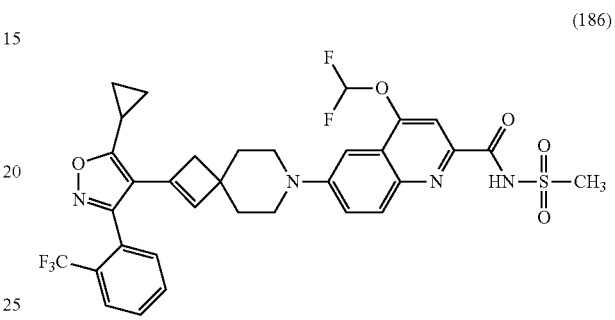

(186)

The title compound was prepared as described in General Method E for the preparation of Example 185 with replacement of 3,5-dichloroisonicotinaldehyde with 2-(trifluoromethyl)benzaldehyde. MS (ESI) m/z: 689.0 [M+H]+; 1H NMR (500 MHz, Methanol-d4) δ 8.03 (d, J=9.35 Hz, 1H), 7.88 (s, 1H), 7.67-7.81 (m, 4H), 7.51 (d, J=7.15 Hz, 1H), 7.20-7.49 (m, 1H), 7.32 (d, J=2.75 Hz, 1H), 5.73 (s, 1H), 3.50-3.68 (m, 1H), 3.23-3.32 (m, 2H), 2.42 (s, 2H), 2.31 (s, 1H), 2.05 (s, 3H), 1.67-1.87 (m, 4H), 1.14-1.29 (m, 4H); FXR EC50=13 nM.

Example 187

6-(2-(5-Cyclopropyl-3-(4-(trifluoromethyl)pyridin-3-yl)isoxazol-4-yl)-7-azaspiro[3.5]non-1-en-7-yl)-4-(difluoromethoxy)-N-(methylsulfonyl)quinoline-2-carboxamide

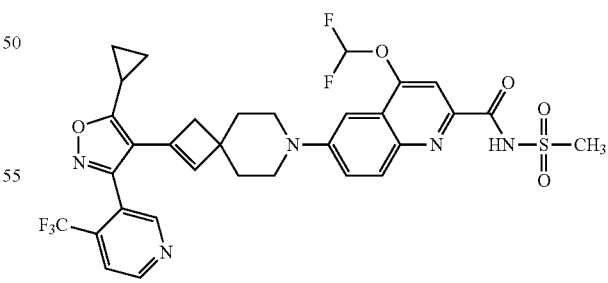

(187)

The title compound was prepared as described in General Method E for the preparation of Example 185 with replacement of 3,5-dichloroisonicotinaldehyde with 4-(trifluoromethyl)nicotinaldehyde. MS (ESI) m/z: 690.3 [M+H]+; 1H NMR (500 MHz, DMSO-d6) δ 8.93 (d, J=4.7 Hz, 1H), 8.15 (d, J=7.9 Hz, 1H), 8.02 (d, J=9.4 Hz, 1H), 7.89 (dd, J=4.8, 7.9 Hz, 1H), 7.86-7.55 (m, 3H), 7.15 (d, J=2.7 Hz, 1H), 3.35

(s, 3H), 3.29-3.21 (m, 2H), 2.38-2.28 (m, 3H). 1.66 (q, J=7.1, 7.7 Hz, 4H), 1.25-1.08 (m, 4H), additional signals missing due to water signal suppression; FXR $EC_{50}$=63 nM.

6-(2-(5-Cyclopropyl-3-(4-(trifluoromethyl)pyridin-3-yl)isoxazol-4-yl)-7-azaspiro[3.5]non-1-en-7-yl)-N-(cyclopropylsulfonyl)-4-(difluoromethoxy)quinoline-2-carboxamide (188)

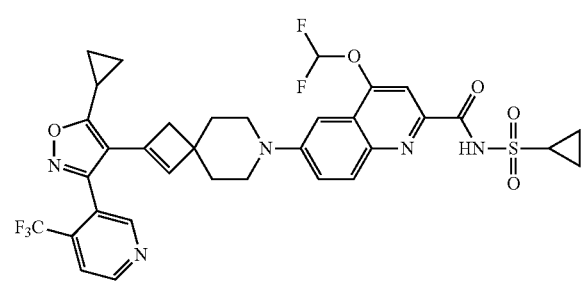

The title compound was prepared as described in General Method E for the preparation of Example 187 with replacement of methanesulfonamide with cyclopropanesulfonamide. MS (ESI) m/z: 716.3 [M+H]+; 1H NMR (500 MHz, DMSO-$d_6$) δ 8.92 (d, J=4.6 Hz, 1H), 8.13 (d, J=7.9 Hz, 1H), 8.02 (d, J=9.4 Hz, 1H), 7.88 (dd, J=4.7, 8.0 Hz, 1H), 7.84-7.49 (m, 3H), 7.15 (d, J=2.7 Hz, 1H), 5.82 (s, 1H), 3.38-3.19 (m, 2H), 3.14-3.06 (m, 1H), 2.36-2.28 (m, 3H), 1.70-1.59 (m, 4H), 1.25-1.01 (m, 8H), additional signals missing due to water signal suppression; FXR $EC_{50}$=43 nM.

Example 189

6-(2-(3-(3-Chloropyridin-2-yl)-5-cyclopropylisoxazol-4-yl)-7-azaspiro[3.5]non-1-en-7-yl)-N-(cyclopropylsulfonyl)-4-(difluoromethoxy)quinoline-2-carboxamide (189)

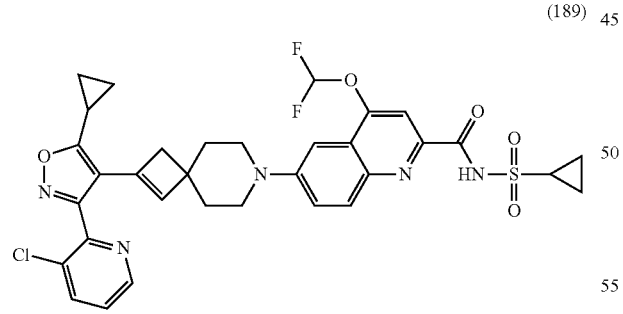

The title compound was prepared as described in General Method E for the preparation of Example 188 with replacement of 4-(trifluoromethyl)nicotinaldehyde with 3-chloropicolinaldehyde. MS (ESI) m/z: 682.0 [M+H]+; 1H NMR (500 MHz, DMSO-$d_6$) δ 8.68 (d, J=4.6 Hz, 1H), 8.14 (d, J=8.2 Hz, 1H), 7.98 (d, J=9.2 Hz, 1H), 7.84-7.45 (m, 4H), 7.15 (s, 1H), 5.88 (s, 1H), 3.26-3.16 (m, 2H), 3.04 (br s, 1H), 2.38-2.28 (m, 3H), 1.73-1.61 (m, 4H), 1.26-0.87 (m, 8H), additional signals missing due to water signal suppression; FXR $EC_{50}$=48 nM.

6-(2-(3-(3-Chloropyridin-2-yl)-5-cyclopropylisoxazol-4-yl)-7-azaspiro[3.5]non-1-en-7-yl)-4-(difluoromethoxy)-N-(methylsulfonyl)quinoline-2-carboxamide (190)

The title compound was prepared as described in General Method E for the preparation of Example 189 with replacement of cyclopropanesulfonamide with methanesulfonamide. MS (ESI) m/z: 655.8 [M+H]+; 1H NMR (500 MHz, DMSO-$d_6$) δ 8.69 (d, J=4.6 Hz, 1H), 8.15 (d, J=8.2 Hz, 1H), 8.02 (d, J=9.5 Hz, 1H), 7.90-7.55 (m, 4H), 7.16 (d, J=2.7 Hz, 1H), 5.89 (s, 1H), 3.61-3.53 (m, 2H), 3.38 (s, 3H), 3.30-3.22 (m, 2H), 2.39-2.29 (m, 3H), 1.74-1.61 (m, 4H), 1.23-1.10 (m, 4H); FXR $EC_{50}$=168 nM.

Example 191

6-(2-(5-Cyclopropyl-3-(2-(trifluoromethyl)pyridin-3-yl)isoxazol-4-yl)-7-azaspiro[3.5]non-1-en-7-yl)-N-(cyclopropylsulfonyl)-4-(difluoromethoxy)quinoline-2-carboxamide (191)

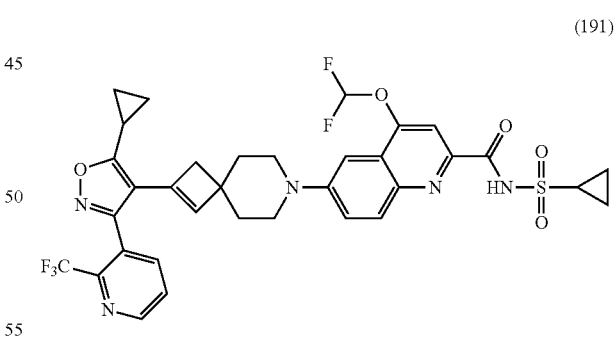

The title compound was prepared as described in General Method E for the preparation of Example 188 with replacement of 4-(trifluoromethyl)nicotinaldehyde with 2-(trifluoromethyl)nicotinaldehyde. MS (ESI) m/z: 716.3 [M+H]+; 1H NMR (500 MHz, DMSO-$d_6$) δ 9.04 (d, J=5.2 Hz, 1H), 8.87 (s, 1H), 8.04-7.96 (m, 2H), 7.88-7.54 (m, 3H), 7.15 (d, J=2.7 Hz, 1H), 5.83 (s, 1H), 3.27-3.18 (m, 2H), 3.09 (dq, J=3.6, 4.2, 8.1 Hz, 1H), 2.39-2.29 (m, 3H), 1.73-1.58 (m, 4H), 1.26-0.97 (m, 8H), additional signals missing due to water signal suppression; FXR $EC_{50}$=140 nM.

Example 192

6-(2-(5-Cyclopropyl-3-(2-(trifluoromethyl)pyridin-3-yl)isoxazol-4-yl)-7-azaspiro[3.5]non-1-en-7-yl)-4-(difluoromethoxy)-N-(methylsulfonyl)quinoline-2-carboxamide

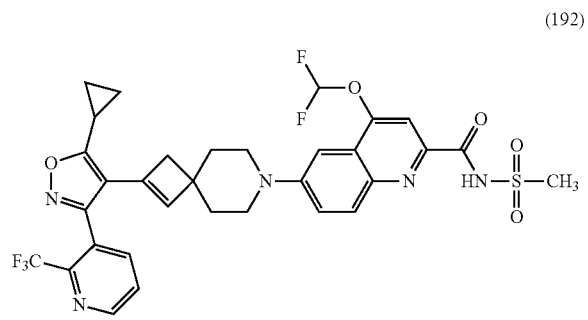 [SMILES: CS(=O)(=O)NC(=O)c1cc(OC(F)F)c2cc(N3CCC4(C=C(c5c(-c6cccnc6C(F)(F)F)noc5C5CC5)C4)CC3)ccc2n1]

(192)

The title compound was prepared as described in General Method E for the preparation of Example 191 with replacement of cyclopropanesulfonamide with methanesulfonamide. MS (ESI) m/z: 690.1 [M+H]$^+$; $^1$H NMR (500 MHz, DMSO-d$_6$) δ 9.03 (d, J=5.2 Hz, 1H), 8.84 (s, 1H), 8.01-7.90 (m, 2H), 7.77-7.42 (m, 3H), 7.13 (d, J=2.7 Hz, 1H), 5.81 (d, J=2.4 Hz, 1H), 3.51-3.40 (m, 2H), 3.19-3.09 (m, 2H), 2.96 (s, 3H), 2.39-2.27 (m, 3H), 1.74-1.57 (m, 4H), 1.26-1.07 (m, 4H); FXR EC$_{50}$=238 nM.

Example 193

6-(2-(5-Cyclopropyl-3-(2,6-dichlorophenyl)isoxazol-4-yl)-7-azaspiro[3.5]non-1-en-7-yl)-N-(cyclopropylsulfonyl)quinoline-2-carboxamide

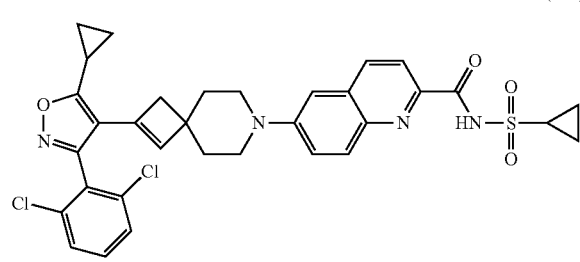

(193)

The title compound was prepared as described for the preparation of Example 179 with replacement of ethyl 2-bromo-4-fluorobenzo[d]thiazole-6-carboxylate with methyl 6-bromoquinoline-2-carboxylate. MS (ESI) m/z: 649.1 [M+H]$^+$; $^1$H NMR (500 MHz, DMSO-d$_6$) δ 8.26 (d, J=8.58 Hz, 1H), 7.94-8.05 (m, 2H), 7.73 (br d, J=9.51 Hz, 1H), 7.65-7.69 (m, 2H), 7.60 (dd, J=7.24, 8.92 Hz, 1H), 7.18-7.33 (m, 1H), 5.76-6.04 (m, 1H), 3.55 (br d, J=12.79 Hz, 2H), 2.55 (s, 2H), 2.27-2.41 (m, 2H), 1.56-1.74 (m, 4H), 1.05-1.27 (m, 8H) additional signals missing due to water signal suppression; FXR EC$_{50}$=178 nM.

Example 194

6-(2-(5-Cyclopropyl-3-(2,6-dichlorophenyl)isoxazol-4-yl)-7-azaspiro[3.5]non-1-en-7-yl)-N-(methylsulfonyl)quinoline-2-carboxamide

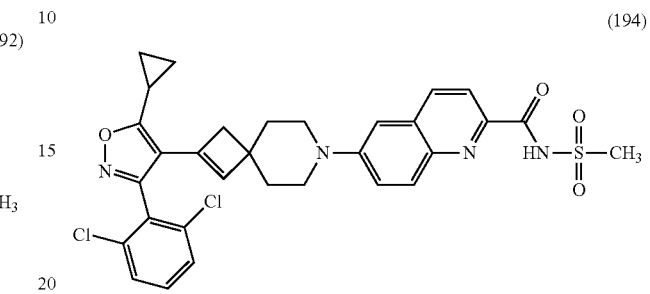

(194)

The title compound was prepared as described in General Method E for the preparation of Example 193 with replacement of cyclopropanesulfonamide with methanesulfonamide. MS (ESI) m/z: 623.1 [M+H]$^+$; $^1$H NMR (500 MHz, DMSO-d$_6$) δ 8.28 (d, J=8.54 Hz, 1H), 7.94-8.07 (m, 2H), 7.75 (dd, J=2.14, 9.46 Hz, 1H), 7.65-7.71 (m, 2H), 7.57-7.64 (m, 1H), 7.26 (d, J=2.14 Hz, 1H), 5.88 (s, 1H), 3.47-3.69 (m, 2H), 3.06-3.39 (m, 2H), 2.56 (s, 3H), 2.37 (m, 3H), 1.53-1.84 (m, 4H), 0.93-1.29 (m, 4H); FXR EC$_{50}$=255 nM.

Example 195

6-(2-(5-Cyclopropyl-3-(3,5-dichloropyridin-4-yl)isoxazol-4-yl)-7-azaspiro[3.5]non-1-en-7-yl)-4-methoxy-N-(methylsulfonyl)quinoline-2-carboxamide

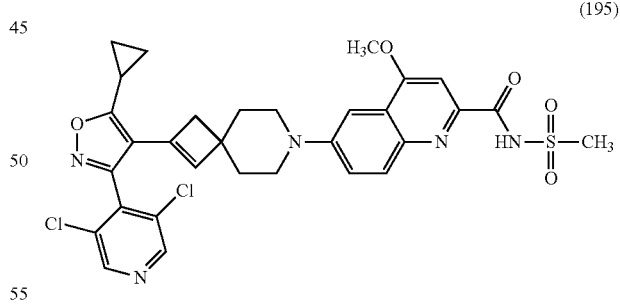

(195)

The title compound was prepared as described in General Method E for the preparation of Example 184 with replacement of ethyl 6-chloro-4-(trifluoromethyl)quinoline-2-carboxylate with methyl 6-bromo-4-methoxyquinoline-2-carboxylate. MS (ESI) m/z: 653.9 [M+H]$^+$; $^1$H NMR (500 MHz, Methanol-d$_4$) δ 8.73 (s, 2H), 8.15 (d, J=9.35 Hz, 1H), 7.83-7.98 (m, 1H), 7.77 (s, 1H), 7.65-7.74 (m, 1H), 5.85-6.07 (m, 1H), 4.28 (s, 3H), 3.59-3.80 (m, 2H), 3.47 (br d, J=13.20 Hz, 2H), 3.39 (s, 3H), 2.54 (s, 2H), 2.34 (s, 1H), 1.74-2.02 (m, 4H), 1.19-1.32 (m, 4H); FXR EC$_{50}$=75 nM.

Example 196

6-(2-(5-Cyclopropyl-3-(2-(trifluoromethyl)phenyl)isoxazol-4-yl)-7-azaspiro[3.5]non-1-en-7-yl)-4-methoxy-N-(methylsulfonyl)quinoline-2-carboxamide

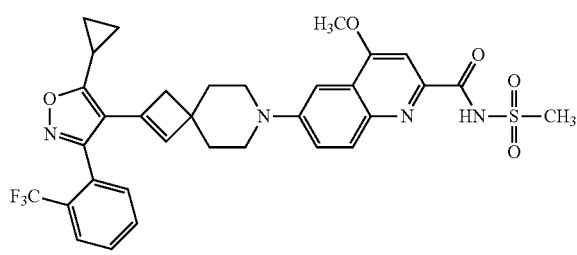

(196)

The title compound was prepared as described in General Method E for the preparation of Example 195 with replacement of 3,5-dichloroisonicotinaldehyde with 2-(trifluoromethyl)benzaldehyde. MS (ESI) m/z: 653.1 [M+H]$^+$; $^1$H NMR (500 MHz, Methanol-d$_4$) δ 8.08 (d, J=9.35 Hz, 1H), 7.89 (br d, J=7.15 Hz, 1H), 7.69-7.83 (m, 4H), 7.42-7.57 (m, 2H), 5.63-5.98 (m, 1H), 4.24 (s, 3H), 3.51-3.63 (m, 2H), 3.33-3.38 (m, 2H), 3.35 (s, 3H), 2.44 (s, 2H), 2.31 (m, 1H), 1.79 (m, 4H), 1.21 (m, 4H); FXR EC$_{50}$=155 nM.

Example 197

2-(2-(5-Cyclopropyl-3-(3,5-dichloropyridin-4-yl)isoxazol-4-yl)-7-azaspiro[3.5]non-1-en-7-yl)-4-fluoro-N-sulfamoylbenzo[d]thiazole-6-carboxamide

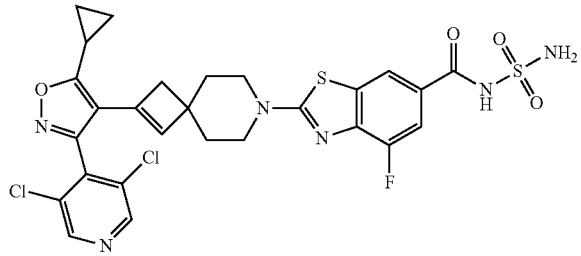

(197)

The title compound was prepared as described in General Method E for the preparation of Example 181 with replacement of cyclopropanesulfonamide with sulfuric diamide. MS (ESI) m/z: 649.0 [M+H]$^+$; $^1$H NMR (500 MHz, CDCl$_3$) δ 8.58 (s, 2H), 7.92 (s, 1H), 7.53 (br d, J=11.28 Hz, 1H), 5.77 (s, 1H), 3.66-3.84 (m, 2H), 3.44-3.59 (m, 2H), 2.40 (s, 2H), 2.07-2.21 (m, 1H), 1.72 (br s, 4H), 1.21-1.34 (m, 2H), 1.16 (br d, J=6.05 Hz, 2H); FXR EC$_{50}$=381 nM.

General Method F

Example 198

2-(2-(5-Cyclopropyl-3-(3,5-dichloropyridin-4-yl)isoxazol-4-yl)-7-azaspiro[3.5]non-1-en-7-yl)-4-fluoro-N-methylbenzo[d]thiazole-6-carboxamide

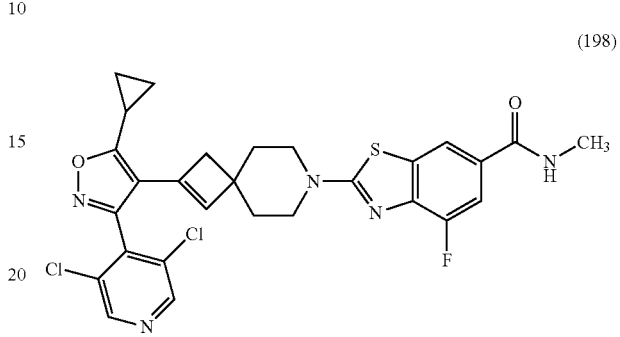

(198)

2-(2-(5-Cyclopropyl-3-(3,5-dichloropyridin-4-yl)isoxazol-4-yl)-7-azaspiro[3.5]non-1-en-7-yl)-4-fluorobenzo[d]thiazole-6-carboxylic acid (15 mg, 0.03 mmol) was dissolved in DCE (1 mL). 2,4,6-Tripropyl-1,3,5,2,4,6-trioxatriphosphinane 2,4,6-trioxide (T3P) (0.03 mL, 0.05 mmol) followed by methylamine (1.6 mg, 0.05 mmol) and pyridine (6.4 µL, 0.08 mmol) were added to the reaction mixture and the resulting solution was stirred at room temperature for 6 h. The crude reaction mixture was directly purified flash chromatography on SiO$_2$ (0-100% EtOAc/hexanes, Isco 12 g column) to yield 2-(2-(5-cyclopropyl-3-(3,5-dichloropyridin-4-yl)isoxazol-4-yl)-7-azaspiro[3.5]non-1-en-7-yl)-4-fluoro-N-methylbenzo[d]thiazole-6-carboxamide (10 mg, 0.016 mmol, 62% yield) as a white solid. MS (ESI) m/z: 584.0 [M+H]$^+$; $^1$H NMR (400 MHz, CDCl$_3$) δ 8.63 (s, 2H), 7.85 (d, J=1.54 Hz, 1H), 7.38 (dd, J=1.54, 11.22 Hz, 1H), 6.04 (br d, J=4.62 Hz, 1H), 5.81 (s, 1H), 3.65-3.88 (m, 2H), 3.42-3.60 (m, 2H), 3.01 (d, J=4.84 Hz, 3H), 2.44 (s, 2H), 2.06-2.24 (m, 1H), 1.66-1.89 (m, 4H), 1.32 (dd, J=2.53, 4.95 Hz, 2H), 1.07-1.21 (m, 2H); FXR EC$_{50}$=311 nM.

Example 199

2-(2-(5-Cyclopropyl-3-(3,5-dichloropyridin-4-yl)isoxazol-4-yl)-7-azaspiro[3.5]non-1-en-7-yl)-4-fluoro-N-isopropylbenzo[d]thiazole-6-carboxamide

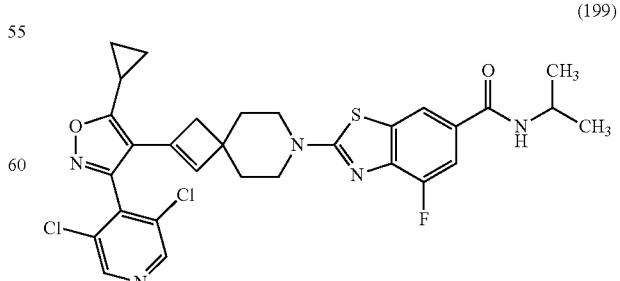

(199)

The title compound was prepared as described in General Method F for the preparation of Example 198 with replacement of methylamine with isopropylamine. MS (ESI) m/z: 612.0 [M+H]$^+$; $^1$H NMR (400 MHz, CDCl$_3$) δ 8.63 (s, 2H), 7.76-7.95 (m, 1H), 7.38 (d, J=11.22 Hz, 1H), 5.81 (s, 1H), 4.29 (m, 2H), 3.64-3.93 (m, 2H), 3.53 (m, 1H), 2.44 (s, 2H), 2.18 (s, 1H), 1.73-1.94 (m, 4H), 1.32 (m, 2H), 1.26 (d, J=6.60 Hz, 6H), 1.20 (m, 2H); FXR EC$_{50}$=431 nM.

Example 200

2-(2-(5-Cyclopropyl-3-(3,5-dichloropyridin-4-yl) isoxazol-4-yl)-7-azaspiro[3.5]non-1-en-7-yl)-N-ethyl-4-fluorobenzo[d]thiazole-6-carboxamide

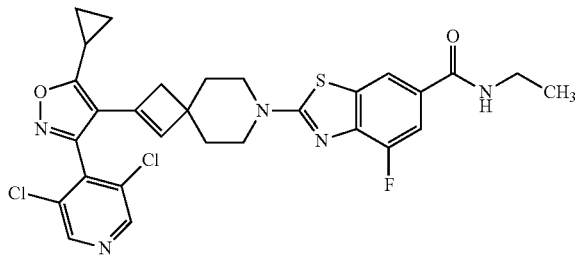

(200)

The title compound was prepared as described in General Method F for the preparation of Example 198 with replacement of methylamine with ethylamine. MS (ESI) m/z: 598.0 [M+H]$^+$; $^1$H NMR (400 MHz, CDCl$_3$) δ 8.56 (s, 2H), 7.78 (d, J=1.76 Hz, 1H), 7.33 (dd, J=1.54, 11.22 Hz, 1H), 6.02 (s, 1H), 5.74 (s, 1H), 3.60-3.80 (m, 2H), 3.30-3.56 (m, 5H), 2.37 (s, 2H), 1.98-2.21 (m, 2H), 1.45-1.77 (m, 7H), 0.74-1.33 (m, 13H); FXR EC$_{50}$=68 nM.

Example 201

N-Cyclopropyl-2-(2-(5-cyclopropyl-3-(3,5-dichloropyridin-4-yl)isoxazol-4-yl)-7-azaspiro[3.5]non-1-en-7-yl)-4-fluorobenzo[d]thiazole-6-carboxamide

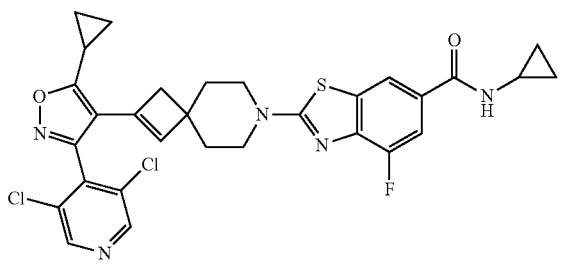

(201)

The title compound was prepared as described in General Method F for the preparation of Example 198 with replacement of methylamine with cyclopropylamine. MS (ESI) m/z: 610.0 [M+H]$^+$; $^1$H NMR (400 MHz, CHLOROFORM-d) δ 8.63 (s, 2H), 7.83 (d, J=1.54 Hz, 1H), 7.36 (dd, J=1.54, 11.22 Hz, 1H), 6.20 (br d, J=2.64 Hz, 1H), 3.76 (td, J=5.06, 13.20 Hz, 2H), 3.45-3.64 (m, 2H), 2.89 (dt, J=3.30, 6.93 Hz, 1H), 2.44 (s, 2H), 2.18 (tt, J=5.03, 8.39 Hz, 1H), 1.69-1.81 (m, 4H), 1.31 (dd, J=2.53, 4.95 Hz, 2H), 1.13-1.24 (m, 2H), 0.87 (br d, J=5.50 Hz, 2H), 0.55-0.69 (m, 2H); FXR EC$_{50}$=150 nM.

Example 202

2-(2-(5-Cyclopropyl-3-(3,5-dichloropyridin-4-yl) isoxazol-4-yl)-7-azaspiro[3.5]non-1-en-7-yl)-4-fluorobenzo[d]thiazole-6-carboxamide

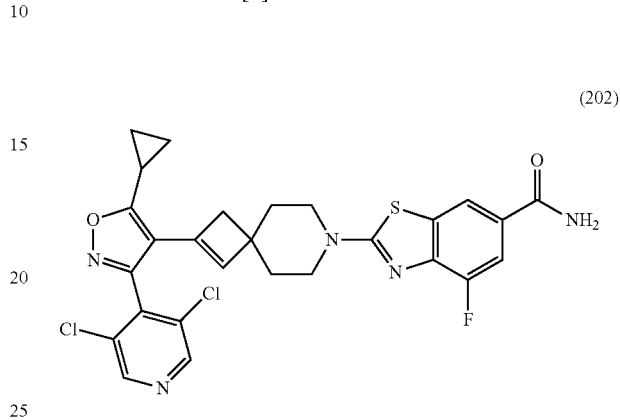

(202)

The title compound was prepared as described in General Method F for the preparation of Example 198 with replacement of methylamine with ammonium chloride. MS (ESI) m/z: 570.0 [M+H]$^+$; $^1$H NMR (400 MHz, Methanol-d$_4$) δ 8.63 (s, 2H), 7.92 (d, J=1.76 Hz, 1H), 7.50 (dd, J=1.54, 11.66 Hz, 1H), 5.72-5.99 (m, 1H), 3.72 (br d, J=13.64 Hz, 2H), 3.43-3.57 (m, 2H), 2.41 (s, 2H), 2.18-2.28 (m, 1H), 1.60-1.79 (m, 4H), 1.08-1.17 (m, 4H); FXR EC$_{50}$=155 nM.

Example 203

Ethyl 6-(2-(5-cyclopropyl-3-(3,5-dichloropyridin-4-yl)isoxazol-4-yl)-7-azaspiro[3.5]non-1-en-7-yl)-4-(trifluoromethyl)quinoline-2-carboxylate

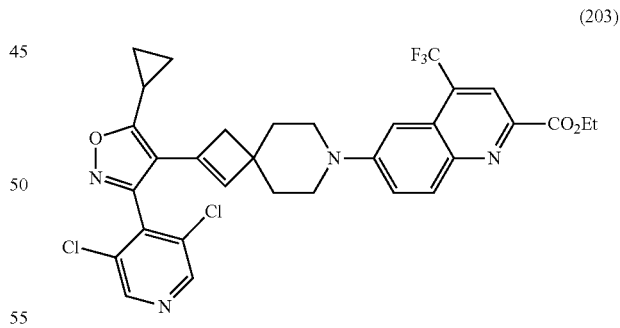

(203)

A slurry of 5-cyclopropyl-3-(3,5-dichloropyridin-4-yl)-4-(7-azaspiro[3.5]non-1-en-2-yl)isoxazole (0.1 g, 0.27 mmol, synthesis described in General Method A), ethyl 6-chloro-4-(trifluoromethyl)quinoline-2-carboxylate (0.097 g, 0.32 mmol) and Cs$_2$CO$_3$ (0.17 g, 0.53 mmol) in dioxane (1.8 mL) was degassed by bubbling nitrogen through the mixture for 5 min. Chloro(2-dicyclohexylphosphino-2',6'-diisopropoxy-1,1'-biphenyl)[2-(2'-amino-1,1'-biphenyl)]palladium(II) (RuPhos-Pd-G2) (10.3 mg, 0.013 mmol) was then added and the reaction mixture was sealed and heated to 70° C. After heating for 3 h the reaction mixture was diluted with EtOAc, filtered and the filtrate was concentrated in vacuo. The residue was purified by flash chromatography on SiO$_2$ (0-80% EtOAc/hexanes, Isco 40 g column) to give ethyl 6-(2-(5-cyclopropyl-3-(3,5-dichloropyridin-4-yl)isoxazol-4-yl)-7-azaspiro[3.5]non-1-en-7-yl)-4-(trifluoromethyl)quinoline-2-carboxylate (61.7 mg, 0.095 mmol, 36% yield) as a red solid. MS (ESI) m/z: 643.1 [M+H]$^+$; $^1$H NMR (400 MHz, CDCl$_3$) δ 8.67 (s, 2H), 8.38 (s, 1H), 8.21 (d, J=9.7 Hz, 1H), 7.63 (dd, J=9.7, 2.6 Hz, 1H), 7.25 (br s, 1H), 5.86 (s, 1H), 4.57 (q, J=7.0 Hz, 2H), 3.66-3.53 (m, 2H), 3.34 (ddd, J=12.8, 8.6, 4.3 Hz, 2H), 2.47 (s, 2H), 2.29-2.18 (m, 2H), 1.87-1.77 (m, 4H), 1.50 (t, J=7.2 Hz, 3H), 1.39-1.31 (m, 2H), 1.26-1.18 (m, 2H); FXR EC$_{50}$=946 nM.

General Method G

Example 204

2-(2-(4-Cyclopropyl-1-(2,6-dichlorophenyl)-1H-1,2,3-triazol-5-yl)-7-azaspiro[3.5]non-1-en-7-yl)-4-fluorobenzo[d]thiazole-6-carboxylic acid (204)

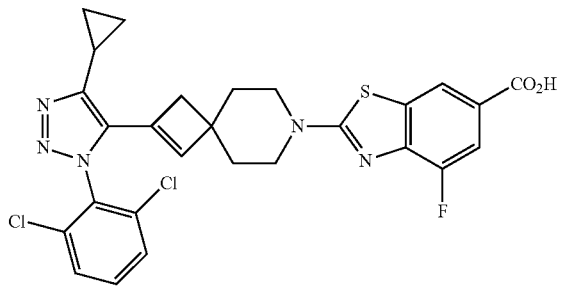

Step 1. (2,6-dichlorophenyl)hydrazine

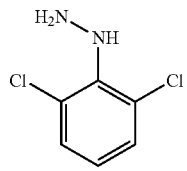

To a solution of 2,6-dichloroaniline (5.0 g, 30.9 mmol) in TFA (50 mL) was added water (10 mL). The reaction mixture was cooled to 0° C. and sodium nitrite (2.1 g, 30.9 mmol) was added over 0.5 hours, followed by gradual addition of sodium azide (5.1 g, 78.0 mmol) dissolved in a minimal volume of water. The mixture was stirred at 0° C. for 10 minutes, and allowed to warm to room temperature. After 2 hours, the reaction mixture was filtered, the solid was washed with water, air dried and collected. The was filtrate diluted with EtOAc, washed with saturated aqueous NaHCO$_3$ and brine, dried over MgSO$_4$, filtered and concentrated in vacuo. The residue was purified by flash chromatography on SiO$_2$ (0-20% EtOAc/hexanes). The solid isolated previously and the product from chromatography were combined to afford 2-azido-1,3-dichlorobenzene (5.6 g, 29.9 mmol, 97% yield) as a tan solid. $^1$H NMR (500 MHz, CDCl$_3$) δ 7.31 (d, J=8.3 Hz, 2H), 7.06 (t, J=8.1 Hz, 1H).

Step 2. 4-cyclopropyl-1-(2,6-dichlorophenyl)-5-iodo-1H-1,2,3-triazole

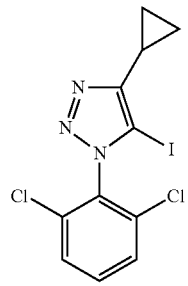 [SMILES: Clc1cccc(Cl)c1-n1nnc(C2CC2)c1I]

To a room temperature solution of 2-azido-1,3-dichlorobenzene (4.5 g, 23.7 mmol) in THF (120 mL) was added potassium iodide (15.8 g, 95 mmol) and copper (II) perchlorate hexahydrate (15.8 g, 42.7 mmol). The reaction mixture was stirred at 50° C. for 5 minutes, followed by addition of DBU (3.9 mL, 26.1 mmol) and cyclopropylacetylene (2.3 mL, 27.3 mmol). The resulting brown mixture was stirred at room temperature overnight. The reaction mixture was filtered through a pad of SiO$_2$ and concentrated to dryness in vacuo. The residue was purified by flash chromatography on SiO$_2$ (0-20% EtOAc/hexanes) to afford 4-cyclopropyl-1-(2,6-dichlorophenyl)-5-iodo-1H-1,2,3-triazole (1.8 g, 4.8 mmol, 20% yield) as a white solid. $^1$H NMR (500 MHz, CDCl$_3$) δ 7.51-7.55 (m, 2H), 7.45-7.50 (m, 1H), 1.85-1.94 (m, 1H), 1.14-1.21 (m, 2H), 1.03-1.10 (m, 2H).

Step 3. tert-Butyl 2-(4-cyclopropyl-1-(2,6-dichlorophenyl)-1H-1,2,3-triazol-5-yl)-2-hydroxy-7-azaspiro[3.5]nonane-7-carboxylate

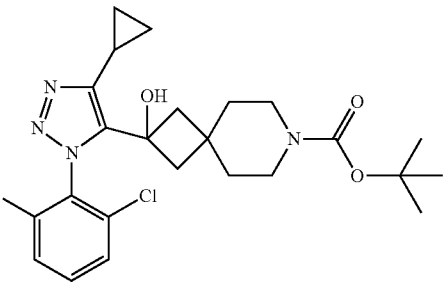

n-Butyllithium (2.5 M in hexanes, 0.26 mL, 0.66 mmol) was added slowly to a −78° C. solution of 4-cyclopropyl-1-(2,6-dichlorophenyl)-5-iodo-1H-1,2,3-triazole (0.2 g, 0.53 mmol) in THF (2.1 mL) giving a dark brown solution. After 5 minutes, a solution of tert-butyl 2-oxo-7-azaspiro[3.5]nonane-7-carboxylate (0.15 g, 0.63 mmol) in 0.25 mL of THF was added slowly via syringe. The reaction was continued at −78° C. for 2 hours and brought to 0° C. for 45 minutes. The reaction was quenched by the slow addition of approximately 1 mL of MeOH and then concentrated onto SiO$_2$ for purification. The residue was purified by flash chromatography on SiO$_2$ (0-100% EtOAc/hexanes, Isco 24 g column) to give tert-butyl 2-(4-cyclopropyl-1-(2,6-dichlorophenyl)-1H-1,2,3-triazol-5-yl)-2-hydroxy-7-azaspiro[3.5]nonane-7-carboxylate (75 mg, 0.15 mmol, 29% yield) as a white foam.

Step 4. 2-(4-Cyclopropyl-1-(2,6-dichlorophenyl)-1H-1,2,3-triazol-5-yl)-7-azaspiro[3.5]nonan-2-ol

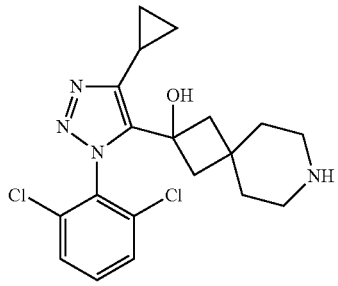 [SMILES: OC1(c2c(C3CC3)nnn2-c2c(Cl)cccc2Cl)CC2(CCNCC2)C1]

tert-Butyl 2-(4-cyclopropyl-1-(2,6-dichlorophenyl)-1H-1,2,3-triazol-5-yl)-2-hydroxy-7-azaspiro[3.5]nonane-7-carboxylate (75 mg, 0.152 mmol) was taken up in TFA (117 µL, 1.520 mmol). After 1 h the excess TFA was removed in vacuo. The solid was dried in vacuo overnight and then used directly in the next step. MS (ESI) m/z: 393.1 [M+H]$^+$.

Step 5. Ethyl 2-(2-(4-cyclopropyl-1-(2,6-dichlorophenyl)-1H-1,2,3-triazol-5-yl)-2-hydroxy-7-azaspiro[3.5]nonan-7-yl)-4-fluorobenzo[d]thiazole-6-carboxylate

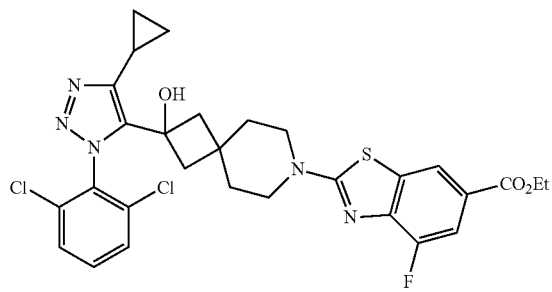 [SMILES: CCOC(=O)c1cc(F)c2nc(N3CCC4(CC3)CC(O)(c3c(C5CC5)nnn3-c3c(Cl)cccc3Cl)C4)sc2c1]

Cesium carbonate (61.9 mg, 0.19 mmol) followed by ethyl 2-bromo-4-fluorobenzo[d]thiazole-6-carboxylate (34.7 mg, 0.11 mmol) were added to a room temperature solution of 2-(4-cyclopropyl-1-(2,6-dichlorophenyl)-1H-1,2,3-triazol-5-yl)-7-azaspiro[3.5]nonan-2-ol, TFA (38.6 mg, 0.08 mmol) in DMA (0.22 mL) and the reaction mixture was heated to 90° C. After 2 hours of heating the crude reaction mixture was loaded directly onto a 12 g Isco SiO$_2$ cartridge for purification by flash chromatography (0-100% EtOAc/hexanes, Isco 12 g column) to give ethyl 2-(2-(4-cyclopropyl-1-(2,6-dichlorophenyl)-1H-1,2,3-triazol-5-yl)-2-hydroxy-7-azaspiro[3.5]nonan-7-yl)-4-fluorobenzo[d]thiazole-6-carboxylate (48 mg, 0.08 mmol, 100% yield). MS (ESI) m/z: 616.2 [M+H]$^+$.

Example 204. 2-(2-(4-Cyclopropyl-1-(2,6-dichlorophenyl)-1H-1,2,3-triazol-5-yl)-7-azaspiro[3.5]non-1-en-7-yl)-4-fluorobenzo[d]thiazole-6-carboxylic acid Phosphorus(V) oxychloride (45.4 µL, 0.49 mmol) followed by Et$_3$N (22.6 µL, 0.16 mmol) were added to a vial containing ethyl 2-(2-(4-cyclopropyl-1-(2,6-dichlorophenyl)-1H-1,2,3-triazol-5-yl)-2-hydroxy-7-azaspiro[3.5]nonan-7-yl)-4-fluorobenzo[d]thiazole-6-carboxylate (intermediate 33, 10 mg, 0.02 mmol). The reaction mixture was heated to 60° C. for 5 hours and concentrated in vacuo to remove excess POCl$_3$. The residue was dissolved in THF (133 µL), water (53.3 µL), MeOH (13.33 µL) and lithium hydroxide monohydrate (8.4 mg, 0.20 mmol) was added to the mixture. The reaction vessel was sealed and heated to 80° C. and after heating over the weekend was quenched with 1N HCl, diluted with MeOH, and filtered. The solution was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 10-60% B over 19 minutes, then a 5-minute hold at 100% B; Flow: 20 mL/min. Fractions containing the desired product were combined and dried via centrifugal evaporation to give 2-(2-(4-cyclopropyl-1-(2,6-dichlorophenyl)-1H-1,2,3-triazol-5-yl)-7-azaspiro[3.5]non-1-en-7-yl)-4-fluorobenzo[d]thiazole-6-carboxylic acid (4.6 mg, 8.1 mmol, 40% yield). MS (ESI) m/z: 570.2 [M+H]$^+$; $^1$H NMR (500 MHz, DMSO-d$_6$) δ 8.19 (s, 1H), 7.85-7.77 (m, 2H), 7.75-7.67 (m, 1H), 7.58 (br d, J=11.6 Hz, 1H), 6.22 (s, 1H), 3.73 (br d, J=13.4 Hz, 1H), 3.53 (br d, J=11.9 Hz, 1H), 2.36 (s, 2H), 2.13-2.00 (m, 1H), 1.77-1.59 (m, 4H), 1.10-1.02 (m, 2H), 0.99 (br d, J=2.7 Hz, 2H); FXR EC$_{50}$=26 nM.

General Method H

Example 205

2-((2-(5-Cyclopropyl-3-(2,6-dichlorophenyl)isoxazol-4-yl)-2-hydroxyspiro[3.5]nonan-7-yl)oxy)-4-fluorobenzo[d]thiazole-6-carboxylic acid (205)

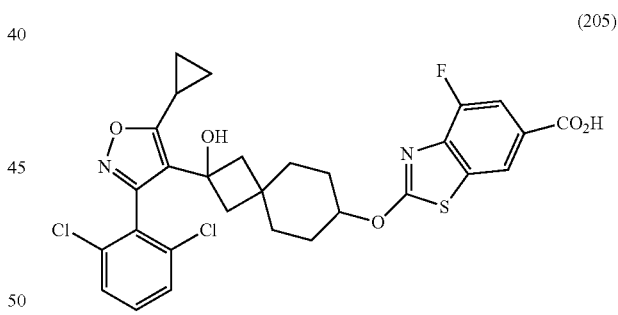

Step 1. 7-(tert-Butyldimethylsilyloxy)spiro[3,5]nonan-2-one

A solution of tert-butyldimethylchlorosilane (0.28 g, 1.9 mmol) in DCM (3 mL) was slowly added to a 0° C. solution of 7-hydroxyspiro[3.5]nonan-2-one (0.25 g, 1.6 mmol) and imidazole (0.22 g, 3.2 mmol) in DCM (5 mL). The ice bath was removed and the reaction mixture was stirred at room temperature overnight. The reaction mixture was concentrated in vacuo and the residue was partitioned between EtOAc and saturated aqueous NaHCO₃. The organic phase was isolated, washed with brine, dried over MgSO₄, filtered and concentrated in vacuo to give 7-((tert-butyldimethylsilyl)oxy)spiro[3.5]nonan-2-one (0.408 g, 1.520 mmol, 94% yield) as a colorless oil. MS (ESI) m/z: 269.2 [M+H]⁺; ¹H NMR (500 MHz, CDCl₃) δ 3.90-3.56 (m, 1H), 2.75 (br d, J=5.5 Hz, 4H), 1.94-1.80 (m, 2H), 1.77-1.64 (m, 2H), 1.62-1.40 (m, 4H), 0.90 (s, 9H), 0.07 (s, 6H).

Step 2. 7-((tert-Butyldimethylsilyl)oxy)-2-(5-cyclopropyl-3-(2,6-dichlorophenyl)isoxazol-4-yl)spiro[3.5]nonan-2-ol

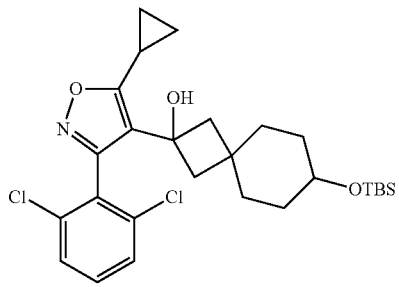 [SMILES: CC(C)(C)[Si](C)(C)OC1CCC2(CC1)CC(O)(c1c(-c3c(Cl)cccc3Cl)noc1C1CC1)C2]

n-Butyllithium (0.74 mL, 1.8 mmol) was added slowly to a −78° C. solution of 4-bromo-5-cyclopropyl-3-(2,6-dichlorophenyl)isoxazole (0.49 g, 1.5 mmol, synthesis described in General Method A) in THF (5.9 mL) giving a light brown solution. After 10 minutes, 7-((tert-butyldimethylsilyl)oxy)spiro[3.5]nonan-2-one (0.40 g, 1.5 mmol) was added as a solution in ~3 mL of THF. The reaction was continued at −78° C., and after 30 minutes, was quenched by the slow addition of 5 mL of MeOH and then concentrated in vacuo. The resulting residue was purified by flash chromatography on SiO₂ (0-30% EtOAc/hexanes, 40 g Isco SiO₂ cartridge) to give 7-((tert-butyldimethylsilyl)oxy)-2-(5-cyclopropyl-3-(2,6-dichlorophenyl)isoxazol-4-yl)spiro[3.5]nonan-2-ol (0.48 g, 0.92 mmol, 62% yield) as a white foam. ¹H NMR (500 MHz, CDCl₃) δ 7.47-7.41 (m, 2H), 7.40-7.34 (m, 1H), 3.61-3.47 (m, 1H), 2.25 (s, 1H), 2.21-2.08 (m, 3H), 2.04-1.88 (m, 3H), 1.60 (br d, J=12.1 Hz, 2H), 1.45-1.36 (m, 1H), 1.34-1.18 (m, 6H), 1.17-1.08 (m, 2H), 0.87 (s, 9H), 0.03 (s, 6H).

Step 3. 2-(5-Cyclopropyl-3-(2,6-dichlorophenyl)isoxazol-4-yl)spiro[3.5]nonane-2,7-diol

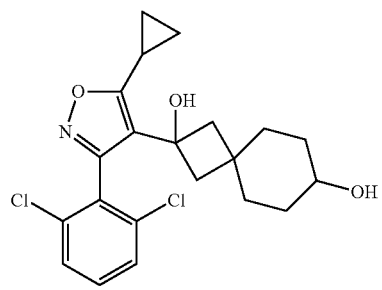 [SMILES: OC1CCC2(CC1)CC(O)(c1c(-c3c(Cl)cccc3Cl)noc1C1CC1)C2]

To a room temperature solution of 7-((tert-butyldimethylsilyl)oxy)-2-(5-cyclopropyl-3-(2,6-dichlorophenyl)isoxazol-4-yl)spiro[3.5]nonan-2-ol (0.23 g, 0.43 mmol) in THF (2 mL) was added tetrabutylammonium fluoride (1 M in THF, 0.86 mL, 0.86 mmol). The reaction mixture was stirred overnight, quenched with 1.5 M aqueous potassium phosphate, and extracted twice with EtOAc. The combined organic extracts were washed with brine, dried over Na₂SO₄, filtered, and concentrated in vacuo. The residue was purified by flash chromatography on SiO₂ (24 g, 0-100% EtOAc/hexanes over 7 minutes, then hold at 100% for 5 minutes, Isco 24 g SiO₂ column) to give 2-(5-cyclopropyl-3-(2,6-dichlorophenyl)isoxazol-4-yl)spiro[3.5]nonane-2,7-diol (0.16 g, 0.39 mmol, 91% yield) as a white foam. ¹H NMR (500 MHz, CDCl₃) δ 7.47-7.42 (m, 2H), 7.41-7.35 (m, 1H), 3.57 (br s, 1H), 2.27 (s, 1H), 2.22-2.09 (m, 3H), 2.04-1.92 (m, 3H), 1.80-1.63 (m, 2H), 1.52-1.50 (m, 1H), 1.48-1.36 (m, 1H), 1.36-1.23 (m, 6H), 1.18-1.08 (m, 3H).

Step 4. Methyl 2-(2-(5-cyclopropyl-3-(2,6-dichlorophenyl)isoxazol-4-yl)-2-hydroxyspiro[3,5]nonan-7-yloxy)-4-fluorobenzo[d]thiazole-6-carboxlate

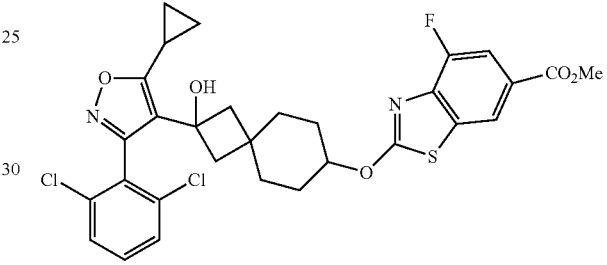

A solution of 2-(5-cyclopropyl-3-(2,6-dichlorophenyl)isoxazol-4-yl) spiro[3.5]nonane-2,7-diol (33 mg, 0.081 mmol) in anhydrous THF (1 mL) at room temperature was added KOtBu (19.0 mg, 0.17 mmol). After 5 minutes, methyl 2-bromo-4-fluorobenzo[d]thiazole-6-carboxylate (28.1 mg, 0.097 mmol) was added and the reaction mixture was stirred at room temperature for 5 minutes. The reaction was quenched with saturated aqueous NH₄Cl, and the resulting mixture was extracted three times with EtOAc. The combined organic extracts were washed with brine, dried over Na₂SO₄, filtered and concentrated in vacuo. The residue was purified by flash chromatography on SiO₂ (0-50% EtOAc/hexanes, Isco 12 g column) to give methyl 2-((2-(5-cyclopropyl-3-(2,6-dichlorophenyl)isoxazol-4-yl)-2-hydroxyspiro[3.5]nonan-7-yl)oxy)-4-fluorobenzo[d]thiazole-6-carboxylate (33 mg, 0.053 mmol, 66% yield) as a white foam. MS (ESI) m/z: 617.2 [M+H]⁺.

Example 205. 2-((2-(5-Cyclopropyl-3-(2,6-dichlorophenyl)isoxazol-4-yl)-2-hydroxyspiro[3,5]nonan-7-yl)oxy)-4-fluorobenzo[d]thiazole-6-carboxylic acid To a mixture of methyl 2-((2-(5-cyclopropyl-3-(2,6-dichlorophenyl)isoxazol-4-yl)-2-hydroxyspiro[3.5]nonan-7-yl)oxy)-4-fluorobenzo[d]thiazole-6-carboxylate (33 mg, 0.053 mmol) was added MeOH (0.1 mL), water (0.40 mL) and THF (0.50 mL), followed by lithium hydroxide monohydrate (9.1 mg, 0.22 mmol). The reaction mixture was stirred at 70° C. for 30 min and concentrated in vacuo to remove THF and MeOH. The reaction mixture was neutralized with 1 N aq. HCl to ~pH 4 and the resulting suspension was extracted with three times with EtOAc. The combined EtOAc extracts were concentrated in vacuo and the crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-100% B) over 19 minutes, then a 5-minute hold at 100% B). The desired fractions were combined and concentrated to give 2-((2-(5-cyclopropyl-3-(2,6-dichlorophenyl)isoxazol-4-yl)-2-hydroxyspiro[3,5]nonan-7-yl)oxy)-4-fluorobenzo[d]thiazole-6-carboxylic acid (5 mg, 8.2 μmol, 15% yield) as an off-white solid. MS (ESI) m/z: 603.2 [M+H]+; 1H NMR (500 MHz, DMSO-d6) δ 8.31 (br s, 1H), 7.72-7.65 (m, 1H), 7.64-7.58 (m, 2H), 7.58-7.51 (m, 1H), 5.18-5.02 (m, 1H), 3.60-3.42 (m, 1H), 2.38-2.30 (m, 1H), 2.17-2.06 (m, 2H), 2.00-1.85 (m, 3H), 1.85-1.75 (m, 1H), 1.65-1.51 (m, 2H), 1.50-1.40 (m, 1H), 1.40-1.32 (m, 1H), 1.31-1.17 (m, 2H), 1.17-1.02 (m, 4H); GAL-FXR EC$_{50}$=2618 nM.

Example 206

3-(((2-(5-Cyclopropyl-3-(2,6-dichlorophenyl)isoxazol-4-yl)-2-hydroxyspiro[3.5]nonan-7-yl)oxy)methyl)benzoic acid

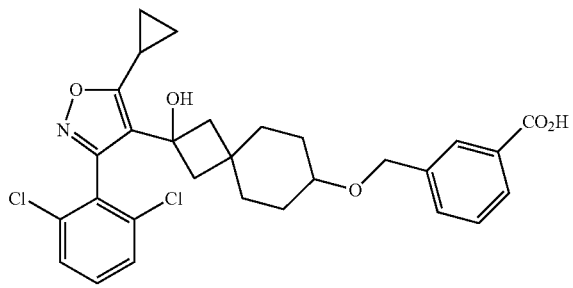

(206)

The title compound was prepared as described in General Method H for the preparation of Example 205 with replacement of methyl 2-bromo-4-fluorobenzo[d]thiazole-6-carboxylate with methyl 3-(bromomethyl)benzoate. MS (ESI) m/z: 542.2 [M+H]+; 1H NMR (500 MHz, DMSO-d6) δ 7.90-7.78 (m, 2H), 7.65-7.59 (m, 2H), 7.58-7.52 (m, 1H), 7.50 (br d, J=7.3 Hz, 1H), 7.46-7.40 (m, 1H), 5.26 (s, 1H), 4.49 (s, 2H), 3.20-3.10 (m, 1H), 2.39-2.29 (m, 1H), 2.12-2.01 (m, 2H), 1.95-1.82 (m, 3H), 1.73-1.55 (m, 2H), 1.41-1.17 (m, 4H), 1.16-1.03 (m, 5H); GAL-FXR EC$_{50}$=4711 nM.

General Method I

Example 207

3-((2-(5-Cyclopropyl-3-(2,6-dichlorophenyl)isoxazol-4-yl)-2-hydroxyspiro[3.5]nonan-7-yl)oxy)benzoic acid Step 1. Methyl 3-((2-(5-cyclopropyl-3-(2,6-dichlorophenyl)isoxazol-4-yl)-2-hydroxyspiro[3.5]nonan-7-yl)oxy)benzoate

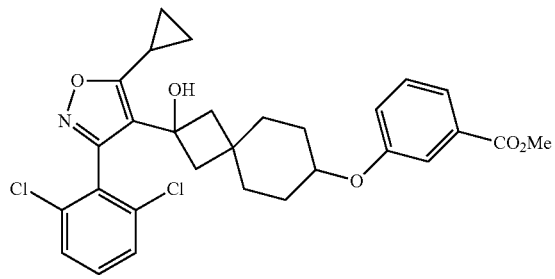 [SMILES: COC(=O)c1cccc(OC2CCC3(CC2)CC(O)(c2c(-c4c(Cl)cccc4Cl)noc2C2CC2)C3)c1]

2-(5-Cyclopropyl-3-(2,6-dichlorophenyl)isoxazol-4-yl)spiro[3.5]nonane-2,7-diol (30 mg, 0.073 mmol, synthesis described in General Method H), methyl 3-hydroxybenzoate (12.3 mg, 0.081 mmol), Bu$_3$P (0.029 mL, 0.12 mmol) and 1,1'-(azodicarbonyl)dipiperidine (29.7 mg, 0.12 mmol) were dissolved in dry dioxane (0.3 mL) in a sealed vial. The reaction mixture was heated with stirring at 110° C. for two hours. After cooling to room temperature, the mixture was diluted with water and extracted three times with EtOAc. The combined organic extracts were washed with brine, dried over Na$_2$SO$_4$, filtered and concentrated in vacuo. The residue was purified by flash chromatography on SiO$_2$ (0-50% EtOAc/hexanes, Isco 12 g column) to give methyl 3-((2-(5-cyclopropyl-3-(2,6-dichlorophenyl)isoxazol-4-yl)-2-hydroxyspiro[3.5]nonan-7-yl)oxy)benzoate (10 mg, 0.018 mmol, 25% yield) as a white foam. MS (ESI) m/z: 542.2 [M+H]+.

Example 207. 3-((2-(5-Cyclopropyl-3-(2,6-dichlorophenyl)isoxazol-4-yl)-2-hydroxyspiro[3.5]nonan-7-yl)oxy)benzoic acid The hydrolysis of methyl 3-((2-(5-cyclopropyl-3-(2,6-dichlorophenyl)isoxazol-4-yl)-2-hydroxyspiro[3.5]nonan-7-yl)oxy)benzoate was accomplished as described in General Method H for the preparation of Example 206. MS (ESI) m/z: 528.1 [M+H]+; 1H NMR (500 MHz, DMSO-d6) δ 7.64-7.58 (m, 2H), 7.57-7.51 (m, 1H), 7.46 (br d, J=7.9 Hz, 1H), 7.39-7.32 (m, 2H), 7.12 (br d, J=6.4 Hz, 1H), 5.35 (s, 1H), 4.35-4.21 (m, 1H), 2.42-2.27 (m, 1H), 2.16-2.02 (m, 2H), 1.96-1.83 (m, 3H), 1.79-1.68 (m, 1H), 1.68-1.59 (m, 1H), 1.54-1.43 (m, 1H), 1.41-1.30 (m, 2H), 1.30-1.20 (m, 2H), 1.15-1.02 (m, 4H); FXR EC$_{50}$=4473 nM.

4-((2-(5-Cyclopropyl-3-(2,6-dichlorophenyl)isoxazol-4-yl)-2-hydroxyspiro[3.5]nonan-7-yl)oxy)benzoic acid

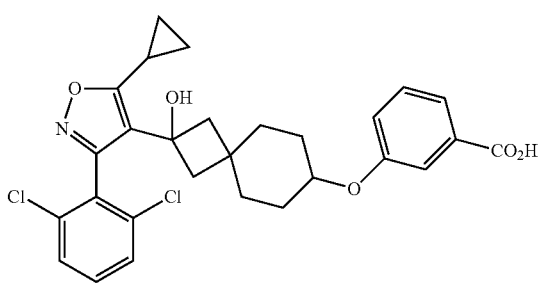

(207)

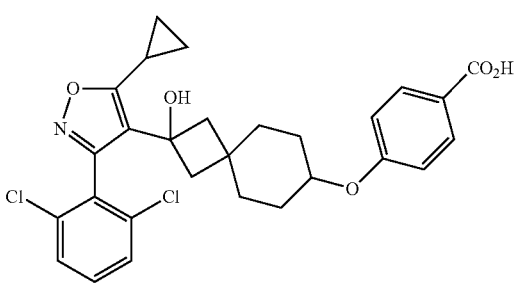

(208)

The title compound was prepared as described in General Method I for the preparation of Example 207 with replacement of methyl 3-hydroxybenzoate with ethyl 4-hydroxybenzoate. MS (ESI) m/z: 528.1 [M+H]+; 1H NMR (500 MHz, DMSO-$d_6$) δ 7.82 (br d, J=8.5 Hz, 2H), 7.63-7.60 (m, 2H), 7.58-7.52 (m, 1H), 6.92 (br d, J=8.5 Hz, 2H), 5.33 (s, 1H), 4.32-4.21 (m, 1H), 2.39-2.30 (m, 1H), 2.16-2.04 (m, 2H), 1.97-1.84 (m, 3H), 1.80-1.60 (m, 2H), 1.55-1.44 (m, 1H), 1.43-1.31 (m, 2H), 1.30-1.18 (m, 2H), 1.15-1.03 (m, 4H); GAL-FXR $EC_{50}$=6660 nM.

Example 209

2-((2-(5-Cyclopropyl-3-(2,6-dichlorophenyl)isoxazol-4-yl)spiro[3.5]non-1-en-7-yl)oxy)-4-fluorobenzo[d]thiazole-6-carboxylic acid

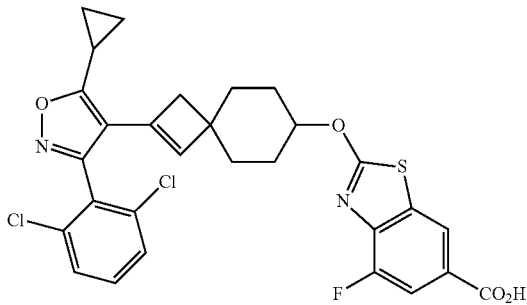

(209)

Step 1. 2-(5-Cyclopropyl-3-(2,6-dichlorophenyl)isoxazol-4-yl)-8,11-dioxadispiro[3.2.4$^7$.2$^4$]tridecan-2-ol

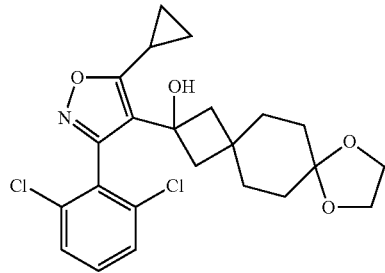 [SMILES: OC1(c2c(-c3c(Cl)cccc3Cl)noc2C2CC2)CC2(CCC3(CC2)OCCO3)C1]

n-Butyllithium (2.5 M in hexanes, 1.2 mL, 3.0 mmol) was added slowly to a −78° C. solution of 4-bromo-5-cyclopropyl-3-(2,6-dichlorophenyl)isoxazole (0.80 g, 2.4 mmol, synthesis described in General Method A) in THF (9.6 mL). After 10 minutes, 8,11-dioxadispiro[3.2.4$^7$.2$^4$]tridecan-2-one (0.47 mg, 2.4 mmol) was added as a solution in ~0.5 mL of THF. After 30 minutes the reaction was quenched by the slow addition of approximately 5 mL of MeOH and then concentrated in vacuo to dryness. The resulting residue was purified by flash chromatography on $SiO_2$ (0-60% EtOAc/hexanes, Isco 40 g column) to give 2-(5-cyclopropyl-3-(2,6-dichlorophenyl)isoxazol-4-yl)-8,11-dioxadispiro[3.2.4$^7$.2$^4$]tridecan-2-ol (0.76 g, 1.69 mmol, 70% yield) as a white foam.

Step 2. 2-(5-Cyclopropyl-3-(2,6-dichlorophenyl)isoxazol-4-yl)-2-hydroxyspiro[3.5]nonan-7-one

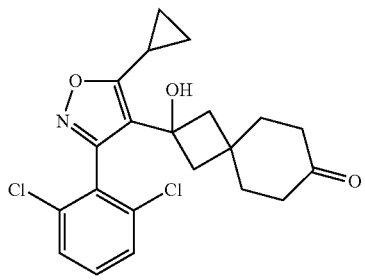 [SMILES: O=C1CCC2(CC1)CC(O)(c1c(-c3c(Cl)cccc3Cl)noc1C1CC1)C2]

To a mixture of 2-(5-cyclopropyl-3-(2,6-dichlorophenyl)isoxazol-4-yl)-8,11-dioxadispiro[3.2.4$^7$.2$^4$]tridecan-2-ol (0.40 g, 0.89 mmol) in MeOH (4 mL) and water (4 mL) at room temperature was added p-toluenesulfonic acid monohydrate (84 mg, 0.44 mmol). The reaction mixture was stirred at room temperature for 16 h and additional p-toluenesulfonic acid monohydrate (84 mg, 0.44 mmol) was added. After one hour, the reaction was quenched with 1M $K_2HPO_4$ (20 mL), and extracted twice with EtOAc. The combined organic extracts were washed with brine, dried over $Na_2SO_4$, filtered and concentrated in vacuo. The residue was purified by flash chromatography on $SiO_2$ (0-100% EtOAc/hex, Isco 24 g column) to give 2-(5-cyclopropyl-3-(2,6-dichlorophenyl) isoxazol-4-yl)-2-hydroxyspiro[3.5]nonan-7-one (0.32 g, 0.79 mmol, 89% yield) as an off-white foam. 1H NMR (400 MHz, $CDCl_3$) δ 7.48-7.43 (m, 2H), 7.41-7.35 (m, 1H), 2.36-2.33 (m, 1H), 2.33-2.30 (m, 1H), 2.30-2.22 (m, 2H), 2.21-2.12 (m, 5H), 2.10-2.02 (m, 2H), 1.75 (t, J=6.6 Hz, 2H), 1.33-1.24 (m, 3H), 1.19-1.10 (m, 2H).

Step 3. 2-(5-Cyclopropyl-3-(2,6-dichlorophenyl)isoxazol-4-yl)spiro[3.5]non-1-en-7-one

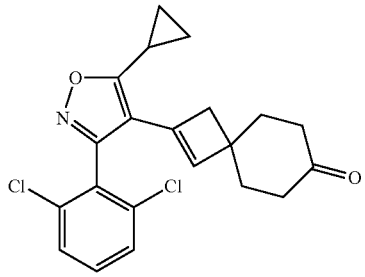 [SMILES: O=C1CCC2(C=C(c3c(-c4c(Cl)cccc4Cl)noc3C3CC3)C2)CC1]

To a reaction flask containing 2-(5-cyclopropyl-3-(2,6-dichlorophenyl)isoxazol-4-yl)-2-hydroxyspiro[3.5]nonan-7-one (0.37 g, 0.91 mmol) was added TFA (1 mL, 13.0 mmol). The reaction mixture was stirred at room temperature for 30 minutes and concentrated in vacuo. The residue was diluted with EtOAc, washed with 1M $K_2HPO_4$, brine, dried over $Na_2SO_4$, filtered, and concentrated in vacuo. The residue was purified by flash chromatography on $SiO_2$ (0-30% EtOAc/hexanes, Isco 24 g cartridge) to give 2-(5-cyclopropyl-3-(2,6-dichlorophenyl)isoxazol-4-yl)spiro[3.5]non-1-en-7-one (0.28 g, 0.73 mmol, 80% yield) as a white foam. 1H NMR (400 MHz, $CDCl_3$) δ 7.45-7.40 (m, 2H), 7.39-7.33 (m, 1H), 5.82 (s, 1H), 2.47 (s, 2H), 2.39-2.28 (m, 4H), 2.18 (tt, J=8.4, 5.0 Hz, 1H), 1.99-1.82 (m, 4H), 1.34-1.28 (m, 2H), 1.21-1.12 (m, 2H).

Step 4. 2-(5-Cyclopropyl-3-(2,6-dichlorophenyl)isoxazol-4-yl)spiro[3.5]non-1-en-7-ol

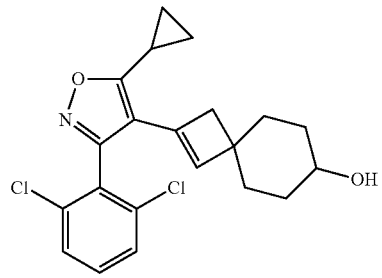 [SMILES: OC1CCC2(C=C(c3c(-c4c(Cl)cccc4Cl)noc3C3CC3)C2)CC1]

To a solution of 2-(5-cyclopropyl-3-(2,6-dichlorophenyl)isoxazol-4-yl) spiro[3.5]non-1-en-7-one (165 mg, 0.42 mmol) in MeOH (2.1 mL) at 0° C. was added NaBH$_4$ (17.7 mg, 0.47 mmol) in several portions. The reaction mixture was stirred at 0° C. for 30 min and concentrated in vacuo. The residue was diluted with EtOAc, washed with H$_2$O and brine, dried over Na$_2$SO$_4$, filtered and concentrated in vacuo. The residue was purified by flash chromatography on SiO$_2$ (0-100% EtOAc/hexanes, Isco 12 g column) to give 2-(5-cyclopropyl-3-(2,6-dichlorophenyl)isoxazol-4-yl)spiro[3.5]non-1-en-7-ol (0.14 g, 0.36 mmol, 84% yield) as a white solid.

Example 209. 2-((2-(5-Cyclopropyl-3-(2,6-dichlorophenyl)isoxazol-4-yl)spiro[3.5]non-1-en-7-yl)oxy)-4-fluorobenzo[d]thiazole-6-carboxylic acid The title compound was prepared as described in General Method H for the preparation of Example 205 with replacement of 2-(5-cyclopropyl-3-(2,6-dichlorophenyl)isoxazol-4-yl)spiro[3.5]nonane-2,7-diol with 2-(5-cyclopropyl-3-(2,6-dichlorophenyl)isoxazol-4-yl)spiro[3.5]non-1-en-7-ol. MS (ESI) m/z: 585.1 [M+H]$^+$; NMR represents 1:1 mixture of isomers. $^1$H NMR (500 MHz, DMSO-d$_6$) δ 8.35 (s, 2H), 7.78-7.56 (m, 8H), 6.00 (s, 1H), 5.77 (s, 1H), 5.29-5.11 (m, 2H), 2.99 (s, 2H), 2.38-2.19 (m, 4H), 2.09-1.74 (m, 8H), 1.69-1.47 (m, 8H), 1.23-1.17 (m, 4H), 1.13-1.08 (m, 4H); FXR EC$_{50}$=1281 nM.

Example 210

6-((2-(5-Cyclopropyl-3-(2,6-dichlorophenyl)isoxazol-4-yl)spiro[3.5]non-1-en-7-yl)oxy)quinoline-2-carboxylic acid (210)

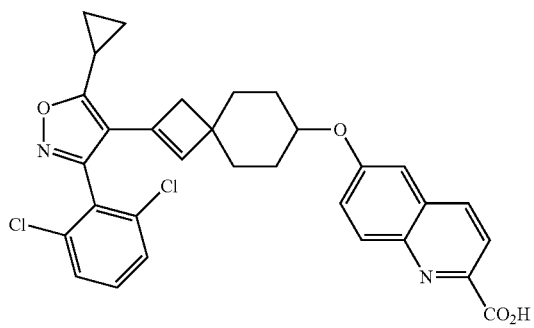

Step 1. Methyl 6-((2-(5-cyclopropyl-3-(2,6-dichlorophenyl)isoxazol-4-yl)spiro[3.5]non-1-en-7-yl)oxy)quinoline-2-carboxylate

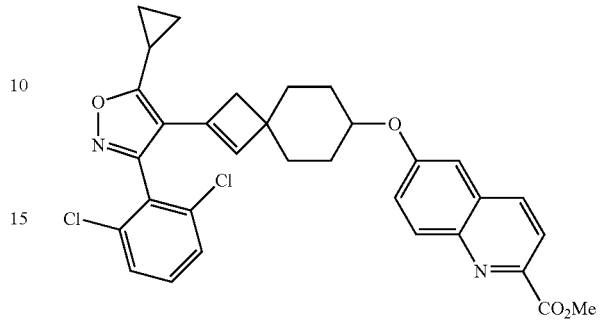

2-(5-Cyclopropyl-3-(2,6-dichlorophenyl)isoxazol-4-yl)spiro[3.5]non-1-en-7-ol) (32 mg 0.082 mmol), methyl 6-hydroxyquinoline-2-carboxylate (20 mg, 0.098 mmol), 1,1'-(azodicarbonyl)dipiperidine (33 mg, 0.13 mmol) and Bu$_3$P (32 µL, 0.13 mmol) were dissolved in dry dioxane (0.41 mL). The reaction mixture was stirred overnight at 100° C. in a sealed pressure vial. After cooling to room temperature, water was added, and the resulting mixture was extracted twice with EtOAc. The combined organic layers were washed with brine, dried over Na$_2$SO$_4$, filtered and concentrated in vacuo. The residue was purified by flash chromatography on SiO$_2$ (0-60% EtOAc/hexanes, 10 minute gradient, then hold at 60% for 5 minutes, Isco 12 g cartridge) to give methyl 6-((2-(5-cyclopropyl-3-(2,6-dichlorophenyl)isoxazol-4-yl)spiro[3.5]non-1-en-7-yl)oxy)quinoline-2-carboxylate (24 mg, 0.042 mmol, 51% yield, mixture of diastereomers) as a colorless oil.

Example 210. 6-((2-(5-Cyclopropyl-3-(2,6-dichlorophenyl)isoxazol-4-yl)spiro[3.5]non-1-en-7-yl)oxy)quinoline-2-carboxylic acid The title compound was prepared as described in General Method H for the preparation of Example 205 with replacement of methyl 2-((2-(5-cyclopropyl-3-(2,6-dichlorophenyl)isoxazol-4-yl)-2-hydroxyspiro[3.5]nonan-7-yl)oxy)-4-fluorobenzo[d]thiazole-6-carboxylate with methyl 6-((2-(5-cyclopropyl-3-(2,6-dichlorophenyl)isoxazol-4-yl)spiro[3.5]non-1-en-7-yl)oxy)quinoline-2-carboxylate. MS (ESI) m/z: 560.9 [M+H]$^+$; $^1$H NMR represents 1:1 mixture. $^1$H NMR (500 MHz, DMSO-d$_6$) δ 8.41-8.32 (m, 2H), 8.03 (d, J=8.5 Hz, 4H), 7.70-7.56 (m, 6H), 7.50-7.38 (m, 4H), 6.00 (s, 1H), 5.76 (s, 1H), 4.64-4.43 (m, 2H), 3.16 (s, 1H), 2.88 (s, 1H), 2.35-2.29 (m, 2H), 2.27 (s, 1H), 2.21 (s, 1H), 2.02-1.80 (m, 4H), 1.71-1.41 (m, 12H), 1.24-1.18 (m, 4H), 1.12-1.07 (m, 4H); FXR EC$_{50}$=485 nM.

Example 211

2-(2-(5-Cyclopropyl-3-(2,6-dichlorophenyl)isoxazol-4-yl)-1,4-dioxa-8-azaspiro[4.5]decan-8-yl)-4-fluorobenzo[d]thiazole-6-carboxylic acid

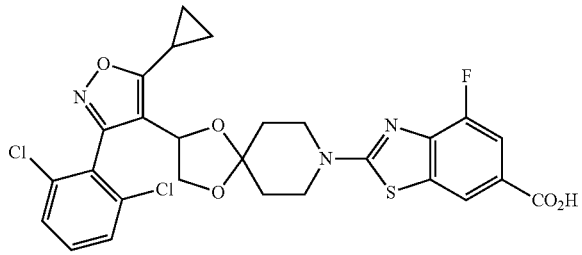
(211)

Step 1. 5-cyclopropyl-3-(2,6-dichlorophenyl)-4-vinylisoxazole

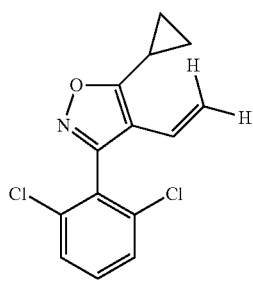 [SMILES: C=Cc1c(-c2c(Cl)cccc2Cl)noc1C1CC1]

To a solution of methyltriphenylphosphonium bromide (1.1 g, 3.2 mmol) in THF (7.5 mL) at 0° C. was added KOtBu (1M in THF, 3.8 mL, 3.8 mmol) dropwise over 10 minutes. The reaction mixture was stirred for 30 minutes followed by addition of 5-cyclopropyl-3-(2,6-dichlorophenyl)isoxazole-4-carbaldehyde (0.6 g, 2.1 mmol, synthesis described in General Method C). The reaction mixture was stirred at 0° C. for 30 minutes and directly purified by flash chromatography on SiO$_2$ (0-25% EtOAc/hexanes) to afford 5-cyclopropyl-3-(2,6-dichlorophenyl)-4-vinylisoxazole (0.59 g, 2.1 mmol, 99% yield) as a white crystalline solid. $^1$H NMR (500 MHz, CDCl$_3$) δ 7.45-7.40 (m, 2H), 7.40-7.32 (m, 1H), 6.39 (dd, J=17.9, 11.6 Hz, 1H), 5.11 (d, J=11.6 Hz, 1H), 5.07-4.98 (m, 1H), 2.21-2.04 (m, 1H), 1.32-1.24 (m, 2H), 1.15 (br dd, J=8.1, 2.3 Hz, 2H).

Step 2. 1-(5-cyclopropyl-3-(2,6-dichlorophenyl)isoxazol-4-yl)ethane-1,2-diol

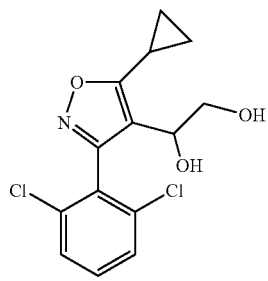 [SMILES: OCC(O)c1c(-c2c(Cl)cccc2Cl)noc1C1CC1]

To a 0° C. solution of 5-cyclopropyl-3-(2,6-dichlorophenyl)-4-vinylisoxazole (0.50 g, 1.8 mmol) in THF (5.3 mL) and water (5.3 mL) was added 4-methylmorpholine n-oxide (0.31 g, 2.7 mmol) and then osmium tetroxide (2.5% in tBuOH, 0.36 mL, 0.036 mmol). The reaction mixture was stirred at 0° C. for 2 hours and then allowed to warm to room temperature. After stirring overnight the reaction mixture was diluted with EtOAc, and washed with water. The organic was concentrated to a crude solid, which was then purified by flash chromatography on SiO$_2$ (0-75% EtOAc/hexanes) to afford 1-(5-cyclopropyl-3-(2,6-dichlorophenyl)isoxazol-4-yl)ethane-1,2-diol (0.49 g, 1.5 mmol, 87% yield) as an off-white crystalline solid. $^1$H NMR (500 MHz, CDCl$_3$) δ 7.40-7.45 (m, 2H), 7.33-7.39 (m, 1H), 4.49-4.68 (m, 1H), 3.71-3.78 (m, 1H), 3.61-3.69 (m, 1H), 2.42 (br d, J=1.93 Hz, 1H), 2.34 (ddd, J=3.58, 5.02, 8.46 Hz, 1H), 2.05 (s, 1H), 1.29-1.36 (m, 1H), 1.21-1.28 (m, 1H), 1.09-1.17 (m, 2H).

Step 3. Ethyl 4-fluoro-2-(4-oxopiperidin-1-yl)benzo[d]thiazole-6-carboxylate

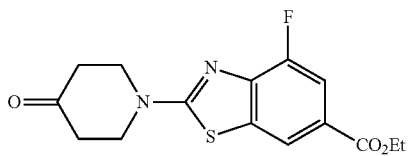 [SMILES: CCOC(=O)c1cc(F)c2nc(N3CCC(=O)CC3)sc2c1]

A mixture of piperidin-4-one (48.9 mg, 0.49 mmol), ethyl 2-bromo-4-fluorobenzo[d]thiazole-6-carboxylate (150 mg, 0.49 mmol) and Cs$_2$CO$_3$ (402 mg, 1.2 mmol) in DMF (1.5 mL) was heated at 60° C. for 1 hour. The reaction mixture was diluted with EtOAc and washed with water. The organic layer was concentrated in vacuo and the residue was purified by flash chromatography on SiO$_2$ (0-60% EtOAc/hexanes) to afford ethyl 4-fluoro-2-(4-oxopiperidin-1-yl)benzo[d]thiazole-6-carboxylate (41 mg, 0.13 mmol, 26% yield) as a tan solid. $^1$H NMR (500 MHz, CDCl$_3$) δ 8.14 (d, J=0.8 Hz, 1H), 7.80-7.68 (m, 1H), 4.46-4.32 (m, 2H), 4.09-3.94 (m, 4H), 2.67 (t, J=6.3 Hz, 4H), 1.47-1.34 (m, 3H).

Step 4. Ethyl 2-(2-(5-cyclopropyl-3-(2,6-dichlorophenyl)isoxazol-4-yl)-1,4-dioxa-8-azaspiro[4.5]decan-8-yl)-4-fluorobenzo[d]thiazole-6-carboxylate

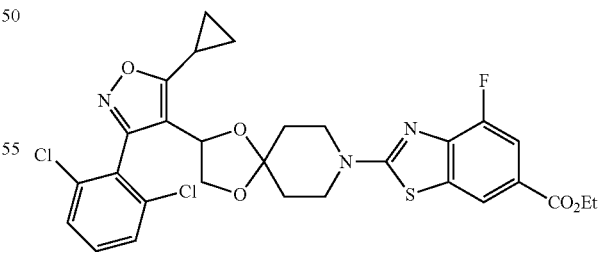

To a mixture of 1-(5-cyclopropyl-3-(2,6-dichlorophenyl)isoxazol-4-yl)ethane-1,2-diol (20.0 mg, 0.064 mmol, from step 2) and ethyl 4-fluoro-2-(4-oxopiperidin-1-yl)benzo[d]thiazole-6-carboxylate (20.5 mg, 0.064 mmol, from step 3) in DCE (0.5 mL) was added p-toluenesulfonic acid monohydrate (24.2 mg, 0.13 mmol). The reaction mixture was stirred at room temperature overnight. The reaction mixture was directly purified by flash chromatography on SiO₂ (0-30% EtOAc/hex) to afford ethyl 2-(2-(5-cyclopropyl-3-(2,6-dichlorophenyl)isoxazol-4-yl)-1,4-dioxa-8-azaspiro[4.5]decan-8-yl)-4-fluorobenzo[d]thiazole-6-carboxylate (19.0 mg, 0.031 mmol, 48% yield) as a tan solid. ¹H NMR (500 MHz, CDCl₃) δ 8.11-8.07 (m, 1H), 7.72 (dd, J=11.3, 1.4 Hz, 1H), 7.47-7.41 (m, 2H), 7.40 (d, J=8.0 Hz, 1H), 5.31 (s, 1H), 5.09-5.03 (m, 1H), 4.41-4.34 (m, 2H), 4.16 (dd, J=8.3, 6.1 Hz, 1H), 3.86-3.67 (m, 4H), 3.60-3.52 (m, 1H), 2.21-2.15 (m, 1H), 1.87-1.81 (m, 2H), 1.44-1.37 (m, 3H), 1.30 (br dd, J=5.0, 2.2 Hz, 3H), 1.20-1.13 (m, 2H).

Example 211. 2-(2-(5-Cyclopropyl-3-(2,6-dichlorophenyl)isoxazol-4-yl)-1,4-dioxa-8-azaspiro[4.5]decan-8-yl)-4-fluorobenzo[d]thiazole-6-carboxylic acid The hydrolysis of ethyl 2-(2-(5-cyclopropyl-3-(2,6-dichlorophenyl)isoxazol-4-yl)-1,4-dioxa-8-azaspiro[4.5]decan-8-yl)-4-fluorobenzo[d]thiazole-6-carboxylate to give the title compound was accomplished as described in General Method C for the preparation of Example 39. MS (ESI) m/z: 590.2 [M+H]⁺; ¹H NMR (500 MHz, DMSO-d₆) δ 8.12-8.21 (m, 1H), 7.64-7.68 (m, 2H), 7.56-7.62 (m, 2H), 5.23 (br t, J=7.36 Hz, 1H), 4.24 (t, J=7.15 Hz, 1H), 3.51 (br d, J=9.51 Hz, 1H), 3.21-3.40 (m, 1H), 2.55 (s, 2H), 2.34-2.40 (m, 1H), 1.68-1.83 (m, 2H), 1.37 (br s, 1H), 1.17 (br d, J=8.25 Hz, 2H), 1.09 (br s, 2H), 0.93-1.07 (m, 2H); FXR EC₅₀=1360 nM.

Example 212

6-(2-(5-Cyclopropyl-3-(dicyclopropylmethyl)isoxazol-4-yl)-7-azaspiro[3.5]non-1-en-7-yl)-4-(trifluoromethyl)quinoline-2-carboxylic acid

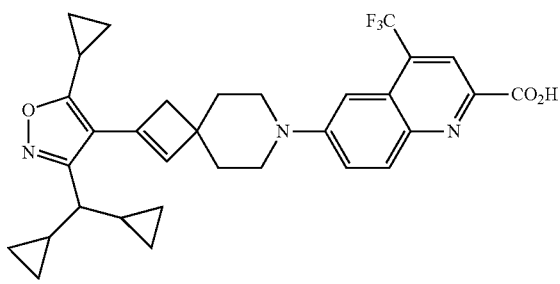

(212)

The title compound was prepared as described for the preparation of Example 82 with replacement of 2,6-difluorobenzaldehyde with 2,2-dicyclopropylacetaldehyde. MS (ESI) m/z: 564.3 [M+H]⁺; ¹H NMR (500 MHz, DMSO-d₆) δ 8.14 (s, 1H), 8.03 (br d, J=9.5 Hz, 1H), 7.83 (br d, J=9.5 Hz, 1H), 7.04 (br s, 1H), 6.37 (s, 1H), 3.60 (br s, 2H), 2.63 (s, 2H), 2.49-2.46 (m, 2H), 2.14 (br s, 1H), 1.82 (br t, J=8.7 Hz, 1H), 1.70 (br s, 4H), 1.15 (br s, 2H), 1.10 (br d, J=7.9 Hz, 2H), 1.01 (br d, J=7.9 Hz, 2H), 0.93 (br s, 2H), 0.43 (br d, J=3.7 Hz, 2H), 0.32-0.24 (m, 2H), 0.21 (br dd, J=9.0, 4.4 Hz, 2H); FXR EC₅₀=1546 nM.

Example 213

2-(2-(4-(Difluoromethyl)-1-(2-(trifluoromethyl)phenyl)-1H-pyrazol-5-yl)-7-azaspiro[3.5]non-1-en-7-yl)-4-fluorobenzo[d]thiazole-6-carboxylic acid

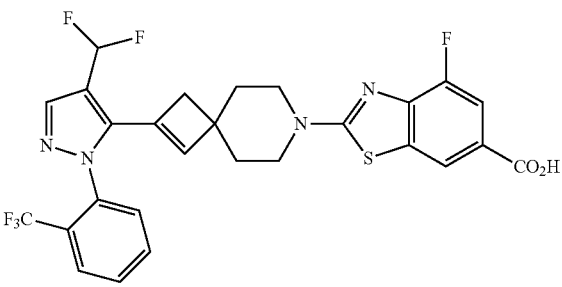

(213)

Step 1. Ethyl 5-amino-1-(2-(trifluoromethyl)phenyl)-1H-pyrazole-4-carboxylate

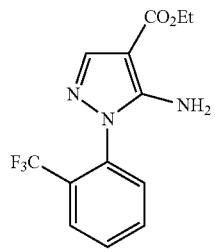

A solution of ethyl (E)-2-cyano-3-ethoxyacrylate (1.6 g, 9.4 mmol) and (2-(trifluoromethyl)phenyl)hydrazine (1.5 g, 8.5 mmol) in ethanol (8.52 mL) was heated to 85° C. in a sealed tube. Heating was continued overnight, the reaction mixture was concentrated to minimal volume and the residue was purified by flash chromatography on SiO₂ (0-100% EtOAc/hex, Isco 40 g column) to give ethyl 5-amino-1-(2-(trifluoromethyl)phenyl)-1H-pyrazole-4-carboxylate (2.6 g, 8.5 mmol, 100% yield as a brown solid. ¹H NMR (400 MHz, CDCl₃) δ 7.89 (dd, J=7.6, 1.2 Hz, 1H), 7.82 (s, 1H), 7.78-7.71 (m, 1H), 7.71-7.64 (m, 1H), 7.48 (d, J=7.7 Hz, 1H), 5.00 (br s, 2H), 4.32 (q, J=7.3 Hz, 2H), 1.38 (t, J=7.2 Hz, 3H). ¹⁹F NMR (377 MHz, CDCl₃) δ -60.60 (s).

Step 2. Ethyl 5-bromo-1-(2-(trifluoromethyl)phenyl)-1H-pyrazole-4-carboxylate

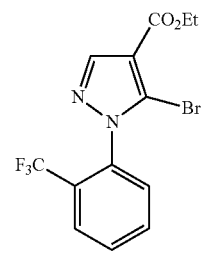

tert-Butyl nitrite (0.14 mL, 1.0 mmol) was added slowly to a room temperature suspension of copper(II) bromide (0.20 g, 0.92 mmol) and ethyl 5-amino-1-(2-(trifluoromethyl)phenyl)-1H-pyrazole-4-carboxylate (0.25 g, 0.84 mmol) in acetonitrile (8.4 mL). After 1 h, the reaction was quenched with saturated aqueous NaHCO$_3$. The mixture was taken up in EtOAc and washed with water and brine. The combined aqueous layers were back extracted with EtOAc and the combined organics were dried over Na$_2$SO$_4$, filtered and concentrated to dryness in vacuo. The residue was purified by flash chromatography on SiO$_2$ (0-50% EtOAc/hex, Isco 12 g column) to give ethyl 5-bromo-1-(2-(trifluoromethyl)phenyl)-1H-pyrazole-4-carboxylate (0.19 g, 0.52 mmol, 62% yield) as a white solid. $^1$H NMR (400 MHz, CDCl$_3$) δ 8.17 (s, 1H), 7.92-7.86 (m, 1H), 7.80-7.69 (m, 2H), 7.43 (dd, J=7.4, 1.4 Hz, 1H), 4.40 (q, J=7.3 Hz, 2H), 1.42 (t, J=7.2 Hz, 3H). $^{19}$F NMR (377 MHz, CDCl$_3$) δ −60.52 (s).

Step 3. tert-Butyl 2-(4-(ethoxycarbonyl)-1-(2-(trifluoromethyl)phenyl)-1H-pyrazol-5-yl)-7-azaspiro [3.5]non-1-ene-7-carboxylate

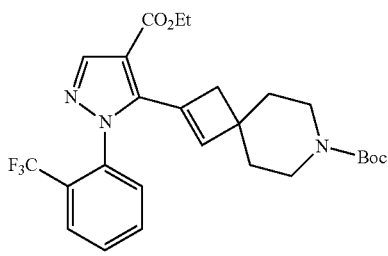 [SMILES: CCOC(=O)c1cnn(-c2ccccc2C(F)(F)F)c1C1=CC2(CCN(C(=O)OC(C)(C)C)CC2)C1]

Tri-o-tolylphosphine (15.8 mg, 0.05 mmol), tert-butyl 2-(4,4,5,5-tetramethyl-1,3,2-dioxaborolan-2-yl)-7-azaspiro [3.5]non-1-ene-7-carboxylate (0.20 g, 0.57 mmol), ethyl 5-bromo-1-(2-(trifluoromethyl)phenyl)-1H-pyrazole-4-carboxylate (0.19 g, 0.52 mmol) and 2.0 M aqueous potassium phosphate (0.85 mL, 1.7 mmol) were dissolved in dioxane (3.3 mL) and the mixture was degassed by bubbling nitrogen through for 20 minutes. PdOAc$_2$ (5.8 mg, 0.03 mmol) was added and nitrogen was bubbled through the resulting mixture for 10 minutes. The reaction vessel was sealed and heated to 80° C. After 3 h the reaction mixture was diluted with EtOAc and washed with water and brine. The combined aqueous layers were back extracted with EtOAc. The organic layers were dried over Na$_2$SO$_4$, filtered and concentrated to dryness in vacuo. The residue was purified by flash chromatography on SiO$_2$ (0-80% EtOAc/hex, Isco 12 g column) to give tert-butyl 2-(4-(ethoxycarbonyl)-1-(2-(trifluoromethyl)phenyl)-1H-pyrazol-5-yl)-7-azaspiro[3.5] non-1-ene-7-carboxylate (0.24 g, 0.48 mmol, 92% yield) as a sticky solid. $^1$H NMR (400 MHz, CDCl$_3$) δ 8.07 (s, 1H), 7.88-7.81 (m, 1H), 7.75-7.65 (m, 2H), 7.47-7.39 (m, 1H), 6.39 (br s, 1H), 4.34 (q, J=7.0 Hz, 2H), 3.47 (dt, J=13.2, 5.1 Hz, 2H), 3.20-3.09 (m, 2H), 2.18 (br s, 2H), 1.55-1.44 (m, 4H), 1.43 (s, 9H), 1.40 (t, J=7.0 Hz, 3H). $^{19}$F NMR (377 MHz, CDCl$_3$) δ −60.51 (s, 1F).

Step 4. tert-Butyl 2-(4-(hydroxymethyl)-1-(2-(trifluoromethyl)phenyl)-1H-pyrazol-5-yl)-7-azaspiro [3.5]non-1-ene-7-carboxylate

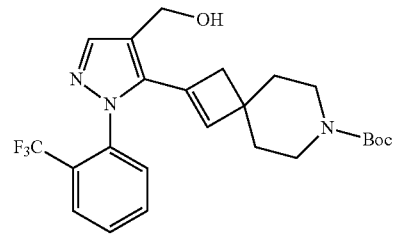 [SMILES: CC(C)(C)OC(=O)N1CCC2(C=C(c3c(CO)cnn3-c3ccccc3C(F)(F)F)C2)CC1]

Lithium aluminum hydride (2.5 mL, 2.5 mmol, 1M solution in THF) was added dropwise to a −50° C. solution of tert-butyl 2-(4-(ethoxycarbonyl)-1-(2-(trifluoromethyl) phenyl)-1H-pyrazol-5-yl)-7-azaspiro[3.5]non-1-ene-7-carboxylate (1.1 g, 2.1 mmol) in THF (8.3 mL). The mixture was warmed to −10° C. for 35 minutes and then brought to 0° C. for 40 minutes. The reaction was quenched at 0° C. with sequential additions of 0.1 mL of water, 0.1 mL of 15% aqueous NaOH and 0.3 mL of water. The mixture was stirred at 0° C. for 10 minutes and at room temperature for 30 minutes. The layers were separated and the organic layer was washed with water and brine. The aqueous layers were back extracted with EtOAc and the combined organics were dried over Na$_2$SO$_4$, filtered and concentrated to dryness in vacuo. The residue was purified by flash chromatography on SiO$_2$ (0-100% EtOAc/hex, Isco 24 g column) to give tert-butyl 2-(4-(hydroxymethyl)-1-(2-(trifluoromethyl)phenyl)-1H-pyrazol-5-yl)-7-azaspiro[3.5]non-1-ene-7-carboxylate (0.78 g, 1.7 mmol, 81% yield) as an off-white foam. $^1$H NMR (400 MHz, CDCl$_3$) δ 7.88-7.83 (m, 1H), 7.81 (s, 1H), 7.75-7.64 (m, 2H), 7.44-7.38 (m, 1H), 4.64 (d, J=5.7 Hz, 2H), 1.59 (t, J=5.8 Hz, 1H). $^{19}$F NMR (377 MHz, CDCl$_3$) δ −60.46 (s).

Step 5. tert-Butyl 2-(4-formyl-1-(2-(trifluoromethyl) phenyl)-1H-pyrazol-5-yl)-7-azaspiro[3.5]non-1-ene-7-carboxylate

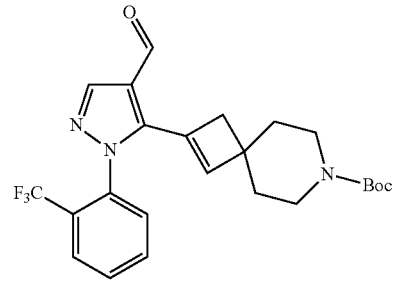 [SMILES: CC(C)(C)OC(=O)N1CCC2(C=C(c3c(C=O)cnn3-c3ccccc3C(F)(F)F)C2)CC1]

Triethylamine (97 μL, 0.69 mmol) followed by 1-propanephosphonic anhydride (0.41 mL, 0.69 mmol, 50% solution in EtOAc) were added to a 0° C. solution of tert-butyl 2-(4-(hydroxymethyl)-1-(2-(trifluoromethyl)phenyl)-1H-pyrazol-5-yl)-7-azaspiro[3.5]non-1-ene-7-carboxylate (0.11 g, 0.23 mmol) in dichloromethane (1.3 mL and DMSO (1.0 mL). After 20 minutes the reaction was quenched with brine and diluted with EtOAc. The aqueous layer was back extracted with EtOAc and the combined organics were dried over Na₂SO₄, filtered and concentrated to dryness in vacuo. The residue was purified by flash chromatography on SiO₂ (0-100% EtOAc/hex, Isco 12 g column) to give tert-butyl 2-(4-formyl-1-(2-(trifluoromethyl)phenyl)-1H-pyrazol-5-yl)-7-azaspiro[3.5]non-1-ene-7-carboxylate (0.085 g, 0.18 mmol, 80% yield) as a white foam. ¹H NMR (500 MHz, CDCl₃) δ 10.05 (s, 1H), 8.14 (s, 1H), 7.91-7.84 (m, 1H), 7.78-7.70 (m, 2H), 7.49-7.44 (m, 1H), 6.27 (br d, J=2.2 Hz, 1H), 3.56-3.43 (m, 2H), 3.16 (ddd, J=13.2, 8.9, 3.7 Hz, 2H), 2.22 (s, 2H), 1.44 (m, 13H).

Step 6. tert-Butyl 2-(4-(difluoromethyl)-1-(2-(trifluoromethyl)phenyl)-1H-pyrazol-5-yl)-7-azaspiro[3.5]non-1-ene-7-carboxylate

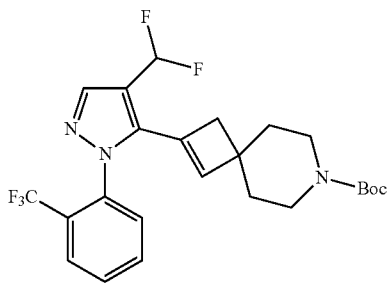 [SMILES: CC(C)(C)OC(=O)N1CCC2(C=C(c3c(C(F)F)cnn3-c3ccccc3C(F)(F)F)C2)CC1]

Diethylaminosulfur trifluoride (73.0 μL, 0.55 mmol) was added to a room temperature solution of tert-butyl 2-(4-formyl-1-(2-(trifluoromethyl)phenyl)-1H-pyrazol-5-yl)-7-azaspiro[3.5]non-1-ene-7-carboxylate (85 mg, 0.18 mmol) in dichloromethane (1.8 mL). After stirring over the weekend, the reaction mixture was purified directly by flash chromatography on SiO₂ (0-80% EtOAc/hex, Isco 12 g column) to give tert-butyl 2-(4-(difluoromethyl)-1-(2-(trifluoromethyl)phenyl)-1H-pyrazol-5-yl)-7-azaspiro[3.5]non-1-ene-7-carboxylate (66 mg, 0.14 mmol, 74% yield) as a white foam. ¹H NMR (400 MHz, CDCl₃) δ 7.91-7.83 (m, 2H), 7.78-7.68 (m, 2H), 7.51-7.45 (m, 1H), 6.98-6.61 (m, 1H), 5.80 (s, 1H), 3.61-3.45 (m, 2H), 3.16 (ddd, J=13.2, 8.7, 4.1 Hz, 2H), 2.21 (s, 2H), 1.55-1.48 (m, 4H), 1.46 (s, 9H).

Step 7. 2-(4-(Difluoromethyl)-1-(2-(trifluoromethyl)phenyl)-1H-pyrazol-5-yl)-7-azaspiro[3.5]non-1-ene

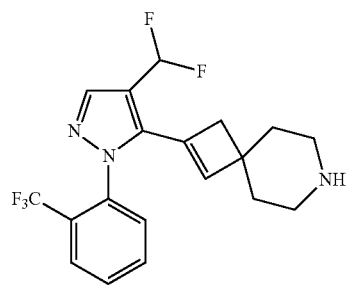 [SMILES: FC(F)c1cnn(-c2ccccc2C(F)(F)F)c1C1=CC2(CCNCC2)C1]

Trifluoroacetic acid (0.21 mL, 2.7 mmol) was added to a room temperature solution of tert-butyl 2-(4-(difluoromethyl)-1-(2-(trifluoromethyl)phenyl)-1H-pyrazol-5-yl)-7-azaspiro[3.5]non-1-ene-7-carboxylate (66 mg, 0.14 mmol) in dichloromethane (1.4 mL). After 2 hours the reaction mixture was concentrated to dryness to give 2-(4-(difluoromethyl)-1-(2-(trifluoromethyl)phenyl)-1H-pyrazol-5-yl)-7-azaspiro[3.5]non-1-ene, TFA. The product was used in subsequent steps without further purification or characterization.

Example 213. 2-(2-(4-(Difluoromethyl)-1-(2-(trifluoromethyl)phenyl)-1H-pyrazol-5-yl)-7-azaspiro[3.5]non-1-en-7-yl)-4-fluorobenzo[d]thiazole-6-carboxylic acid A slurry of 2-(4-(difluoromethyl)-1-(2-(trifluoromethyl)phenyl)-1H-pyrazol-5-yl)-7-azaspiro[3.5]non-1-ene, TFA (30 mg, 0.06 mmol, from step 7), ethyl 2-bromo-4-fluorobenzo[d]thiazole-6-carboxylate (19 mg, 0.06 mmol) and Cs₂CO₃ (59 mg, 0.18 mmol) in dioxane (0.3 mL) was heated to 80° C. in a sealed flask. After 1.5 h, the reaction mixture was cooled to room temperature and THF/H₂O/MeOH (10:4:1, 0.6 mL) and LiOH monohydrate (13 mg, 0.3 mmol) were added. The reaction mixture was sealed and heated to 80° C. for 2 h. The reaction was quenched by the addition of 0.5 mL of AcOH and concentrated to dryness in vacuo. The residue was dissolved in 2 mL of MeOH, filtered, and the crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 19% B, 19-59% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation to give 2-(2-(4-(difluoromethyl)-1-(2-(trifluoromethyl)phenyl)-1H-pyrazol-5-yl)-7-azaspiro[3.5]non-1-en-7-yl)-4-fluorobenzo[d]thiazole-6-carboxylic acid (23 mg, 0.04 mmol, 67% yield). MS (ESI) m/z: 579.3 [M+H]⁺; ¹H NMR (500 MHz, DMSO-d₆) δ 8.17 (s, 1H), 8.03-7.93 (m, 2H), 7.93-7.81 (m, 2H), 7.66 (d, J=7.6 Hz, 1H), 7.57 (d, J=11.6 Hz, 1H), 7.30-7.02 (m, 1H), 5.95 (s, 1H), 3.76-3.65 (m, 1H), 3.62-3.49 (m, 1H), 3.50-3.40 (m, 1H), 2.22 (br s, 2H), 1.69-1.48 (m, 4H) additional peaks missing due to water suppression; EC₅₀=48 nM.

Example 214

6-(2-(4-(Difluoromethyl)-1-(2-(trifluoromethyl)phenyl)-1H-pyrazol-5-yl)-7-azaspiro[3.5]non-1-en-7-yl)-4-(trifluoromethyl)quinoline-2-carboxylic acid

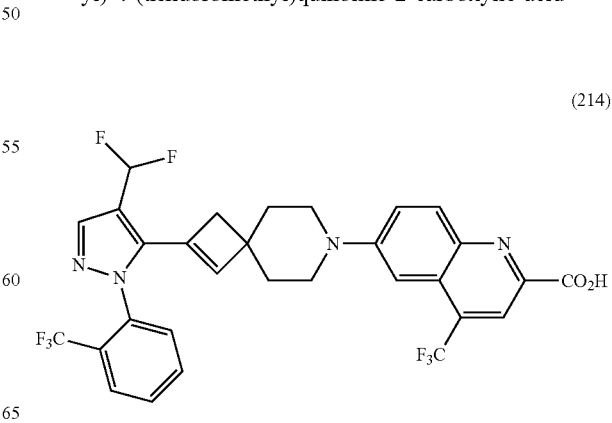

(214)

The title compound was prepared as described in General Method B for the preparation of Example 82 with replacement of 5-cyclopropyl-3-(2,6-difluorophenyl)-4-(7-azaspiro[3.5]non-1-en-2-yl)isoxazole with 2-(4-(difluoromethyl)-1-(2-(trifluoromethyl)phenyl)-1H-pyrazol-5-yl)-7-azaspiro[3.5]non-1-ene. MS (ESI) m/z: 623.3 [M+H]+; 1H NMR (500 MHz, DMSO-d6) δ 8.20 (s, 1H), 8.07 (d, J=9.4 Hz, 1H), 8.04-7.93 (m, 2H), 7.93-7.80 (m, 3H), 7.73-7.65 (m, 1H), 7.33-7.02 (m, 2H), 5.98-5.92 (m, 1H), 3.33-3.22 (m, 1H), 2.23 (br s, 2H), 1.72-1.62 (m, 2H), 1.60 (br s, 2H) additional peaks missing due to water suppression; $EC_{50}$=26 nM.

Example 215

2-(2-(4-(Difluoromethyl)-1-(2-(trifluoromethyl)phenyl)-1H-pyrazol-5-yl)-7-azaspiro[3.5]nonan-7-yl)-4-fluorobenzo[d]thiazole-6-carboxylic acid

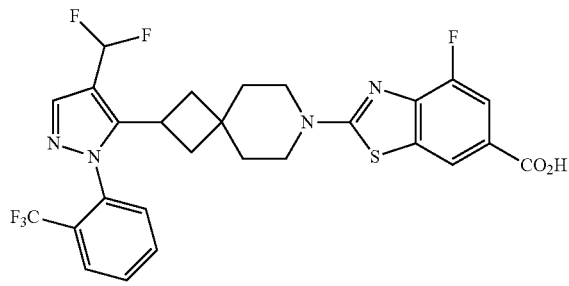

(215)

Step 1. 2-(4-(Difluoromethyl)-1-(2-(trifluoromethyl)phenyl)-1H-pyrazol-5-yl)-7-azaspiro[3.5]nonane

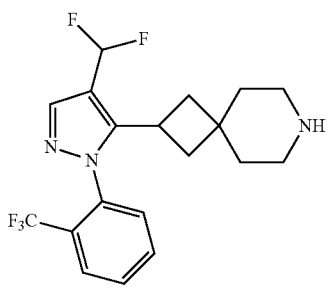 [SMILES: FC(F)c1cnn(-c2ccccc2C(F)(F)F)c1C1CC2(CCNCC2)C1]

A solution of tert-butyl 2-(4-(difluoromethyl)-1-(2-(trifluoromethyl)phenyl)-1H-pyrazol-5-yl)-7-azaspiro[3.5]non-1-ene-7-carboxylate (23.4 mg, 0.048 mmol) in MeOH (0.69 mL) was deoxygenated by bubbling nitrogen through the mixture for 5 minutes. To the mixture was added palladium on carbon (10% by wt., 25.8 mg, 0.024 mmol) and the reaction flask was sparged with hydrogen. A balloon of hydrogen was affixed and the mixture was stirred at room temperature. After 2 h the reaction mixture was filtered through celite (EtOAc wash) and concentrated in vacuo. The residue was dissolved in dichloromethane (0.47 mL) and trifluoroacetic acid (46.8 µL) was added to the solution. After 1 h the solvent was removed in vacuo and the resulting material was used directly in the next step.

Example 215. 2-(2-(4-(Difluoromethyl)-1-(2-(trifluoromethyl)phenyl)-1H-pyrazol-5-yl)-7-azaspiro[3.5]nonan-7-yl)-4-fluorobenzo[d]thiazole-6-carboxylic acid The title compound was prepared as described in General Method A for the preparation of Example 213 with replacement of 2-(4-(difluoromethyl)-1-(2-(trifluoromethyl)phenyl)-1H-pyrazol-5-yl)-7-azaspiro[3.5]non-1-ene with 2-(4-(difluoromethyl)-1-(2-(trifluoromethyl)phenyl)-1H-pyrazol-5-yl)-7-azaspiro[3.5]nonane. MS (ESI) m/z: 581.2 [M+H]+; 1H NMR (500 MHz, DMSO-d6) δ 8.16 (s, 1H), 8.01-7.91 (m, 1H), 7.90-7.84 (m, 2H), 7.83-7.77 (m, 1H), 7.62 (br d, J=7.9 Hz, 1H), 7.56 (br d, J=11.3 Hz, 1H), 7.33-7.06 (m, 1H), 2.88 (s, 1H), 2.72 (s, 1H), 2.11-2.02 (m, 1H), 1.97 (br t, J=10.4 Hz, 1H), 1.86 (br d, J=8.2 Hz, 2H), 1.63 (br d, J=1.5 Hz, 2H), 1.50 (br s, 2H) Additional peaks lost under water peak; $EC_{50}$=995 nM.

Example 216

2-(2-(1-(3,5-Dichloropyridin-4-yl)-4-(difluoromethyl)-1H-pyrazol-5-yl)-7-azaspiro[3.5]non-1-en-7-yl)-4-fluorobenzo[d]thiazole-6-carboxylic acid

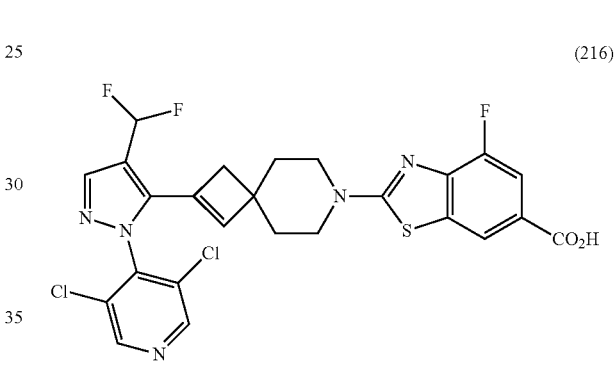

(216)

The title compound was prepared as described in General Method A for the preparation of Example 213 with replacement of (2-(trifluoromethyl)phenyl)hydrazine with 3,5-dichloro-4-hydrazineylpyridine. MS (ESI) m/z: 580.1 [M+H]+; 1H NMR (500 MHz, CDCl3) δ 8.74 (s, 2H), 8.15 (s, 1H), 7.97 (s, 1H), 7.76 (br d, J=11.0 Hz, 1H), 7.01-6.62 (m, 1H), 6.03 (s, 1H), 3.91-3.78 (m, 2H), 3.74 (s, 1H), 3.61-3.46 (m, 2H), 2.42 (s, 2H), 1.89-1.68 (m, 4H); $EC_{50}$=88 nM.

Example 217

2-(2-(4-(Difluoromethyl)-1-(2-(trifluoromethoxy)phenyl)-1H-pyrazol-5-yl)-7-azaspiro[3.5]non-1-en-7-yl)-4-fluorobenzo[d]thiazole-6-carboxylic acid

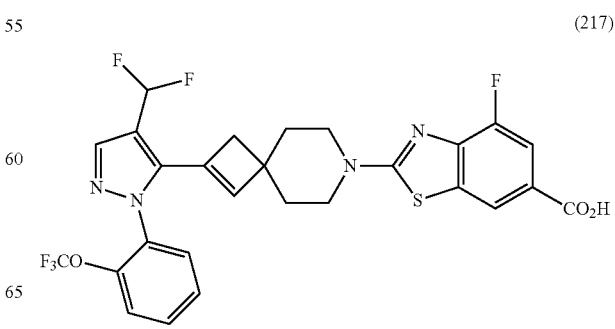

(217)

The title compound was prepared as described in General Method A for the preparation of Example 213 with replacement of (2-(trifluoromethyl)phenyl)hydrazine with (2-(trifluoromethoxy)phenyl)hydrazine. MS (ESI) m/z: 559.2 [M+H]⁺; ¹H NMR (500 MHz, DMSO-d₆) δ 8.16 (s, 1H), 7.98 (s, 1H), 7.74 (t, J=7.8 Hz, 1H), 7.69 (d, J=7.6 Hz, 1H), 7.66-7.54 (m, 3H), 7.15 (t, J=55.0 Hz, 1H), 6.06 (s, 1H), 3.67-3.44 (m, 4H), 2.31 (s, 2H), 1.63 (dt, J=4.9, 17.0 Hz, 4H); EC₅₀=230 nM.

Example 218

6-(2-(4-(Difluoromethyl)-1-(2-(trifluoromethoxy)phenyl)-1H-pyrazol-5-yl)-7-azaspiro[3.5]non-1-en-7-yl)nicotinic acid

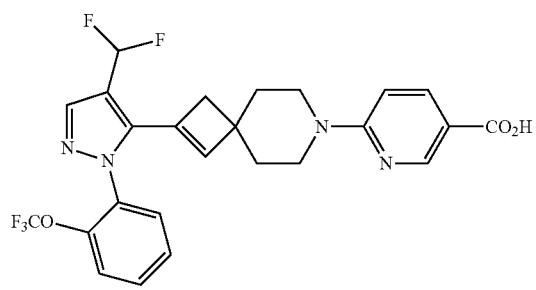
(218)

The title compound was prepared as described in General Method A for the preparation of Example 217 with replacement of ethyl 2-bromo-4-fluorobenzo[d]thiazole-6-carboxylate with methyl 6-fluoronicotinate. MS (ESI) m/z: 521.3 [M+H]⁺; ¹H NMR (500 MHz, DMSO-d₆) δ 8.58 (s, 1H), 7.99 (s, 1H), 7.89 (d, J=8.9 Hz, 1H), 7.78-7.68 (m, 2H), 7.67-7.57 (m, 2H), 7.16 (t, J=55.1 Hz, 1H), 6.83 (d, J=9.2 Hz, 1H), 6.04 (s, 1H), 3.86-7.78 (m, 2H), 3.45-3.36 (m, 2H), 2.29 (s, 2H), 1.59-1.45 (m, 2H); EC₅₀=1085 nM.

Example 219

6-(2-(4-(Difluoromethyl)-1-(2-(trifluoromethyl)phenyl)-1H-pyrazol-5-yl)-7-azaspiro[3.5]non-1-en-7-yl)-1-methyl-1H-indole-3-carboxylic acid

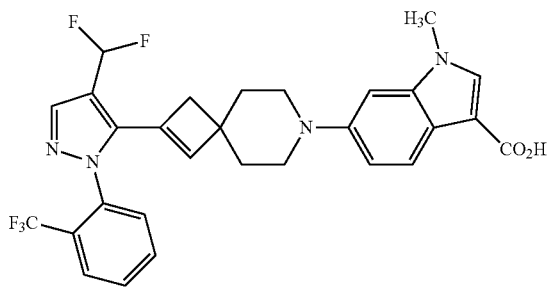
(219)

The title compound was prepared as described in General Method B for the preparation of Example 214 with replacement of ethyl 6-bromo-4-(trifluoromethyl)quinoline-2-carboxylate with methyl 6-bromo-1-methyl-1H-indole-3-carboxylate. MS (ESI) m/z: 557.3 [M+H]⁺; ¹H NMR (500 MHz, DMSO-d₆) δ 8.01 (d, J=7.5 Hz, 1H), 7.96 (s, 1H), 7.94-7.83 (m, 2H), 7.81 (s, 1H), 7.77 (d, J=8.5 Hz, 1H), 7.68 (d, J=7.7 Hz, 1H), 7.18 (t, J=55.1 Hz, 1H), 6.95-6.89 (m, 2H), 5.93 (s, 1H), 3.75 (s, 3H), 3.27-3.19 (m, 2H), 2.91 (br t, J=10.4 Hz, 2H), 2.18 (s, 2H), 1.72-1.63 (m, 2H), 1.60-1.53 (m, 2H); EC₅₀=180 nM.

Example 220

2-(2-(4-(Difluoromethyl)-1-(2-(trifluoromethyl)phenyl)-1H-pyrazol-5-yl)-7-azaspiro[3.5]nonan-7-yl)-4-methylbenzo[d]thiazole-6-carboxylic acid

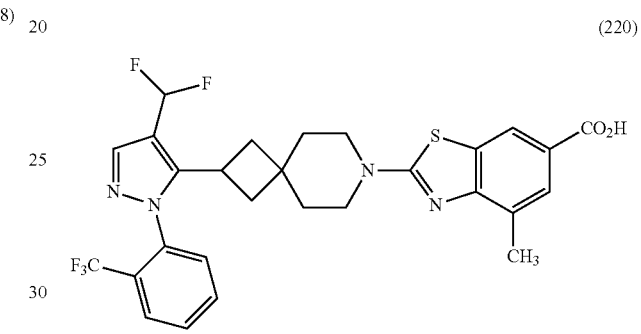
(220)

The title compound was prepared as described in General Method A for the preparation of Example 215 with replacement of ethyl 2-bromo-4-fluorobenzo[d]thiazole-6-carboxylate with methyl 2-bromo-4-methylbenzo[d]thiazole-6-carboxylate. MS (ESI) m/z: 577.2 [M+H]⁺; ¹H NMR (500 MHz, DMSO-d₆) δ 8.12 (s, 1H), 7.98 (d, J=7.6 Hz, 1H), 7.91-7.79 (m, 3H), 7.66 (s, 1H), 7.62 (d, J=7.8 Hz, 1H), 7.19 (t, J=55.6 Hz, 1H), 3.70-3.40 (m, 5H), 2.44 (s, 3H), 2.11-2.02 (m, 2H), 2.01-1.92 (m, 2H), 1.86 (br d, J=9.3 Hz, 2H), 1.63 (br s, 2H), 1.50 (br s, 2H); EC₅₀=378 nM.

Example 221

2-(2-(4-(Difluoromethyl)-1-(2-(trifluoromethoxy)phenyl)-1H-pyrazol-5-yl)-7-azaspiro[3.5]non-1-en-7-yl)-4-methylbenzo[d]thiazole-6-carboxylic acid

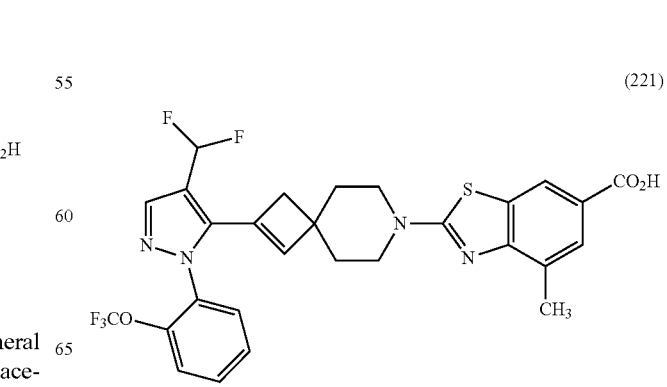
(221)

The title compound was prepared as described in General Method A for the preparation of Example 217 with replacement of ethyl 2-bromo-4-fluorobenzo[d]thiazole-6-carboxylate with methyl 2-bromo-4-methylbenzo[d]thiazole-6-carboxylate. MS (ESI) m/z: 591.1 [M+H]$^+$; $^1$H NMR (500 MHz, DMSO-d$_6$) δ 8.14 (s, 1H), 7.99 (s, 1H), 7.78-7.56 (m, 5H), 7.16 (t, J=55.0 Hz, 1H), 6.07 (s, 1H), 3.63-3.43 (m, 4H), 2.45 (s, 3H), 2.32 (s, 2H), 1.71-1.56 (m, 4H); EC$_{50}$=182 nM.

Example 222

6-(2-(4-(Difluoromethyl)-1-(2-(trifluoromethyl)phenyl)-1H-pyrazol-5-yl)-7-azaspiro[3.5]nonan-7-yl)-1-methyl-1H-indole-3-carboxylic acid (222)

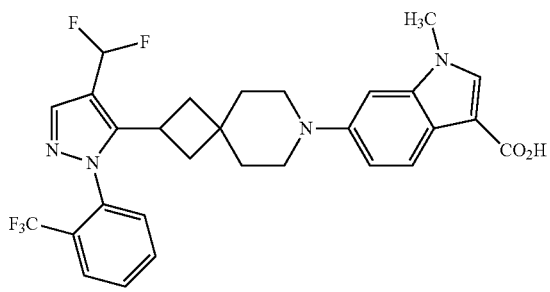

The title compound was prepared as described in General Method B for the preparation of Example 219 with replacement of 2-(4-(difluoromethyl)-1-(2-(trifluoromethyl)phenyl)-1H-pyrazol-5-yl)-7-azaspiro[3.5]non-1-ene, TFA with 2-(4-(difluoromethyl)-1-(2-(trifluoromethyl)phenyl)-1H-pyrazol-5-yl)-7-azaspiro[3.5]nonane, TFA. MS (ESI) m/z: 559.1 [M+H]$^+$; $^1$H NMR (500 MHz, DMSO-d$_6$) δ 7.98 (d, J=7.8 Hz, 1H), 7.91-7.85 (m, 2H), 7.84-7.79 (m, 2H), 7.76 (d, J=8.7 Hz, 1H), 7.64 (d, J=7.8 Hz, 1H), 7.19 (t, J=55.5 Hz, 1H), 6.94-6.84 (m, 2H), 3.73 (s, 2H), 3.03 (br s, 2H), 2.93 (br s, 2H), 2.07-1.99 (m, 2H), 1.96-1.89 (m, 2H), 1.81 (br d, J=9.5 Hz, 2H), 1.65 (br s, 2H), 1.52 (br s, 2H), additional peak missing due to water suppression; EC$_{50}$=275 nM.

Example 223

6-(2-(4-(Difluoromethyl)-1-(2-(trifluoromethoxy)phenyl)-1H-pyrazol-5-yl)-7-azaspiro[3.5]non-1-en-7-yl)nicotinic acid (223)

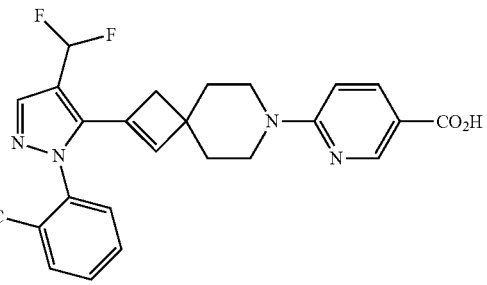

The title compound was prepared as described in General Method A for the preparation of Example 218 with replacement of (2-(trifluoromethoxy)phenyl)hydrazine with (2-(trifluoromethyl)phenyl)hydrazine. MS (ESI) m/z: 505.3 [M+H]$^+$; $^1$H NMR (500 MHz, DMSO-d$_6$) δ 8.56 (d, J=2.4 Hz, 1H), 7.98 (d, J=7.6 Hz, 1H), 7.95 (s, 1H), 7.92-7.81 (m, 3H), 7.64 (d, J=7.6 Hz, 1H), 7.14 (t, J=55.0 Hz, 1H), 6.80 (d, J=9.0 Hz, 1H), 5.91 (s, 1H), 3.83-3.74 (m, 2H), 3.39-3.31 (m, 2H), 2.19 (s, 2H), 1.60-1.39 (m, 4H); EC$_{50}$=205 nM.

Example 224

(2S,3S,4S,5R,6S)-6-((6-(2-(5-Cyclopropyl-3-(3,5-dichloropyridin-4-yl)isoxazol-4-yl)-7-azaspiro[3.5]non-1-en-7-yl)-4-(trifluoromethyl)quinoline-2-carbonyl)oxy)-3,4,5-trihydroxytetrahydro-2H-pyran-2-carboxylic acid (224)

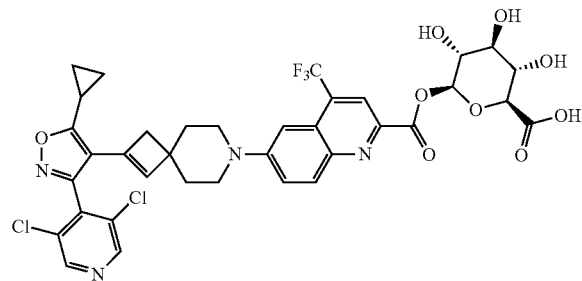

Step 1. (2S,3R,4S,5S,6S)-6-((Allyloxy)carbonyl)-3,4,5-trihydroxytetrahydro-2H-pyran-2-yl 6-(2-(5-cyclopropyl-3-(3,5-dichloropyridin-4-yl)isoxazol-4-yl)-7-azaspiro[3.5]non-1-en-7-yl)-4-(trifluoromethyl)quinoline-2-carboxylate

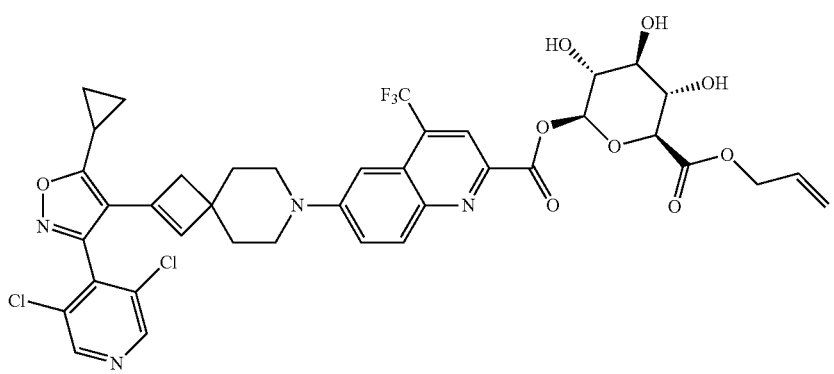 [SMILES: C=CCOC(=O)[C@H]1O[C@@H](OC(=O)c2cc(C(F)(F)F)c3cc(N4CCC5(C=C(c6c(-c7c(Cl)cncc7Cl)noc6C6CC6)C5)CC4)ccc3n2)[C@H](O)[C@@H](O)[C@@H]1O]

To a mixture of 6-(2-(5-cyclopropyl-3-(3,5-dichloropyridin-4-yl)isoxazol-4-yl)-7-azaspiro[3.5]non-1-en-7-yl)-4-(trifluoromethyl)quinoline-2-carboxylic acid (Example 85, 36.5 mg, 0.059 mmol) and HATU (24.8 mg, 0.065 mmol) in acetonitrile (0.5 mL) was added N-methylmorpholine (0.013 mL, 0.12 mmol) at room temperature. The reaction mixture was stirred at room temperature for 25 min followed by addition of allyl (2S,3S,4S,5R,6R)-3,4,5,6-tetrahydroxytetrahydro-2H-pyran-2-carboxylate (16.7 mg, 0.071 mmol). The resulting mixture was stirred at room temperature for 1.5 hours and purged with nitrogen to remove the solvent. The residue was purified by flash chromatography on SiO$_2$ (0-100% EtOAc/CH$_2$Cl$_2$, Isco 12 g column) to give (2S,3R,4S,5S,6S)-6-((allyloxy)carbonyl)-3,4,5-trihydroxytetrahydro-2H-pyran-2-yl 6-(2-(5-cyclopropyl-3-(3,5-dichloropyridin-4-yl)isoxazol-4-yl)-7-azaspiro[3.5]non-1-en-7-yl)-4-(trifluoromethyl)quinoline-2-carboxylate (31.8 mg, 0.038 mmol, 64% yield) as an orange solid. MS (ESI) m/z: 831.5[M+H].

Step 2. Example 224

To a mixture of (2S,3R,4S,5S,6S)-6-((allyloxy)carbonyl)-3,4,5-trihydroxytetrahydro-2H-pyran-2-yl 6-(2-(5-cyclopropyl-3-(3,5-dichloropyridin-4-yl) isoxazol-4-yl)-7-azaspiro [3.5]non-1-en-7-yl)-4-(trifluoromethyl)quinoline-2-carboxylate (0.50 g, 0.60 mmol) and tetrakis(triphenylphosphine)palladium(0) (69.5 mg, 0.060 mmol) in THF (8.0 mL) at 0° C. was added Et$_3$N (0.13 mL, 0.96 mmol). After stirring at 0° C. for 40 min, acetonitrile was added followed by Celite. The mixture was then evaporated to remove the solvents, loaded into a cartridge and then purified by C-18 reverse phase flash chromatography (100 g Isco HP C-18 column, 10-100% B in A, mobile phase A=10:90 acetonitrile: water with 0.05% trifluoroacetic acid; mobile phase B=90:10 acetonitrile: water with 0.05% trifluoroacetic acid). The collected fractions containing desired product were purged with nitrogen to remove the solvents and the residue was lyophilized to give (2S,3S,4S,5R,6S)-6-((6-(2-((5-cyclopropyl-3-(2-(trifluoromethyl)phenyl) isoxazol-4-yl)methyl)-7-azaspiro[3.5]nonan-7-yl)-4-(trifluoromethyl)quinoline-2-carbonyl)oxy)-3,4,5-trihydroxytetrahydro-2H-pyran-2-carboxylic acid (0.34 g, 0.43 mmol, 67% yield) as a light brown solid. MS (ESI) m/z: 791.2[M+H]$^+$; 1H NMR (500 MHz, DMSO-d$_6$) δ 12.98-12.86 (m, 1H), 8.87 (s, 2H), 8.26 (s, 1H), 8.11 (d, J=9.5 Hz, 1H), 7.89 (br dd, J=9.8, 2.5 Hz, 1H), 7.06 (br s, 1H), 5.99 (s, 1H), 5.76 (d, J=7.6 Hz, 1H), 3.90 (d, J=9.5 Hz, 1H), 3.68-3.57 (m, 2H), 3.46-3.43 (m, 1H), 3.43-3.41 (m, 1H), 3.40-3.38 (m, 1H), 3.33 (s, 2H), 2.41 (s, 2H), 2.37-2.33 (m, 1H), 1.72-1.63 (m, 4H), 1.26-1.19 (m, 2H), 1.19-1.12 (m, 2H); FXR EC50=73 nM.

Biological Assays

The exemplified compounds of the present invention were tested in the transient human FXR/Gal4-luciferase reporter assay, and assay results were reported in the Examples section with other analytical data.

A Gal4-hFXR fusion construct reporter system was used as the primary assay to characterize compound activity. A construct including 5 copies of the Gal4 promoter response element upstream of a firefly luciferase reporter cDNA was stably expressed in HEK293 cells. This reporter cell line was maintained in Dulbecco's Modified Eagle's medium (DMEM; Gibco) supplemented with 1% penicillin-streptomycin (P/S) solution, 500 μg/mL Zeocin and 10% charcoal/dextran-treated fetal bovine serum (cs-FBS) at 37° C. in a humidified 5% CO$_2$ atmosphere. Another plasmid was constructed in which the human cytomegalovirus promoter in the pcDNA3.1 vector directs the expression of the cDNA encoding a fusion protein comprised of the DNA binding domain from the Gal4 transcription factor fused to the ligand binding domain from human FXR.

The day prior to transfection, the reporter cells in culture are detached from the plate with trypsin and plated into a T75 flask at a sufficient density to achieve approximately 90% confluence the next morning. The transfection reagents are prepared by separately diluting 25 μg of the pcDNA3.1-Gal4-FXR plasmid into 1.87 mL of Opti-MEM (Thermo-Fisher), and 40 μL of Lipofectamine 2000 (Thermo-Fisher) into 1.87 mL of Opti-MEM, and then adding the diluted DNA solution into the diluted Lipofectamine 2000 solution and incubating at room temperature for 15-20 minutes. The mixture is further diluted with 10 mL of a solution comprised of DMEM, 10% cs-FBS, and 1% P/S immediately prior to transferring to the cells. The maintenance culture media is aspirated from the cells and the final transfection mixture is added before the cells are incubated overnight at 37° C. in a humidified 5% CO$_2$ atmosphere. This protocol can be scaled up, and the transiently transfected cells can be cryopreserved in an assay-ready format.

For compound testing, 100 nL of the compounds (serial dilutions in DMSO) are dispensed with an Echo acoustic dispenser (Labcyte) into the wells of a Corning/Costar clear bottom 384-well white plate. The transfected cells are harvested, counted, and diluted such that 10-25,000 cells in 25 μL are plated into each well of the 384-well compound assay plate. The compound-treated cells are incubated overnight at 37° C. in a humidified 5% CO$_2$ atmosphere. The next morning 25 μL of Steady-Glo (Promega) are added to each well of the plate, the mixture is incubated for 15 min. with shaking, and luminescence is measured on an Envision (Perkin Elmer) plate reader. Background counts from cells treated with DMSO alone are subtracted from all raw counts, and the corrected values are converted to a percentage of the control response attained with 8 μM GW-4064. These data are fit to a 4-parameter log agonist-response equation to calculate an EC$_{50}$ value.

Acute Mouse In Vivo Assay:

Male, C57BL6/NTac mice, weighing 25-28 g, are purchased from Taconic Labs (Hudson, N.Y.) and maintained on Teklad Global 18% Protein Rodent Diet (Harlan Laboratories). After 1 week acclimation, mice are sorted into groups based upon body weight. Mice are administered a single oral dose of vehicle or experimental compound. Systemic compound exposure is evaluated in plasma derived from blood collected via the submandibular vein at 1 hour post-dose, and at study termination (6 h). At study termination, the animals are euthanized and rapidly dissected. The medial lobe of the liver is divided, with one half being homogenized and analyzed for compound exposure, and the other half saved in RNAlater (Thermo-Fisher Scientific). The ileum is also dissected and preserved in RNAlater. Tissue samples in RNAlater are homogenized with MP Biomedicals' beads. RNA is extracted using the MagMax-96 Total RNA Isolation kit (Thermo-Fisher Scientific) according to the manufacturer's protocol. RNA Concentration is determined with the Nano-Drop 8000 Spectrophotometer (Thermo Fisher). Reverse transcription is done with Invitrogen's SuperScript® VILO cDNA Synthesis Kit according to the manufacturer's protocol. Real time PCR is done with Applied Biosystems' Taqman PCR master mixture according to the manufacturer's protocol. All primers are purchased from Thermo-Fisher Scientific. Mouse genes analyzed include Nr0b2 (which encodes the small heterodimer partner, SHP), Abcb11 (which encodes the bile salt excretion pump, BSEP), Cyp7a1, & Cyp8b1 in liver, and Fgf15, Fabp6 (which encodes ileal bile acid binding protein, I-BABP), Slc51a (which encodes organic solute transporter alpha subunit, OSTA), and Slc51b (which encodes organic solute transporter beta subunit, OSTB) in the ileum. The statistical significant changes in FGF15 gene expression are expressed as fold increase and $CYP_{7A1}$ expression as a percent reduction relative to vehicle control.

Other features of the invention should become apparent in the course of the above descriptions of exemplary embodiments that are given for illustration of the invention and are not intended to be limiting thereof. The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

What is claimed is:

1. A compound of Formula (I):

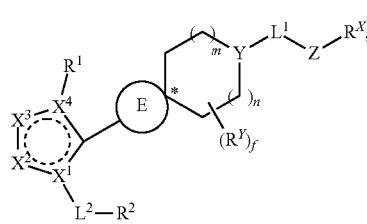

or a stereoisomer, a tautomer, a pharmaceutically acceptable salt, or a solvate thereof; wherein:

the

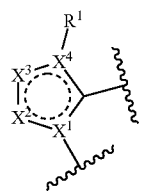

moiety is

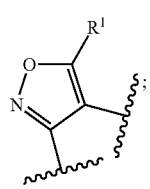

E ring is a 4- to 6-membered carbocyclyl or heterocyclyl, wherein the carbocyclyl and heterocyclyl are each independently substituted with 0 to 3 $R^3$;
* denotes a spiro carbon atom;
Y is $CR^7$ or N;

m and n are each independently an integer of 0, 1, or 2;
f is an integer of 0, 1, 2, or 3;
Z is 6- to 10-membered aryl, 5- to 10-membered heteroaryl containing 1 to 3 heteroatoms independently selected from N, O, and S, 3- to 10-membered carbocyclyl, or 4- to 10-membered heterocyclyl containing 1 to 3 heteroatoms independently selected from N, O, and S, wherein the aryl, heteroaryl carbocyclyl, and heterocyclyl are independently substituted with 0 to 5 $R^8$;
$L^1$ is a covalent bond, O, S, —$NR^{16}$—, —$S(O)_2$—, $C_{1-3}$ alkylene, $C_{1-3}$ heteroalkylene, $C_{2-4}$ alkenylene, $C_{2-4}$ alkynylene, aryl, or a 5- to 6-membered heteroaryl containing 1 to 3 heteroatoms independently selected from N, O, and S; wherein the alkylene, alkenylene, aryl, heteroalkylene, and heteroaryl are each independently substituted with 0 to 3 $R^{17}$;
$L^2$ is a covalent bond, O, S, —$NR^{17}$—, $C_{1-3}$ alkylene, or $C_{1-3}$ heteroalkylene, wherein the alkylene and heteroalkylene are independently substituted with 0 to 3 $R^{15}$;
$R^X$ is -$L^3$-$R^Z$;
$L^3$ is a covalent bond, $C_{1-3}$ alkylene, —$C(O)NR^{12}$—$CH_2$—, or —$OCH_2$—, wherein the $C_{1-3}$ alkylene is substituted with 0 to 3 $R^4$;
$R^Z$ is —CN, —$C(O)OR^{13}$, —$C(O)NR^{14a}R^{14b}$,

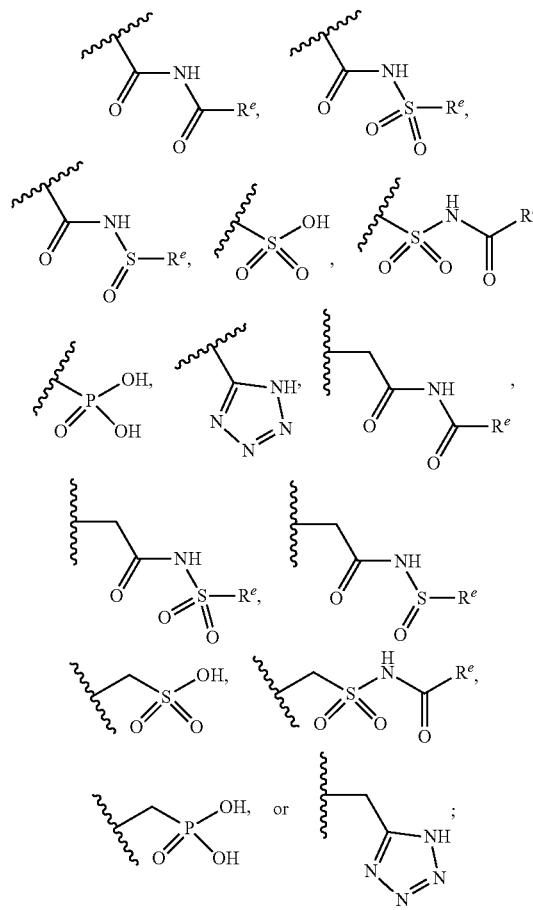

$R^e$ is $C_{1-6}$ alkyl, $C_{3-6}$ cycloalkyl, haloalkyl, hydroxyalkyl, aminoalkyl, alkoxyalkyl, haloalkoxyalkyl, or aryl;
$R^Y$ is each independently hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy; or alternatively two $R^Y$, together with the carbon atoms to which they are attached, form a bridge moiety; and with the proviso that when Y is N and $R^Y$ is attached to a carbon atom adjacent to Y, then $R^Y$ is not halo, cyano, hydroxyl, amino, alkoxy, or haloalkoxy;

$R^1$ is $C_{1-6}$ alkyl, $C_{3-5}$ cycloalkyl, or $C_{4-6}$ heterocyclyl, wherein the alkyl, cycloalkyl, and heterocyclyl are each substituted with 0 to 3 $R^9$;

$R^2$ is 6- to 10-membered aryl, 5- to 10-membered heteroaryl containing 1 to 3 heteroatoms independently selected from N, O, and S, 3- to 10-membered carbocyclyl, or 4- to 10-membered heterocyclyl containing 1 to 3 heteroatoms independently selected from N, O, and S, wherein the aryl, heteroaryl, carbocyclyl, and heterocyclyl are independently substituted with 0 to 5 $R^{10}$;

$R^3$, $R^5$, and $R^7$ are each independently hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy;

$R^4$ is each independently halo, oxo, cyano, hydroxyl, amino, alkyl, alkoxy, or alkylamino; or alternatively, two $R^4$, taken together with the atom(s) to which they are attached, form a carbocyclyl or heterocyclyl moiety;

$R^6$, $R^{16}$ and $R^{17}$ are each independently hydrogen, $C_{1-6}$ alkyl, haloalkyl, hydroxyalkyl, aminoalkyl, alkoxyalkyl, or haloalkoxyalkyl;

$R^8$ and $R^{10}$ are each independently halo, cyano, hydroxyl, amino, oxo, —$OR^a$, —$SR^a$, =S, $NR^cR^c$, =NH, =N—OH, =$NR^a$, =N—$OR^a$, —$NO_2$, —$S(O)_2R^a$, —$S(O)_2NHR^b$, —$S(O)_2NR^cR^c$, —$S(O)_2OR^b$, —OS(O)$_2R^b$, —OS(O)$_2OR^b$, —P(O)(OR$^b$)(OR$^b$), —C(O)R$^b$, —C(NR$^b$)R$^b$, —C(O)OR$^b$, —C(O)NR$^c$R$^c$, —C(NR$^b$)NR$^c$R$^c$, —OC(O)R$^b$, —NR$^b$C(O)R$^b$, —OC(O)OR$^b$, —NR$^b$C(O)OR$^b$, —NR$^b$C(O)NR$^c$R$^c$, —NR$^b$C(NR$^b$)R$^b$, —NR$^b$C(NR$^b$)NR$^c$R$^c$, $C_{1-6}$ alkyl, $C_{1-6}$ haloalkyl, aryl, arylalkyl, heteroaryl, carbocyclyl, or heterocyclyl; wherein the alkyl, aryl, heteroaryl, carbocyclyl, and heterocyclyl, by themselves or as part of another group, are each independently substituted with 0 to 5 $R^d$;

$R^a$ is each independently $C_{1-6}$ alkyl, haloalkyl, hydroxyalkyl, aminoalkyl, alkoxyalkyl, haloalkoxyalkyl, aryl, arylalkyl, heteroaryl, heteroarylalkyl, carbocyclyl, carbocyclylalkyl, heterocyclyl, or heterocyclylalkyl;

$R^b$ is each independently hydrogen or $R^a$;

$R^c$ is each independently $R^b$ or alternatively, the two $R^c$ are taken together with the nitrogen atom to which they are bonded form a 4-, 5-, 6- or 7-membered heterocyclyl containing 1 to 3 heteroatoms independently selected from N, O, and S;

$R^d$ is each independently $R^a$, alkoxy, haloalkoxy, alkylamino, cycloalkylamino, heterocyclylamino, haloalkyl, hydroxyalkyl, aminoalkyl, cycloalkoxy, heterocyclyloxy, haloalkoxy, alkoxyalkoxy, haloalkylamino, alkoxyalkylamino, haloalkoxyalkylamino, arylamino, aralkylamino, aryloxy, aralkyloxy, heteroaryloxy, heteroarylalkyloxy, alkylthio, halo, cyano, hydroxyl, amino, oxo, —$OR^a$, —$SR^a$, =S, —$NR^cR^c$, =NH, =N—OH, =$NR^a$, =N—$OR^a$, —$NO_2$, —$S(O)_2R^a$, —$S(O)_2NHR^b$, —$S(O)_2NR^cR^c$, —$S(O)_2OR^b$, —OS(O)$_2R^b$, —OS(O)$_2OR^b$, —P(O)(oR$^b$)(OR$^b$), —C(O)R$^b$, —C(NR$^b$)R$^b$, —C(O)OR$^b$, —C(O)NR$^c$R$^c$, —C(NR$^b$)NR$^c$R$^c$, —OC(O)R$^b$, —NR$^b$C(O)R$^b$, —OC(O)OR$^b$, —NR$^b$C(O)OR$^b$, —NR$^b$C(O)NR$^c$R$^c$, —NR$^b$C(NR$^b$)R$^b$, or —NR$^b$C(NR$^b$)NR$^c$R$^c$;

$R^9$ is each independently halo, cyano, hydroxyl, amino, or $C_{1-6}$ alkyl;

$R^{11}$ and $R^{15}$ are each independently halo, oxo, cyano, hydroxyl, amino, $C_{1-6}$ alkyl, $C_{3-6}$ cycloalkyl, $C_{4-6}$ heterocyclyl, alkylamino, haloalkyl, hydroxyalkyl, aminoalkyl, alkoxyalkyl, haloalkoxyalkyl, alkoxy, or haloalkoxy;

$R^{12}$ is hydrogen or $C_{1-4}$ alkyl;

$R^{13}$ is hydrogen, $C_{1-10}$ alkyl, glycosyl, or carboxy(trihydroxy)tetrahydropyranyl; and $R^{14a}$ and $R^{14b}$ are each independently hydrogen, $C_{1-6}$ alkyl, $C_{3-6}$ cycloalkyl, $C_{4-6}$ heterocyclyl, alkylamino, haloalkyl, hydroxyalkyl, aminoalkyl, alkoxyalkyl, haloalkoxyalkyl, alkoxy, or haloalkoxy.

2. The compound according to claim 1, or a stereoisomer, a tautomer, a pharmaceutically acceptable salt, or a solvate thereof; wherein:

$L^1$ is a covalent bond, O, S, NH, or C1-3 alkylene, wherein the $C_{1-3}$ alkylene is substituted with 0 to 3 $R^{11}$; and $L^2$ is a covalent bond.

3. The compound according to claim 1, or a stereoisomer, a tautomer, a pharmaceutically acceptable salt, or a solvate thereof; wherein:

the

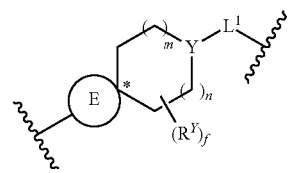

moiety is selected from:

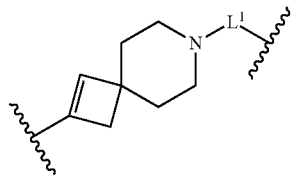

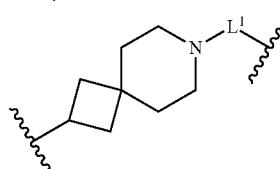

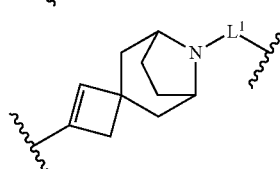

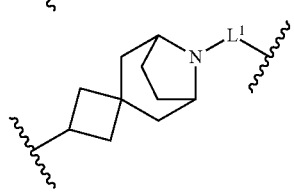

-continued

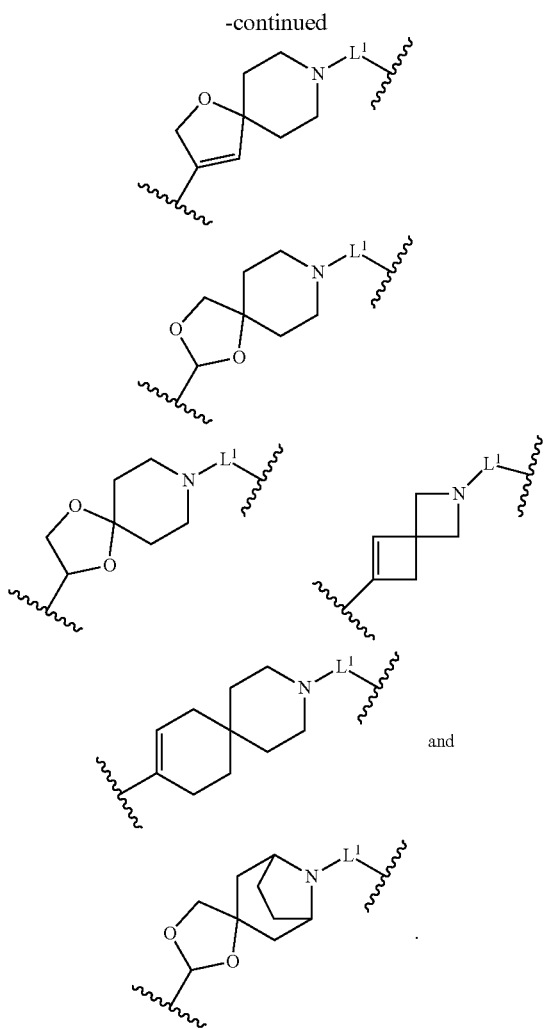

and

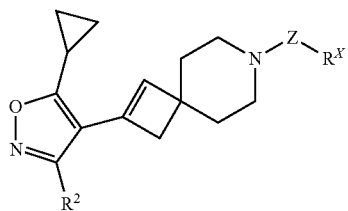

4. The compound according to claim 1, or a stereoisomer, a tautomer, a pharmaceutically acceptable salt, or a solvate thereof; wherein Z is phenyl or 5- to 10-membered heteroaryl containing 1 to 3 heteroatoms independently selected from N, O, and S, wherein the phenyl and heteroaryl are independently substituted with 0 to 5 $R^8$.

5. The compound according to claim 1, which is represented by Formula (III):

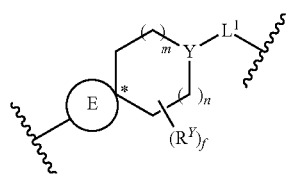

(III)

or a stereoisomer, a tautomer, a pharmaceutically acceptable salt, or a solvate thereof; wherein:

Z is 6-membered monocyclic heteroaryl containing 1 or 2 nitrogen atoms, or a 9- to 10-membered bicyclic heteroaryl containing 1 or 3 heteroatoms independently selected from N, O, and S, wherein the monocyclic or bicyclic heteroaryl is independently substituted with 0 to 3 $R^8$;

$R^2$ is phenyl or pyridinyl, wherein the phenyl and pyridinyl are each independently substituted with 0 to 2 $R^{10}$;

$R^8$ is each independently halo, cyano, hydroxyl, $C_{1-4}$ alkyl, $C_{1-4}$ haloalkyl, $C_{1-4}$ alkoxy, or $C_{1-4}$ haloalkoxy;

$R^{10}$ is each independently halo, $C_{1-4}$ alkyl, $C_{1-4}$ haloalkyl, $C_{1-4}$ alkoxy, or $C_{1-4}$ haloalkoxy;

$R^x$ is —C(O)OH or —C(O)NH—S(O)$_2$R$^e$; and $R^e$ is $C_{1-6}$ alkyl or $C_{3-6}$ cycloalkyl.

6. The compound according to claim 1, or a stereoisomer, a tautomer, a pharmaceutically acceptable salt, or a solvate thereof; wherein:

Y is CH or N;

the

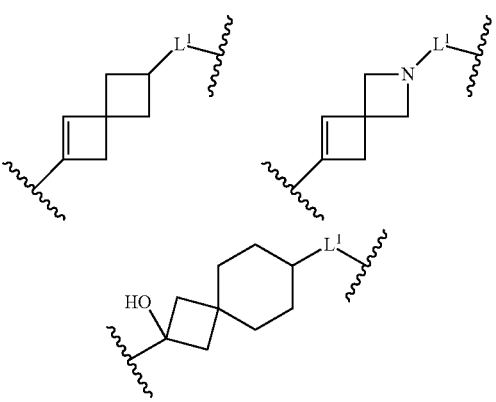

moiety is selected from:

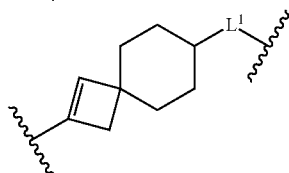

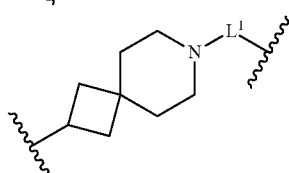

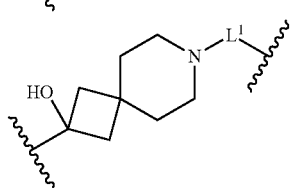

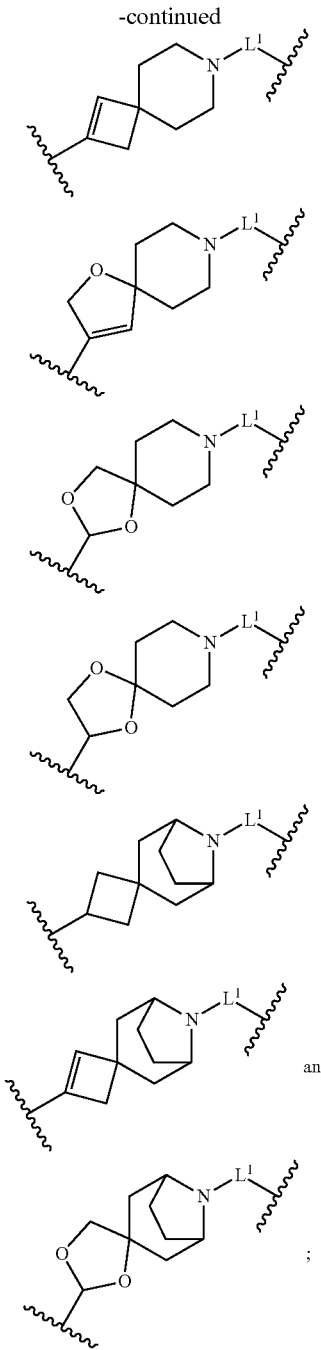

L¹ is a covalent bond, O, or —OCH₂—, provided that L¹ is a covalent bond when Y is N;

Z is phenyl, pyridinyl, pyridazinyl, pyrimidinyl, pyrazinyl, benzo[d]imidazolyl, benzo[d]isoxazolyl, benzo[d]oxadiazolyl, benzo[d]thiazolyl, imidazolo[1,5-a]pyridinyl, indazolyl, indolyl, pyrazolo[4,3-b]pyridinyl, pyrrolo[2,1-f][1,2,4]triazinyl, pyrrolo[2,3-b]pyridinyl, pyrrolo[2,3-c]pyridinyl, pyrrolo[2,3-d]pyrimidinyl, pyrrolo[3,2-c]pyridinyl, thiazolo[4,5-b]pyridinyl, thiazolo[5,4-b]pyridinyl, cinnolinyl, isoquinolinyl, quinolinyl, or quinoxalinyl, each substituted with zero to 1 $R^8$;

$R^8$ is F, —CH₃, —CF₃, —OCH₃, —OCH₂CH₃, —OCH(CH₃)₂, —OCHF₂, —OCF₃, —OCH₂CH₂OH, or —CH₂OCH₂CH₂Si(CH₃)₃;

$R^x$ is —CN, —C(O)OH, —C(O)OCH₂CH₃, —C(O)NH₂, —C(O)NH(CH₃), —C(O)NHCH₂CH₃, —C(O)NHCH(CH₃)₂, —C(O)NH(cyclopropyl), —C(O)NHCH₂C(O)OH, —C(O)NHS(O)₂CH₃, —C(O)NHS(O)₂(cyclopropyl), —OCH₂C(O)OH, or —C(O)O(carboxy(trihydroxy)tetrahydropyranyl);

L² is a covalent bond;

$R^1$ is —CHF₂, —CH(CH₃)₂, cyclopropyl, or methylcyclopropyl;

$R^2$ is cyclohexyl, phenyl, or pyridinyl, wherein the phenyl and the pyridinyl are independently substituted with 1 to 3 $R^{10}$; and $R^{10}$ is each independently F, Cl, —CH₃, —CF₃, —OCH₃, or —OCF₃.

7. The compound according to claim 1, or a stereoisomer, a tautomer, a pharmaceutically acceptable salt, or a solvate thereof, selected from:

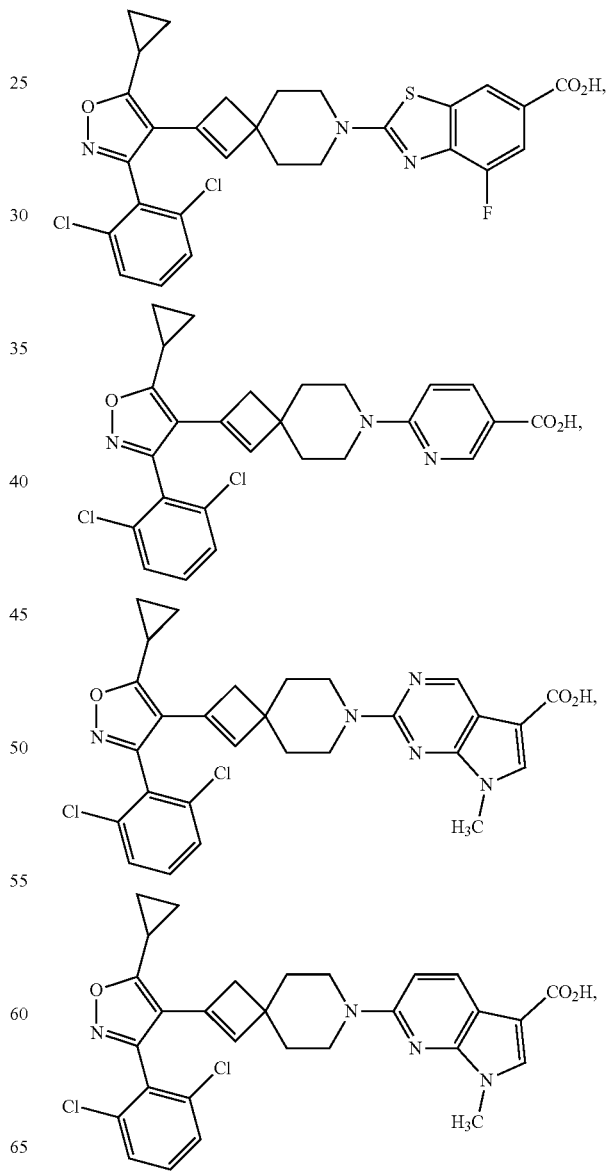

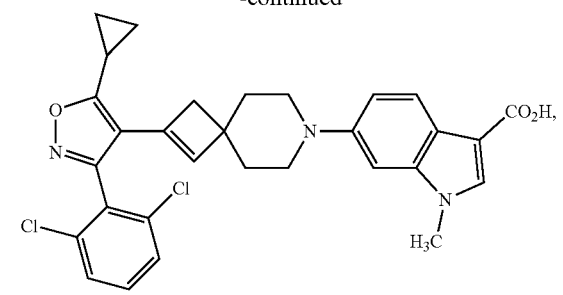
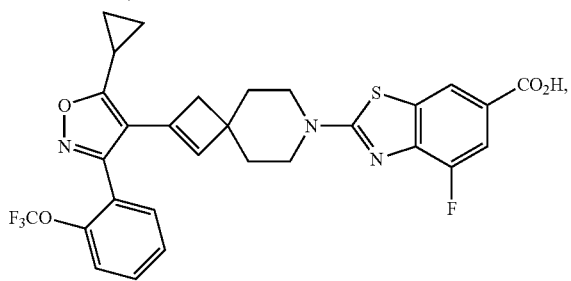
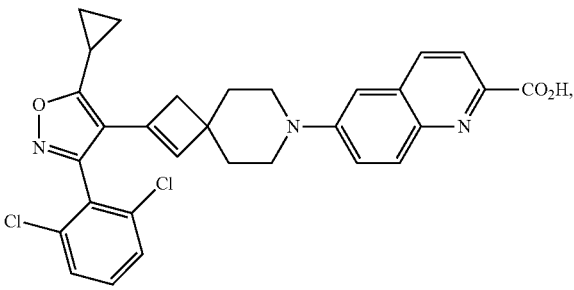
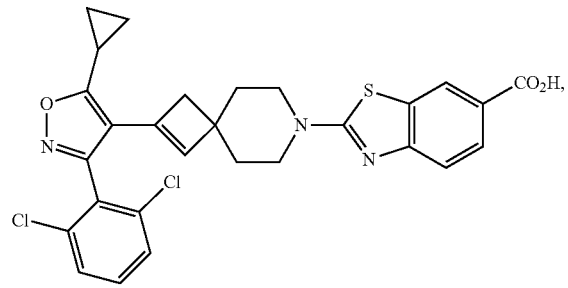
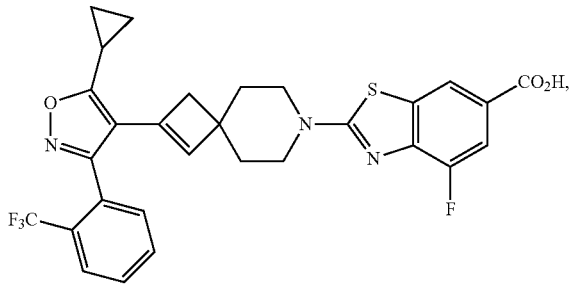
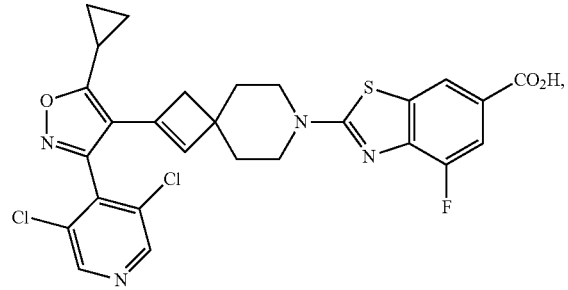
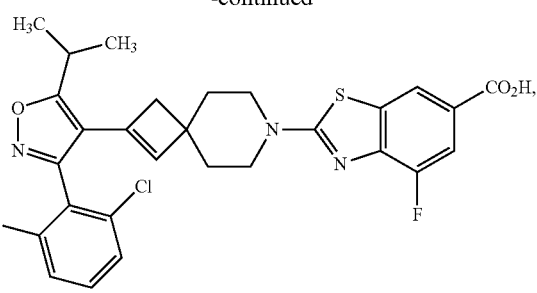
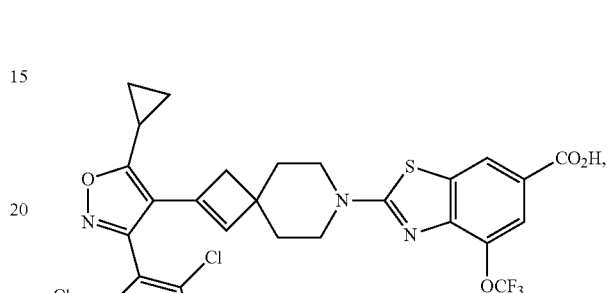
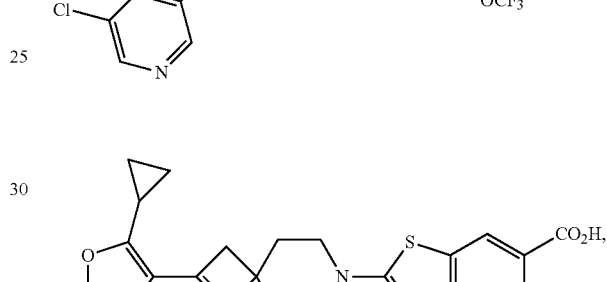
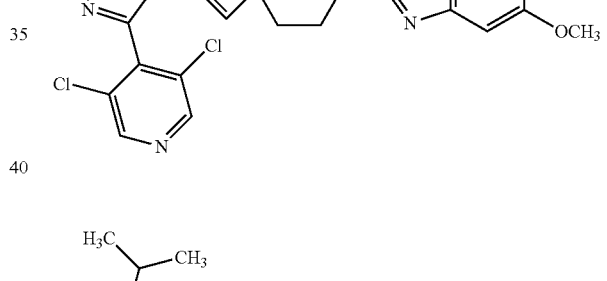
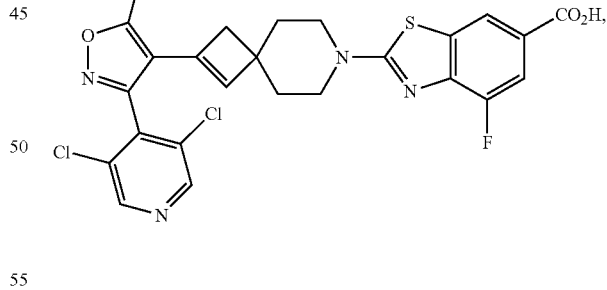
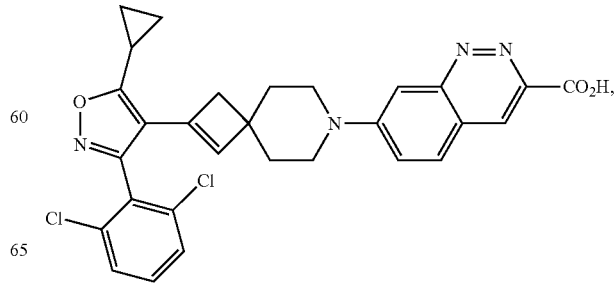

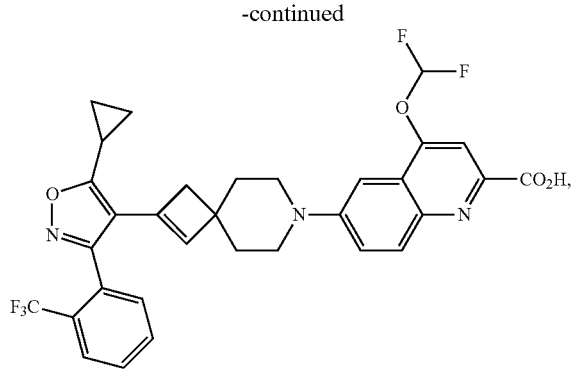
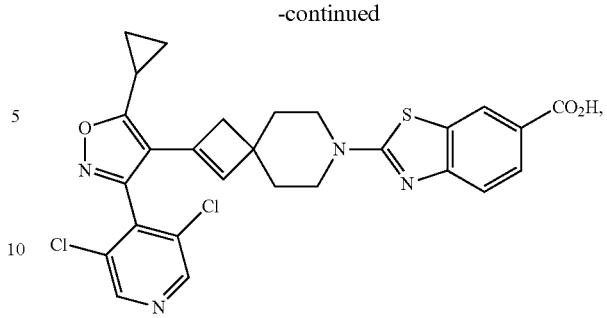
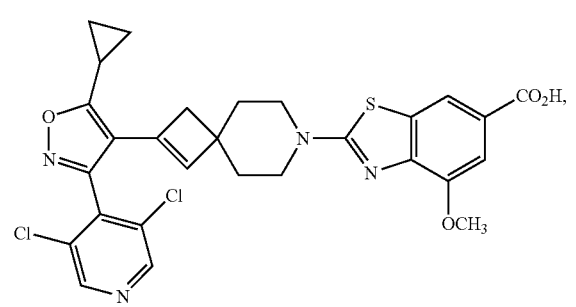
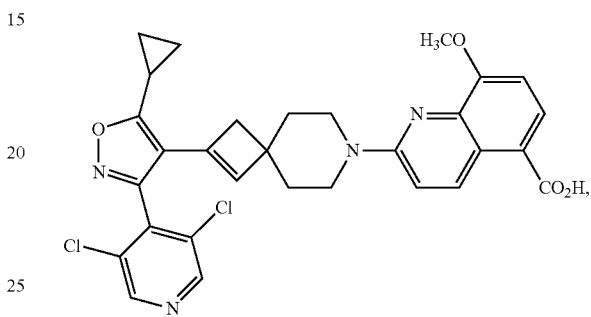
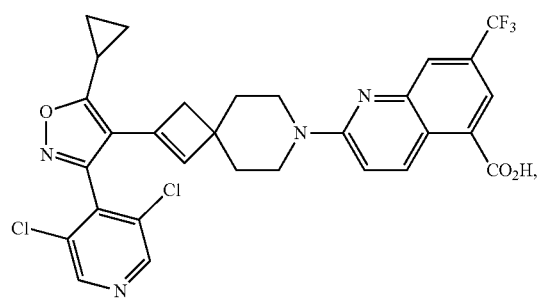
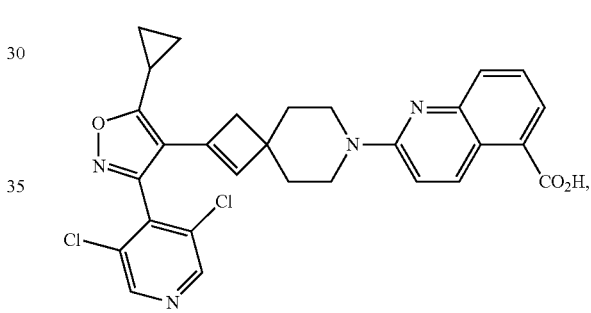
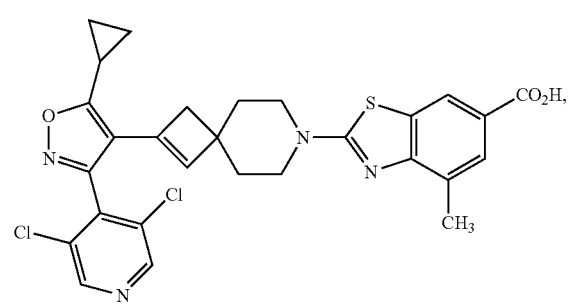
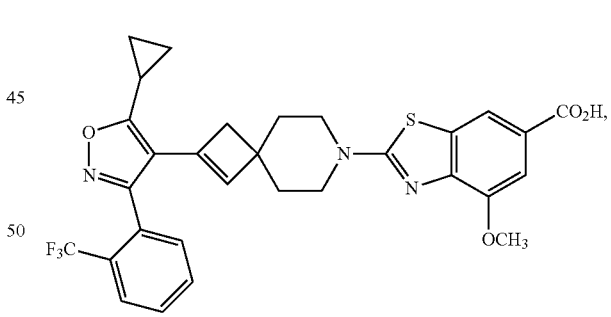
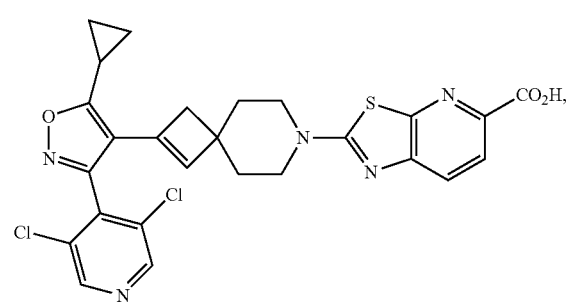
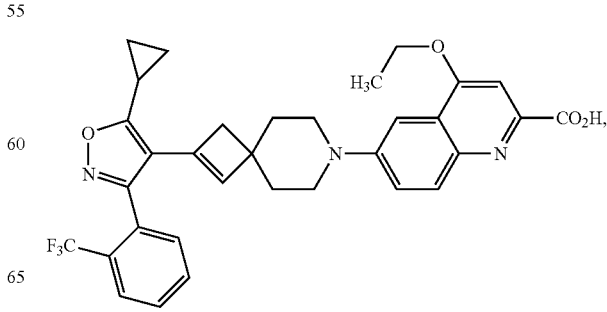

249
-continued
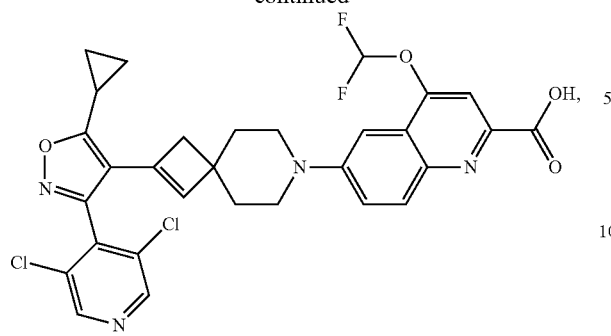
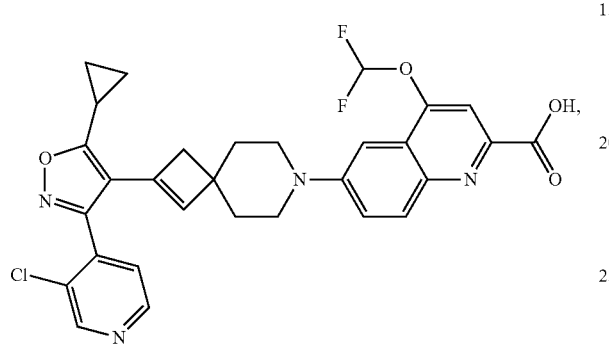
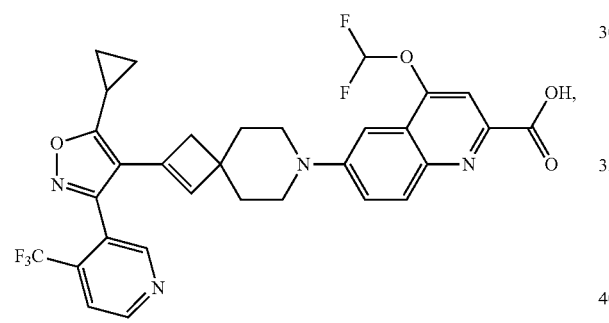
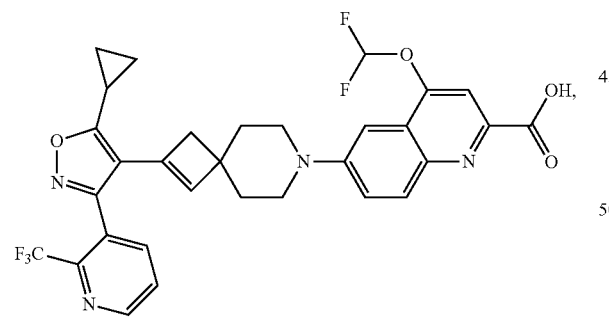
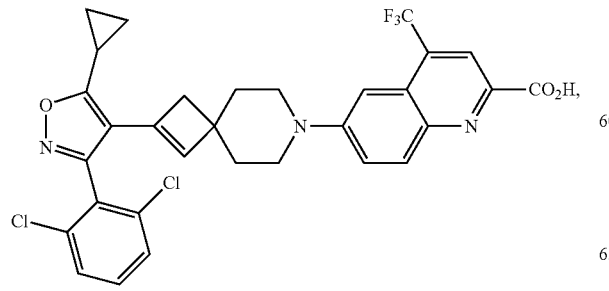
250
-continued
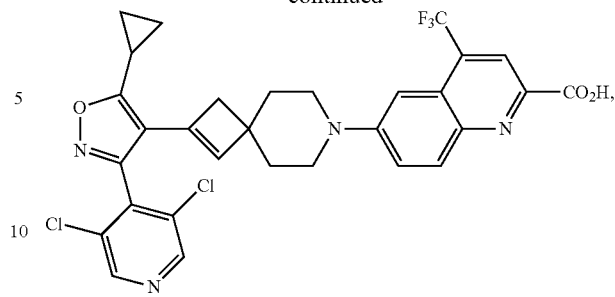
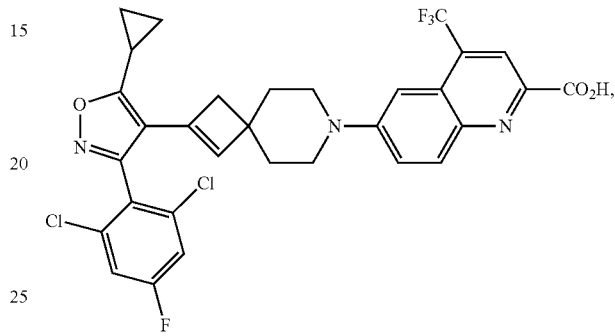
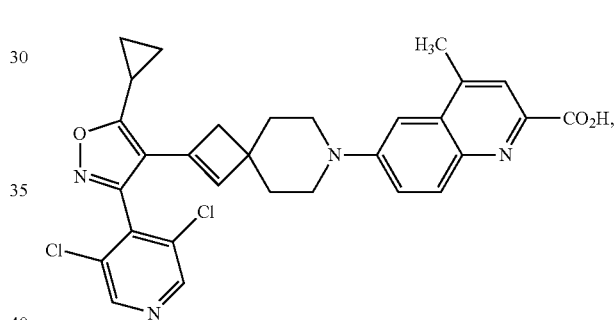
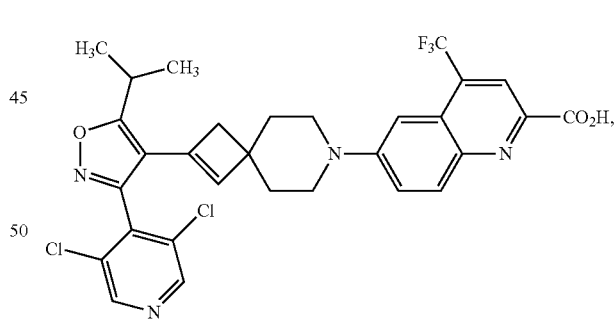
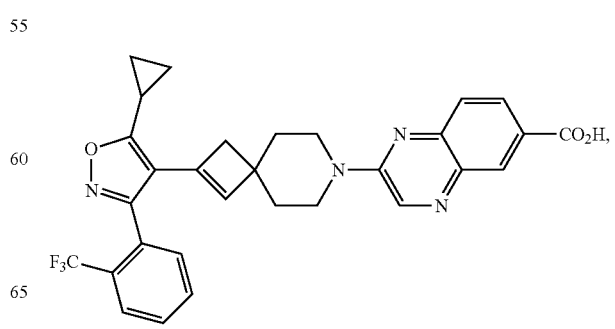

251
-continued
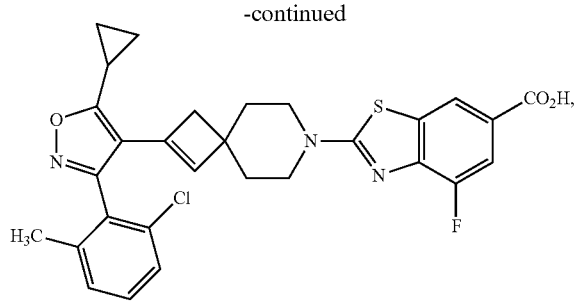
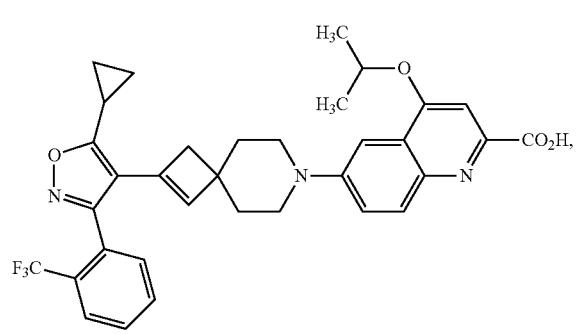
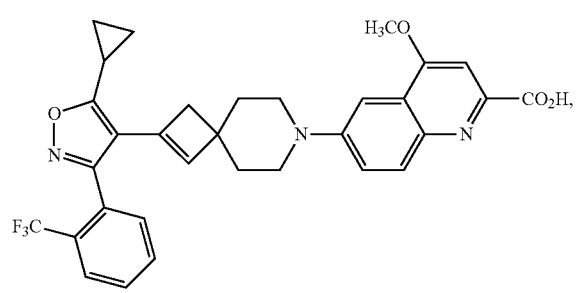
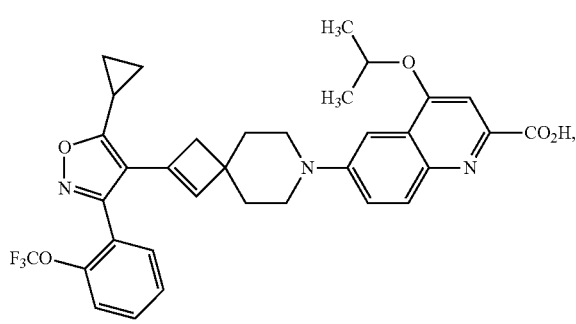
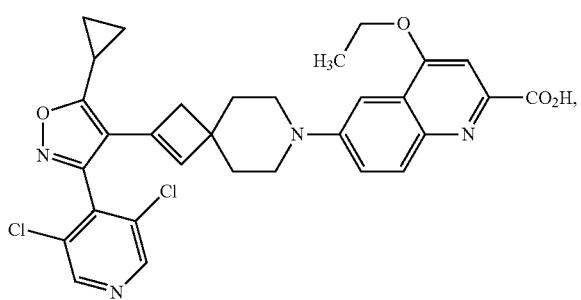
252
-continued
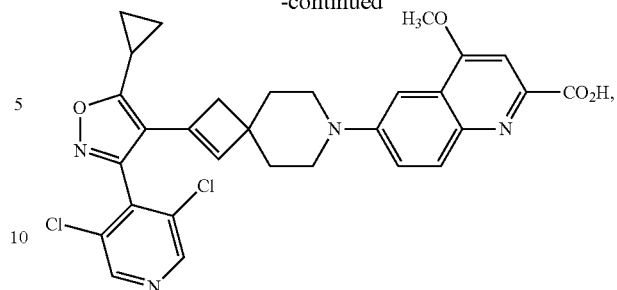
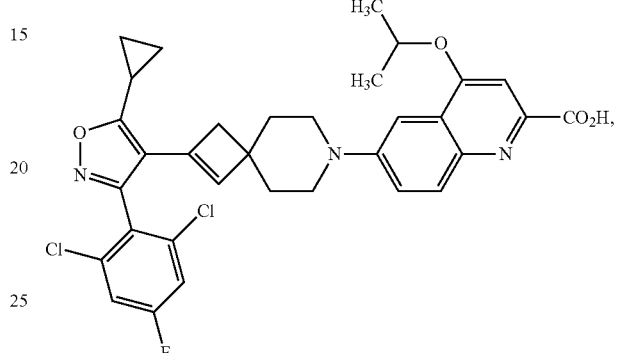
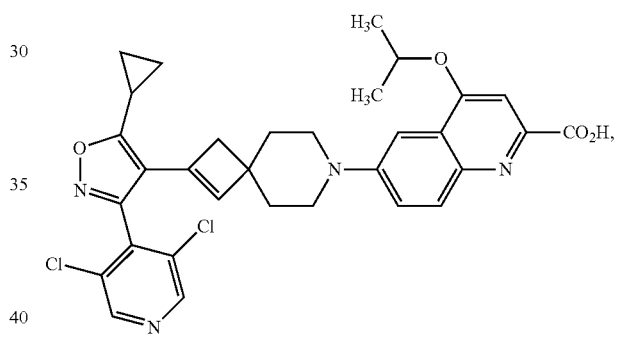
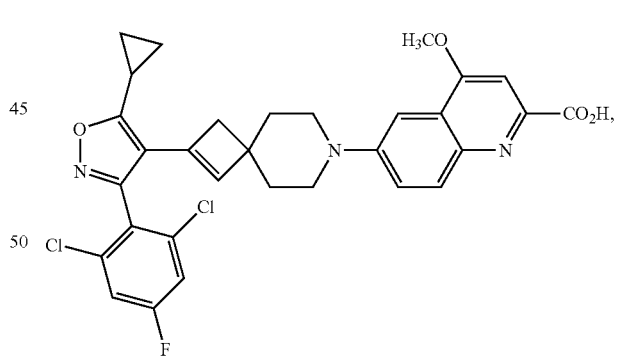
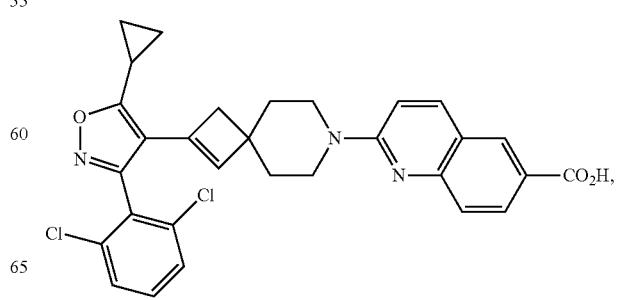

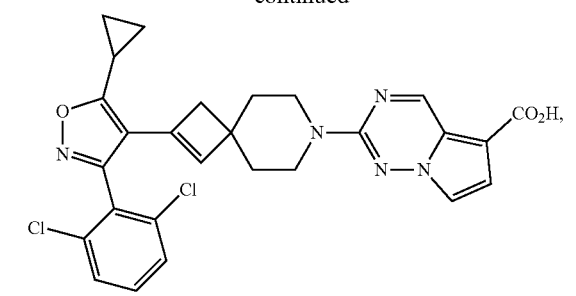
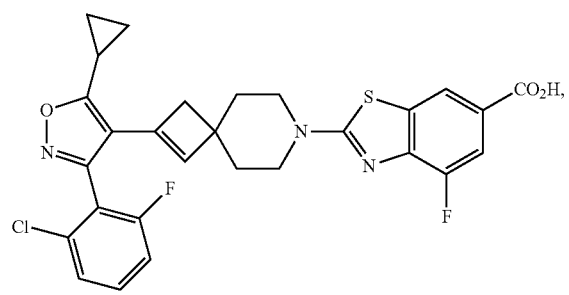
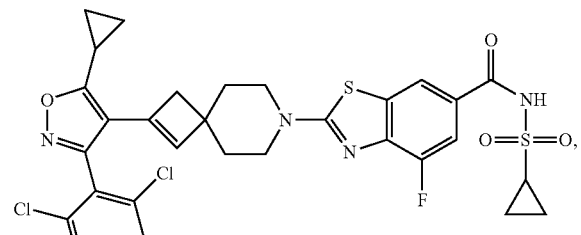
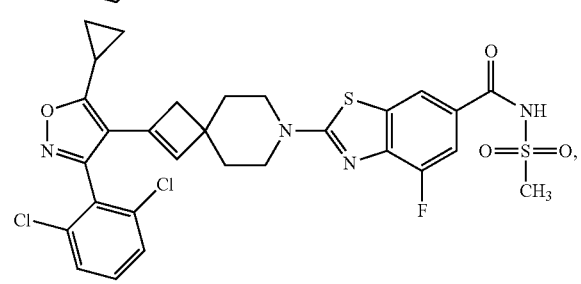
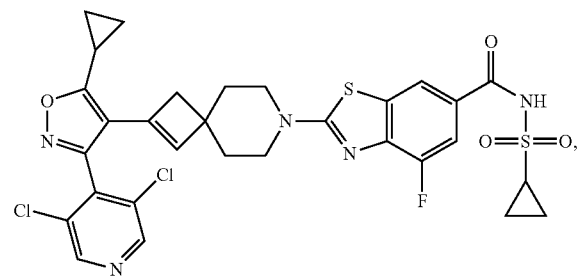
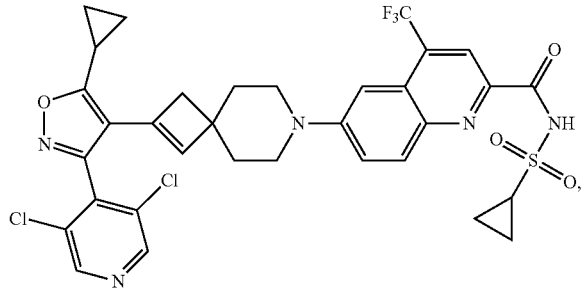
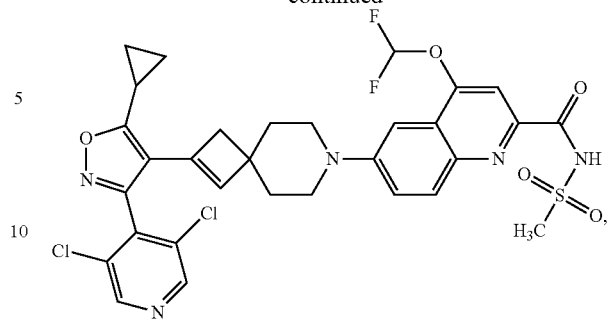
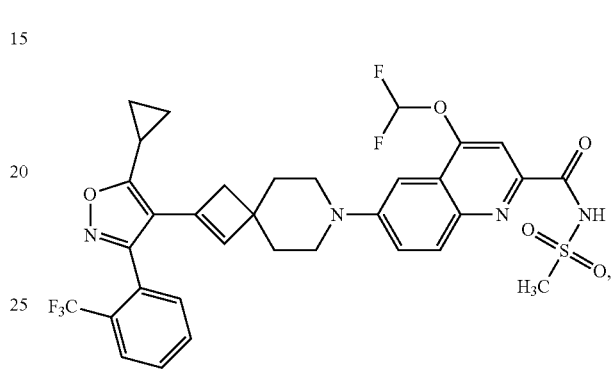
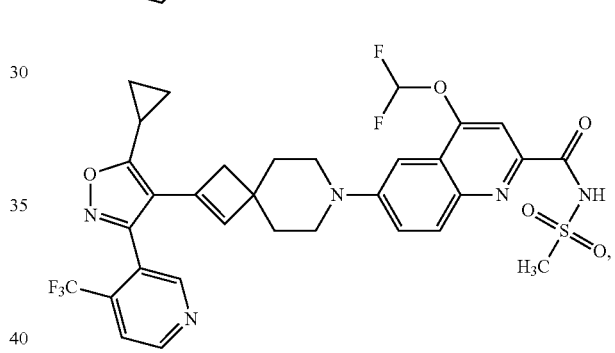
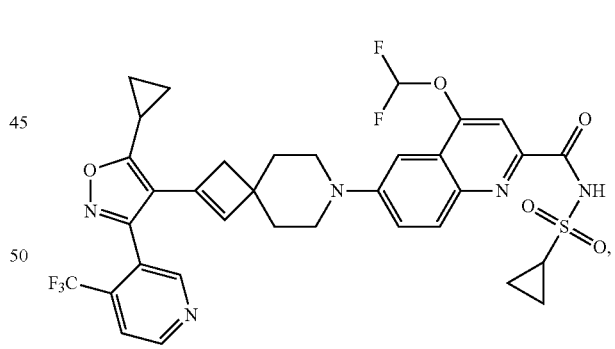
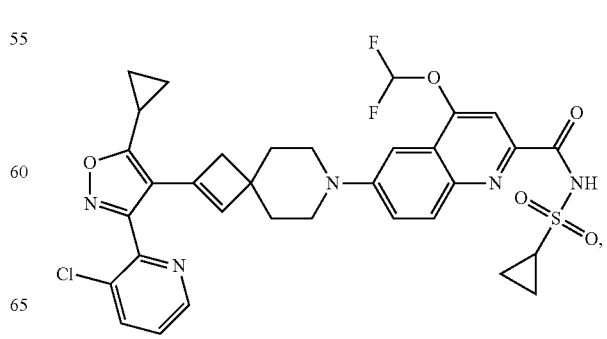

255
-continued
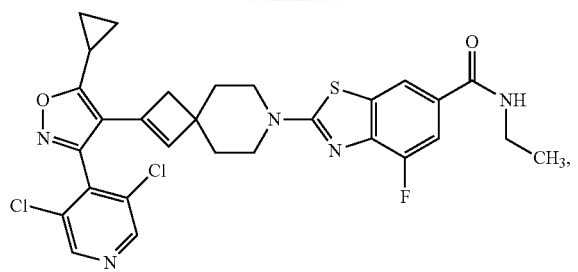
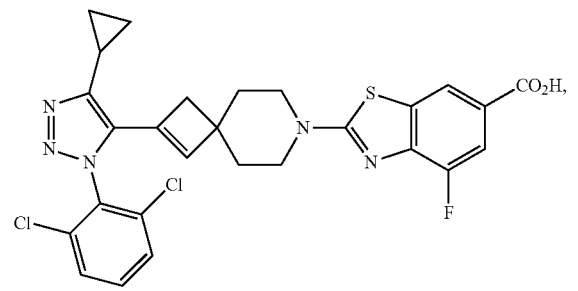
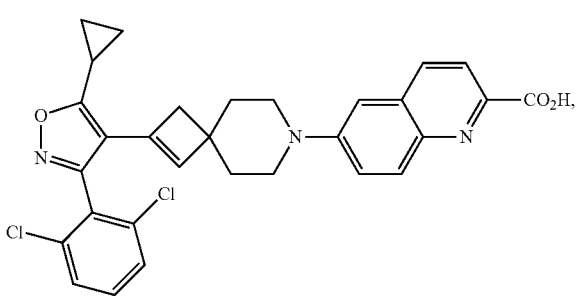
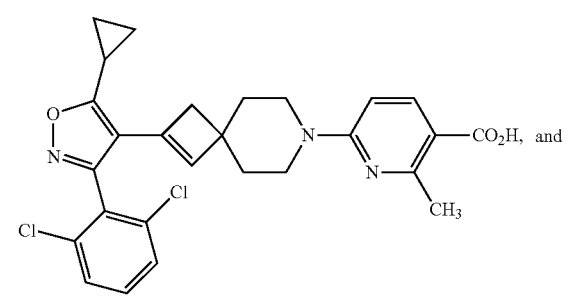
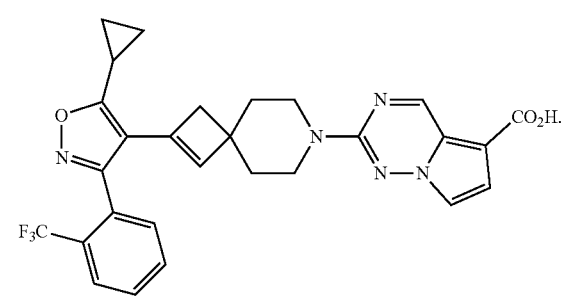
8. The compound according to claim 1, or a stereoisomer, a tautomer, a pharmaceutically acceptable salt, or a solvate thereof, selected from:
256
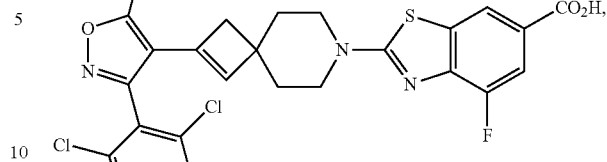
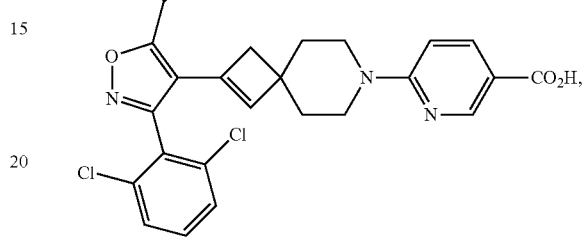
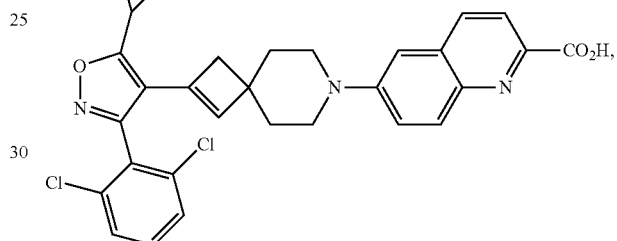
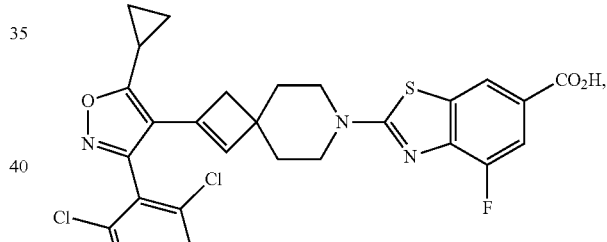
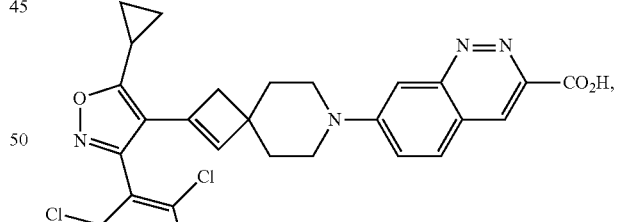
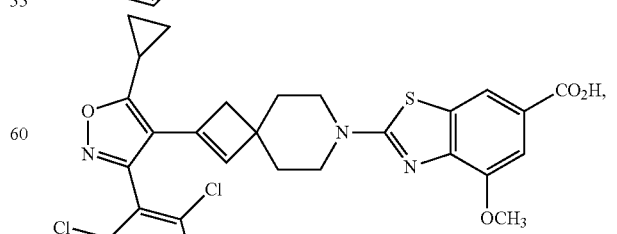

257
-continued

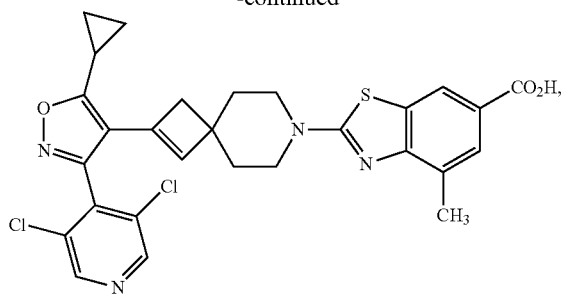

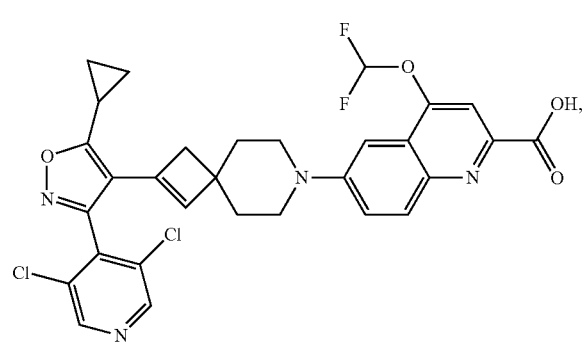

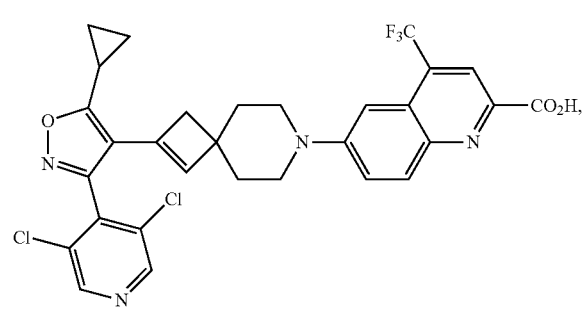

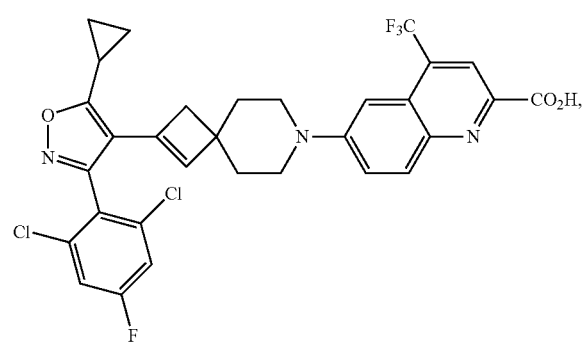

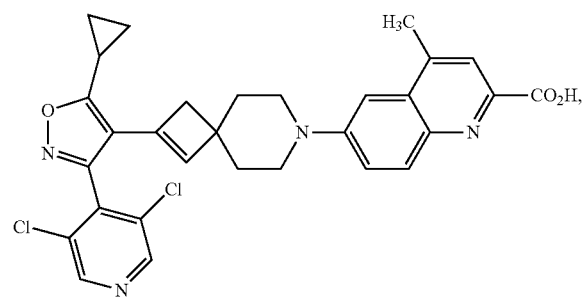

258
-continued

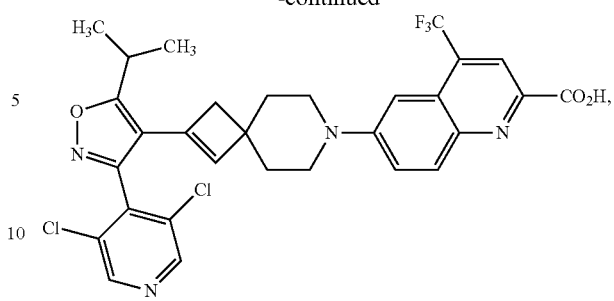

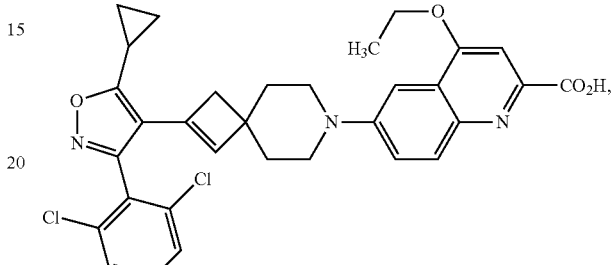

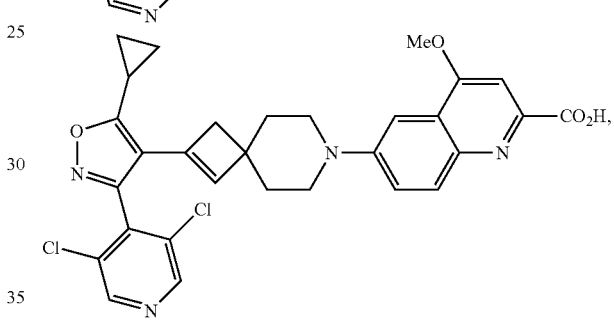

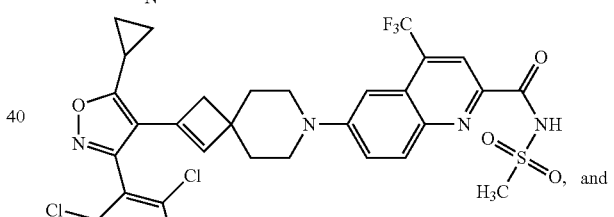, and

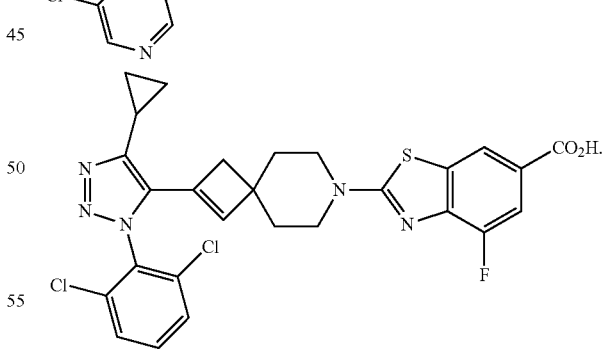

9. A pharmaceutical composition comprising a pharmaceutically acceptable carrier and a compound according to claim 1, or a stereoisomer, a tautomer, a pharmaceutically acceptable salt, or a solvate thereof.

10. A pharmaceutical composition comprising a pharmaceutically acceptable carrier and a compound according to claim 8, or a stereoisomer, a tautomer, a pharmaceutically acceptable salt, or a solvate thereof.

11. A compound having the structure:
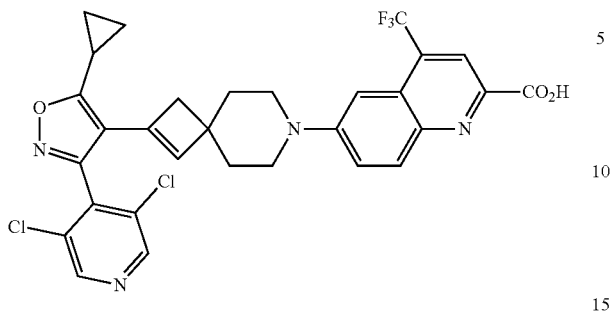
or a stereoisomer, a tautomer, a pharmaceutically acceptable salt, or a solvate thereof.
12. A pharmaceutical composition comprising a pharmaceutically acceptable carrier and a compound according to claim 11 or a stereoisomer, a tautomer, a pharmaceutically acceptable salt, or a solvate thereof.
* * * * *